US008956616B2

(12) United States Patent
Thorpe et al.

(10) Patent No.: US 8,956,616 B2
(45) Date of Patent: Feb. 17, 2015

(54) CONSTRUCTS BINDING TO PHOSPHATIDYLSERINE AND THEIR USE IN DISEASE TREATMENT

(75) Inventors: Philip E. Thorpe, Dallas, TX (US); Troy A. Luster, Dallas, TX (US); Steven W. King, Ladera Ranch, CA (US)

(73) Assignees: Board of Regents, The University of Texas System, Austin, TX (US); Peregrine Pharmaceuticals, Inc., Tustin, CA (US)

( * ) Notice: Subject to any disclaimer, the term of this patent is extended or adjusted under 35 U.S.C. 154(b) by 685 days.

(21) Appl. No.: 11/339,392

(22) Filed: Jan. 24, 2006

(65) Prior Publication Data

US 2006/0228299 A1 Oct. 12, 2006

Related U.S. Application Data

(60) Provisional application No. 60/646,333, filed on Jan. 24, 2005.

(51) Int. Cl.

| | |
|---|---|
| ***A61K 38/00*** | (2006.01) |
| ***C07K 16/44*** | (2006.01) |
| ***A61K 47/48*** | (2006.01) |
| ***B82Y 5/00*** | (2011.01) |
| ***C07K 14/775*** | (2006.01) |
| ***C07K 16/30*** | (2006.01) |
| *A61K 39/00* | (2006.01) |

(52) U.S. Cl.

CPC ........... *C07K 16/44* (2013.01); *A61K 47/48384* (2013.01); *A61K 47/48415* (2013.01); *A61K 47/48492* (2013.01); *A61K 47/48507* (2013.01); *A61K 47/48569* (2013.01); *A61K 47/48753* (2013.01); *B82Y 5/00* (2013.01); *C07K 14/775* (2013.01); *C07K 16/3076* (2013.01); *A61K 38/00* (2013.01); *A61K 2039/505* (2013.01); *C07K 2317/622* (2013.01); *C07K 2317/73* (2013.01); *C07K 2317/77* (2013.01); *C07K 2319/00* (2013.01); *C07K 2319/30* (2013.01)

USPC ...................................................... 424/178.1

(58) Field of Classification Search

CPC .................. A61K 2039/505; A61K 47/48569; A61K 38/00; C07K 16/3076; C07K 2319/30; C07K 2317/73

See application file for complete search history.

(56) References Cited

U.S. PATENT DOCUMENTS 5,245,015 A * 9/1993 Fung et al. ............... 530/388.35
5,344,758 A 9/1994 Krilis et al. .................... 433/4.1
5,472,883 A 12/1995 Matsuura et al. ............. 436/518
5,650,269 A 7/1997 Rucheton et al. ................. 435/5
5,859,213 A 1/1999 Stefas et al. .................. 530/415
5,874,409 A 2/1999 Victoria et al. ................. 514/15
5,900,359 A 5/1999 Matsuura et al. .............. 435/7.1
5,998,223 A 12/1999 Matsuura et al. ............. 436/518
6,027,921 A 2/2000 Heartlein et al. ............ 435/69.7
6,203,980 B1 3/2001 Kamboh et al. .................. 435/6
6,312,694 B1 11/2001 Thorpe et al. ............. 424/178.1
6,406,693 B1 6/2002 Thorpe et al.
6,465,191 B1 10/2002 Stefas et al. .................. 435/7.1
6,783,760 B1 8/2004 Thorpe et al.
6,818,213 B1 11/2004 Thorpe et al.
6,825,319 B1 11/2004 Blank et al. ................... 530/328
6,858,210 B1 2/2005 Marquis et al. ............ 424/185.1
6,951,939 B2 10/2005 Jones ............................ 544/357
7,053,178 B2 5/2006 Blank et al. ................... 530/328
7,067,109 B1 6/2006 Thorpe et al.
7,247,303 B2 7/2007 Thorpe et al.
7,422,738 B2 9/2008 Thorpe et al.
7,455,833 B2 11/2008 Thorpe et al.
7,550,141 B2 6/2009 Thorpe et al.
7,572,442 B2 8/2009 Thorpe et al.
7,572,448 B2 8/2009 Thorpe et al.
7,611,704 B2 11/2009 Thorpe et al.
7,615,223 B2 11/2009 Thorpe et al.
7,622,118 B2 11/2009 Thorpe et al.
7,625,563 B2 12/2009 Thorpe et al.
7,678,386 B2 3/2010 Thorpe et al.
7,714,109 B2 5/2010 Thorpe et al.
7,790,159 B2 9/2010 Thorpe et al.

(Continued)

FOREIGN PATENT DOCUMENTS

JP 2000-028607 1/2000
JP 2003-107088 4/2003

(Continued)

OTHER PUBLICATIONS de Groot et al. (Thrombosis Research, vol. 114, pp. 455-459, 2004).*
Callahan et al. (Journal of Immunology, 170: 4840-4845, 2003).*
Arvieux et al., "Neutrophil Activation by anti-$\beta_2$ Glycoprotein I Monoclonal Antibodies via Fcγ Receptor II", *J. Leukoc. Biol.*, 57(3):387-394, 1995.
de Groot et al., "β2-Glycoprotein 1 and LDL-Receptor Family Members", *Thromb. Res*,, 114(5-6),455-459, 2004.

(Continued)

*Primary Examiner* — Brad Duffy
*Assistant Examiner* — Nelson B Moseley, II
(74) *Attorney, Agent, or Firm* — Shelley P. M. Fussey

(57) ABSTRACT

Disclosed are new phosphatidylserine binding constructs with surprising combinations of properties, and a range of diagnostic and therapeutic conjugates thereof. The new constructs effectively bind phosphatidylserine targets in disease and enhance their destruction, and can also specifically deliver attached imaging or therapeutic agents to the disease site. Also disclosed are methods of using the new construct compositions, therapeutic conjugates and combinations thereof in tumor vasculature targeting, cancer diagnosis and treatment, and for treating viral infections and other diseases.

31 Claims, 28 Drawing Sheets

(56) References Cited

U.S. PATENT DOCUMENTS

| | | | | |
|---|---|---|---|---|
| 7,790,860 | B2 | 9/2010 | Thorpe et al. | |
| 7,906,115 | B2 | 3/2011 | Thorpe et al. | |
| 8,486,391 | B2 | 7/2013 | Thorpe et al. | |
| 8,709,430 | B2 | 4/2014 | Thorpe et al. | |
| 2001/0025026 | A1 | 9/2001 | Heartlein et al. | 514/12 |
| 2002/0025321 | A1 | 2/2002 | Shoenfeld et al. | 424/184.1 |
| 2003/0100036 | A1 | 5/2003 | Vojdani | 435/7.92 |
| 2003/0114367 | A1 | 6/2003 | Shoenfeld et al. | 514/12 |
| 2003/0138419 | A1 | 7/2003 | Radic et al. | 424/143.1 |
| 2003/0219406 | A1 | 11/2003 | Schroit et al. | 424/85.7 |
| 2004/0171071 | A1 | 9/2004 | Stefas | 435/7.1 |
| 2004/0248200 | A1 | 12/2004 | Koike et al. | 435/7.1 |
| 2005/0004351 | A1 | 1/2005 | Marquis et al. | 530/387.2 |
| 2005/0107584 | A1 | 5/2005 | Blank et al. | 530/327 |
| 2005/0113297 | A1 | 5/2005 | Francois et al. | 514/12 |
| 2005/0148499 | A1 | 7/2005 | Harats et al. | 514/8 |
| 2005/0175620 | A1 | 8/2005 | Jones | 424/178.1 |
| 2005/0192224 | A1 | 9/2005 | Huizinga et al. | 514/12 |
| 2005/0197283 | A1 | 9/2005 | Harats et al. | 514/8 |
| 2006/0094073 | A1 | 5/2006 | Vojdani | 435/7.92 |
| 2006/0234392 | A1 | 10/2006 | Watkins et al. | 436/518 |

FOREIGN PATENT DOCUMENTS

| | | | |
|---|---|---|---|
| WO | WO 94/13323 | 6/1994 | |
| WO | WO 96/04006 | 2/1996 | |
| WO | WO 01/18541 | 3/2001 | |
| WO | WO 01/66785 | 9/2001 | C12P 21/06 |
| WO | WO 02-058638 | 8/2002 | |
| WO | WO/02/060919 | * 8/2002 | |
| WO | WO 02-100445 | 12/2002 | |
| WO | WO/03/099833 | * 4/2003 | |
| WO | WO 03/099833 | 12/2003 | |
| WO | WO 2004-006847 | 1/2004 | |
| WO | WO 2004-101740 | 11/2004 | |
| WO | WO 2006/054281 | 5/2006 | |
| WO | WO 2006/109312 | 10/2006 | |

OTHER PUBLICATIONS

Miyakis et al., "Beta 2 Glycoprotein I—Function in Health and Disease", *Thromb. Res.*, 114(5-6):335-346, 2004.

Ran and Thorpe, "Phosphatidylserine is a Marker of Tumor Vasculature and a Potential Target for Cancer Imaging and Therapy", *Int. J. Radiation Oncology Biol. Phys.*, 54(5):1479-1484, 2002.

Thorpe, "Antibodies to Anionic Phospholipids as Vascular Targeting Agents for Cancer Treatment", *Euroconferences—Angiogenesis 2* (Online), Jun. 19-20, 2003; http://www.pasteur.fr/applications/euroconf/angio2/12Thorpe.pdf.

Thorpe, "Targeting Tumor Vasculature", *Euroconferences—Angiogenesis 2* [Online] Jun. 19-20, 2003; http://www.pasteur.fr/applications/euroconf/angio2/angiogenesis-micabs.html.

International Search Report for PCT/US2006/002964 mailed May 18, 2007.

Beccken et al., "An Endogenous Inhibitor of Angiogenesis Derived From a Transitional Cell Carcinoma; Clipped $\beta_2$-Glycoprotein-I", *Ann. Surg. Oncol.*, 13(9):1241-1251, 2006.

Hammel et al., "Mechanism of the Interaction of $\beta_2$-Glycoprotein I with Negatively Charged Phospholipid Membranes", *Biochemistry*, 40:14173-14181, 2001.

Horbach et al., "$\beta_2$-Glycoprotein I is Proteolytically Cleaved In Vivo Upon Activation of Fibrinolysis", *Thromb. Haemost.*, 81:87-95, 1999.

Hum et al., "Identification of a Region of $\beta_2$-Glycoprotein I Critical for Lipid Binding and Anti-Cardiolipin Antibody Cofactor Activity", *Proc. Natl. Acad Sci. USA*, 90:2141-2145, 1993.

Hunt and Krilis, "The Fifth Domain of $\beta_2$-Glycoprotein I Contains a Phospholipid Binding Site (Cys281-Cys288) and a Region Recognized by Anticardiolipin Antibodies", *J. Immunol.*, 152:653-659, 1994.

Itoh et al., "Highly Increased Plasma Concentrations of the Nicked Form of $\beta_2$ Glycoprotein I in Patients with Leukemia and with Lupus Anticoagulant: Measurement with a Monoclonal Antibody Specific for a Nicked Form of Domain V", *J. Biochem.*, 128(6):1017-1024, 2000.

Lin et al., "$\beta_2$-Glycoprotein I Protects J774A 1 Macrophages and Human Coronary Artery Smooth Muscle Cells Against Apoptosis", *J. Cell. Biochem.*, 94:485-496, 2005.

Ma et al., "High Affinity Binding of $\beta_2$-Glycoprotein I to Human Endothelial Cells is Mediated by Annexin II", *J. Biol. Chem.*, 275(20):15541-15548, 2000.

Matsuura et al., "Proteolytic Cleavage of $\beta_2$-Glycoprotein I: Reduction of Antigenicity and the Structural Relationship", *International Immunology*, 12(8):1183-1192, 2000.

Ohkura et al., "Plasmin Can Reduce the Function of Human $\beta_2$ Glycoprotein I by Cleaving Domain V Into a Nicked Form", *Blood*, 91(11):4173-4179, 1998.

Shi et al., "$\beta_2$-Glycoprotein I Binds Factor XI and Inhibits its Activation by Thrombin and Factor XIIa: Loss of Inhibition by Clipped B2-Glyooprotein I", *Proc. Natl. Acad. Sci. USA*, 101(11):3939-3944, 2004.

Shi et al., "Domain V of $\beta_2$-Glycoprotein I Binds Factor XI/Xia and is Cleaved at $Lys^{317}$-$Th4^{318}$", *J. Biol. Chem.*, 280(2):907-912, 2005.

Zhang and McCrae, "Annexin A2 Mediates Endothelial Cell Activation by Antiphopholipid/Anti-$\beta_2$ Glycoprotein I Antibodies", *Blood*, 105(5):1964-1969, 2005.

Balasubramanian and Schroit, "Aminophospholipid Asymmetry: A Matter of Life and Death", *Annu. Rev. Physiol.*, 65:701-734, 2003.

Bevers et al., "The Effect of Phospholipids on the Formation of Immune Complexes Between Autoantibodies and $\beta_2$-Glycoprotein I or Prothrombin", *Clin. Immunol*, 112:150-160, 2004.

Bevels et al., "Quantitative Determination of the Binding of $\beta_2$-Glycoprotein I and Prothrombin to Phosphatidylserine-Exposing Blood Platelets", *Biochem. J.*, 386:271-279, 2005.

de Laat et al., "IgG Antibodies that Recognize Epitope Gly40-Arg43 in Domain I of $\beta_2$-Glycoprotein I Canse LAC, and their Presence Correlates Strongly with Thrombosis", *Blood*, 105(4):1540-1545, 2005.

de Laat et al., "Pathogenic Anti-$\beta_2$-Glycoprotein I Antibodies Recognize Domain I of β2-Glycoprotein I Only After a Conformational Change", *Blood*, 107(5):1916-1924, 2006.

del Papa et al., "Human β2-Glycoprotein I Binds to Endothelial Cells Through a Cluster of Lysine Residues that are Critical for Anionic Phospholipid Binding and Offers Epitopes for Anti-$\beta_2$-Glycoprotein I Antibodies", *J. Immunol.*, 160:5572-5578, 1998.

Lozier et al., "Complete Amino Acid Sequence of Human Plasma $\beta_2$-Glycoprotein I", *Proc. Natl. Acad. Sci. USA*, 81:3640-3644, 1984.

Luster et al., "Binding of a Monoclonal Antibody that Targets Anionic Phospholipids on Tumor Vasculature is Dependent upon Interaction with Plasma Protein Beta2-Glycoprotein I", *97th Annual Meeting of the American Association for Cancer Research (AACR)*, Washington, DC, USA, Apr. 1-5, 2006, Poster #2179; *Proceedings of the American Association for Cancer Research*, 47:515, 2006.

Luster et al., "Plasma Protein Beta-2-Glycoprotein 1 Mediates Interaction Between the Anti-tumor Monoclonal Antibody 3G4 and Anionic Phospholipids on Endothelial Cells", *J. Biol. Chem.*, 281(40):29863-29871, 2006.

Luster & Thorpe, "Fusion Proteins Composed of Mouse IgG2a Fc and Mouse Beta-2-Glycoprotein 1 Bind to Endothelial Cells with Exposed Phosphatidylserine", *98th Annual Meeting of the American Association for Cancer Research (AACR)*, Los Angeles, USA, Apr. 14-18, 2007, Poster #4089.

Lutters et al., "Dimers of $\beta_2$-Glycoprotein I Mimic in Vitro Effects of $\beta_2$-Glycoprotein I—Anti-$\beta_2$-Glycoprotein I Antibody Complexes", *J. Biol. Chem.*, 276(5):3060-3067, 2001.

Lutters et al., "Dimers of $\beta_2$-Glycoprotein I Increase Platelet Deposition to Collagen via Interaction with Phospholipids and the Apolipoprotein E Receptor 2", *J. Biol. Chem.*, 278(36):33831-33838, 2003.

McNeil et al., "Anti-Phospholipid Antibodies are Directed Against a Complex Antigen that Includes a Lipid-Binding Inhibitor of Coagulation: $\beta_2$-Glycoprotein I (Apolipoprotein H)", *Proc. Natl. Acad. Sci. USA*, 87:4120-4124, 1990.

Okkels et al, "Structure of the Human $\beta_2$-Glycoprotein I (Apolipoprotein H) Gene", *Eur. J. Biochem.*, 259:435-440, 1999.

(56) References Cited

OTHER PUBLICATIONS

Price et al., "Anti-Phospholipid Autoantibodies Bind to Apoptotic, but Not Viable, Thymocytes in a $\beta_2$-Glycoprotein I-Dependent Manner", *J. Immunol.*, 157:2201-2208, 1996.

Steinkasserer et al., "Complete Nucleotide and Deduced Amino Acid Sequence of Human $\beta_2$-Glycoprotein I", *Biochem. J.*, 277:387-391, 1991.

Strausberg et al., "Generation and Initial Analysis of More than 15,000 Full-Length Human and Mouse cDNA Sequences", *Proc. Natl. Acad. Sci. USA*, 99(26):16899-16903, 2002.

van Lummel et al., "The Binding Site in $\beta_2$-Glycoprotein I for ApoER2' on Platelets is Located in Domain V", *J. Biol. Chem.*, 280(44):36729-36736, 2005.

Willems et al., "Role of Divalency in the High-Affinity Binding of Anticardiolipin Antibody-$\beta_2$-Glycoprotein I Complexes to Lipid Membranes", *Biochemistry*, 35:13833-13842, 1996.

Yasuda et al., "Nicked $\beta_2$-Glycoprotein I: A Marker of Cerebral Infarct and a Novel Role in the Negative Feedback Pathway of Extrinsic Fibrinolysis", *Blood*, 103(10):3766-3772, 2004.

Davis and Gillies, "Immunocytokines: Amplification of Anti-Cancer Immunity", *Cancer Immunol. Immunother.*, 52(5):297-308, 2003.

Esmon et al., "Antiphospholipid Antibodies and the Protein C Pathway", *J. Autoimmun.*, 15(2):221-225, 2000.

Ran et al., "Increased Exposure of Anionic Phospholipids on the Surface of the Tumor Blood Vessels", *Cancer Res.*, 62(21):6132-6140, 2002.

Stenflo, "Contributions of Gla and EGF-Like Domains to the Function of Vitamin K-Dependent Coagulation Factors", *Critical Reviews in Eukaryotic Gene Expression*, 9(1):59-88, 1999.

Sugiura, "Baculoviral Expression of Correctly Processed ADAMTS Proteins Fused with the Human IgG-Fc Region", *J. Biotechnol.*, 100(3):193-201, 2003.

Wang et al., "A Single Fc Binding Domain—Alkaline Phosphatase Gene Fusion Expresses a Protein with Both IgG Binding Ability and Alkaline Phosphatase Enzymatic Activity", *Protein Engineering*, 7(5):715-722, 1994.

Zwaal et al., "Lipid-Protein Interactions in Blood Coagulation", *Biochim. Biophys. ACTA*, 1376(3):433-453, 1998.

International Search Report for PCT/US2006/002964, mailed Mar. 8, 2007.

Hagihara et al., "Role of the N- and C-Terminal Domains of Bovine $\beta_2$-Glycoprotein I in Its in Interaction with Cardiolipin[1]", *J. Biochem.*, 118:129-136, 1995.

Mehdi et al., "A Hydrophobic Sequence at Position 313-316 (Leu-Ala-Phe-Trp) in the Fifth Domain of Apolipoprotein H ($\beta_2$-Glycoprotein I) is Crucial for Cardiolipin Binding", *Eur. J. Biochem.*, 267:1770-1776, 2000.

Sanghera et al., "Identification of Structural Mutations in the Fifth Domain of Apolipoprotein H ($\beta_2$-Glycoprotein I) which Affect Phospholipid Binding", *Hum. Mol. Genet.*, 6(2):311-316, 1997.

Schwarzenbacher et al., "Crystal Structure of Human $\beta_2$-Glycoprotein I: Implications for Phospholipid Binding and the Antiphospholipid Syndrome", *EMBO J.*, 18(22):6228-6239, 1999.

Sheng et al., "Site-Directed Mutagenesis of Recombinant Human $\beta_2$-Glycoprotein I Identifies a Cluster of Lysine Residues that are Critical for Phosopholipid Binding and Anti-Cardiolipin Antibody Activity", *J. Immunol.*, 157:3744-3751, 1996.

Anthony Prakasam and Perumal Thiagarajan (2012). β2-Glycoprotein I—A Protein in Search of Functions, Antiphospholipid Syndrome, Dr. Alena Bulikova, (Ed.), ISBN:978-953-51-0526-8, InTech, Available from: http://www.intechopen.com/books/antiphospholipid-syndrome/beta2-glycoprotein-i-in-search-of-function.

Hartwig Cleve, "Genetic Studies on the Deficiency of β2-Glycoprotein I of Human Serum", Humangenetik 5, 294-304 (1968).

Balasubramanian et al., "Estimation of Plasma Beta-2-Glycoprotein Levels by Competitive ELISA", Thrombosis Research 92, 91-97 (1998).

* cited by examiner

FIG. 2A

3G4-2BVH original sequence:

```
                                      M   G   W   T   W   I   F   I   L   I   L   S   V
121                                  ATG GGA TGG ACC TGG ATC TTT ATT TTA ATC CTG TCA GTA
                                     TAC CCT ACC TGG ACC TAG AAA TAA AAT TAG GAC AGT CAT
                                         PvuII
                                         ~~~~~~~~
      T   T   G   V   H   S   E   V   Q   L   Q   Q   S   G   P   E   L   E   K   P
181  ACT ACA GGT GTC CAC TCT GAG GTC CAG CTG CAG CAG TCT GGA CCT GAG CTG GAG AAG CCT
     TGA TGT CCA CAG GTG AGA CTC CAG GTC GAC GTC GTC AGA CCT GGA CTC GAC CTC TTC GGA
      G   A   S   V   K   L   S   C   K   A   S   G   Y   S   F   T   G   Y   N   M
241  GGC GCT TCA GTG AAG CTA TCC TGC AAG GCT TCT GGT TAC TCA TTC ACT GGC TAC AAC ATG
     CCG CGA AGT CAC TTC GAT AGG ACG TTC CGA AGA CCA ATG AGT AAG TGA CCG ATG TTG TAC
      N   W   V   K   Q   S   H   G   K   S   L   E   W   I   G   H   I   D   P   Y
301  AAC TGG GTG AAA CAG AGC CAT GGA AAG AGC CTT GAA TGG ATT GGA CAT ATT GAT CCT TAC
     TTG ACC CAC TTT GTC TCG GTA CCT TTC TCG GAA CTT ACC TAA CCT GTA TAA CTA GGA ATG
      Y   G   D   T   S   Y   N   Q   K   F   R   G   K   A   T   L   T   V   D   K
361  TAT GGT GAT ACT TCC TAC AAC CAG AAG TTC AGG GGC AAG GCC ACA TTG ACT GTA GAC AAA
     ATA CCA CTA TGA AGG ATG TTG GTC TTC AAG TCC CCG TTC CGG TGT AAC TGA CAT CTG TTT
      S   S   S   T   A   Y   M   Q   L   K   S   L   T   S   E   D   S   A   V   Y
421  TCC TCC AGC ACA GCC TAC ATG CAG CTC AAG AGC CTG ACA TCT GAG GAC TCT GCA GTC TAT
     AGG AGG TCG TGT CGG ATG TAC GTC GAG TTC TCG GAC TGT AGA CTC CTG AGA CGT CAG ATA
      Y   C   V   K   G   G   Y   Y   G   H   W   Y   F   D   V   W   G   A   G   T
481  TAC TGT GTA AAG GGG GGT TAC TAC GGG CAC TGG TAC TTC GAT GTC TGG GGC GCA GGG ACC
     ATG ACA CAT TTC CCC CCA ATG ATG CCC GTG ACC ATG AAG CTA CAG ACC CCG CGT CCC TGG
      BstEII
      ~~~~~~~~~~
      T   V   T   V   S   S   A   T   T   T   A   P   S   V   Y   P   L   V   P
541  ACG GTC ACC GTC TCC TCA GCT ACA ACA ACA GCC CCA TCT GTC TAT CCC TTG GTC CCG GGC
     TGC CAG TGG CAG AGG AGT CGA TGT TGT TGT CGG GGT AGA CAG ATA GGG AAC CAG GGC CCG
     BamHI                   EcoRI                                       XhoI
     ~~~~~~~~                ~~~~~~~~                                    ~~~~~~~~
601  GGA TCC CCC GGG CTG CAG GAA TTC GAT ATC AAG CTT ATC GAT ACC GTC GAC CTC GAG GGG
     CCT AGG GGG CCC GAC GTC CTT AAG CTA TAG TTC GAA TAG CTA TGG CAG CTG GAG CTC CCC
```

The RACE product 3G4-2BVH is cloned and grafted onto the human γ1 constant region at the BstEII site. Thus, it contains the mouse leader sequence and its VH is joined with the human CH1 sequence in the following way: leader/3G4VH/VSS-AST…

```
       Mouse Leader           ↓mature protein
  1    MGWTWIFILI LSVTTGVHSE VQLQQSGPEL EKPGASVKLS CKASGYSFTG
 51    YNMNWVKQSH GKSLEWIGHI DPYYGDTSYN QKFRGKATLT VDKSSSTAYM
                                                ↓BstEII graft site
101    QLKSLTSEDS AVYYCVKGGY YGHWYFDVWG AGTTVTVSS ASTKGPSVFPL
151    APSSKSTSG                                 ↑human γ1CH1
```

FIG. 2B

3G4-2BVL original sequence:

```
                                                                  M   D   M   R   A
 61                                                              ATG GAC ATG AGG GCT
                                                                 TAC CTG TAC TCC CGA
          P   A   Q   I   L   G   F   L   L   L   F   P   G   T   R   C   D   I   Q
121      CCT GCA CAG ATT TTG GGC TTC TTG TTG CTC TTG TTT CCA GGT ACC AGA TGT GAC ATC CAG
         GGA CGT GTC TAA AAC CCG AAG AAC AAC GAG AAC AAA GGT CCA TGG TCT ACA CTG TAG GTC
          M   T   Q   S   P   S   S   L   S   A   S   L   G   E   R   V   S   L   T   C
181      ATG ACC CAG TCT CCA TCC TCC TTA TCT GCC TCT CTG GGA GAA AGA GTC AGT CTC ACT TGT
         TAC TGG GTC AGA GGT AGG AGG AAT AGA CGG AGA GAC CCT CTT TCT CAG TCA GAG TGA ACA
          R   A   S   Q   D   I   G   S   S   L   N   W   L   Q   Q   G   P   D   G   T
241      CGG GCA AGT CAG GAC ATT GGT AGT AGC TTA AAC TGG CTT CAG CAG GGA CCA GAT GGA ACT
         GCC CGT TCA GTC CTG TAA CCA TCA TCG AAT TTG ACC GAA GTC GTC CCT GGT CTA CCT TGA
          I   K   R   L   I   Y   A   T   S   S   L   D   S   G   V   P   K   R   F   S
301      ATT AAA CGC CTG ATC TAC GCC ACA TCC AGT TTA GAT TCT GGT GTC CCC AAA AGG TTC AGT
         TAA TTT GCG GAC TAG ATG CGG TGT AGG TCA AAT CTA AGA CCA CAG GGG TTT TCC AAG TCA
          G   S   R   S   G   S   D   Y   S   L   T   I   S   S   L   E   S   E   D   F
361      GGC AGT AGG TCT GGG TCA GAT TAT TCT CTC ACC ATC AGC AGC CTT GAG TCT GAA GAT TTT
         CCG TCA TCC AGA CCC AGT CTA ATA AGA GAG TGG TAG TCG TCG GAA CTC AGA CTT CTA AAA
          V   D   Y   Y   C   L   Q   Y   V   S   S   P   P   T   F   G   A   G   T   K
421      GTA GAC TAT TAC TGT CTA CAA TAT GTT AGT TCT CCT CCC ACG TTC GGT GCT GGG ACC AAG
         CAT CTG ATA ATG ACA GAT GTT ATA CAA TCA AGA GGA GGG TGC AAG CCA CGA CCC TGG TTC
                                                            BbsI                BamHI
                                                            ~~~~~~~             ~~~~~~~
          L   E   L   K   R   A   D   A   A   P   T   V   F   I   F   G   R   I   P
481      CTG GAG CTG AAA CGG GCT GAT GCT GCA CCA ACT GTC TTC ATC TTC GGG CGG ATC CCC CGG
         GAC CTC GAC TTT GCC CGA CTA CGA CGT GGT TGA CAG AAG TAG AAG CCC GCC TAG GGG GCC
```

The RACE product 3G4-2BVL is grafted to human κ constant region at the BbsI site. Thus, it contains the mouse leader sequence and its VL is joined withIN the human CL1 sequence in the following way: leader/3G4-VL/TVF-IFP...

```
            Mouse Leader      ↓mature protein
  1    MDMRAPAQIL  GFLLLLFPGT  RCDIQMTQSP  SSLSASLGER  VSLTCRASQD
 51    IGSSLNWLQQ  GPDGTIKRLI  YATSSLDSGV  PKRFSGSRSG  SDYSLTISSL
                               FR4↓                    ↓BbsI graft site
101    ESEDFVDYYC  LQYVSSPPTF  GAGTKLELKR  ADAAPTVF    IFPPSDEQLKSGTAS
                                                      ↑ human kappa constant
```

FIG. 2C

3G4 IgG2a Heavy Chain (SEQ ID NO:10)

```
        /-------Leader-----\/-------------------------------------------------------------
  1     MGWTWIFILI LSVTTGVHSE VQLQQSGPEL EKPGASVKLS CKASGYSFTG YNMNWVKQSH GKSLEWIGHI

        ------------------3G4 VH---------------------------------------------------\/
 71     DPYYGDTSYN QKFRGKATLT VDKSSSTAYM QLKSLTSEDS AVYYCVKGGY YGHWYFDVWG AGTTVTVSSA

        -----------------------------------mouse IgG2a CH1 domain------------------
141     KTTAPSVYPL APVCGDTTGS SVTLGCLVKG YFPEPVTLTW NSGSLSSGVH TFPAVLQSDL YTLSSSVTVT

        --------------------------\/----hinge-------\/------------------------------
211     SSTWPSQSIT CNVAHPASST KVDKKEPRGP TIKPCPPCKC PAPNLLGGPS VFIFPPKIKD VLMISLSPIV

        -------------------------------mouse IgG2a CH2 domain----------------------
281     TCVVVDVSED DPDVQISWFV NNVEVHTAQT QTHREDYNST LRVVSALPIQ HQDWMSGKEF KCKVNNKDLP

        -----------\/-------------------mouse IgG2a CH3 domain---------------------
351     APIERTISKP KGSVRAPQVY VLPPPEEEMT KKQVTLTCMV TDFMPEDIYV EWTNNGKTEL NYKNTEPVLD

        ---------------------------------------------------\
421     SDGSYFMYSK LRVEKKNWVE RNSYSCSVVH EGLHNHHTTK SFSRTPGK
```

FIG. 2D

3G4 Light Chain ($C_\kappa$) (SEQ ID NO:11)

```
        /------Leader----------\/-------------------------------------------------------
  1     MDMRAPAQIL GFLLLLFPGT RCDIQMTQSP SSLSASLGER VSLTCRASQD IGSSLNWLQQ GPDGTIKRLI

        ---------3G4 VL-----------------------------------------------------\/-----------
 71     YATSSLDSGV PKRFSGSRSG SDYSLTISSL ESEDFVDYYC LQYVSSPPTF GAGTKLELKR ADAAPTVSIF

        -----------------------------mouse C-kappa-----------------------------------
141     PPSSEQLTSG GASVVCFLNN FYPKDINVKW KIDGSERQNG VLNSWTDQDS KDSTYSMSST LTLTKDEYER

        ---------------------------\
211     HNSYTCEATH KTSTSPIVKS FNRNEC
```

FIG. 12
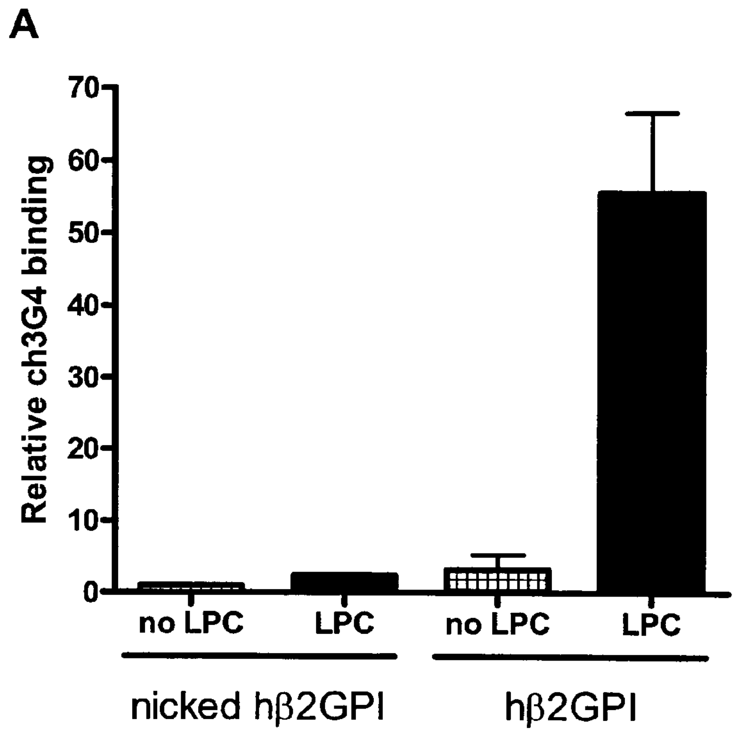
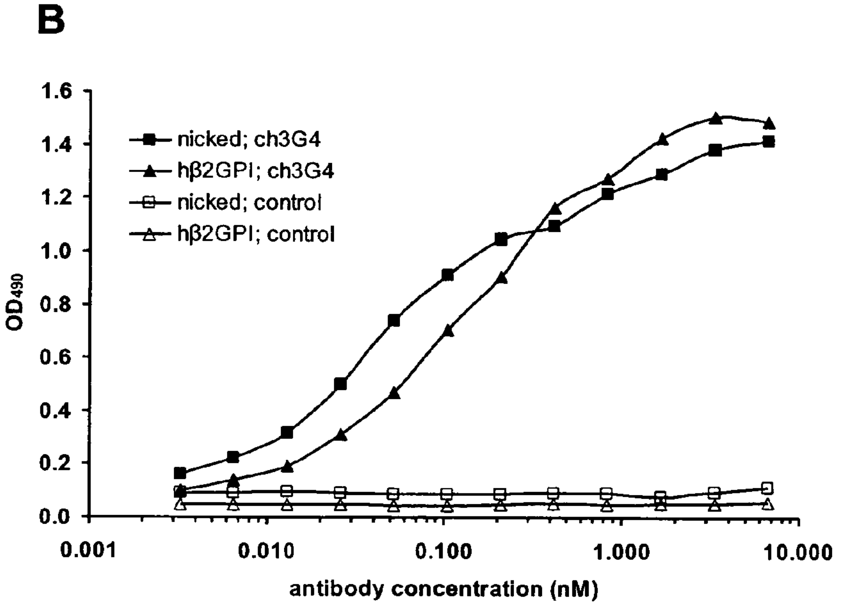

FIG. 18A

Fc-mβ2GPI protein sequence:

```
                                      1
        /---mIgGκ signal seq-----\/----hinge------\ /-----------------------------------------------
-24     MDMPAPAQIL GFLLLLFPGT RCLREPRGPT IKPCPPCKCP APNLLGGPSV FIFPPKIKDV LMISLSPIVT CVVVDVSEDD

        --------------------------mouse IgG2a CH2 domain-----------------------------------\ /---------
56      PDVQISWFVN NVEVHTAQTQ THREDYNSTL RVVSALPIQH QDWMSGKEFK CKVNNKDLPA PIERTISKPK GSVRAPQVYV

        -----------------------mouse IgG2a CH3 domain-------------------------------------------------
136     LPPPEEEMTK KQVTLTCMVT DFMPEDIYVE WTNNGKTELN YKNTEPVLDS DGSYFMYSKL RVEKKNWVER NSYSCSVVHE

        -----------------------\/---------------------------------------------------------------------
216     GLHNHHTTKS FSRTPGKTGG RICPKPDDLP FATVVPLKTS YDPGEQIVYS CKPGYVSRGG MRRFTCPLTG MWPINTLRCV
                               [------------------------Domain I-----------------------------------]

        ----------------------------------------------------------------------------------------------
296     PRVCPFAGIL ENGIVRYTTF EYPNTISFAC NTGFYLNGTS SAKCTEEGKW SPDLPACAPI TCPPPPVPKF ALLKDYRPSA
        [-------------------------------Domain II-----------------------------][----------------------

        --------------------------------------------mouse β2GPI---------------------------------------
376     GNNSLYQDTV VFKCLPHHAM IGNDTVTCTE QGNWTPLPEC LEVRCPFPPR PENGYVNHPA KPVLLYKDKA TFGCHETYKL
        ----Domain III----------------------------------][-----------------------------Domain IV--------

        ----------------------------------------------------------------------------------------------
456     DGPEEAECTK TGTWSFLPTC RESCKLPVKK ATVLYQGMRV KIQEQFKNGM MHGDKIHFYC KNKEKKCSYT VEAHCRDGTI
        ------------------------][-----------------------------------------Domain V---------------------

        ---------------------------------------\
536     EIPSCFKEHS SLAFWKTDAS ELTPC
        ---------------------------------------}
```

FIG. 18B

Human IgG$_1$ heavy chain constant region protein sequence:

```
/------------------------------------------CH1 region-------------------------------------------
ASTKGPSVFP LAPSSKSTSG GTAALGCLVK DYFPEPVTVS WNSGALTSGV HTFPAVLQSS GLYSLSSVVT VPSSSLGTQT

--------------------\/-----hinge-----\/-------------------------------------------------------
YICNVNHKPS NTKVDKKVEP KSCDKTHTCP PCPAPELLGG PSVFLFPPKP KDTLMISRTP EVTCVVVDVS HEDPEVKFNW

-----------------CH2 region----------------------------------------------------\/---------------
YVDGVEVHNA KTKPREEQYN STYRVVSVLT VLHQDWLNGK EYKCKVSNKA LPAPIEKTIS KAKGQPREPQ VYTLPPSRDE

---------------------------------------------CH3 region----------------------------------------
LTKNQVSLTC LVKGFYPSDI AVEWESNGQP ENNYKTTPPV LDSDGSFFLY SKLTVDKSRW QQGNVFSCSV MHEALHNHYT

----------\
QKSLSLSPG
```

Human β2GPI protein sequence:

```
    /-------------------------Domain I--------------------------------------\/--------------------
1   GRTCPKPDDL PFSTVVPLKT FYEPGEEITY SCKPGYVSRG GMRKFICPLT GLWPINTLKC TPRVCPFAGI LENGAVRYTT

    ----Domain II-------------------------------\/------------------------------------Domain III---
81  FEYPNTISFS CNTGFYLNGA DSAKCTEEGK WSPELPVCAP IICPPPSIPT FATLRVYKPS AGNNSLYRDT AVFECLPQHA

    ------------------------------\/-----------------------------------Domain IV--------------------
161 MFGNDTITCT THGNWTKLPE CREVKCPFPS RPDNGFVNYP AKPTLYYKDK ATFGCHDGYS LDGPEEIECT KLGNWSAMPS

    --\/--------------------------------------------Domain V-----------------------------------------
241 CKASCKLPVK KATVVYQGER VKIQEKFKNG MLHGDKVSFF CKNKEKKCSY TEDAQCIDGT IEVPKCFKEH SSLAFWKTDA

    -------\
321 SDVKPC
```

CONSTRUCTS BINDING TO PHOSPHATIDYLSERINE AND THEIR USE IN DISEASE TREATMENT

The present application claims priority to U.S. provisional application Ser. No. 60/646,333, filed Jan. 24, 2005, the disclosure of which application, including the specification, claims, drawings and sequences, is specifically incorporated herein by reference without disclaimer.

BACKGROUND OF THE INVENTION

1. Field of the Invention

The present invention relates to the fields of phosphatidylserine biology, and to treating tumors and viral infections. It provides surprising new constructs, compositions, methods and combinations for tumor vasculature targeting and cancer treatment, and for treating viral infections and other diseases. The invention particularly provides new phosphatidylserine binding constructs with surprising combinations of properties and diagnostic and therapeutic conjugates thereof. The new constructs effectively bind phosphatidylserine disease targets and enhancing their destruction, and can also deliver therapeutic agents to specific sites, and thus provide a range of methods for treating cancer, viral infections and other diseases.

2. Description of the Related Art

Tumor cell resistance to chemotherapeutic agents represents a significant problem in clinical oncology. Another major problem to address in tumor treatment is the desire for a "total cell kill", i.e., killing all so-called "clonogenic" malignant cells that have the ability to grow uncontrolled and replace any tumor mass that might be removed by the therapy. Despite certain advances in the field, these are two of the main reasons why many prevalent forms of human cancer still resist effective chemotherapeutic intervention.

Due to the goal of developing treatments that approach a total cell kill, certain types of tumors have been more amenable to therapy than others. For example, the soft tissue tumors, e.g., lymphomas, and tumors of the blood and blood-forming organs, e.g., leukemias, have generally been more responsive to chemotherapeutic therapy than have solid tumors, such as carcinomas.

One reason for the susceptibility of soft and blood-based tumors to chemotherapy is the greater accessibility of lymphoma and leukemic cells to chemotherapeutic intervention. Simply put, it is much more difficult for most chemotherapeutic agents to reach all of the cells of a solid tumor mass than it is the soft tumors and blood-based tumors, and therefore much more difficult to achieve a total cell kill. Increasing the dose of chemotherapeutic agents most often results in toxic side effects, which generally limits the effectiveness of conventional anti-tumor agents.

Another tumor treatment strategy is the use of an "immunotoxin", in which an anti-tumor cell antibody is used to deliver a toxin to the tumor cells. However, in common with chemotherapeutic approaches, immunotoxin therapy also suffers from significant drawbacks when applied to solid tumors. For example, antigen-negative or antigen-deficient cells can survive and repopulate the tumor or lead to further metastases. A further reason for solid tumor resistance to antibody-based therapies is that the tumor mass is generally impermeable to macromolecular agents such as antibodies and immunotoxins. Both the physical diffusion distances and the interstitial pressure within the tumor are significant limitations to this type of therapy.

An improved treatment strategy is to target the vasculature of solid tumors. Targeting the blood vessels of the tumors, rather than the tumor cells themselves, has certain advantages in that it is not likely to lead to the development of resistant tumor cells, and that the targeted cells are readily accessible. Moreover, destruction of the blood vessels leads to an amplification of the anti-tumor effect, as many tumor cells rely on a single vessel for their oxygen and nutrients. Exemplary vascular targeting agents (VTAs) are described in U.S. Pat. Nos. 5,855,866, 5,965,132, 6,261,535, 6,051,230 and 6,451,312, which describe the targeted delivery of anti-cellular agents and toxins to markers of tumor vasculature.

Another effective version of the vascular targeting approach is to target a coagulation factor to a marker expressed or adsorbed within the tumor vasculature or stroma (Huang et al., 1997; U.S. Pat. Nos. 6,093,399, 6,004,555, 5,877,289, and 6,036,955). The delivery of coagulants, rather than toxins, to tumor vasculature has the further advantages of reduced immunogenicity and even lower risk of toxic side effects. As disclosed in U.S. Pat. No. 5,877,289, a preferred coagulation factor for use in such tumor-specific "coaguligands" is a truncated version of the human coagulation-inducing protein, Tissue Factor (TF), the major initiator of blood coagulation.

More recently, phosphatidylserine (PS) was identified as a specific marker of tumor vasculature (Ran et al., 1998). This led to the development of new anti-PS immunoconjugates for delivering anti-cellular agents, toxins and coagulation factors to tumor blood vessels (U.S. Pat. Nos. 6,312,694, 6,783,760 and 6,818,213). In addition, it was discovered that unconjugated antibodies to PS exerted an anti-cancer effect without attachment to a therapeutic agent, which became known as the phosphatidylserine "naked antibody" approach to tumor vascular targeting and treatment (U.S. Pat. No. 6,406,693).

Although the foregoing methods have furthered the art of tumor treatment, the development of additional therapeutic and vascular targeting agents is needed to expand the number and effectiveness of therapeutic options. An important advance would be the identification of a group of therapeutic agents with anti-cancer properties and therapeutic effects in other systems, such as in treating viral infections. The generation of new targeted constructs that can be made from two human components, particularly those that do not rely on the use of antibodies for targeting, would be a significant development, providing improved safety. Designing and developing new agents that enhance a patients' own response against disease, i.e., that increase host effector functions, would be of great value in maximizing therapeutic responses, particularly where the same mechanisms could be leveraged against cancer and other diseases, such as viral infections and diseases.

SUMMARY OF THE INVENTION

The present invention addresses the foregoing and other needs of the prior art by providing new constructs, compositions, methods and combinations for tumor vasculature targeting and cancer treatment, and for treating viral infections and other diseases. The invention particularly provides new phosphatidylserine binding constructs with surprising combinations of properties, which effectively bind phosphatidylserine targets in disease and enhance their destruction, such as by increasing host effector functions. A range of conjugate compositions are also provided, in which the new constructs are attached to further biological, diagnostic and therapeutic agents, which can be specifically delivered to disease sites. The invention further provides effective methods for using the new constructs and conjugates and combinations thereof in tumor vasculature targeting, cancer treatment and for treating viral infections and other diseases.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, a "construct", as used herein, means "at least a first construct". The operable limits and parameters of combinations, as with the amounts of any single agent, will be known to those of ordinary skill in the art in light of the present disclosure.

ReceptorBodies and BetaBodies:

The invention first provides a range of phosphatidylserine binding construct compositions, in which the constructs comprise at least a first phosphatidylserine binding protein, polypeptide or receptor operatively attached to at least a first antibody Fc region. Joining a phosphatidylserine binding protein, polypeptide or "receptor" to an "antibody" Fc region gives rise to the terms "receptorbody" and "receptorbodies", which are used herein to refer to the phosphatidylserine-binding Fc constructs of the invention.

The constructs or receptorbodies of the invention typically comprise at least a first antibody Fc region operatively attached to at least a first phosphatidylserine binding protein or polypeptide, receptor, ligand or peptide. The term "phosphatidylserine binding protein" is succinctly used herein to refer to all phosphatidylserine binding proteins, polypeptides, receptors, ligands and peptides.

In many embodiments, the "phosphatidylserine binding protein" will retain the phosphatidylserine binding property when attached to an antibody Fc region to form a construct of the invention. Naturally, retention of phosphatidylserine binding function is important in those constructs intended for use in targeting phosphatidylserine exposed in disease sites. However, not all embodiments of the invention are limited to phosphatidylserine binding proteins that retain phosphatidylserine binding properties when attached to an antibody Fc region.

Notably, the invention encompasses an antibody Fc region linked to "nicked β2-glycoprotein I", wherein nicked β2-glycoprotein I no longer binds phosphatidylserine (see below). As nicked β2-glycoprotein I is known to be an inhibitor of angiogenesis (U.S. patent application publication No. US 2003/0219406, specifically incorporated herein by reference), the "Fc-nicked β2" of the present invention will be useful as an inhibitor of angiogenesis and has the advantage of having a longer half life and additional effector functions, if needed.

Accordingly, the term "phosphatidylserine binding protein" refers to the origin of the protein, polypeptide, receptor, ligand or peptide for use in the constructs of the invention, notwithstanding that some constructs of the invention will not bind phosphatidylserine and yet will have important biological and therapeutic uses, as set forth above. That is, β2-glycoprotein I is known as a phosphatidylserine binding protein and yet nicked β2 no longer binds phosphatidylserine.

In terms of binding phosphatidylserine, the original phosphatidylserine binding proteins and the phosphatidylserine binding proteins of the resultant constructs will bind to phosphatidylserine under biologically appropriate conditions, preferably under physiological conditions. Such phosphatidylserine binding proteins may optionally bind to other anionic phospholipids, under biologically appropriate conditions, preferably under physiological conditions.

In certain preferred embodiments, the phosphatidylserine binding proteins of the constructs do not substantially bind to the aminophospholipid, phosphatidylethanolamine (PE). In other preferred embodiments, the phosphatidylserine binding proteins of the constructs show no detectable binding to phosphatidylethanolamine.

A range of phosphatidylserine binding proteins may be used in the constructs of the invention. Certain exemplary phosphatidylserine binding proteins that may be used include Protein C, Protein S, Factor II (prothrombin), Factor V, Factor VII, Factor IX or Factor X.

Other exemplary phosphatidylserine binding proteins that may be used include Mer, a PS-binding scavenger receptor, $\alpha_5\beta_3$ integrin, the CR3 complement receptor, the CR4 complement receptor and the phosphatidylserine receptor, PSr (Balasubramanian and Schroit, 2003, specifically incorporated herein by reference, see Table 2 in particular).

Other exemplary phosphatidylserine binding proteins that may be used in the constructs of the invention are annexins, preferably annexin V, which are particularly contemplated for use in certain embodiments, such as in further conjugates, liposomes and the like. However, in certain embodiments, the present invention provides constructs comprising an antibody Fc region operatively attached to at least a first phosphatidylserine binding protein, wherein said phosphatidylserine binding protein is not an annexin or a phosphatidylserine binding fragment thereof, i.e., is not annexin V or a phosphatidylserine binding fragment thereof.

Preferred examples of phosphatidylserine binding proteins, polypeptides and peptides for use in the constructs of the invention are Beta2-glycoprotein I (β2-glycoprotein I or β2GP1) proteins, polypeptides and peptides. Joining a "Beta"2-glycoprotein I binding protein, polypeptide or peptide to an "antibody" Fc region gives rise to the terms "betabody" and "betabodies", which are used herein to refer to the preferred Fc-β2GP1 constructs of the invention.

β2GP1, previously known as apolipoprotein H, is a 50 kDa plasma glycoprotein that binds phosphatidylserine. The DNA and amino acid sequences of β2GPI from various mammalian species are known, including mouse, rat, dog, cow, chimp and human β2GPI. β2GP1 has five domains, I, II, III, IV and V, and the domain structure is conserved across mammals, as represented by domains I-V of mouse and human β2GPI shown in FIG. 18A and FIG. 18B, respectively.

β2GP1 binds phosphatidylserine through its C terminal domain, domain V. As the lipid and phosphatidylserine binding region(s) from β2GPI domain V are known, the phosphatidylserine binding part of the constructs of the invention need only contain "a lipid binding region from domain V of β2GPI".

With exemplary reference to the human β2GPI amino acid sequence provided herein as SEQ ID NO:22 (Accession number 1C1ZA), as shown in FIG. 18B, and the counterpart mouse β2GPI sequence shown in FIG. 18A, the lipid binding regions from domain V of β2GPI include a cluster of positively charged amino acids (282-287) and a conserved hydrophobic region (311-317) responsible for binding of β2GPI to anionic phospholipids (underlined italics and double underlined italics in FIG. 18B and FIG. 18A).

Accordingly, in certain embodiments, the phosphatidylserine binding part of the constructs of the invention will comprise a peptide having an amino acid sequence as set forth by amino acids 282-287 of SEQ ID NO:22, or a peptide having an amino acid sequence as set forth by amino acids 311-317 of SEQ ID NO:22. In other embodiments, the phosphatidylserine binding part of the constructs of the invention will comprise a peptide spanning these regions, i.e., a peptide having the amino acid sequence of SEQ ID NO:24 (human) or a peptide having the amino acid sequence of SEQ ID NO:20 (mouse).

As the foregoing smaller peptides and polypeptides may not be optimal, other preferred constructs of the invention are those in which the phosphatidylserine binding portion is a β2GPI polypeptide that contains the full or intact domain V of β2GPI, including β2GPI polypeptides that comprise at least domain V and those that contain only domain V.

Although there are no concerns regarding the safety of the methods of the present invention, antibodies from patients with Anti-Phospholipid Syndrome(s) or APS commonly recognize domain I of β2GPI (de Laat et al., 2005a). Antibodies that recognize β2GPI domain II are not pathogenic. Therefore, in certain embodiments, the phosphatidylserine binding part of the constructs of the invention may comprise a β2GPI polypeptide that comprises at least a lipid binding region from β2GPI domain V and that substantially lacks domain I of β2GPI. In preferred embodiments, these constructs will comprise a β2GPI polypeptide that comprises at least domain V of β2GPI and that substantially lacks domain I of β2GPI.

Exemplary β2GPI DNA and amino acid sequences are provided herein, including the human β2GPI amino acid sequence of SEQ ID NO:22 (Accession number 1C1ZA), as shown in FIG. 18B, and the counterpart mouse β2GPI amino acid sequence shown in FIG. 18A (the sequence of an expression plasmid encoding an exemplary Fc-β2GPI construct of the invention is also provided as SEQ ID NO:25). With reference to these figures, sequences and the Accession numbers, optionally in light of the working examples herein, those of ordinary skill in the art will be able to make and use a range of polypeptides that comprise at least domain V of β2GPI.

As set forth above, certain preferred β2GPI polypeptides will comprise at least β2GPI domain V and substantially lack β2GPI domain I. β2GPI polypeptides in accordance with this description may comprise at least domain IV and domain V of β2GPI; comprise at least domain III, domain IV and domain V of β2GPI; or comprise domain II, domain III, domain IV and domain V of β2GPI.

Nonetheless, the presence of β2GPI domain I will not be a significant drawback in the use of the invention, and it may be convenient to prepare constructs in which the β2GPI polypeptide comprises domain I, e.g., for ease of preparation and use. Accordingly, the invention further comprises constructs in which the phosphatidylserine binding portion is a full length β2GPI polypeptide, i.e., a β2GPI polypeptide comprising domain I, domain II, domain III, domain IV and domain V. A full length β2GPI polypeptide may be a human β2GPI polypeptide that comprises the amino acid sequence of SEQ ID NO:22.

In certain embodiments of the invention, it is important that the construct retains phosphatidylserine binding functions when the at least a first phosphatidylserine binding protein is attached to the Fc region, particularly where the construct is intended for use in targeting phosphatidylserine exposed in disease sites. An example where phosphatidylserine binding is not necessary is where at least a first nicked β2GPI polypeptide is attached to an antibody Fc region, which will have use as an angiogenesis inhibitor.

A "nicked" β2GPI polypeptide is where the β2GPI sequence has been nicked, such as by cleavage with the enzyme plasmin, at the Lys317/Thr318 cleavage site. A construct comprising a "nicked β2GPI polypeptide", as used herein, may contain only a nicked domain V. Alternatively, a nicked β2GPI polypeptide may comprise "at least a nicked domain V", such that the polypeptide may comprise a nicked domain V in conjunction with any one or more of domains IV, III, II and I.

Where retention of phosphatidylserine binding is required in a construct of the invention, the present invention provides further surprising and advantageous features in connection with the use of β2GPI polypeptides attached to an Fc region. It was surprisingly found that when an antibody Fc region was operatively attached to two β2GPI polypeptides, the β2GPI polypeptides formed a dimer in the resultant Fc-β2GPI construct and the dimeric construct effectively bound phosphatidylserine.

Thus, additional embodiments of the invention are wherein an antibody Fc region is operatively attached to two β2GPI polypeptides, preferably where each β2GPI polypeptide comprises at least domain V of β2GPI. More preferably, wherein the antibody Fc region is operatively attached to two β2GPI polypeptides, which each comprise at least domain V of β2GPI, and wherein the β2GPI polypeptides form a dimer when attached to the Fc region. Preferably, wherein the antibody Fc region is operatively attached to two β2GPI polypeptides, which each comprise at least domain V of β2GPI, and wherein the β2GPI polypeptides form a dimer when attached to the Fc region and wherein the resultant construct binds phosphatidylserine, i.e., the β2GPI polypeptides form a dimer and bind to phosphatidylserine when attached to the Fc region.

Also, preferably wherein an antibody Fc region is operatively attached to two β2GPI polypeptides; wherein the β2GPI polypeptides each comprise at least domain V of β2GPI and substantially lack domain I of β2GPI; and wherein the β2GPI polypeptides form a dimer and bind to phosphatidylserine when attached to the Fc region. Further, preferably wherein first and second β2GPI polypeptides, which each comprise at least domain V of β2GPI, are operatively attached to the antibody Fc region, thereby forming an Fc-β2GPI dimer.

However, even where phosphatidylserine binding is required in a β2GPI-containing construct of the invention, it is not necessary that the construct comprise two β2GPI polypeptides, nor that any two or more β2GPI polypeptides form a dimer when attached to the Fc region. For example, an Fc region may be attached to a single β2GPI polypeptide, or attached to two or more β2GPI polypeptides that do not form a dimer when attached, and the resultant constructs can still be used to bind phosphatidylserine, e.g., by formulation in a scaffold that provides the required valency. Examples of such formulations or scaffolds are nanoparticles, liposomes and such like, containing the constructs.

For use in humans, any phosphatidylserine binding protein, such as one or more β2GPI polypeptides, should be a human phosphatidylserine binding protein, such as a human β2GPI polypeptide(s). As human Fc regions can also be used, this has the advantage of providing a totally human therapeutic agent, which should reduce side-effects, such as those associated with immunogenicity.

The Fc regions for use in the invention are derived from an antibody or "immunoglobulin", including polyclonal and monoclonal antibodies. The Fc region provides the resultant construct with the ability to stimulate host effector functions, in order to enhance disease treatment.

Although human Fc regions are preferred for use in humans, Fc regions from other sources may be used, such as mouse, rat, hamster, rabbit, monkey and the like. For pre-clinical testing, both the Fc region and the phosphatidylserine binding protein can be selected from the same animal species in which the pre-clinical testing is to be conducted, e.g., a mouse Fc region and a mouse β2GPI polypeptide.

In the art, antibodies are typically depicted as "Y" shaped molecules, made from four polypeptides—two heavy chains and two light chains. The antigen binding or "variable" region, which gives the antibody its specificity for binding antigen, resides in the ends of the light and heavy chains Treating an antibody with a protease can cleave this region, producing separate Fab ("fragment antigen binding") and Fc (fragment crystallizable) regions, domains or fragments. Accordingly, the term "Fc" is used in the art to mean an antibody region, domain or fragment "without an antigen binding region, domain or fragment". This is the meaning intended in the present application, such that the "Fc region" of the constructs is an antibody region, domain or fragment "that does not comprise an antigen binding region, domain or fragment", i.e., that does not specifically bind to an antigen. Thus, the invention provides constructs with effector functions that are not complicated by targeting issues.

The constant regions determine the mechanism used to destroy antigen, i.e., contain determinants of effector function. Antibodies are divided into five major classes, IgM, IgG, IgA, IgD and IgE, based on their constant region structure and immune function. The heavy-chain constant domains that correspond to the difference classes of immunoglobulins are termed μ, γ, α, δ and ϵ, respectively. Several of these are further divided into subclasses or isotypes, such as IgG1, IgG2, IgG3, and IgG4. The subunit structures of different classes of immunoglobulins are well known. The constant regions of heavy chains γ, α and δ have three domains, whereas the constant region of heavy chains μ and ϵ have four domains.

In the constructs of the invention, it is preferred to use an antibody Fc region that has an antibody hinge and antibody heavy chain constant domains $C_H2$ and $C_H3$. The antibody hinge may be important for structural considerations, such as flexibility, which may facilitate formation of a dimer when two or more phosphatidylserine binding proteins, such as two or more β2GPI polypeptides, are attached. The hinge region and hinge link or lower hinge region may also provide effector functions. Although it is not required, the Fc region of the constructs may also comprise at least one of antibody heavy chain constant domains $C_H1$ or $C_H4$.

In light of the effector functions provided, such as complement activation (C1q binding), Fc Receptor binding, and the ability to effectively stimulate processes such as ADCC and cell lysis (Bruggemann et al., 1987; Riechmann et al., 1988; Clark, 1997; Padlan, 1994; each specifically incorporated herein by reference), it is currently preferred that the antibody Fc region is an Fc region from a human IgG1 (γ1) or human IgG3 (γ3) antibody. For a mouse antibody, the Fc region is preferably an Fc region from a mouse IgG2a (γ2a) or mouse IgG2b (γ2b) antibody.

The antibody Fc region will be attached, linked or conjugated to the at least a first phosphatidylserine binding protein, such as a β2GPI polypeptide, by any operative means. For example, by a direct covalent bond, such as via a chemical cross-linker, or wherein the antibody Fc region and the phosphatidylserine binding protein are prepared by recombinant expression as a fusion protein. Indirect attachment may be used, such as avidin:biotin and other such linkages.

The Fc region and the phosphatidylserine binding protein are operatively attached or conjugated, such that the Fc region and phosphatidylserine binding protein each function sufficiently as intended after attachment or conjugation. For example, "operatively" attached means that the Fc region substantially retains the desired effector functions, and the phosphatidylserine binding protein substantially retains desired properties, particularly phosphatidylserine binding where desired, or anti-angiogenic activity.

In certain embodiments, "operatively attaching" will comprise attaching the phosphatidylserine binding proteins to the Fc region in a manner effective to permit the phosphatidylserine binding proteins to form a dimer when attached, particularly where the phosphatidylserine binding proteins are two or more β2GPI polypeptides. In other embodiments, operatively attaching will produce clustering of phosphatidylserine binding proteins.

Where the chosen phosphatidylserine binding protein is a β2GPI polypeptide, and/or where dimerization on the Fc region is particularly desired, it is currently preferred to use the Fc region as the N-terminal portion of the construct and to attach the phosphatidylserine binding proteins or β2GPI polypeptides to become the C-terminal portion of the construct (FIG. 16).

However, other schemes for operatively attaching are contemplated, such that the phosphatidylserine binding proteins or β2GPI polypeptides become the C-terminal portion of the construct, i.e., are inserted in place of an antigen binding region or in place of a $C_H1$ domain and an antigen binding region. In such embodiments, it may be preferred to use a peptide or chemical linker that provides additional flexibility to the resultant construct, such as, e.g., a peptide linker with four glutamine residues and one serine residue (G4S flexible linker).

After operatively attaching the two or more components, the resultant construct will exhibit desired biological properties. Exemplary desired biological properties in the construct as a whole include, binding phosphatidylserine; stimulating host effector functions; targeting phosphatidylserine on activated cells, such as activated, dividing, injured or apoptotic endothelial cells, tumor cells or virally infected cells; localizing to target sites, such as tumor blood vessels and tumor cells; and exerting therapeutic effects, such as anti-cancer and/or anti-viral effects.

The biological properties of the resultant construct will also preferably include desired safety features. For example, the construct will preferably not significantly damage quiescent cells, significantly inhibit coagulation reactions in vitro, cause significant thrombosis in vivo or have significant lupus anticoagulant activities.

The present invention thus provides new receptorbody and betabody constructs effective in the treatment of cancer, viral infections and other diseases. These constructs include those that effectively bind phosphatidylserine targets in disease and enhance their destruction by increasing host effector functions.

Additional Conjugates, Compositions and Kits:

Although highly effective alone, the present invention nonetheless also provides further conjugates, compositions and related methods in which the constructs, receptorbodies and betabodies of the invention are further attached to additional biological, diagnostic and therapeutic agents. Such "additional conjugates" of the invention are "trifunctional agents", as they have the three properties of binding phosphatidylserine, stimulating host effector functions and delivering the attached biological, diagnostic or therapeutic agent to the desired target.

In the following descriptions of the conjugates, compositions, pharmaceuticals, combinations, cocktails, kits, first and second medical uses and all methods in accordance with this invention, the "constructs" include all the constructs, receptorbodies and betabodies of the primary invention described above.

In the additional conjugate embodiments, the invention still further provides new categories of conjugates, compositions, kits and methods in which the original construct, receptorbody or betabody is operatively attached to an "additional", further or exogenous biological, diagnostic or therapeutic agent. The "exogenous" biological, diagnostic or therapeutic agent is "an agent distinct from the Fc domain already present in the original construct".

The additional or exogenous "biological agent" need not directly be a therapeutic or diagnostic agent. For example, as the invention can be used in connection with prodrugs, including ADEPT embodiments, the biological agent may be an agent, preferably an enzyme, which cleaves a substantially inactive prodrug to release a substantially active drug. Such agents and enzymes are described below in relation to the prodrug and ADEPT method embodiments.

As to "diagnostic agents", preferred diagnostic agents for attachment are in vivo diagnostic, imaging or detectable agent agents. Such diagnostic conjugates may be used in imaging pre-apoptotic and apoptotic cells in a range of diseases, in combined tumor imaging and treatment, and in methods of using the invention as a surrogate marker to monitor chemotherapy. Preferred diagnostic agents include an X-ray detectable compound, a radioactive ion, a nuclear magnetic spin-resonance isotope and a CEST or paraCEST agent.

Suitable detectable labels include an X-ray detectable compound, such as bismuth (III), gold (III), lanthanum (III) or lead (II); a radioactive ion, such as copper$^{67}$, gallium$^{67}$, gallium$^{68}$, indium$^{111}$, indium$^{113}$, iodine$^{123}$, iodine$^{125}$, iodine$^{131}$, mercury$^{197}$, mercury$^{203}$, rhenium$^{186}$, rhenium$^{188}$, rubidium$^{97}$, rubidium$^{103}$, technetium$^{99m}$ or yttrium$^{90}$; a nuclear magnetic spin-resonance isotope, such as cobalt (II), copper (II), chromium (III), dysprosium (III), erbium (III), gadolinium (III), holmium (III), iron (II), iron (III), manganese (II), neodymium (III), nickel (II), samarium (III), terbium (III), vanadium (II) or ytterbium (III); or rhodamine or fluorescein.

Regarding "therapeutic agents", certain preferred therapeutic agents are cytotoxic, cytostatic, anticellular and anticancer agents. A construct, receptorbody or betabody of the invention may therefore be linked to at least a first chemotherapeutic agent, anti-angiogenic agent, apoptosis-inducing agent, anti-tubulin drug, antibiotic, radioisotope or coagulant.

Within the cytotoxic agents, currently preferred are ricin, gelonin, abrin, diphtheria, pseudomonas and pertussis toxins. Of the cytokines and chemokines, currently preferred agents are IL-2, IL-12, TNF-α, interferon-α (IFN-α), IFN-β, IFN-γ, and LEC (liver-expressed chemokine). V-type ATPase inhibitors are also currently preferred, such as salicylihalamide, concanamycin or bafilomycin, as are protein synthesis inhibitors, such as psymberin, pederin, irciniastatin A.

Taxol, docetaxel, paclitaxel, cisplatin, gemcitabine, a combretastatin, doxorubicin and adriamycin are currently preferred anti-cancer agents. Arsenic radioisotopes are also currently preferred as additional or exogenous agents. In terms of coagulants, truncated Tissue Factor is currently preferred.

A construct, receptorbody or betabody of the invention may also be further operatively attached to an anti-viral agent or drug, such as a nucleoside reverse transcriptase inhibitor, a non-nucleoside reverse transcriptase inhibitor or a protease inhibitor. AZT, cidofovir and ribavirin are currently preferred as exogenous anti-viral agents.

Again, in the additional conjugate embodiments, the term "conjugate" is used to define the operative association of the original construct, receptorbody or betabody and the additional agent, and is not intended to refer solely to any type of operative association, and is particularly not limited to chemical "conjugation". Recombinant fusion proteins may again be used. So long as the phosphatidylserine binding protein, Fc region and additional attached agent(s) function sufficiently as intended, particularly when delivered to a target site in vivo, any mode of attachment will be suitable.

Where a β2GPI polypeptide is used as the phosphatidylserine binding protein of a construct, it will generally be preferred not to attach any additional agent in β2GPI domain V, or at least not within the lipid binding region(s) of domain V. In certain embodiments, such as those exemplified in FIG. 16, it is therefore preferred for simplicity to operatively attach any additional agent to the N-terminal portion of the construct, i.e., towards the hinge or $C_H2$ area.

The invention also provides compositions comprising a biologically effective amount of at least a first construct, receptorbody or betabody. Preferred compositions are "pharmaceutical compositions" comprising, in a pharmaceutically acceptable carrier, a biologically or therapeutically effective amount of at least a first construct, receptorbody or betabody of the invention, or a conjugate thereof. These compositions are intended for pharmaceutical, pharmacological, therapeutic, medical and veterinary uses, preferably for use in treating cancer and viral infections.

The pharmaceutical compositions include those formulated for parenteral administration, such as for intravenous administration, or for administration as a liposome or as an aerosol. The aerosol formulations are particularly suitable for treating viral infections. The "biologically or therapeutically effective amounts" in the pharmaceutical compositions are amounts effective for treating a disease or disorder, particularly amounts effective for treating cancer or a viral infection.

Although uniquely effective, the various constructs, receptorbodies or betabodies of the invention, and conjugates thereof, and the related methods of the invention, can also be used to advantage in combination with other agents and therapies to provide combined, compositions, pharmaceuticals and kits of the invention and related combined treatment methods. In further embodiments, therefore, the invention further provides particular combined compositions, methods and kits, e.g. for cancer and anti-viral treatment, which have been selected to work surprisingly well together, as explained in more detail herein.

Aspects of the invention thus further include compositions, pharmaceutical compositions, combinations, mixtures, medicaments and/or medicinal cocktails of agents, comprising at least a first construct, receptorbody or betabody of the invention, or a conjugate thereof, in combination with a biologically or therapeutically effective amount of at least a second biological agent. All such combinations preferably comprise "combined biologically or therapeutically effective amounts", such as a combined amount effective to treat a disease, such as to treat cancer or a viral infection.

In the compositions, the "at least a second biological agent" will often be a diagnostic or therapeutic agent, but it need not be. For example, the second biological agent may be a component of a pharmaceutical composition such as a dispersion agent or an absorption delaying agent. Other biological agents, such as agents for making conjugates and prodrugs for use in prodrug and ADEPT methods, and diagnostic agents, are preferably maintained in combination, but separately, from the first composition of the invention and are therefore discussed below in reference to the kits of the invention. "In combination, but separately" means in close confinement together, but not part of the same composition, such as not part of the same solution or pharmaceutical composition.

As to the "at least a second therapeutic agent", the term "second" is in reference to the construct, receptorbody or betabody of the invention, or conjugate thereof, being the "first" therapeutic agent.

Where the invention is intended for use in cancer treatment, the at least a second therapeutic agent will preferably be "at least a second, distinct anti-cancer agent". The second, anti-cancer agents for combined use may be radiotherapeutic, chemotherapeutic, anti-angiogenic or apoptosis-inducing agents, cytokines or antibodies or an antibody-therapeutic agent constructs that bind to a tumor cell, an intracellular antigen released from a necrotic tumor cell or to a component of tumor vasculature (i.e., anti-cancer immunotoxins or coaguligands). The term "chemotherapeutic agent", as used herein, includes genes, vectors, antisense constructs and ribozymes.

Certain preferred second, anti-cancer agents for combined use are those that complement or enhance the therapeutic effect of the first construct, receptorbody or betabody of the invention, or conjugate thereof, and/or those selected for a particular tumor type or patient. "Therapeutic agents that complement or enhance the therapeutic effect" include radiotherapeutic agents, vascular permeability enhancing agents, anti-angiogenic agents, apoptosis-inducing agents, certain cytokines, anti-tumor cell immunotoxins, as well as selected chemotherapeutic agents. Currently preferred "selected chemotherapeutic agents" are chemotherapeutic agents with anti-angiogenic effects, as in Table E; chemotherapeutic agents that induce apoptosis, as in Table F; calcium flux inducing agents, inflammatory cytokines, $H_2O_2$, thrombin, and anti-tubulin drugs from the combretastatin family. Doxorubicin, etoposide and actinomycin-D are further preferred, with docetaxel being most preferred.

Where the invention is intended for use in viral treatment, the at least a second therapeutic agent will preferably be "at least a second, distinct anti-viral agent". The second, anti-viral agents for combined use may be selected from any anti-viral agent or drug available at the time of practicing the invention, including the range of anti-viral agents and drugs described herein for attachment to the constructs of the invention. By way of example, anti-retroviral drugs such as NTRIs, non-nucleoside RT inhibitors and protease inhibitors, anti-viral agents as set forth in Table G, and preferably, AZT or cidofovir.

The invention further provides a liposome, lipid carrier, complex, mixture, supramolecular structure multimolecular aggregate or lipid-based drug delivery system comprising at least a first construct, receptorbody or betabody of the invention, or a conjugate thereof. The liposome or liposome-like composition may be in the form of a monolayer, bilayer, multimolecular aggregate, vesicle, helix, disc, tube, fiber, torus, hexagonal phase, gel phase, liquid-crystalline phase, liquid-crystalline multimolecular aggregate, micelle, reverse micelle, microemulsion, emulsion, microreservoir, oil globule, fat globule, wax globule and/or colloidal particle.

Liposomes or liposome-like compositions generally comprise an "outer membrane" or bulk aqueous phase and "central core" or inner aqueous phase. In preferred embodiments, the liposome or liposome-like composition is a stealthed liposome, lipid carrier, complex, mixture, supramolecular structure multimolecular aggregate or lipid-based drug delivery system. "Stealthed" liposomes and liposome-like compositions comprise a biologically effective amount of at least a first stealthing agent in operative association with the outer membrane. A "stealthing agent" is a component that increases the biological half life of a liposome or liposome-like composition when operatively associated with the outer membrane of the liposome or liposome-like composition. In "operative association", the outer membrane of the liposome or liposome-like composition is preferably "coated" with the one or more stealthing agents.

Effective stealthing agents include a range of biocompatible hydrophilic polymers, such as polyamines, polylactic acid, polyglycolic acid, polylactic-polyglycolic acid (PLGA), polypeptides and related materials. A preferred stealthing agent is polyethylene glycol (PEG) component, wherein the resulting stealthed liposomes are termed "PEGylated liposomes".

Preferred liposomes of the invention are stealthed or PEGylated liposomes wherein at least a first construct, receptorbody or betabody of the invention, or a conjugate thereof, is operatively associated with the outer membrane of the liposome, preferably where the liposome is "coated" therewith.

Particularly preferred liposomes are such "coated" and stealthed or PEGylated liposomes wherein at least a first therapeutic agent, such as an anti-viral agent or preferably an anti-cancer agent, is operatively associated with the liposome or dispersed within the liposomal formulation. Preferably, the therapeutic, anti-viral or anti-cancer agent is operatively associated with or maintained within the central core of the liposome. Exemplary anti-cancer agents are radionuclide(s) and chemotherapeutic agents, such as anti-tubulin drugs, docetaxel and paclitaxel, with docetaxel being preferred.

Further embodiments of the invention concern kits comprising, in at least a first composition or container, at least a first construct, receptorbody or betabody of the invention, or a conjugate thereof, in combination with a biologically or therapeutically effective amount of at least a second biological agent, component or system.

The "second biological agents, components or systems" are not limited to therapeutic or diagnostic agents. For example, second biological agents, components or systems may comprise components for modification of the construct and/or for attaching other agents. Certain preferred second biological agents, components or systems are prodrugs or components for making and using prodrugs, including components for making the prodrug itself and components for adapting the constructs of the invention to function in such prodrug or ADEPT embodiments.

The at least a "second diagnostic agent, component or system" may be a diagnostic agent, component or system directly or indirectly detectable by an in vitro diagnostic test. "Directly detectable in vitro reporter agents" include radiolabels, reporter agents detectable by immunofluorescence and luciferase. "Indirectly detectable in vitro reporter agents" function in conjunction with further exogenous agent(s), such as detectable enzymes that yield a colored product on contact with a chromogenic substrate. These include "secondary antibodies", which are attached to a direct or indirect detectable agent, such a radiolabel or enzyme, and "secondary and tertiary antibody detection systems" in which the tertiary antibody is attached to the detectable agent.

Preferred diagnostic kits of the invention are those comprising a diagnostic agent, component or system detectable by in vivo diagnosis or imaging. An advantage of the imaging embodiments of the invention is that the same construct can be used for imaging and treatment. The invention therefore provides kits and medicaments that comprise:

(a) a first pharmaceutical composition comprising a diagnostically effective amount of a construct, receptorbody or betabody of the invention, operatively attached to a detectable label or diagnostic agent; and (b) a second pharmaceutical composition comprising a therapeutically effective amount of a construct, receptorbody or betabody of the invention, preferably a therapeutically effective amount of the same construct, receptorbody or betabody used in the first pharmaceutical composition.

For use in therapeutic embodiments, the kits will comprise "at least a second therapeutic agent". Preferably, such kits comprise a combined biologically or therapeutically effective amount of at least the two specified agents, such as combined amounts effective to inhibit proliferation or viral replication, or to treat a disease such as cancer or a viral infection.

In terms of cancer treatment, the kits of the invention include antibodies for use in combination with prodrugs and ADEPT. In such compositions, the construct, receptorbody or betabody is "modified to provide a converting or enzymatic capacity". Preferably, the construct, receptorbody or betabody is operatively associated with, preferably covalently linked or conjugated to, at least a first converting agent or enzyme capable of converting at least one prodrug to the active form of the drug.

The enzymatic or enzyme-conjugated construct, receptorbody or betabody will combined with an initially separate formulation of the "prodrug". The prodrug will be an inactive or weakly active form of a drug that is that is converted to the active form of the drug on contact with the enzymatic capacity, converting function or enzyme associated with the construct, receptorbody or betabody of the invention.

Accordingly, kits are provided that comprise, preferably in separate compositions and/or containers:

(a) a biologically effective amount of at least a first construct, receptorbody or betabody of the invention, wherein the construct, receptorbody or betabody is operatively associated with, covalently linked or conjugated to, at least a first enzyme; and (b) a biologically effective amount of at least a first substantially inactive prodrug that is converted to a substantially active drug by the enzyme associated with, linked to or conjugated to the construct, receptorbody or betabody.

Suitable enzymes that cleave a substantially inactive prodrug to release a substantially active drug include arylsulfatase, serratia protease, thermolysin, subtilisin, a carboxypeptidase, a cathepsin, D-alanylcarboxypeptidase, β-galactosidase, neuraminidase, β-lactamase, penicillin amidase and cytosine deaminase.

Other than prodrugs, the at least a second, anti-cancer agent may be any of the second, anti-cancer agents described above in relation to the combined anti-cancer compositions of the invention. For treating viral infections, the at least a second, anti-viral agent may also be any of the second, anti-viral agents described above in relation to the combined anti-viral compositions of the invention. However, the "kits" may comprise the at least two recited the agents "in combination, but separately", thus providing even more flexibility in the selection of agents.

The kits of the invention may therefore comprise combined biologically or therapeutically effective amounts of at least the two specified agents within a single container or container means, or within distinct containers or container means. The kits may also comprise instructions for using the biological and therapeutic agents included therein. Imaging components may also be included in combination, but separately with the therapeutic kits.

Tumor Treatment and Related Methods:

The present invention provides a number of methods and uses for a construct, receptorbody or betabody of the invention, or a conjugate thereof. Concerning all methods, the terms "a" and "an" are used to mean "at least one", "at least a first", "one or more" or "a plurality" of steps in the recited methods, except where specifically stated. This is particularly relevant to the administration steps in the treatment methods. Thus, not only may different doses be employed with the present invention, but different numbers of doses, e.g., injections or inhalations, may be used, up to and including multiple injections or inhalations.

Various useful in vitro methods and uses are provided that have important biological implications. Thus provided are methods of, and uses in, binding phosphatidylserine, which generally comprise effectively contacting a composition comprising phosphatidylserine with at least a first construct, receptorbody or betabody of the invention, or a conjugate thereof. The "contacting" is under conditions effective to allow the formation of bound complexes, and any complexes so formed are detected.

The detection methods and uses may be used in connection with biological samples, e.g., in diagnostics for apoptosis, tumors and virally infected cells, and diagnostic kits based thereon are also provided. These methods and kits provide specific and credible uses for the constructs, receptorbodies, betabodies and conjugates of the present invention. For example, annexin V is currently used in methods and kits to detect apoptotic cells. However, annexin V binds to phosphatidylethanolamine as well as phosphatidylserine, whereas the constructs, receptorbodies, betabodies and conjugates of the present invention bind to phosphatidylserine with no significant, or preferably no detectable, binding to phosphatidylethanolamine. Thus, the constructs of the invention are better able to specifically detect phosphatidylserine in detection methods and diagnostic assays.

The invention further provides many useful in vivo methods and uses. For example, methods for tumor vascular targeting, tumor imaging and treatment based upon localization to phosphatidylserine, which is an accessible and stably targetable marker of tumor vasculature. The constructs, receptorbodies and betabodies of the invention, and conjugates thereof, specifically localize to the vasculature of solid tumors upon administration to an animal with a tumor. Thus, translocation of phosphatidylserine to the surface of tumor vascular endothelial cells occurs, at least in a significant part, independently of complete apoptosis and cell death, such that phosphatidylserine is exposed on morphologically intact vascular endothelial cells.

The methods and uses can be performed in vitro and in vivo, in the latter case, wherein the tissues or cells are located within an animal and the construct, receptorbody or betabody of the invention, or conjugate thereof, is administered to the animal. Where tissues or cells are maintained ex vivo, the present invention has utility in drug discovery programs. In vitro screening assays, with reliable positive and negative controls, are useful as a first step in the development of drugs. Where the tissues or cells are located within an animal or patient, the composition is administered to the animal as a form of therapy.

Anti-angiogenic and anti-vascular therapies are provided in terms of animals and patients that have, or are at risk for developing, any disease or disorder characterized by undesired, inappropriate, aberrant, excessive and/or pathological angiogenesis or vascularization. The methods and uses of the present invention are particularly intended for use in animals and patients that have, or are at risk for developing, any form of vascularized tumor; macular degeneration, including age-related macular degeneration; arthritis, including rheumatoid arthritis; atherosclerosis and atherosclerotic plaques; diabetic retinopathy and other retinopathies; thyroid hyperplasias, including Grave's disease; hemangioma; neovascular glaucoma; and psoriasis. In certain embodiments, the use of an Fc region operatively attached to a β2GPI polypeptide that comprises nicked domain V will be preferred for use in inhibiting angiogenesis.

As disclosed in U.S. Pat. Nos. 5,712,291 and 6,524,583, specifically incorporated herein by reference, each of the foregoing treatment groups are by no means exhaustive of the types of conditions that are to be treated by the present invention. U.S. Pat. Nos. 5,712,291 and 6,524,583 are incorporated herein by reference for certain specific purposes, including the purpose of identifying a number of other conditions that may be effectively treated once a defined category of compounds have been disclosed and claimed; and the purpose of showing that the treatment of other diseases is enabled by data from only a single model system.

In addition to the treatment of vascular diseases, important and unified aspects of the present invention are compositions and methods for treating cancer. Such methods comprise administering to an animal or patient that has, or is at risk for developing, cancer, a biologically or therapeutically effective amount of at least a first construct, receptorbody or betabody of the invention, or a conjugate thereof.

The cancer treatment methods and uses of the invention are suitable for treating all forms of cancer, including animals and patients that have, or are at risk for developing, a vascularized solid tumor, a metastatic tumor or metastases from a primary tumor. The cancer treatment methods of the invention do not rely solely on exerting anti-vascular effects, such as by targeting phosphatidylserine exposed on the luminal surface of tumor blood vessel endothelial cells, as the constructs of the invention can also target phosphatidylserine exposed on the surface of tumor cells. The methods of the invention preferably exert an anti-cancer effect without causing significant thrombotic complications.

Either the unconjugated construct, receptorbody or betabody of the original invention, or an additional conjugate thereof, may be used in the cancer treatment aspects of the invention. As to the use of immunoconjugates, the invention provides methods for delivering selected diagnostic or therapeutic agents to tumors. Such embodiments comprise administering to an animal or patient having a tumor a biologically effective amount of at least a first conjugate in which a diagnostic or therapeutic agent is operatively attached to a construct, receptorbody or betabody of the invention.

The invention also provides tumor diagnostic, prognostic, imaging and related methods using a construct, receptorbody or betabody of the invention to detect pre-apoptotic and apoptotic cells. Such methods can be used as a surrogate marker to monitor the progress of other treatment, particularly chemotherapy, or to form an image of a tumor prior to treatment.

The use of the invention as a surrogate marker to monitor the progress of cancer treatment, particularly chemotherapy, comprises:

(a) subjecting an animal or patient with a tumor to at least a first treatment designed to exert an anti-tumor effect; and (b) subsequently administering to the same animal or patient a diagnostically effective amount of at least a first construct, receptorbody or betabody of the invention, operatively attached to a detectable label or diagnostic agent, thereby forming a detectable image of the tumor, preferably an image of pre-apoptotic or apoptotic tumor cells or tumor vascular endothelial cells within the tumor; and preferably (c) analyzing the detectable image of the tumor, preferably the image of the pre-apoptotic or apoptotic tumor cells or tumor vascular endothelial cells within the tumor, thereby assessing the progress or effectiveness of the at least a first treatment designed to exert an anti-tumor effect.

The combined imaging and cancer treatment methods comprise:

(a) forming an image of a tumor by administering to an animal or patient having a tumor a diagnostically minimal or effective amount of at least a first construct, receptorbody or betabody of the invention, operatively attached to a detectable label or diagnostic agent, thereby forming a detectable image of the tumor; and (b) subsequently administering to the same animal or patient a therapeutically optimized or effective amount of at least a first construct, receptorbody or betabody of the invention, or a conjugate thereof, thereby causing an anti-tumor effect.

Within the cancer treatment methods of the invention, the invention further provides prodrug treatment methods, which generally comprise:

(a) administering to an animal or patient with a tumor a first pharmaceutical composition comprising a first construct, receptorbody or betabody of the invention, operatively associated with, covalently linked or conjugated to, at least a first enzyme; wherein the construct, receptorbody or betabody localizes to the tumor after administration and (b) subsequently administering to the animal or patient, after an effective time period, at least a second pharmaceutical composition comprising a biologically effective amount of at least one substantially inactive prodrug; wherein the prodrug is converted to a substantially active drug by the enzyme associated with, linked to or conjugated to the construct, receptorbody or betabody of the invention localized within the tumor.

The present invention further provides a range of combination cancer treatment methods, comprising administering to an animal or patient with cancer a therapeutically effective combined amount of at least a first construct, receptorbody or betabody of the invention, or a conjugate thereof, and at least a second, distinct therapeutic or anti-cancer agent.

Generally speaking, the at least a second anti-cancer agent may be administered to the animal or patient before, during or after administration of the construct, receptorbody or betabody of the invention, or conjugate thereof. The at least a second anti-cancer agent may be administered to the animal or patient "substantially simultaneously" with the construct, receptorbody or betabody of the invention, or conjugate thereof; such as from a single pharmaceutical composition or from two pharmaceutical compositions administered closely together.

Alternatively, the at least a second anti-cancer agent may be administered to the animal or patient at a time sequential to the administration of the construct, receptorbody or betabody of the invention, or conjugate thereof. "At a time sequential", as used herein, means "staggered", such that the at least a second anti-cancer agent is administered to the animal or patient at a time distinct to the administration of construct, receptorbody or betabody of the invention, or conjugate thereof.

In sequential administration, the two agents are administered at times effectively spaced apart to allow the two agents to exert their respective therapeutic effects, i.e., they are administered at "biologically effective time intervals". The at least a second anti-cancer agent may be administered to the animal or patient at a biologically effective time prior to the construct, receptorbody or betabody of the invention, or conjugate thereof, or at a biologically effective time subsequent to that therapeutic.

Any therapeutic or anti-cancer agent may be used as the second, therapeutic or anti-cancer agent in the combined cancer treatment methods of the invention, including any of the therapeutic or anti-cancer agents described above in relation to the anti-cancer compositions and kits of the invention. Preferred agents are those that complement or enhance the therapeutic effects of the construct, receptorbody or betabody of the invention, or conjugate thereof, such as vascular permeability enhancing agents, anti-angiogenic agents, apoptosis-inducing agents, calcium flux inducing agents, inflammatory cytokines, antibodies and immunotoxins to tumor cells and necrotic tumor cells, chemotherapeutic agents from Table E or Table F, a combretastatin, doxorubicin, etoposide and actinomycin-D.

Docetaxel is a particularly preferred agent for use in combination therapy. Docetaxel may be administered separately to the construct, receptorbody or betabody of the invention, or conjugate thereof, either before or afterwards. As to simultaneous administration, docetaxel may be given in separate or the same formulations, optionally within a liposome or stealthed liposome, and preferably within the core of a stealthed liposome coated with a construct, receptorbody or betabody of the invention.

Treating Viral Infections:

In another overall embodiment, the invention further provides an important new class of compositions and methods for inhibiting viral replication, infection and spread for use in treating viral infections and diseases. These methods are based on the use of a construct, receptorbody or betabody of the invention, whether conjugated to an anti-viral agent or not. Importantly, a construct, receptorbody or betabody of the invention will exert an anti-viral effect without attachment to any additional agent. If attachment to additional agents is desired, cytotoxic and other agents will be effective in anti-viral treatment, as well as classic anti-viral agents. Such constructs and conjugates are therefore broadly applicable in the treatment of a range of viral infections and associated diseases.

In a first instance, the anti-viral methods of the invention concern contacting a composition comprising, or population of cells or tissue(s) that contains or is suspected to contain, a virally infected cell with a biologically effective amount of at least a first construct, receptorbody or betabody of the invention, or a conjugate thereof. The virally infected cell is preferably a eukaryotic cell, such as an animal cell, and preferably a mammalian or human cell.

The anti-viral methods and uses can be performed in vitro and in vivo. In the in vitro embodiments, the methods have important utilities. For example, in drug discovery programs for the development of anti-viral drugs or combinations thereof, as well as in the delineation of further information on viral infection, replication and spread. The in vitro anti-viral methods may also be used in purging viruses from biological samples, such as cell populations and tissue cultures for laboratory use, from samples, tissues, seeds, plant parts and plants for agricultural use, and from blood and tissue samples for therapeutic use.

In the in vivo methods, where the cells, populations or tissues are located within an animal, the construct, receptorbody or betabody of the invention, or a conjugate thereof, is administered to the animal as anti-viral therapy. A construct, receptorbody or betabody of the invention, or a conjugate thereof, may bind to phosphatidylserine exposed on the surface of virally-infected cells, or may bind to phosphatidylserine exposed on the surface of viral particles.

In all cases, the compositions, methods and uses inhibit one or more steps or stages necessary for a productive or ongoing viral infection, including inhibiting viral entry. Preferably, the compositions, methods and uses inhibit viral replication and/or spread, such as inhibiting one or more steps of viral transcription, translation, assembly, packaging and/or egress within or from an infected host cell, such as a mammalian or human cell. The invention therefore preferably limits or substantially confines viral infections to initially infected cells and cell populations, thus substantially inhibiting or preventing the subsequent or ongoing infection of additional host cells or tissues.

The anti-viral treatment methods of the invention preferably concern administering to an animal or patient having, suspected of having or at risk for developing a viral infection or associated disease a biologically effective amount of at least a first construct, receptorbody or betabody of the invention, or a conjugate thereof. The conjugates may be operatively attached to a V-type ATPase inhibitors, such as salicylihalamide, concanamycin or bafilomycin; a protein synthesis inhibitor, such as psymberin, pederin, irciniastatin A; a ricin, gelonin, abrin, diphtheria, pseudomonas or pertussis toxin; or to at least a second, distinct anti-viral agent. Suitable anti-viral agents for attachment include those set forth in Table G, such as AZT or cidofovir.

As the invention inhibits one or more steps or stages necessary for productive or ongoing infection common to all viruses, the anti-viral methods and uses of the invention are suitable for treating all viruses, both enveloped and non-enveloped viruses, including those that infect plants, animals, vertebrates, mammals and human patients. The invention is suitable for treating all viruses that infect vertebrates, as listed herein in Table H, particularly humans, and particularly viruses that are pathogenic in animals and humans. The viral infections and associated and resultant diseases that can be treated by the invention include those viruses and diseases set forth in Table J, as exemplified by treating CMV, RSV, arenavirus and HIV infections, and the diseases hepatitis, influenza, pneumonia, Lassa fever and AIDS. Treating enveloped viruses is particularly preferred.

The anti-viral treatment methods of the invention may also be used in combination with other therapeutics and diagnostics. The combined treatment methods comprise administering to an animal or patient with a viral infection a therapeutically effective combined amount of at least a first construct, receptorbody or betabody of the invention, or a conjugate thereof, and at least a second, distinct therapeutic or anti-viral agent.

The at least a "second, distinct" anti-viral agent is in reference to the construct, receptorbody or betabody of the invention, or a conjugate thereof, being the "first" anti-viral agent. The at least a second anti-viral agent may be administered to the animal or patient during administration of, or substantially simultaneously with, the first anti-viral agent of the invention; or before or after, i.e., sequential to the administration of the first anti-viral agent of the invention.

Any therapeutic or anti-viral agent may be used as the second therapeutic or anti-viral agent in the combined anti-viral treatment methods of the invention, including any of the anti-viral agents described above in relation to the anti-viral conjugates, compositions and kits of the invention.

The foregoing cancer and anti-viral treatment methods and uses will often involve the administration of a pharmaceutically effective composition to the animal or patient systemically, such as by transdermal, intramuscular, intravenous injection and the like. For treating viral infections, particularly respiratory viral infections, delivery to the lung is another preferred embodiment, as may be achieved using an aerosol. However, any route of administration that allows the therapeutic agent to localize to the site of the tumor or viral infection will be acceptable. Therefore, other suitable routes of delivery include oral, rectal, nasal, topical, and vaginal. For uses and methods for the treatment of arthritis, e.g., intrasynovial administration may be employed, as described for other immunological agents in U.S. Pat. No. 5,753,230, specifically incorporated herein by reference. For conditions associated with the eye, ophthalmic formulations and administration are contemplated.

"Administration", as used herein, means provision or delivery of a construct, receptorbody or betabody of the invention, or a conjugate thereof, in an amount(s) and for a period of time(s) effective to exert a therapeutic effect. The passive administration of proteinaceous therapeutics is generally preferred, in part, for its simplicity and reproducibility.

However, the term "administration" is herein used to refer to any and all means by which the therapeutics are delivered. "Administration" therefore includes the provision of cells that produce the construct, receptorbody or betabody of the invention, or conjugates thereof, in an effective manner. In such embodiments, it may be desirable to formulate or package the cells in a selectively permeable membrane, structure or implantable device, generally one that can be removed to cease therapy. Exogenous administration will still generally be preferred, as this represents a non-invasive method that allows the dose to be closely monitored and controlled.

The therapeutic methods and uses of the invention also extend to the provision of nucleic acids that encode a construct, receptorbody or betabody of the invention, or a conjugate thereof, in a manner effective to result in expression in vivo. Any gene therapy technique may be employed, such as naked DNA delivery, recombinant genes and vectors, cell-based delivery, including ex vivo manipulation of patients' cells, and the like. Viral vectors may be used, such as comprised within a recombinant retrovirus, herpes simplex virus (HSV), adenovirus, adeno-associated virus (AAV), cytomegalovirus (CMV), and the like. Liposomes and stealthed liposomes will be preferred for use in some embodiments.

The pharmaceutical compositions and treatment methods of the invention employ "therapeutically effective amounts" of a construct, receptorbody or betabody of the invention, or a conjugate thereof. The "therapeutic effects" and consequent "therapeutically effective amounts" are measured by different parameters in cancer treatment vs. anti-viral treatment.

In cancer treatment, the amounts of the agents are effective to kill or specifically kill at least a portion of tumor cells, tumor or intratumoral vascular endothelial cells; to induce apoptosis or specifically induce apoptosis in at least a portion of tumor cells, tumor or intratumoral vascular endothelial cells; to promote coagulation or specifically promote coagulation in at least a portion of tumor or intratumoral blood vessels; to occlude or destroy, or specifically occlude or destroy at least a portion of blood transporting vessels of the tumor; to induce necrosis or specifically induce necrosis in at least a portion of a tumor; and/or to induce tumor regression or remission upon administration to an animal or patient.

In treating viral infections and related diseases, the amounts of the agents are effective to inhibit one or more requirements for ongoing viral infection, such as viral entry, and preferably, viral replication, egress and spread from the infected host cells. The amounts may also kill or remove at least a portion of the virally infected cells in a manner that counteracts viral replication, spread and ongoing infection. Overall, the amounts of the agents are effective to reduce, significantly reduce or eradicate the viral infection upon administration to an animal or patient.

The terms "preferentially" and "specifically", as used herein, mean that the construct, receptorbody or betabody of the invention, or a conjugate thereof, achieve anti-cancer or anti-viral effects that are substantially confined to the disease site, and do not substantially cause coagulation, destruction and/or tissue necrosis in normal, healthy tissues of the animal or subject. The structure and function of healthy cells and tissues is therefore maintained substantially unimpaired by the practice of the invention.

BRIEF DESCRIPTION OF THE DRAWINGS

FIG. 2A, FIG. 2B, FIG. 2C and FIG. 2D. DNA and amino acid sequences of the complementarity determining regions (CDRs) of the 3G4 antibody and the 2aG4 antibody. DNA and amino acid sequences for the heavy (FIG. 2A; SEQ ID NO: 1 and SEQ ID NO:2) and light (FIG. 2B; SEQ ID NO:3 and SEQ ID NO:4) chains of the 3G4 antibody are presented, and the restriction sites in the DNA sequences are shown. The leader sequence is distinguished from the mature protein, which begins as shown by the first arrow in each of FIG. 2A and FIG. 2B. Exemplary means of grafting each variable sequence with a human constant region are set forth, wherein the first part of the respective human constant region sequences (SEQ ID NO:7 and SEQ ID NO:8) is shown by the second arrow in each of FIG. 2A and FIG. 2B. The amino acid sequences of the IgG2a heavy chain and the 3G4 Light Chain ($C_k$) are represented by SEQ ID NO: 10 and SEQ ID NO: 11, respectively, as shown in FIG. 2C and FIG. 2D.

FIG. 5A, HUVEC or MDA-MB-435 cells were treated with $H_2O_2$ (200 μM) for 1 h at 37° C. The cells were washed and detached from the culture dish with trypsin. Cells were stained with 3G4 (solid line) or control mouse $IgG_3$ (BBG3) (dotted line) and were analyzed by cytofluorometry using a FACS. The instrument was gated on intact cells (propidium iodide negative). FIG. 5A, top left, HUVEC; top right, $H_2O_2$-treated HUVEC; lower left, MDA-MB-435; lower right, $H_2O_2$-treated MDA-MB-435. FIG. 5B, FIG. 5C, FIG. 5D and FIG. 5E, the morphology of 3G4 binding to intact, non-permeablized $H_2O_2$-treated HUVEC was determined by treating adherent cells with $H_2O_2$ as above, washing the cells and staining them with 3G4 or control mouse $IgG_3$, BBG3, followed by FITC-labeled goat anti-mouse IgG antibody (green). The cells were then fixed with paraformaldehyde and permeabilized. The cytoskeleton was stained with Texas-red labeled phalloidin (red) and nuclei were counterstained with DAPI (blue). 3G4 bound to discrete regions of the plasma membrane, having the appearance of membrane blebs. FIG. 5B, HUVEC stained with BBG3; FIG. 5C, HUVEC stained with 3G4; FIG. 5D, MDA-MB-435 cells stained with BBG3; and FIG. 5E, MDA-MB-435 cells stained with 3G4. Cells not treated with $H_2O_2$ were not stained by 3G4. Scale bar represents 50 μm.

FIG. 6A, tumor from mouse treated with control BBG3 showing sparse infiltration by macrophages. FIG. 6B, tumor from mouse treated with 3G4 showing abundant macrophage infiltration. FIG. 6C, control tumor from mouse treated with BBG3 showing absence of monocytes attaching to vessel. FIG. 6D, tumor from mouse treated with 3G4 showing monocytes attaching to the luminal surface of tumor vascular endothelium (arrows). Scale bars in FIG. 6A and FIG. 6B represent 50 μm and in FIG. 6C and FIG. 6D represent 10 μm.

FIG. 9A, the 3G4 antibody was purified from cells grown in bovine serum-containing media (SCM) or serum-free media (SFM). A microtiter plate was coated with PS and blocked in 1% OVA,. Serial dilutions of 3G4 were performed in 10% fetal bovine serum (FBS) or 1% ovalbumin from chicken egg white (OVA). FIG. 9A, the microtiter plate was coated with PS and blocked in 1% OVA. Serial dilutions of 3G4 SFM were performed in 10% serum from the species mouse, rat, human and bovine, as indicated.

FIG. 10A, a microtiter plate was coated with human β2GPI (hβ2GPI) purified from human plasma and blocked in 1% OVA. Serial dilutions of a commercial mouse anti-human β2GPI (anti-β2GPI or "α-β2GPI"), 3G4 SFM, and a control mouse IgG (mIgG) were performed in 1% OVA. FIG. 10B, the wells of a microtiter plate were coated with recombinant full-length hβ2GPI (domain I-V) or hβ2GPI peptides absent domain I (II-V), absent domains I & II (III-V), absent domains I-III (IV-V) or absent domains I-IV (V). The plate was blocked in 1% OVA and serial dilutions of 3G4 SFM were performed in 1% OVA.

FIG. 12A and FIG. 12B. The lipid binding region of β2GPI is required to mediate binding of ch3G4 to endothelial cells with exposed PS. FIG. 12A, ABAE cells were incubated with ch3G4 plus (i) a non-lipid binding form of β2GPI (nicked hβ2GPI) or (ii) intact hβ2GPI. The incubations were performed in the presence or absence of 200 μM LPC in DMEM+10% MS for 30 min. Cells were then washed, fixed, and stained with fluorescent markers to detect binding of ch3G4. ch3G4, hβ2GPI, and nicked hβ2GPI were used at a concentration of 2 μg/ml. The pixel area of ch3G4 binding was quantified using MetaVue software. Values are relative to the binding of ch3G4 under condition (i) no LPC, which was set to one. FIG. 12B, the wells of a microtiter plate were coated with hβ2GPI or nicked hβ2GPI and blocked in 1% OVA. Serial dilutions of ch3G4 or a control mIgG were performed in 1% OVA.

FIG. 14A, ABAE cells were incubated for 30 min with 20 nM 3G4, 3G4 $F(ab')_2$, or 3G4 Fab' monomer in the presence or absence of 200 μM LPC in DMEM+10% FBS. Cells were then washed, fixed, and stained with fluorescent markers to detect binding of 3G4 or 3G4 fragments. The pixel area of antibody binding was quantified using MetaVue software. Values are relative to the binding of 3G4 in the absence of LPC, which was set to one. FIG. 14B, ABAE cells were incubated for 30 min with 200 μM LPC, 40 nM purified hβ2GPI, and a titer of 3G4 Fab' monomer in DMEM+10% MS. Cells were then washed, fixed, and stained with fluorescent markers to detect binding of 3G4 Fab'. The pixel area of 3G4 Fab' binding was quantified using MetaVue software. Values are relative to the binding of 2 nM 3G4 Fab', which was set to one. FIG. 14C, ABAE cells were incubated for 30 min with 200 μM LPC, 40 μM purified hβ2GPI, 20 nM ch3G4, and a titer of 3G4 Fab' monomer in DMEM+10% MS. Cells were then washed, fixed, and stained with fluorescent markers to detect binding of ch3G4. The pixel area of ch3G4 binding was quantified using MetaVue software. Values are relative to the binding of ch3G4 without competing 3G4 Fab', which was set to 100.

FIG. 18A. Fc-mβ2GPI amino acid sequence. The signal peptide ("mIgGκ signal seq") MDMRAPAQILGFLLLLFPGTRCLR, which is cleaved, is represented by SEQ ID NO: 18. Position 1 indicates the start of the mature Fc-mβ2GPI protein after the signal peptide has been cleaved. The amino acid sequence of the mature Fc-mβ2GPI is SEQ ID NO: 19. The hinge, $C_H2$ and $C_H3$ domains of the Fc region are indicated, as are domains I, II, III, IV and V of mouse β2GPI. The Cys residues involved in intra-domain disulfide bond formation in β2GPI are shown in bold and shading. The amino acids in underlined italics are part of the positively charged region involved in recognition of anionic phospholipids. The amino acids in double underlined italics are part of the hydrophobic loop required for binding to lipid membranes. The sequence of amino acids beginning with those involved in recognition of anionic phospholipids and concluding with those that are part of the hydrophobic loop required for binding to lipid membranes, KNKEKKCSYTVEAHCRDGTIEIPSCFKEHSSLAFWK, is SEQ ID NO:20.

FIG. 18B. Amino acid sequences for human a heavy chain constant region and human β2GPI to prepare human Fc-β2GPI (Fc-hβ2GPI). The human $IgG_1$ heavy chain constant region (Accession number P01857; SEQ ID NO:21) is presented starting with the $C_H1$ domain, which may be deleted. In a human Fc-hβ2GPI, the hinge (hinge start matches position 1 in FIG. 18A), human $C_H2$ and human $C_H3$ domains are followed by human β2GPI (Accession number 1C1ZA; SEQ ID NO:22), shown to include domains I, II, III, IV and V. The amino acid sequence of an Fc-hβ2GPI is SEQ ID NO:23. The domain structure of human β2GPI closely matches that of mouse β2GPI (FIG. 18A), including the location of the Cys residues involved in intra-domain disulfide bond formation (bold and shaded), amino acids that are part of the positively charged region involved in recognition of anionic phospholipids (underlined italics) and amino acids that are part of the hydrophobic loop required for binding to lipid membranes (double underlined italics). The sequence of amino acids beginning with those involved in recognition of anionic phospholipids and concluding with those that are part of the hydrophobic loop required for binding to lipid membranes, KNKEKKCSYTEDAQCIDGTIEVPKCFKEHSSLAFWK, is SEQ ID NO:24.

FIG. 23A and FIG. 23B each depict binding of Fc-mβ2GPI, seen as small pinpoints of green staining.

FIG. 24D, the binding area of β2GPI-monomers and β2GPI-dimers was quantified using MetaVue software. All values are relative to the binding of hβ2GPI-dimers to non-LPC treated cells, which was set to one.

DESCRIPTION OF ILLUSTRATIVE EMBODIMENTS

Figure 1:
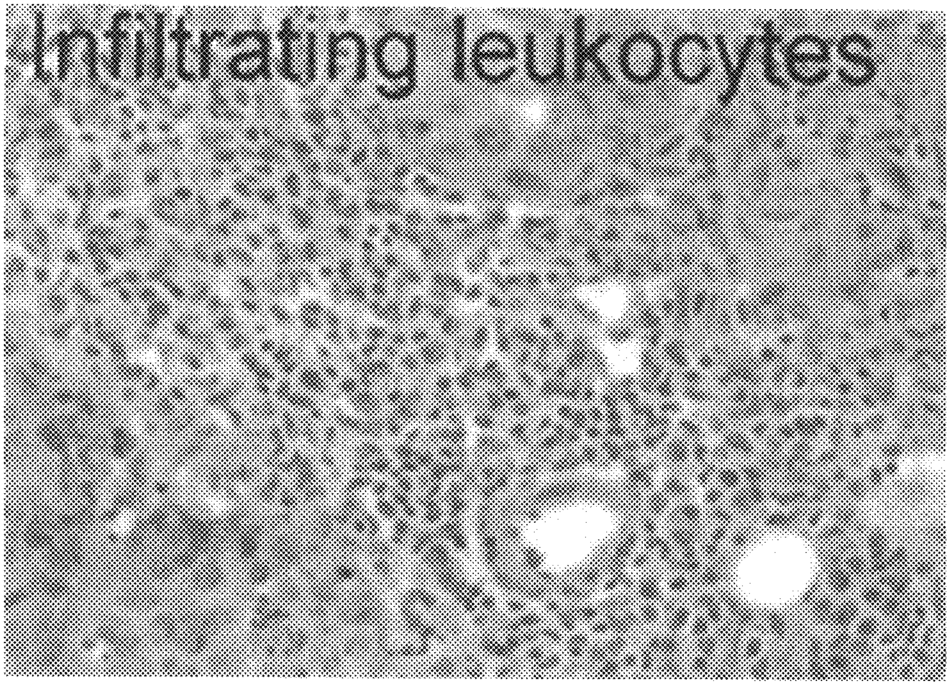
FIG. 1. Leukocytes infiltrate the tumor in mice treated with the 3G4 antibody. Nude mice bearing MDA-MB-231 orthotopic tumors were treated 3 times a week with 100 μg/dose 3G4 antibody or with the same dose of an isotype-matched, control antibody. At the conclusion of treatment, animals were perfused and tumors were snap-frozen, cut and stained to detect leukocytes. The leukocytes infiltrating the tumor are shown in the figure.

Solid tumors and carcinomas account for more than 90% of all cancers in man. Although the use of monoclonal antibodies and immunotoxins has been investigated in the therapy of lymphomas and leukemias (Vitetta et al., 1991), these agents have been disappointingly ineffective in clinical trials against carcinomas and other solid tumors (Abrams and Oldham, 1985). A principal reason for the ineffectiveness of antibody-based treatments is that macromolecules are not readily transported into solid tumors. Even once within a tumor mass, these molecules fail to distribute evenly due to the presence of tight junctions between tumor cells, fibrous stroma, interstitial pressure gradients and binding site barriers (Denekamp, 1990; Dvorak et al., 1991).

In developing new strategies for treating solid tumors, the methods that involve targeting the vasculature of the tumor, rather than the tumor cells, offer distinct advantages. An effective destruction or blockade of the tumor vessels arrests blood flow through the tumor, resulting in an avalanche of tumor cell death. Antibody-toxin and antibody-coagulant constructs, examples of VTA which selectively destroy and/or occlude tumor blood vessels, have already been used to great effect in the specific targeting and destruction of tumor vasculature, resulting in tumor necrosis (Burrows et al., 1992; Burrows and Thorpe, 1993; WO 93/17715; WO 96/01653; Huang et al., 1997; each incorporated herein by reference).

VTAs exert their primary action on the pre-existing blood vessels of solid tumors, and differ from anti-angiogenic agents that prevent new blood vessel formation. There are numerous advantages of VTAs over other cancer therapies. First, a single vessel provides the nutrition for and facilitates removal of waste products of metabolism from hundreds or thousands of tumor cells, and only has to be damaged at one point to block blood flow upstream and downstream. VTAs are thus particularly effective on established tumors. Second, endothelial cell killing, although one useful mechanism, is not required. A change of shape or local initiation of blood coagulation can be sufficient. Third, the endothelial cell is adjacent to the blood stream, ensuring adequate drug delivery. Fourth, the target is a normal diploid cell that is unlikely to acquire genetic mutations that render it drug resistant. Fifth, a surrogate marker of biological activity, i.e., blood flow, is measurable.

Sixth, temporary effects on vascular function may be sufficient for significant anti-tumor effects. Studies indicate that over 99% of tumor cells in vivo can be killed during a 2 hour period of ischemia. Finally, unlike angiogenesis inhibitors, VTAs only require intermittent administration to synergize with conventional treatments, rather than chronic administration over months or years.

Cytotoxic VTAs are described in the following patents: U.S. Pat. Nos. 5,660,827, 5,776,427, 5,855,866, 5,863,538, 5,965,132, 6,004,554, 6,051,230, 6,261,535 and 6,451,312, each incorporated herein by reference. Where antibodies, growth factors or other binding ligands are used to specifically deliver a coagulant to the tumor vasculature, such agents are termed "coaguligands". Coaguligand VTAs are described in the following patents: U.S. Pat. Nos. 6,093,399, 6,004,555, 5,877,289 and 6,036,955, each incorporated herein by reference.

A currently preferred coagulant for use in coaguligands is truncated Tissue Factor (tTF) (Huang et al., 1997; WO 96/01653; U.S. Pat. No. 5,877,289). TF is the major initiator of blood coagulation (Ruf et al., 1991; Edgington et al., 1991). At sites of injury, Factor VII/VIIa in the blood comes into contact with, and binds to, TF on cells in the perivascular tissues. The TF:VIIa complex, in the presence of the phospholipid surface, activates factors IX and X. This, in turn, leads to the formation of thrombin and fibrin and, ultimately, a blood clot (Ruf and Edgington, 1994).

The recombinant, truncated form of tissue factor (tTF), lacking the cytosolic and transmembrane domains, is a soluble protein that has about five orders of magnitude lower coagulation inducing ability than native TF (Stone et al., 1995; Huang et al., 1997). This is because TF needs to be associated with phospholipids for the complex with VIa to activate IXa or Xa efficiently. However, when tTF is delivered to tumor vascular endothelium by means of a targeting antibody or agent, it is brought back into proximity to a lipid surface and regains thrombogenic activity (Huang et al., 1997; U.S. Pat. Nos. 6,093,399, 6,004,555, 5,877,289 and 6,036,955). A coaguligand is thus created that selectively thromboses tumor vasculature.

Truncated TF has several advantages that commend its use in vascular targeted coaguligands: human tTF is readily available, and the human protein will have negligible or low immunogenicity in man; human tTF is fully functional in experimental animals, including mice; and targeted tTF is highly potent because it triggers the activation of a cascade of coagulation proteins, giving a greatly amplified effect (U.S. Pat. Nos. 6,093,399, 6,004,555, 5,877,289 and 6,036,955).

A range of suitable target molecules that are available on tumor endothelium, but largely absent from normal endothelium, have been described. For example, expressed targets may be utilized, such as endoglin, E-selectin, P-selectin, VCAM-1, ICAM-1, PSMA, a TIE, a ligand reactive with LAM-1, a VEGF/VPF receptor, an FGF receptor, $\alpha_v\beta_3$ integrin, pleiotropin or endosialin (U.S. Pat. Nos. 5,855,866 5,877,289; Burrows et al., 1992; Burrows and Thorpe, 1993; Huang et al., 1997; Liu et al., 1997; Ohizumi et al., 1997; each incorporated herein by reference).

Adsorbed targets are another suitable group, such as VEGF, FGF, TGFβ, HGF, PF4, PDGF, TIMP, a ligand that binds to a TIE or a tumor-associated fibronectin isoform (U.S. Pat. Nos. 5,877,289, 5,965,132, 6,051,230 and 6,004,555). Fibronectin isoforms are ligands that bind to the integrin family of receptors. Tumor-associated fibronectin isoforms are targetable components of both tumor vasculature and tumor stroma. The monoclonal antibody BC-1 (Carnemolla et al., 1989) specifically binds to tumor-associated fibronectin isoforms.

Other targets inducible by the natural tumor environment or following intervention by man are also targetable entities, as described in U.S. Pat. Nos. 5,776,427, 5,863,538 and 6,036,955. When used in conjunction with prior suppression in normal tissues and tumor vascular induction, MHC Class II antigens may also be employed as targets (U.S. Pat. Nos. 5,776,427, 5,863,538, 6,004,554 and 6,036,955).

One currently preferred target for clinical applications is vascular endothelial adhesion molecule-1 (VCAM-1) (U.S.

Pat. Nos. 5,855,866, 5,877,289, 6,051,230, 6,004,555 and 6,093,399). VCAM-1 is a cell adhesion molecule that is induced by inflammatory cytokines IL-1α, IL-4 (Thornhill et al., 1990) and TNFα (Munro, 1993) and whose role in vivo is to recruit leukocytes to sites of acute inflammation (Bevilacqua, 1993).

VCAM-1 is present on vascular endothelial cells in a number of human malignant tumors including neuroblastoma (Patey et al., 1996), renal carcinoma (Droz et al., 1994), non-small lung carcinoma (Staal-van den Brekel et al., 1996), Hodgkin's disease (Patey et al., 1996), and angiosarcoma (Kuzu et al., 1993), as well as in benign tumors, such as angioma (Patey et al., 1996) and hemangioma (Kuzu et al., 1993). Constitutive expression of VCAM-1 in man is confined to a few vessels in the thyroid, thymus and kidney (Kuzu et al., 1993; Bruijn and Dinklo, 1993), and in the mouse to vessels in the heart and lung (Fries et al., 1993).

Certain of the data presented herein even further supplement those provided in U.S. Pat. Nos. 5,855,866, 5,877,289, 6,051,230, 6,004,555 and 6,093,399, and show the selective induction of thrombosis and tumor infarction resulting from administration of an anti-VCAM-1•tTF coaguligand. The results presented were generated using mice bearing L540 human Hodgkin lymphoma. When grown as a xenograft in SCID mice, this tumor shows close similarity to the human disease with respect to expression of inflammatory cytokines (Diehl et al., 1985) and the presence of VCAM-1 and other endothelial cell activation molecules on its vasculature.

Using a covalently-linked anti-VCAM-1•tTF coaguligand, in which tTF was directly linked to the anti-VCAM-1 antibody, it is shown herein that the coaguligand localizes selectively to tumor vessels, induces thrombosis of those vessels, causes necrosis to develop throughout the tumor and retards tumor growth in mice bearing solid L540 Hodgkin tumors. Tumors generally needed to be at least about 0.3 cm in diameter to respond to the coaguligand, because VCAM-1 was absent from smaller tumors. Presumably, in small tumors, the levels of cytokines secreted by tumor cells or host cells that infiltrate the tumor are too low for VCAM-1 induction. This is in accordance with the studies in U.S. Pat. Nos. 5,855,866, 5,877,289, 6,051,230, 6,004,555 and 6,093,399, where the inventions were shown to be most useful in larger solid tumors.

Although VCAM-1 staining was initially observed more in the periphery of the tumor, the coaguligand evidently bound to and occluded blood transporting vessels—as it was capable of curtailing blood flow in all tumor regions. Furthermore, one of the inventors contemplates that the thrombin generation caused by the initial administration of the coaguligand likely leads to further VCAM-1 induction on central vessels (Sluiter et al., 1993), resulting in an amplified signal and evident destruction of the intratumoral region. This type of coagulant-induced expression of further targetable markers, and hence signal amplification, is also disclosed in U.S. Pat. No. 6,036,955.

As shown herein, although localization to VCAM-1-expressing vessels in the heart and lungs of mice was observed upon administration of an anti-VCAM-1 coaguligand, this construct did not induce thrombosis in such non-tumor sites. Furthermore, the anti-VCAM-1 coaguligand was no more toxic to mice than was a control coaguligand of irrelevant specificity, again indicating that the constitutive expression of VCAM-1 on heart and lung vessels did not lead to toxicity. This data is important to the immediate clinical progress of coaguligand therapy, given that VCAM-1 is a naturally occurring marker of tumor vascular endothelium in humans. However, this phenomenon also provided the inventors with a unique insight, leading to a different approach to tumor vasculature destruction.

A. Discovery of Naked Anti-Phosphatidylserine Antibodies for Tumor Treatment

The inventors sought to understand the mechanism behind the ability of the anti-VCAM-1 coaguligand to bind to the VCAM-1 constitutively expressed on blood vessels in the heart and lungs, and yet not to cause thrombosis in those vessels. There are numerous scientific possibilities for this empirical observation, generally connected with the prothrombotic nature of the tumor environment and any fibrinolytic predisposition in the heart and lungs.

Generally, there is a biological equilibrium between the coagulation system (fibrin deposition) and the fibrinolytic system (degradation of fibrin by enzymes). However, in malignant disease, particularly carcinomas, this equilibrium is disrupted, resulting in the abnormal activation of coagulation (hypercoagulability or the "prothrombotic state"). Despite extensive research, a clear molecular explanation for the prothrombotic nature of the tumor environment could not be discerned until recently.

After detailed analyses of many possible options, the inventors reasoned that the failure of the anti-VCAM-1 coaguligand to cause thrombosis in vessels of normal tissues was due to the absence of phosphatidylserine from the luminal surface of such vessels. To complete the theory, therefore, not only would phosphatidylserine have to be shown to be absent from these normal vessels, but its presence on the luminal side of tumor-associated vessels would have to be demonstrated.

The inventors therefore used immunohistochemical staining to evaluate the distribution of a monoclonal anti-phosphatidylserine (anti-PS) antibody injected intravenously into tumor-bearing mice. These studies revealed that the VCAM-1 expressing vessels in the heart and lungs lacked PS, whereas the VCAM-1 expressing vessels in the tumor expressed PS. The need for surface PS expression in coaguligand action is further indicated by the inventors' finding that annexin V, which binds to PS, blocks anti-VCAM-1•tTF coaguligand action, both in vitro and in vivo.

The lack of thrombotic effect of the anti-VCAM-1 coaguligand on normal heart and lung vessels was thus explained, at least in part: the absence of phosphatidylserine, means that the normal vessels lack a procoagulant surface upon which coagulation complexes can assemble. In the absence of surface PS, anti-VCAM-1•-tTF binds to VCAM-1 expressing heart and lung vessels, but cannot induce thrombosis. In contrast, VCAM-1 expressing vessels in the tumor show coincident expression of surface PS. The coaguligand thus binds to tumor vessels and activates coagulation factors locally to form an occlusive thrombus.

In addition to delineating the tumor-specific thrombotic effects of anti-VCAM-1 coaguligands, the specific expression of phosphatidylserine on the luminal surface of tumor blood vessels also allowed the inventors to explain the prothrombotic phenotype observed, but not understood, in earlier studies. The PS expression plays a significant role in the prothrombotic state of tumor vasculature.

Following their discovery that the representative aminophospholipid, phosphatidylserine, was specifically expressed on the luminal surface of tumor blood vessels, but not in normal blood vessels, the inventors reasoned that other aminophospholipids had potential as targets for therapeutic intervention. The inventors therefore developed tumor vasculature targeting and treatment methods based on targeting the aminophospholipids phosphatidylserine and phosphatidylethanolamine (PE).

Once the discovery of phosphatidylserine as a specific marker of tumor vasculature had been proven, the inventors began to develop a range of phosphatidylserine-targeted immunotoxins and coaguligands for use in tumor treatment. As explained in U.S. Pat. No. 6,406,693, whilst investigating the potential of phosphatidylserine targeting in the context of delivering a toxin or coagulant to the tumor vasculature, the inventors serendipitously found that naked anti-PS antibodies had a destructive effect on tumor vasculature in vivo in the absence of any additional effector moiety. The ability of anti-aminophospholipid antibodies to both specifically localize to tumor vasculature and to exert a concomitant destructive effect, leading to tumor necrosis, was most unexpected.

These discoveries gave rise to tumor treatment using unconjugated or "naked" antibodies that bind to phosphatidylserine, as described in U.S. Pat. No. 6,406,693, incorporated herein by reference. Although anti-tumor effects in art-accepted animal models are demonstrated in U.S. Pat. No. 6,406,693, and extended herein, the ability of aminophospholipids to act as safe and effective targetable markers of tumor vasculature could not have been predicted from studies previous to U.S. Pat. No. 6,406,693.

B. Extensive Tumor Treatment with Anti-Phosphatidylserine Antibodies

Phosphatidylserine is normally segregated to the inner surface of the plasma membrane bilayer in different cells (Gaffet et al., 1995; Julien et al., 1995) and this lipid segregation creates an asymmetric transbilayer (Williamson and Schlegel, 1994). The inventors earlier demonstrated that PS is translocated to the surface of tumor vascular endothelial cells and that this occurs, at least in significant part, independently of apoptotic or other cell-death mechanisms (U.S. Pat. No. 6,406,693). Thus, PS surface expression in the tumor environment is not a consequence of cell death, nor does it trigger immediate cell destruction. Despite PS exposure being detected consistently on intact vascular endothelial cells in various solid tumors, the tumor vascular endothelium is not frankly apoptotic, but is morphologically sound (although different to that in normal tissues) and metabolically active. This is important for therapeutic methods based on PS targeting, meaning that PS translocation to the outer membrane in tumor vascular endothelial cells is sufficiently stable for PS to serve as a targetable entity for successful therapy (using either naked antibodies or therapeutic conjugates).

Through the development of biological tools with exquisite specificity for different phospholipids, the present inventors identified that anionic phospholipids are also upregulated on tumor vascular endothelial cells. Anionic phospholipids are thus specific and stable markers of tumor vasculature, permitting therapeutic intervention using both naked antibodies and immunoconjugates that bind to anionic phospholipids.

Anionic phospholipids are largely absent from the surface of resting mammalian cells under normal conditions. Phosphatidylserine, which is the most abundant anionic phospholipid of the plasma membrane, is tightly segregated to the internal leaflet of the plasma membrane in most cell types under normal conditions (Williamson and Schlegel, 1994; Zwaal and Schroit, 1997). Phosphatidylinositol (PI), another major anionic phospholipid, is also predominantly situated in the internal leaflet of the plasma membrane (Calderon and DeVries, 1997). The minor anionic phospholipids, phosphatidic acid (PA) and phosphatidylglycerol (PG), have only been examined in a few cells types, but they also appear to be mainly situated in the internal leaflet of the plasma membrane (Hinkovska-Galcheva et al., 1989). Cardiolipin (CL), another anionic phospholipid, is present in the mitochondrial membrane and is absent from the plasma membrane (Daum, 1985).

The neutral phospholipids are also asymmetrically distributed in the plasma membrane. The neutral aminophospholipid, phosphatidylethanolamine (PE) is predominately on the internal leaflet. The choline-containing neutral phospholipids, phosphatidylcholine (PC) and sphingomyelin (SM), are predominantly on the external leaflet.

PS asymmetry is maintained by an ATP-dependent transporter, aminophospholipid translocase ($Mg^{2+}$ ATPase), which catalyzes the transport of aminophospholipids from the external leaflet to the internal leaflet of the plasma membrane (Seigneuret and Devaux, 1984). Loss or collapse of PS asymmetry results from the outward movement of these phospholipids in the plasma membrane and is caused either by inhibition of the translocase (Bitbol et al., 1987; Comfurius et al., 1990), activation of PS transporters and/or activation of scramblase enzymes (Zhao et al., 1998) or the ABC-1 floppase (Hamon et al., 2000), $Ca^{2+}$ dependent enzymes that transport all lipids bidirectionally. Sphingomyelinase might also be activated to generate ceramide, which facilitates transbilayer lipid translocation (Contreras et al., 2003).

Loss of PS asymmetry is observed under different pathological and physiological conditions, including cell injury, programmed cell death and apoptosis (Blankenberg et al., 1998; Bombeli et al., 1997), cell aging (Herrmann and Devaux, 1990), activation of platelets (Rote et al., 1993; Zwaal et al., 1989), injury (Boyle et al., 1996) and malignant transformation (Sugimura et al., 1994). Exposure of PS also plays a role in intercellular fusion of myoblasts (Sessions and Horwitz, 1981) and trophoblasts (Adler et al., 1995), cell migration (Vogt et al., 1996) and cell degranulation (Demo et al., 1999). Endothelial cells externalize PS in response to increased $Ca^{2+}$ fluxes induced by thrombin (Qu et al., 1996), calcium ionophore or phorbol esters (Julien et al., 1997), hyperlipidemia (Lupu et al., 1993), and non-lytic concentrations of complement proteins C5b-9 (Christiansen et al., 1997). Spontaneous PS exposure has been also observed in malignant cells in the absence of exogenous activators or cell injury (Utsugi et al., 1991).

Several major consequences follow membrane PS exposure. Phagocytic macrophages recognize, attach and eliminate PS-positive senescent and apoptotic cells (McEvoy et al., 1986; Tait and Smith, 1999). PS also mediates attachment of T lymphocytes to thrombin-activated endothelial cells (Qu et al., 1996). The complement system is activated by PS and contributes to the lysis of PS-positive cells (Test and Mitsuyoshi, 1997). Finally, PS exposure contributes to a procoagulant shift on the endothelium (Williamson and Schlegel, 1994; Bombeli et al., 1997) by providing a negatively charged lipid surface for assembly and activation of coagulation complexes (Bevers et al., 1985; Dachary-Prigent et al., 1996). The prothrombotic character of the tumor endothelium has long been recognized (Donati and Falanga, 2001).

The inventors realized that injury and activation of tumor endothelium are caused by: 1) tumor-derived cytokines, such as interleukin-1 and tumor necrosis factor, which activate the endothelium and induce expression of cell adhesion molecules (Shaughnessy et al., 1989; Orr et al., 2000); 2) reactive oxygen species (ROS) generated by leukocytes that adhere to the endothelium (Orr et al., 2000); and 3) ROS generated by tumor cells themselves as a byproduct of metabolism (Shaughnessy et al., 1989; Soares et al., 1994) or as a result of exposure to hypoxia followed by reoxygenation (Zulueta et al., 1995). These observations suggested that $Ca^{2+}$ fluxes might be generated by these stresses within the tumor endothelium that, in turn, cause exposure of PS, through activation of scramblase or inhibition of aminophospholipid translocase.

To detect cell surface anionic phospholipids, the inventors generated a new monoclonal antibody, 9D2, which reacts with anionic but not neutral phospholipids. 9D2 thus differentiates from general aminophospholipid binding agents, as it binds to the anionic aminophospholipid, phosphatidylserine, but not to the neutral aminophospholipid, phosphatidylethanolamine (PE). The 9D2 antibody is also more specific for anionic phospholipids than is the natural ligand, annexin V, which strongly binds to PE, in addition to anionic phospholipids (Blankenberg et al., 1998).

As detailed in the present application, the inventors found that 9D2 and annexin V localize specifically to tumor endothelium after intravenous injection to mice bearing various types of solid tumors. This finding validates the inventors' hypothesis that phosphatidylserine and anionic phospholipids routinely become exposed on the surface of tumor vascular endothelium and can be used as target molecules for tumor therapy (and imaging).

One of the major findings to emerge from the present inventors is that phosphatidylserine and anionic phospholipids are exposed on the surface of tumor endothelium (Example VI; Ran and Thorpe, 2002; Ran et al., 2002b). This phenomenon was demonstrated using two independent reagents that bind selectively to anionic phospholipids: a monoclonal antibody, 9D2, developed by the inventors particularly to validate this point, and annexin V.

9D2 antibody and annexin V bind with high affinity and specificity to phosphatidylserine and anionic phospholipids adsorbed to plastic, as liposomes, or presented on the membrane surface of activated or apoptotic endothelial cells in vitro. 9D2 binds strongly to PS, PA and CL, but more weakly to PI and PG. Annexin V binds to PE in addition to PS, CL, PA, PI and PG, as found previously (Andree et al., 1990; Schlaepfer et al., 1987; Boustead et al., 1993; Blackwood and Ernst, 1990). Recognition of phosphatidylserine and anionic phospholipids by 9D2 antibody was identical in the presence and absence of serum, indicating that binding does not require serum co-factors. Binding of 9D2 to anionic phospholipids, did not require $Ca^{2+}$ ions, whereas the binding of annexin V did require $Ca^{2+}$.

Cross-blocking studies on PS-coated plates showed that 9D2 and annexin V do not block each other's binding to PS. This indicates that the two reagents recognize different epitopes on the PS molecule, or, more likely, differently packed forms of PS. Annexin V is thought to bind to planar PS surfaces, whereas anti-PS antibodies are thought to bind to hexagonally packed PS (Rauch and Janoff, 1990). Both forms are probably present on PS-coated plates. These practical cross-blocking studies (Example VI) also serve to show that antibodies which effectively compete for binding to anionic phospholipids, i.e., bind to essentially the same epitope, can be readily identified once a reference antibody (e.g. 9D2) is provided.

The present application also shows that 9D2 antibody and annexin V specifically localize to tumor vessels, and to tumor cells in and around necrotic regions of all tumors examined in vivo (Example VI). Between 15 and 40% of blood vessels in the tumors had phosphatidylserine-positive endothelium. In contrast, none of the blood vessels in normal tissues had detectable externalized anionic phospholipids. The PS-expressing tumor endothelial cells are viable. They lack markers of apoptosis (active caspase-3, TUNEL), are morphologically intact and metabolically active, and the vessels are functional at transporting blood and solutes.

The specificity of staining of tumor vasculature by 9D2 was demonstrated by: 1) the lack of tumor vessel staining by control rat IgM; 2) the blocking of 9D2 or annexin V binding to $H_2O_2$-treated endothelial cells in vitro by liposomes prepared from anionic phospholipids, but not neutral phospholipids; 3) the finding that extraction of phospholipids from tumor sections with detergents or organic solvents abolished staining; and 4) the lack of localization of either 9D2 or annexin V to the quiescent endothelium in normal organs.

The main anionic phospholipid that is localized by 9D2 or annexin V on tumor vasculature is phosphatidylserine, as this is the most abundant anionic phospholipid and its exposure on the cell surface is regulated by environmental influences or injury. To examine the mechanism of exposure of anionic phospholipids on tumor endothelial cells, a series of studies was performed in which endothelial cells in vitro were treated with various factors and conditions known to be present in the tumor microenvironment (Example VII). Hypoxia followed by re-oxygenation, acidity, and thrombin increased PS exposure on viable endothelial cells to between 10 and 22% of the level seen when all cells are apoptotic. Inflammatory cytokines (TNFα and IL-1) also caused a weak but definite induction of PS exposure.

These findings are consistent with the possibility that, in tumors, exposure of phosphatidylserine on the vascular endothelium is induced by hypoxia/reoxygenation in combination with inflammatory cytokines, thrombin and acidity. Although the precise mechanism does not need to be understood to practice the present invention, ROS may be generated by tumor cells as a bi-product of metabolism or in response to hypoxia (Zulueta et al., 1995). Cytokines released by tumor cells may induce leukocytes adhesion molecules on the endothelium that mediate adherence of activated macrophages, polymorphonuclear cells and platelets to tumor endothelium and further secretion of ROS. The ROS may then induce PS translocation through oxidation of thiol-containing transport molecules or peroxidation of lipids (Herrmann and Devaux, 1990), possibly by causing an influx of $Ca^{2+}$ or release of $Ca^{2+}$ from intracellular stores (Wang and Joseph, 2000). Indeed, peroxides have been shown to induce PS-exposure on viable endothelial cells in vitro by a mechanism that relates to glutathione oxidation and/or lipid peroxidation, not apoptosis (van Gorp et al., 1999).

Exposure of PS and other anionic phospholipids in part explains the procoagulant status of tumor endothelium that has long been recognized (Donati and Falanga, 2001). The anionic phospholipids provide the surface upon which coagulation factors concentrate and assemble (Bevers et al., 1985; Dachary-Prigent et al., 1996). It also provides an attachment site for circulating macrophages (McEvoy et al., 1986), T lymphocytes (Qu et al., 1996) and polyrnorphonuclear cells that assists in leukocyte infiltration into tumors.

In further studies detailed herein, the inventors generated and characterized the monoclonal antibody termed 3G4, which is directed against phosphatidylserine and anionic phospholipids. This antibody is also shown to localize specifically to vascular endothelial cells in tumors, reduce tumor vascularity and plasma volume and to retard tumor growth.

The 3G4 antibody binds with high affinity to anionic phospholipids absorbed to plastic, and on the surface of activated or apoptotic cells in the presence of serum or β2-glycoprotein I. The binding pattern of 3G4 on cells was indistinguishable from that of annexin A5 or the 9D2 antibody against anionic phospholipids. All three reagents bound to clusters of plasma membrane resembling membrane blebs, consistent with other observations on endothelial cells treated with $H_2O_2$ (van Gorp et al., 1999). Like 9D2, 3G4 recognizes all anionic phospholipids tested, including synthetic phospholipids having saturated fatty acids, which are resistant to oxidation, and lysophospholipids.

Unlike 9D2, 3G4 binding to anionic phospholipids was partially inhibited in the complete absence of serum and restored when β2-glycoprotein I was added. 3G4 recognizes thus an epitope in lipid-β2-glycoprotein I complexes. Irrespective, 3G4 is shown to be safe when administered to animals, and not to be associated with pathological effects reported in the literature for antibodies associated with antiphospholipid syndrome(s) (APS).

3G4 localized specifically to tumor vessels and to tumor cells in and around necrotic regions of tumors after injection into mice bearing orthotopic human breast MDA-MB-435 tumors. An average of 40±10% of vessels were bound by 3G4. Staining patterns were similar to those reported herein using 9D2 and annexin A5. Vascular endothelium in normal tissues was unstained. In this regard, 3G4 differs from other antibodies that recognize tumor vessel markers. Most tumor vessel markers are present on vessels in the ovary, a site of physiological angiogenesis, or in the kidney and pancreatic islets where vessels have high permeability (Thorpe, 2004).

Phosphatidylserine is the anionic phospholipid primarily detected by 3G4. PS is the most abundant anionic phospholipid and the one whose exposure is best known to be regulated by environmental conditions or injury (Zwaal and Schroit, 1997; Balasubramanian and Schroit, 2003). In vivo, the exposed PS on tumor vessels is probably complexed with serum components, such as β2-glycoprotein I, and 3G4 probably binds to these complexes. As noted throughout the present studies, the PS-positive tumor vessels in untreated mice appear to be intact and functional. They transport blood and are perfusible. The vascular endothelium of PS-positive vessels does not display markers of advanced apoptosis (active caspase 3, TUNEL), is morphologically intact and is metabolically active, as judged by co-expression of the rapidly turned over protein, VCAM-1.

Treatment with 3G4 retarded tumor growth in various murine models, including established (0.6-0.7 cm diameter) orthotopic human MDA-MB-231 and MDA-MB-435 breast cancers, large (1 cm diameter) subcutaneous L540 human Hodgkin's tumors, and small syngeneic Meth A fibrosarcomas. 3G4 treatment resulted in 75%, 65%, 50% and 90% retardation of growth of these tumors, respectively. Other studies in the present application demonstrate that these tumors are nourished by vasculature with exposed anionic phospholipids.

The antitumor effect of 3G4 is mediated, at least in part, through damage to tumor vasculature. Histological examination of orthotopic MDA-MB-231 tumors from mice treated with 3G4 revealed a marked reduction in the vascular density and plasma content of the tumors. Localization of 3G4 to tumor vessels preceded macrophage binding to tumor vessels, impairment of vascular function and the development of necrosis. The vascular shutdown and pattern of necrosis are consistent with the primary effect being on tumor vessels. Central necrosis of tumors with survival of a peripheral rim of tumor cells was observed. This pattern of tumor cell killing is characteristic of VTAs (U.S. Pat. No. 5,855,866; Thorpe, 2004). It is thought that VTAs are most effective against vessels in the interior of the tumor because high interstitial pressure in these regions contributes to vascular collapse. In contrast, many direct-acting tumor therapies are most effective against the rapidly dividing tumor cells in the well-oxygenated periphery of the tumor. The inventors therefore expect that combining 3G4 with antiproliferative antitumor therapies will to lead to additive or even synergistic antitumor activity, as has been observed with other VTAs in experimental solid tumors (U.S. Pat. No. 5,855,866; Burrows and Thorpe, 1993; Siemann et al., 2002; Siim et al., 2004).

As with the other antibodies used herein, 3G4 therapy is well-tolerated in tumor-bearing animals treated repeatedly with the therapeutic dose (4 mg/kg in mice, three times a week). The mice retained normal physical signs, coagulation parameters, bone marrow cellularity, white blood cell counts and histology. Manifestations of APS were not observed, in contrast to those observed with anticardiolipin antibodies (Matzinger, 1998; Fadok et al., 1998; Fadok et al., 2001a;b). Despite effects of high concentrations of 3G4 in partially inhibiting phospholipid-dependent coagulation pathways, a substantial safety margin exists between the therapeutic dose and the dose that prolongs coagulation times in vivo.

The inventors have considered the question as to whether PS becomes exposed on vascular endothelium in nonmalignant lesions (e.g., atherosclerotic lesions, sites of inflammation), where cytokines, hypoxia and ROS might induce PS translocation (Moldovan et al., 1994). Is this occurred, it is possible this could lead to some toxicity with an anti-PS antibody, making it advisable to exclude patients with these conditions from treatment. However, other studies of the inventors showed that treatment of atherosclerotic rabbits with a chimeric version of the 3G4 antibody did not exacerbate aortic atherosclerotic lesions.

Vascular targeting agents employing drugs or coagulants have been shown to be highly effective, and sometimes curative, in mice with large solid tumors (Huang et al., 1997; Nilsson et al., 2001; U.S. Pat. Nos. 5,660,827, 5,776,427, 5,855,866, 5,863,538, 5,965,132, 6,004,554, 6,051,230, 6,261,535, 6,093,399, 6,004,555, 5,877,289 and 6,036,955). The present inventors provide naked antibodies and vascular targeting agents directed against phosphatidylserine for use in targeting tumor vasculature in the diagnosis and treatment of cancer in man.

Although a precise molecular understanding of how naked antibodies directed against phosphatidylserine function in tumor treatment is not necessary in order to practice the treatment, the inventors have contemplated several mechanisms that may account for the observed endothelial cell killing. The favored mechanisms (particularly for the 3G4 antibody described herein) are Fc domain-mediated immune effector functions, such as antibody-dependent cellular cytotoxicity (ADCC), complement-dependent cytotoxicity (CDC) and antibody mediated phagocytosis. Cell-mediated cytotoxicity, complement-mediated lysis and/or apoptosis, antibody-induced cell signaling and/or disturbances to the cytoskeleton may also be involved.

Binding of intact antibodies against phosphatidylserine, particularly 3G4, to the vascular endothelial cell surface means that the Fc portions of the antibodies protrude into the vessel lumen. As antibody Fc fragments activate the complement pathway, the observed cellular destruction may be a result of complement-directed lysis. Antibody binding thus activates the complement-dependent coagulation cascade, causing multi-component complexes to assemble and, ultimately, to generate a lytic complex that permeabilizes the target cell. "Complement-activated ADCC" may also be operating in the destruction, in which complement binds to the antibody-coated target cell, and in which cells, such as neutrophils, having receptors for complement, lyse the target cell.

As the naked or unconjugated antibodies, including the antigen binding fragments thereof, bind to phosphatidylserine at the surface of the tumor vascular endothelial cells, they will form an antibody coating on the luminal surface. This may function to attract immune effector cells, such as cytotoxic T cells and/or natural killer (NK) cells, which will then exert a cell-mediated cytotoxic effect on the vascular endothelial cells.

Antibody binding to phosphatidylserine may also induce apoptosis in the tumor vascular endothelial cells. Although there are no known reports of antibody binding to PS actually inducing apoptosis (rather than PS being a marker resulting from apoptosis), the inventors consider this to be another possible mechanism for the observed anti-tumor effects.

It is also possible that antibody binding to phosphatidylserine at the surface of tumor vascular endothelial cells may cause disturbances in the cytoskeletalal organization of the cell. As the cytoskeleton plays a role in the organization of surface membranes, and as antibody binding may disturb (or further disturb) the membrane, binding of antibodies to phosphatidylserine may transmit changes to cytoskeletal proteins that interact with the bilayer. It is already known that the spatial organization of cytoskeletal proteins controls membrane stability and cell shape, and it is possible that perturbation of some cytoskeletal equilibrium may have far-reaching consequences on cell integrity.

A further mechanism of operation of the invention may be that antibody binding to phosphatidylserine at the endothelial cell surface may initiate signal transduction by, as yet, undefined pathways. Antibody binding may also disturb known signal transduction pathways, e.g., by altering the conformation and/or interactions of membrane receptors, signal transduction proteins, membrane channels, and the like. Signals for cell destruction (apoptosis) may be initiated or mimicked, and/or preservation/homeostatic signals may be inhibited.

Although of scientific interest, determining the exact nature of the vascular destruction achieved by the naked antibodies to phosphatidylserine is not necessary to practice the treatment. Given that the administration of these antibodies is shown to advantageously result in specific anti-tumor effects in vivo, the treatment can be utilized irrespective of the molecular mechanism that underlies this phenomenon. The use of naked antibodies that bind to phosphatidylserine thus represents an important advance in tumor therapy, providing advantages in preparation and cost.

C. Detailed Analysis of the 3G4 Antibody

As shown herein, 3G4 is an effective and well-tolerated anti-tumor agent, which acts by homing to phosphatidylserine on tumor blood vessels, and causing host cell-mediated antitumor effects. Since PS is the same molecule in the human and mouse, and has the same cellular distribution, regulation and induction by ROS in both species (Balasubramanian and Schroit, 2003; Whitworth et al., 1990), these studies further support the use of antibodies and other constructs that bind to phosphatidylserine to treat cancer in man. Indeed, chimeric and humanized versions of 3G4 have already been prepared for this and other purposes.

Antibodies and other ligands that bind to phosphatidylserine can thus be used for the targeting, imaging and/or treatment of tumor blood vessels. Phosphatidylserine is attractive as tumor target vessels for several reasons: it is abundant (PS is present at $3\times10^6$ molecules per cell); it is on the luminal surface of tumor endothelium, which is directly accessible for binding by vascular targeting agents in the blood; it is present on a major percentage of tumor endothelial cells in diverse solid tumors; and it is essentially absent from endothelium in all normal tissues.

The 3G4 antibody has been shown to localize specifically to vascular endothelial cells in tumors, reduce tumor vascularity and plasma volume and to retard tumor growth (the present examples; Ran et al., 1998; Ran and Thorpe, 2002; Ran et al., 2002b; Ran et al., 2005; Huang et al., 2005).

Ongoing studies have shown that 3G4 treatment inhibits growth of murine tumor allografts and human tumor xenografts (the present examples; Ran et al., 2005), including orthotopic human breast tumors (Example XX; Huang et al., 2005) and orthotopic human pancreatic tumors (Example XX; Beck et al., 2005). 3G4 also inhibits metastatic spread and growth of these tumors (Example XX; Huang et al., 2005; Beck et al., 2005). When used in combination, 3G4 enhances the therapeutic efficacy of the chemotherapeutic drugs docetaxel and gemcitabine for treatment of breast and pancreatic tumors, respectively (Example XX; Huang et al., 2005; Beck et al., 2005).

As with the other antibodies used herein, 3G4 therapy is well-tolerated in tumor-bearing animals treated repeatedly with the therapeutic dose (4 mg/kg in mice, three times a week). The mice retained normal physical signs, coagulation parameters, bone marrow cellularity, white blood cell counts and histology. Despite effects of very high concentrations of 3G4 in partially inhibiting phospholipid-dependent coagulation pathways, a substantial safety margin exists between the therapeutic dose and the dose that prolongs coagulation times in vivo. 3G4 is thus an effective and well-tolerated anti-tumor agent, which acts by homing to anionic phospholipids on tumor blood vessels and causing host cell-mediated antitumor effects. 3G4 is not associated with pathogenic effects reported in the literature for antibodies associated with anti-phospholipid syndrome(s).

Anti-phospholipid syndrome(s) (APS) are associated with autoantibodies termed "anti-cardiolipin" antibodies and "lupus anticoagulant antibodies". These syndromes are associated with a predisposition towards venous and arterial thromboemboli, thrombocytopenia and a number of neurological syndromes. The anti-phospholipid antibodies in these patients are thus "pathogenic antibodies". Such anti-phospholipid antibodies in the human population occur in systemic lupus erythematosus (Branch et al., 1987; Staub et al., 1989; Drouvalakis and Buchanan, 1998; Smimov et al., 1995; Rauch et al., 1986; Rauch and Janoff, 1990) and are associated with recurrent pregnancy loss (Rote et al., 1995; Rote, 1996; Vogt et al., 1996; 1997; Katsuragawa et al., 1997).

Although described for years as "anti-phospholipid antibodies" and "anti-PS antibodies", such pathogenic antibodies in fact recognize protein cofactors that bind to cardiolipin, PS or both, not the phospholipids themselves (Galli et al., 1990; 1993; McNeil et al., 1990; Rote, 1996). There is considerable heterogeneity in the pathogenic antibodies. Certain anti-cardiolipin antibodies have been reported to recognize particular regions on β2-glycoprotein I, whereas lupus anticoagulant antibodies recognize prothrombin. Similarly, anti-PE antibodies that occur in disease states bind to PE in combination with proteins, such as low and high molecular weight kininogen (HK), prekallikrein and factor XI (Sugi and McIntyre, 1995; 1996a; 1996b).

In selecting antibodies for administration as therapeutics, it was thus thought that such antibodies should be identified on the basis of not binding to phosphatidylserine in combination with protein cofactors, but rather "true" anti-phosphatidylserine antibodies should be sought (WO 2004/006847).

However, further in vitro studies of the 3G4 antibody revealed that, unlike 9D2, binding of 3G4 to phosphatidylserine and anionic phospholipids was partially inhibited in the complete absence of serum. Moreover, binding was found to be restored when β2-glycoprotein I (β2GPI) was added. This prompted the inventors to believe that 3G4 recognizes an epitope in lipid-β2GPI complexes, such that the interaction between 3G4 and PS is dependent on β2GPI (U.S. provisional application Ser. No. 60/646,333, filed Jan. 24, 2005; Ran et al., 2005). The inventors reasoned that PS exposed on tumor vessels in vivo is probably complexed with serum components, such as β2GPI, and that 3G4 probably binds to these complexes.

The potential for 3G4 to bind to a PS-β2GPI complex was very surprising, not least because 3G4 has been shown to be safe when administered to animals in numerous studies, and not to be associated with pathogenic effects reported in the literature for antibodies associated with APS, which antibodies are known to bind to lipid-serum protein complexes, including PS-β2GPI complexes. No manifestations of APS have been observed in any 3G4 treatment, in contrast to those observed with anticardiolipin antibodies against β2GPI (Matzinger, 1998; Fadok et al., 1998; Fadok et al., 2001a;b). Mice treated with 3G4 at high doses for prolonged periods showed no changes in coagulation capability, yet mice respond with APS when injected with anticardiolipin or lupus anticoagulant antibodies.

The present invention resolves this discrepancy, elucidates the interaction of 3G4 and β2GPI required for binding to endothelial cells with exposed PS, and explains how 3G4 can bind to a PS-β2GPI complex without succumbing to the toxicities associated with previously known pathogenic antibodies.

As shown in Example XXX, the interaction between 3G4 and PS is dependent on β2GPI. Although β2GPI binds anionic phospholipids weakly under physiological conditions, the present invention shows that 3G4 greatly enhances the binding of β2GPI to PS-positive endothelial cells. The data show that divalent 3G4/β2GPI complexes are required for enhanced binding, since 3G4 Fab' fragments do not bind endothelial cells with exposed PS. It is also demonstrated that an artificial dimeric β2GPI construct binds to endothelial cells with exposed PS without the need for 3G4. Together, these data suggest that 3G4 targets PS-positive cells, including tumor endothelial cells, by increasing the affinity of β2GPI for PS via the formation of a divalent 3G4/β2GPI complex.

Example XXX also shows that 3G4 binds to domain II of β2GPI. This is important, as antibodies from APS patients that recognize β2GPI domain II are not pathogenic. In contrast, a significant recent study demonstrated that pathogenic anti-β2GPI antibodies isolated from patients with APS commonly recognize domain I of β2GPI (de Laat et al., 2005a). The ability of the 3G4 antibody to bind PS-β2GPI complexes without binding β2GPI domain I is important in the lack of toxicity that the antibody exhibits. β2GPI can also interact with the apolipoprotein E receptor 2' (apoER2') (Lutters et al., 2003). Another recent study indicated that domain V of β2GPI interacts with apoER2' and is involved in the activation of platelets, which causes increased platelet deposition to collagen (van Lummel et al., 2005).

Accordingly, by binding neither domain I nor domain V, the 3G4 antibody can bind to a PS-β2GPI complex and yet show no toxicity following extensive toxicological studies performed in a variety of animal models. In light of these findings, other antibodies that bind to PS-β2GPI complexes can now be made and used safely in the treatment of various conditions, such as cancer and viral infections. The selection of antibodies that do not significantly bind to β2GPI domain I is currently the primary requirement, and the selection of antibodies that do not significantly bind to β2GPI domain I or to β2GPI domain V is envisioned to provide additional advantages.

In review, the new studies have characterized the interaction between the 3G4 antibody and its main anionic phospholipid target, phosphatidylserine. The data demonstrate that the interaction between 3G4 and PS is serum-dependent. β2GPI was identified as the serum factor required to mediate the 3G4-PS interaction.

3G4 was originally generated by immunizing mice with murine endothelial cells treated with $H_2O_2$ to induce PS exposure (Example IV; Ran et al., 2005). The cells were grown in FBS-containing media and likely injected with a small amount of bovine β2GPI, leading to the production of anti-PS/β2GPI antibodies. Initial antibody screens for reactivity with PS were performed in the presence of bovine serum. Later screens were performed in the absence of serum, but as indicated herein, antibody purified from SCM is co-purified with the β2GPI antigen. Therefore, "purified" antibody can bind PS in the absence of serum due the presence of contaminating bovine β2GPI. Only when 3G4 was grown and purified from serum-free media was the serum-dependence identified. Other groups have reported similar concerns regarding obtaining β2GPI free preparations of anti-β2GPI antibodies (Roubey et al., 1995). Therefore, it is quite possible that many so-called "antiphospholipid antibodies" reported to bind phospholipids directly, actually recognize serum proteins with affinity for phospholipids.

β2GPI is a 50-kDa glycoprotein that is present in plasma at a concentration of ~200 μg/mL (4 μM) (Cleve et al., 1969). The protein is a member of the complement control protein (CCP) family (Steinkasserer et al., 1991). β2GPI has five CCP repeats in which the first four domains are regular repeats consisting of ~60 amino acids. The fifth domain differs from the other four domains as it has 82 amino acids, including a cluster of positively charged amino acids (282-287) and a conserved hydrophobic region (311-317) responsible for binding of β2GPI to anionic phospholipids (Steinkasserer et al., 1992; Hunt and Krilis, 1994; Sheng et al., 1996; Mehdi et al., 2000; each specifically incorporated herein by reference).

There is little known about the normal biological function of β2GPI. Proposed functions include facilitating apoptotic cell clearance (Balasubramanian et al., 1997b; Balasubramanian et al., 2005), modulation of platelet function (Nimpf et al., 1985; Nimpf et al., 1987), and inhibition of coagulation (Nimpf et al., 1986; Schousboe, 1985); however, no definitive phenotype has been observed in mice or patients with β2GPI deficiency (Miyakis et al., 2004; Yasuda et al., 2000).

In contrast, β2GPI is well known for its involvement in the autoimmune disorder APS, where it has been identified as a plasma co-factor required for binding of so-called antiphospholipid (aPL) antibodies to anionic phospholipid surfaces (de Laat et al., 2004a; Bevers et al., 2004). Antiphospholipid antibodies are known to interact with a variety of serum proteins, but aPL antibodies recognizing β2GPI correlate most strongly with the clinical symptoms of APS (de Laat et al., 2004b). Therefore, the interaction between β2GPI, anti-β2GPI antibodies, and anionic phospholipid membrane surfaces has been studied extensively (Bevers et al., 2004).

The present studies also examined the characteristics of 3G4 binding to PS-coated microtiter plates and to endothelial cells with exposed PS. Using a live-cell binding assay, it was determined that neither 3G4 nor β2GPI bind endothelial cells with exposed PS unless both molecules are present simultaneously (Example XXX). This observation is consistent with the ELISA-based findings demonstrating that 3G4 depends on β2GPI for binding to anionic lipid surfaces. Furthermore, this observation supports reports that β2GPI has low affinity for anionic phospholipid membranes under physiological conditions (Willems et al., 1996; Bevers et al., 2004; Bevers et al., 2005), and suggests that the affinity is greatly enhanced by the presence of 3G4.

The data also demonstrate that 3G4 enhances the affinity of β2GPI for anionic phospholipid surfaces via the formation of divalent β2GPI complexes. When the β2GPI concentration is held constant and the 3G4 concentration is increased, binding of 3G4/β2GPI to endothelial cells with exposed PS peaks at a 3G4 to β2GPI ratio of 2:1. At higher concentrations of 3G4, the binding decreases. The bell-shaped curve suggests competition between monovalent and divalent complexes, leading to a decrease in overall 3G4/β2GPI complex binding. A bell-shaped relationship has been reported for anti-β2GPI antibodies in a thrombosis model (Jankowski et al., 2003). In other studies, 3G4 Fab fragments did not bind endothelial cells with exposed PS in the presence of β2GPI, demonstrating that monovalent 3G4/β2GPI complexes cannot bind anionic phospholipid surfaces.

It is also demonstrated that artificial dimeric β2GPI constructs can bind endothelial cells with exposed PS without the need for 3G4. Thus, anti-β2GPI antibodies increase the affinity of β2GPI for anionic phospholipid surfaces by crosslinking two β2GPI molecules, forming a divalent β2GPI complex.

Importantly, although 3G4/β2GPI complexes interact with PS much like aPL antibodies from patients with APS, 3G4 has not caused clinical manifestations of APS in any animal model tested. The mechanism(s) by which aPL cause APS remains largely unknown. Some studies suggest that aPL/β2GPI can bind and activate resting endothelial cells (which do not expose PS), causing them adopt a more thrombogenic phenotype (Simantov et al., 1995; Pierangeli et al., 1999). More recent studies demonstrate that β2GPI and aPL/β2GPI complexes cannot bind and fully activate endothelial cells unless they are already “pre-activated” (Chen et al., 2004). Pre-activation causes endothelial cells to expose PS, providing the appropriate anionic phospholipid surface for binding of aPL/β2GPI complexes.

3G4 does not bind resting ABAE cells or HUVECs in a live-cell assay. Furthermore, 3G4 does not activate resting HUVECs or HUVECs pre-activated with low concentrations of LPS. Recent studies report a high correlation between the presence of aPL antibodies recognizing domain I of β2GPI in patient sera and clinical symptoms of APS (de Laat et al., 2005), and a conformational change may be required for antibody binding (de Laat et al., 2005b). Antibodies recognizing the other domains of β2GPI are also detected in patient sera, but do not correlate with pathogenesis. Importantly, the present invention demonstrates that 3G4 recognizes domain II of β2GPI, which likely explains the lack of endothelial cell activation in vitro and the lack of toxicity in vivo.

Domain II of mouse β2GPI differs from domain II of rat, dog, cow, chimp and human β2GPI at only 7 of 60 amino acids. Therefore, the inability of 3G4 to bind PS in the presence of mouse serum or to detect murine β2GPI by immunoblot is unexpected, especially in light of the documented anti-tumor activity of 3G4 in mice (the present examples; Ran et al., 2005; Huang et al., 2005; Beck et al., 2005). Importantly, these studies were performed using 3G4 purified from SCM. As shown herein, 3G4 SCM is able to bind PS, due to co-purification of bovine β2GPI. When 3G4 SCM was run on an SDS-PAGE gel, transferred to membrane support, and probed for the presence of bovine β2GPI, a band of 50 kDa was clearly visible. Furthermore, 3G4 present in sera collected from mice following injection with 3G4 SCM binds PS. Therefore, bovine β2GPI is able to mediate binding of 3G4 to PS in mouse plasma and likely contributed to the anti-tumor effect of 3G4. All tumor studies performed in mice using 3G4 should be supplemented with bovine or human β2GPI to ensure targeting of tumor endothelial cells with exposed PS.

The identification of β2GPI as an important co-factor required for the interaction between 3G4 and PS greatly enhances the understanding of this unique tumor vascular targeting agent. 3G4 targets tumor endothelial cells with exposed PS by enhancing the affinity of β2GPI for anionic phospholipid surfaces via the formation of dimeric β2GPI complexes. In addition to clarifying these properties, the present studies now permit the development of third generation antibodies that bind to aminophospholipids and anionic phospholipids in complexes with serum proteins, without duplicating the properties of pathogenic antibodies.

In summary, preferred “third generation” or “non-pathogenic PS-β2GPI antibodies” can now be selected that bind to PS and β2GPI at a position other than within β2GPI domain I, or other than within β2GPI domain I or domain V. In light of the data herein the most preferred antibodies are currently those that bind β2GPI within domain II. A range of non-pathogenic PS-β2GPI antibodies can be prepared following the methodology and screening techniques described herein, e.g., using the sequence information in FIG. 18A and FIG. 18B and the binding assays in Example XXX. Such antibodies and immunoconjugates thereof can be advantageously used in the safe and effective treatment of viral infections and in treating cancer and other diseases.

D. ReceptorBodies and BetaBodies

The foreoing detailed analyses of the 3G4 antibody, and particularly the interaction of 3G4 with β2GPI, which contrasts with that set forth in WO 2004/006847, also contributed to the inventors' development of the receptorbodies of the present invention. Importantly, this invention also provides a range of constructs, termed “receptorbodies”, which bind to phosphatidylserine, and evoke host effector functions. Aspects of the development of the receptorbodies are described below.

Data are presented herein to show that targeting tumor vasculature with antibodies to phosphatidylserine is effective in tumor treatment. Antibodies to phosphatidylserine are also shown to be effective in treating viral infections. Considering the tumor studies as an example, it is shown herein that stress conditions in the tumor microenvironment induce phosphatidylserine exposure on tumor vascular endothelium (Example VII, Example II, Example V and Example VI). The exposed phosphatidylserine provide a selective marker of tumor vasculature for imaging and therapy (Example IX, Example X, Example XI and Example XX).

In conjunction with the tumor treatment, antibodies to phosphatidylserine damage blood vessels within tumors and cause leukocyte infiltration (e.g., FIG. 1). Moreover, administration of such antibodies recruits macrophages into tumors. For example, in tumor treatment studies using the 3G4 antibody, extensive binding of blood monocytes to tumor vascular endothelium and profuse infiltration of macrophages into the tumor interstitium were seen (e.g., Example XXVII; FIG. 6A, FIG. 6B, FIG. 6C and FIG. 6D).

The infiltration of macrophages into the treated tumor, taken together with the finding that 3G4 enhances the rate of phagocytosis of PS-expressing cells by bone-marrow derived mouse macrophages in vitro by 5-fold in an Fc-dependent fashion, are consistent with antibodies such as 3G4 provoking macrophage cytotoxicity towards tumor vessels or tumor cells. Also, 3G4 does not directly inhibit the proliferation of PS-expressing endothelial cells or tumor cells, or mediate complement lysis of the cells in vitro, suggesting that the antibody is not directly cytotoxic.

The inventors therefore propose two feasible mechanisms of macrophage-mediated damage to tumor vessels or tumor cells. First, antibodies such as 3G4 bind to complexes of anionic phospholipids, mainly phosphatidylserine, and serum proteins on tumor vessels and tumor cells. The antibodies then stimulate the binding of monocytes and macrophages via Fcγ receptors, thereby enhancing antibody-dependent cellular cytotoxicity (ADCC) and antibody-dependent macrophage phagocytosis. Activated macrophages have long been recognized as having direct tumoricidal activity (Whitworth et al., 1990). In support of this, Manfredi et al. (1998) have reported that anti-phospholipid antibodies can facilitate opsonization of PS-expressing cells by scavenger macrophages with massive induction of TNF-α secretion. Although macrophages have PS receptors and can bind to, and engulf, PS-expressing cells (Balasubramanian and Schroit, 2003; Utsugi et al., 1991; Fadok et al., 2001a), PS exposure alone is insufficient to stimulate engulfment (Devitt et al., 2003).

Figure 7:
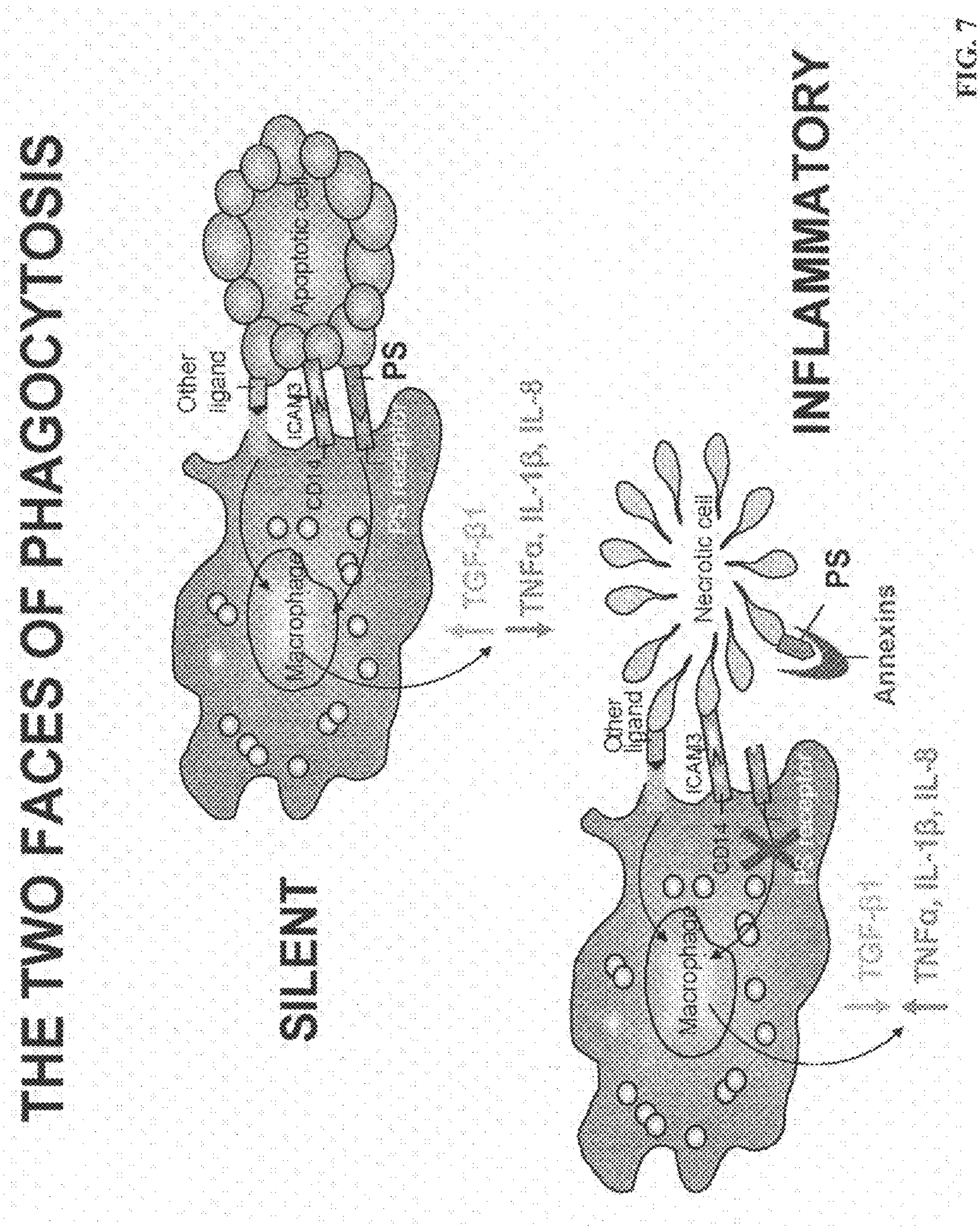
FIG. 7. The silent and inflammatory phases of phagocytosis. From tumor treatment studies using the 3G4 antibody, it is proposed that antibodies such as 3G4 cause a blockade of PS signaling from PS-expressing tumor endothelial cells. Normally, PS on the tumor endothelial cells would suppress inflammatory responses by macrophages that bind to the tumor vessels and tumor cells (silent phase). When antibodies such as 3G4 are present, the antibodies bind to PS such that the PS receptor on the macrophage does not have a binding partner. The macrophage then secretes TNF-α, IL-1 and other inflammatory cytokines that directly damage tumor endothelium and recruit further host cells into the tumor (inflammatory phase).

Second, antibodies such as 3G4 may block PS-mediated "quiescence" signals from PS-expressing tumor endothelial cells, which normally would suppress inflammatory responses by macrophages that bind to the tumor vessels and tumor cells (FIG. 7). Analogous mechanisms are thought to explain the lack of inflammatory response of macrophage-lineage cells to apoptotic cells (Henson et al., 2001; Matzinger, 1998; Gallucci and Matzinger, 2001; Fadok et al., 2001b). Accordingly, antibodies such as 3G4 may evoke tumor vessel damage by provoking macrophages to secrete TNF-α, IL-1 and other inflammatory cytokines that directly damage tumor endothelium (FIG. 7) and recruit further host cells into the tumor (Fadok et al., 1998).

Ideally, each of the above possible mechanisms should be reconciled with the proposal that tumor-associated macrophages can induce tumor angiogenesis, which promotes tumor growth (e.g., Sunderkotter et al., 1994). The inventors therefore reason that there is a balance between the proangiogenic effects of macrophages and their direct cytotoxic effects on tumor vessels and tumor cells that is determined by local conditions (e.g., hypoxia, TGF-β) in the tumor microenvironment (Breier et al., 2002). It is currently envisioned that antibodies such as 3G4 alter the tumor microenvironment in a manner that favors a direct cytotoxic response from macrophages.

Considering phosphatidylserine biology, and optionally in light of the data presented herein concerning macrophage behaviour in tumor treatment, the inventors therefore provide a range of advantageous constructs or "receptorbodies" that bind to phosphatidylserine, and optionally to other anionic phospholipids, and related conjugates and methods of use.

Such a construct or receptorbody of the invention will typically comprise a binding protein or polypeptide, receptor, ligand or peptide that recognizes and binds to phosphatidylserine, and optionally to other anionic phospholipids, which binding protein or polypeptide, receptor, ligand or peptide is linked to an antibody or immunoglobulin Fc region or domain. The Fc region modifies the binding protein or polypeptide, receptor, ligand or peptide to increase its biological half life, but more importantly, provides the resultant construct with the ability to stimulate host effector functions to enhance disease treatment.

The receptorbodies of the invention may be used in any of the embodiments in which antibodies against phosphatidylserine may be used. Such receptorbodies therefore have multiple applications, including binding phosphatidylserine on tumor blood vessels and tumor cells, leading to host cell mediated anti-vascular and anti-cellular effects on the tumor, and binding phosphatidylserine on viruses or virally infected cells, leading to an anti-viral effect in animals.

One of the advantages of these aspects of the invention is that the receptorbodies use natural phosphatidylserine binding proteins, polypeptides or receptors to achieve specific binding. Although the use of antibodies against phosphatidylserine is herein shown to be effective in many treatment embodiments, the receptorbodies could have higher avidity or specificity than anti-PS antibodies. By dimerizing phosphatidylserine binding proteins or polypeptides, particularly β2GPI, onto an Fc immunoglobulin region, the constructs achieve better avidity, stability, longer in vivo half lives, and possibly superior localization to phosphatidylserine-expressing tissues, as well as stimulating host effector functions in vivo. Anti-PS antibodies are herein shown to be both effective and safe when administered to animals, including monkeys. Likewise, the receptorbodies containing the natural ligands will be effective and safe and will not cause antiphospholipid syndromes. Accordingly, the receptorbodies of the present invention are simple, human, specific and safe therapeutics, which may be used to treat a range of tumors and viral infections.

D1. Phosphatidylserine Binding Proteins

The binding protein or polypeptide, receptor, ligand or peptide in the receptorbodies may be any one of several phosphatidylserine binding proteins, including cell-derived receptors, factor V, prothrombin (factor II), and such like. The use of β2-glycoprotein I is much preferred.

Certain factors in the coagulation cascade also bind phosphatidylserine and can thus be used in the receptorbodies of the invention. For example, factor V and prothrombin (factor II) bind phosphatidylserine. In the prothrombinase complex, binding of factor Va to an anionic lipid surface promotes $Ca^{2+}$-dependent binding of factor Xa, which converts prothrombin to thrombin. In both complexes, phosphatidylserine is the most effective anionic phospholipid. The phosphatidylserine binding proteins Protein C, Protein S, Factor II/IIa, Factor V/Va, Factor VII/VIIa, Factor IX/IXa and Factor X/Xa may thus be used.

Fadok et al. (2000, specifically incorporated herein by reference) reported the cloning of a PS receptor that directly binds apoptotic cells. This receptor is expressed in many cells types, including macrophages, fibroblasts and epithelial cells. Studies using antibodies and PS vesicles indicated that the receptor does recognize phosphatidylserine on the cell surface. Hence, this is a PS-specific receptor, "the PS receptor" or "PSr" (Accession Number AF304118). This receptor is present on phagocytes, such as macrophages, and also on other cell types. The PS receptor of Fadok et al. (2000, specifically incorporated herein by reference) may therefore be used in the receptorbodies of the invention.

Other phosphatidylserine binding proteins that could be used in the receptorbodies of the invention are described in Balasubramanian and Schroit, 2003 (specifically incorporated herein by reference), in particular, see Balasubramanian and Schroit, 2003, Table 2, and the references cited therein, which are all specifically incorporated herein by reference. These phosphatidylserine binding proteins include, for example, CD14; integrins, such as α5β3 (vitronectin, CD51/CD61) and α5β3/CD36; several scavenger receptors, such as SRB (CD36), SRC (LOX-1, SRCL), SRD (CD68, macrosialin) and PSOX; complement receptors, such as CR3 (CD11b/CD18) (Accession Number NM 000632), CR4 (CD11c/CD18) (Accession Number NM 000887), and CD93 (cClqr, calreticulin)/CD91 (α2-macroglobulin receptor); and other receptors such as the Mer/Gas 6 phagocyte recognition partners for PS-expressing apoptotic cells (Accession Number AH010001).

Although annexins, such as annexin V, may be used as a phosphatidylserine binding protein in a receptorbody, their use is not a universal part of the present invention. Therefore, in certain embodiments, the present invention provides constructs in which the phosphatidylserine binding protein is not an annexin. Nonetheless, the following information is provided for use in those embodiments in which an annexin is contemplated. In addition, the technical information in the annexin patent documents specifically incorporated herein by reference, e.g., regarding expression and conjugation, may be used to support the other Fc-phosphatidylserine binding protein constructs of the invention.

At least nine members of the annexin family have been identified in mammalian tissues (Annexin I through Annexin IX). Currently preferred amongst these is annexin V (also known as PAP-I). The protein and DNA sequences for annexins are known in the art, facilitating the ready production of recombinant fusion proteins for use in these aspects of the invention.

U.S. Pat. No. 5,658,877, incorporated herein by reference, describes Annexin I, effective amounts of Annexin I and pharmaceutical compositions thereof. Also described are methods of treating an animal to prevent or alleviate the adverse effects of endotoxin in the lung that comprise administering into the airway of an animal a safe amount of 33 kDa Annexin I fragment.

Annexin V contains one free sulfhydryl group and does not have any attached carbohydrate chains. The primary structure of annexin V deduced from the cDNA sequence shows that annexin V comprises four internal repeating units (U.S. Pat. No. 4,937,324; incorporated herein by reference). U.S. Pat. No. 5,296,467 and WO 91/07187 are also each incorporated herein by reference as they provide pharmaceutical compositions comprising 'annexine' (annexin).

WO 91/07187 provides natural, synthetic or genetically prepared derivatives and analogues of 'annexine' (annexin). Particular annexins are provided of 320 amino acids, containing variant amino acids and, optionally, a disulphide bridge between the 316-Cys and the 2-Ala.

U.S. Pat. No. 5,296,467 is incorporated herein by reference in its entirety, including all figures and sequences, for purposes of even further describing annexins and pharmaceutical compositions thereof. U.S. Pat. No. 5,296,467 describes annexin cloning, recombinant expression and preparation. Aggregates of two or more annexines, e.g., linked by disulfide bonds between one or more cysteine groups on the respective annexine, are also disclosed. Yet a further example of suitable annexin starting materials is provided by WO 95/27903 (incorporated herein by reference), which provides annexins for use in detecting apoptotic cells.

U.S. Pat. No. 6,197,278 is specifically incorporated herein by reference for purposes including further enabling and providing written description support for annexins in a generic sense, their safe and effective administration in vivo and imaging embodiments. To the extent that they clearly describe appropriate annexin starting materials for preparing constructs of the present invention, each of the diagnostic approaches of U.S. Pat. No. 5,627,036; WO 95/19791; WO 95/27903; WO 95/34315; WO 96/17618; and WO 98/04294; are also specifically incorporated herein by reference. Various of these documents also concern useful recombinant expression vectors.

U.S. Pat. No. 5,632,986 is also provided for purposes of further describing annexin isolation from tissue extracts (U.S. Pat. No. 4,937,324; also incorporated herein by reference) and annexin production by recombinant methods. Each of the cDNA clones and expression vectors of U.S. Pat. No. 5,632,986 are thus specifically incorporated herein by reference.

U.S. Pat. No. 5,632,986 is also specifically incorporated herein by reference for purposes of further describing mutants and variants of the annexin molecule that are subdivided or altered at one or more amino acid residues so long as the phospholipid binding capability is not reduced substantially. Appropriate annexins for use can thus be truncated, for example, to include one or more domains or contain fewer amino acid residues than the native protein, or can contain substituted amino acids. Any changes are acceptable so long as the mutein or second generation annexin molecule does not contain substantially lower affinity for aminophospholipid. The same reasoning applies to proteins other than annexin.

The chemical cross-linking of annexins and other agents is also described in U.S. Pat. No. 5,632,986, incorporated herein by reference. All such techniques can be adapted for use herewith simply by substituting the thrombolytic agents for the Fc regions described herein. Aliphatic diamines; succinimide esters; hetero-bifunctional coupling reagents, such as SPDP; maleimide compounds; linkers with spacers; and the like, may thus be used. These agents may also be used with proteins other than annexins.

U.S. Pat. No. 5,632,986 is yet further specifically incorporated herein by reference for purposes of describing the recombinant production of annexin-containing conjugates. Appropriate nucleic acid sequences are thus joined to produce chimeric coding sequences that, in turn, produce chimeric proteins. Exemplary expression vectors are said to be pKK233-2 (*E. coli*), DPOT (yeast) and pDSP1.1BGH (mammalian). Such teaching is supplemented by further information provided herein.

U.S. Pat. Nos. 6,312,694, 6,783,760 and 6,818,213 are each specifically incorporated herein by reference for purposes including further enabling and providing written description support for phosphatidylserine binding proteins in a generic sense, and their safe and effective administration in vivo. These patents disclose binding ligand compositions in which a therapeutic agent is operatively attached to a targeting agent that binds to phosphatidylserine, preferably phosphatidylserine exposed on the luminal surface of blood vessels of a vascularized tumor, and cancer treatment methods using such binding ligands and combinations thereof. Although these patents do not teach or suggest phosphatidylserine binding proteins linked to an Fc region, their disclosures concerning phosphatidylserine binding proteins, attached therapeutic agents and safe and effective in vivo treatment methods are specifically incorporated herein by reference.

U.S. Pat. Nos. 6,312,694, 6,783,760 and 6,818,213 particularly concern binding ligands in which a therapeutic agent is operatively attached to at least a first phosphatidylserine binding protein. Although the proteins in these patents are linked to therapeutic agents and are used to deliver the therapeutic agents to the tumor vasculature without an Fc region, and hence do not eleicit host cell effector functions, these patents are specifically incorporated herein by reference for purposes including further enabling and describing protein conjugates and their safe and effective administration in vivo, including to treat cancer. Using the information in these patents and the teaching in the present disclosure, a range of receptorbodies can thus be prepared in which a phosphatidylserine binding protein, or a phosphatidylserine-binding fragment thereof, is now linked to an Fc region or domain.

β2-glycoprotein I (β2GP1) is the currently preferred phosphatidylserine binding protein for use in the receptorbodies of the invention. β2GP1, also known as apoplipoprotein H, is a 50 kDa plasma glycoprotein that binds negatively charged phospholipids through its C terminal (Wurm, 1984, specifically incorporated herein by reference). The following accession numbers are provided for human B2GPI (NP 000033, AAP72014 and 1C1ZA) and for mouse B2GPI (AAH53338, NP 038503, CAA69401, BAB2721). In vitro and in vivo evidence indicates that β2GPI plays a role in the clearance of PS-expressing apoptotic cells (Chonn et al., 1995; Balasubramanian et al., 1997; Balasubramanian and Schroit, 1998). β2GP1 interactions with phagocytes are electrostatic in nature and protein glycosylation is not critical for phagocyte recognition. Accordingly, there are no significant obstacles to recombinant production of β2GP 1 for use in receptorbodies.

When using a β2GPI protein, polypeptide or peptide in the invention, the resulting Fc-β2GPI construct is termed a "betabody". Betabodies will preferably include a lipid binding region from domain V of β2GPI, as shown herein in FIG. 18A and FIG. 18B. Constructs containing all of domain V may be preferred to ensure lipid binding. Domain V may be used alone, or with one or more of the other four domains. Although using the full length β2GPI protein will be convenient, betabodies that do not contain domain I of β2GPI may be preferred in certain aspects, as antibodies from patients with APS commonly recognize domain I of β2GPI (de Laat et al., 2005a).

Other preferred betabodies are those in which two β2GPI polypeptides are dimerized onto an Fc region. Such betabodies are shown herein to be effective in binding to phosphatidylserine on plates and exposed on cell surfaces. However, other means of preparing dimerized and multimerized betabodies are provided, such as nanoparticles, liposomes and other molecular scaffolds.

D2. Fc Regions

The Fc region will be attached, linked or conjugated to the phosphatidylserine binding protein or polypeptide, receptor, ligand or peptide so that the desired activity of the resultant receptorbody is not substantially destroyed by attaching the Fc region. Any of the conjugation or linker technologies known in the art may be employed, such as, e.g., those described in the relevant section herein. If desired, fusion proteins can be created using molecular biological techniques, which are now standard practice to those of ordinary skill in the art, as again exemplified herein. Thus, the receptorbody can be made as a chemical conjugate or as a fusion protein.

Within the heavy chains of an immunoglobulin, the amino terminal domains are the variable domains ($V_H$). The variable domains of the heavy and light chains function together in antigen binding. In the heavy chains, the variable domains are followed by three constant domains: $C_H1$, $C_H2$, and the carboxy terminal $C_H3$. In certain antibodies, a fourth constant domain, $C_H4$, is present. A short stretch, the switch, connects the heavy chain variable and constant regions. The hinge connects $C_H2$ and $C_H3$ (the Fc fragment) to the remainder of the antibody (the Fab fragments).

The nature of the constant region determines various mechanisms of action other than antigen binding. Antibodies are divided into five major classes, IgM, IgG, IgA, IgD and IgE, based on their constant region structure and immune function. The heavy-chain constant domains that correspond to the difference classes of immunoglobulins are termed μ, γ, α, δ and ϵ, and respectively.

In light of the effector functions provided by the Fc regions (Bruggemann et al., 1987; Riechmann et al., 1988; Clark, 1997; Padlan, 1994; each specifically incorporated herein by reference), currently preferred Fc regions are human IgG1 (γ1) and human IgG3 (γ3) for clinical use, and mouse IgG2a (γ2a) and mouse IgG2b (γ2b) for pre-clinical testing in mice. γ2 is believed to be silent and thus would not be chosen to provide effector functions, although it is still a useful human protein for use as a dimerization domain. Although chosen for effector functions, the Fc piece of immunoglobulins also contributes to prolonged half-life, which can result from the active readsorption of antibodies within the kidney.

Although recombinant expression of Fc regions and binding constructs is convenient, such fragments can also be obtained by proteolysis of the whole immunoglobulin, preferably by the non-specific thiol protease, papain. Papain digestion yields two identical antigen-binding fragments, termed "Fab fragments", each with a single antigen-binding site, and the residual "Fc fragment".

Papain should first be activated by reducing the sulphydryl group in the active site with cysteine, 2-mercaptoethanol or dithiothreitol. Heavy metals in the stock enzyme should be removed by chelation with EDTA (2 mM) to ensure maximum enzyme activity. Enzyme and substrate are normally mixed together in the ratio of 1:100 by weight. After incubation, the reaction can be stopped by irreversible alkylation of the thiol group with iodoacetamide or simply by dialysis. The completeness of the digestion should be monitored by SDS-PAGE and the various fractions separated by protein A-Sepharose or ion exchange chromatography.

In certain embodiments, two Fc fragments may be used, preferably two human Fc fragments. In such aspects, two binding proteins, receptors or ligands can be combined with the two Fc fragments to prepare another type of divalent receptorbody. Human Fc fragments will be preferred to make receptorbodies for human administration. Indeed, this is an advantage of the invention, as a totally human therapeutic construct results. Thus, Fc-β2GPI constructs include completely human betabody therapeutics.

D3. Other Constructs and Carriers

Although linking an Fc region to a phosphatidylserine binding protein or polypeptide is the preferred embodiment of the receptorbody invention, phosphatidylserine binding proteins may also be linked to inert carriers to impart longevity to the biologically active molecules. As such, the present invention further provides constructs comprising at least a first aminophospholipid binding protein, including β2GPI, operatively attached to at least a first inert carrier.

As known in the art, carrier proteins can be used to increase biological half life, and exemplary proteins are albumins and globulins, such as neutravidin and streptavidin. Non-protein carriers can also be used to increase biological half life, such as natural or synthetic polymers, including polysaccharides and PEG. Any such inert carrier may be attached to any of the phosphatidylserine binding proteins described herein.

Other aspects of the present invention concern compositions of β2GPI dimers prepared by means other than using an Fc region, and various methods of use. The invention particularly provides methods of treating cancer and methods of treating viral infections, comprising administering to an animal in need thereof a therapeutically effective amount of a β2GPI dimer.

Still further aspects of the invention are liposomes comprising β2GPI polypeptides, whether or not in dimeric form, and including β2GPI polypeptides other than those attached to an Fc region. As such, the invention concerns a nanoparticle, liposome, lipid carrier, complex, mixture, supramolecular structure multimolecular aggregate or lipid-based drug delivery system comprising at least a first β2GPI polypeptide.

The β2GPI polypeptide may be a dimer, but it need not be. The β2GPI polypeptide may, or may not, be attached to an additional therapeutic agent. Such liposomes will preferably be stealthed liposomes, and may contain a therapeutic agent in the liposome core.

Yet further aspects of the present invention concern compositions of β2GPI polypeptides (other than β2GPI polypeptides attached to an Fc region) where the β2GPI polypeptide is operatively attached to at least a first therapeutic agent, and various methods of use. Particularly preferred are compositions wherein a β2GPI polypeptide is operatively attached to at least a first cytokine, such as TNFα, IL-2 or IFNα. In certain embodiments, the β2GPI polypeptide will be a dimer and dimeric β2GPI polypeptide will be operatively attached to at least a first therapeutic agent, such as a cytokine. Any such β2GPI-cytokine constructs or conjugates are particularly contemplated for use in treating diseases, including viral infections.

The invention thus further provides methods of treating cancer and methods of treating viral infections, comprising administering to an animal in need thereof a therapeutically effective amount of a construct comprising a β2GPI polypeptide operatively attached to at least a first cytokine, preferably to TNFα, IL-2 or IFNα. The β2GPI polypeptide may be a dimeric β2GPI polypeptide.

E. Conjugates of Additional Agents

The constructs and receptorbodies of the invention may also be used to deliver attached therapeutic agents to specific targets, such as tumor and intratumoral vasculature, tumor cells, virally infected cells and viral particles. Although not concerning constructs with Fc regions, U.S. Pat. Nos. 6,312,694, 6,783,760 and 6,818,213 are each specifically incorporated herein by reference for their general teaching regarding aminophospholipid-binding proteins attached to therapeutic agents. As the constructs and receptorbodies of the present invention may also be used in safe and effective anti-viral therapy, these constructs may also be advantageously linked to a range of known anti-viral agents.

In these aspects of the invention, any construct, receptorbody or betabody of the invention can be used to prepare a conjugate. Agents for use in such conjugates preferably include an anticellular or cytotoxic agent, cytokine, chemokine, V-type ATPase inhibitor, protein synthesis inhibitor, chemotherapeutic agent, anti-angiogenic agent, apoptosis-inducing agent, anti-tubulin drug, radioisotope, coagulant or anti-viral agent. In the anti-viral conjugates, there is no requirement to use a second anti-viral agent as the attached agent.

E1. Anti-Cellular and Cytotoxic Agents

For certain applications, the therapeutic agents will be cytotoxic or pharmacological agents, particularly cytotoxic, cytostatic or otherwise anti-cellular agents having the ability to kill or suppress the growth or cell division of cells, particularly tumor endothelial cells, tumor cells or virally infected cells.

Exemplary anti-cellular agents include chemotherapeutic agents, as well as cytotoxins. Chemotherapeutic agents that may be used include: hormones, such as steroids; antimetabolites, such as cytosine arabinoside, fluorouracil, methotrexate or aminopterin; anthracyclines; mitomycin C; vinca alkaloids; demecolcine; etoposide; mithramycin; anti-tumor alkylating agents, such as chlorambucil or melphalan. Other embodiments may include agents such as cytokines. Basically, any anti-cellular agent may be used, so long as it can be successfully conjugated to a construct in a manner that will allow its targeting, internalization, release and/or presentation to blood components at the site of the targeted cells, such as endothelial cells.

There may be circumstances, such as when the target antigen does not internalize by a route consistent with efficient intoxication by the toxic compound, where one will desire to target chemotherapeutic agents, such as anti-tumor drugs, cytokines, antimetabolites, alkylating agents, hormones, and the like. A variety of chemotherapeutic and other pharmacological agents have now been successfully conjugated and shown to function pharmacologically, including doxorubicin, daunomycin, methotrexate, vinblastine, neocarzinostatin, macromycin, trenimon and α-amanitin.

In other circumstances, any potential side-effects from cytotoxin-based therapy may be eliminated by the use of DNA synthesis inhibitors, such as daunorubicin, doxorubicin, adriamycin, and the like. These agents are therefore preferred examples of anti-cellular agents for use in certain aspects of the present invention. In terms of cytostatic agents, such compounds generally disturb the natural cell cycle of a target cell, preferably so that the cell is taken out of the cell cycle.

A wide variety of cytotoxic agents are known that may be conjugated. Examples include numerous useful plant-, fungus- or bacteria-derived toxins, which, by way of example, include various A chain toxins, particularly ricin A chain; ribosome inactivating proteins, such as saporin or gelonin; α-sarcin; aspergillin; restrictocin; ribonucleases, such as placental ribonuclease; diphtheria toxin; and *pseudomonas* exotoxin, to name just a few.

The well-known 1992 toxin book, "Genetically Engineered Toxins", edited by Arthur E. Frankel, including the appendix, which includes the primary amino acid sequences of a large number of toxins, is specifically incorporated herein by reference, for purposes of further describing and enabling the use of toxins in targeted constructs.

Of the toxins, the use of gelonin and ricin A chains are preferred. The use of gelonin as the effector or toxin portion of immunoconjugates that bind to markers expressed, accessible to binding, adsorbed or localized on intratumoral blood vessels of a vascularized tumor is described in U.S. Pat. No. 6,051,230, specifically incorporated herein by reference, and in U.S. Pat. No. 6,451,312, which particularly concerns gelonin linked to VEGF as a targeting agent.

As to ricin A chains, a further preferred toxin moiety is toxin A chain that has been treated to modify or remove carbohydrate residues, so-called deglycosylated A chain (dgA). Deglycosylated ricin A chain is preferred because of its extreme potency, longer half-life, and because it is economically feasible to manufacture it in a clinical grade and scale.

It may be desirable from a pharmacological standpoint to employ the smallest molecule possible that nevertheless provides an appropriate biological response. One may thus desire to employ smaller A chain peptides that will provide an adequate anti-cellular response. To this end, it has been discovered that ricin A chain may be "truncated" by the removal of 30 N-terminal amino acids by Nagarase (Sigma), and still retain an adequate toxin activity. It is proposed that where desired, this truncated A chain may be employed in conjugates in accordance with the invention.

Alternatively, one may find that the application of recombinant DNA technology to the toxin A chain moiety will provide additional benefits in accordance the invention. In that the cloning and expression of biologically active ricin A chain has been achieved, it is now possible to identify and prepare smaller, or otherwise variant peptides, which nevertheless exhibit an appropriate toxin activity. Moreover, the fact that ricin A chain has now been cloned allows the application of site-directed mutagenesis, through which one can readily prepare and screen for A chain-derived peptides and obtain additional useful moieties for use in connection with the present invention.

E2. Cytokines

Cytokines and chemokines are particular examples of agents for linking to a construct, receptorbody or betabody of the present invention. A range of cytokines may be used, including IL-3, IL-4, IL-5, IL-7, IL-8, IL-9, IL-11, IL-13, TGF-β, M-CSF, G-CSF, TNFβ, LAF, TCGF, BCGF, TRF, BAF, BDG, MP, LIF, OSM, TMF, IFN-α, IFN-β. More preferred cytokines include IL-1α, IL-1β, IL-2, IL-6, IL-10, GM-CSF, IFN-γ, monocyte chemoattractant protein-1 (MCP-1), platelet-derived growth factor-BB (PDGF-BB) and C-reactive protein (CRP) and the like. Particularly preferred examples are TNFα, TNFα inducers, IL-2, IL-12, IFN-α, IFN-β, IFN-γ and LEC.

TNFα increases vascular permeability. This agent is contemplated for attachment to a construct, receptorbody or betabody of the invention, particularly where the resultant conjugate is used in combination therapy for the treatment of cancer. The construct will deliver the attached TNFα to the tumor environment, and the enhanced vascular permeability cause in the tumor will facilitate the penetration of a second anti-cancer agent into the tumor, thus amplifying the overall anti-tumor effect.

IL-12, for example, may be attached to a construct, receptorbody or betabody and used to redirect host defenses to attack the tumor vessels. The chemokine LEC (liver-expressed chemokine, also known as NCC-4, HCC-4, or LMC) is another preferred component (Giovarelli et al., 2000). LEC is chemotactic for dendritic cells, monocytes, T cells, NK cells and neutrophils and can therefore improve host-mediated anti-tumor responses.

E3. Coagulation Factors

A construct, receptorbody or betabody of the invention may be linked to a component that is capable of directly or indirectly stimulating coagulation, to form a coaguligand. U.S. Pat. Nos. 6,093,399, 6,004,555, 5,877,289 and 6,036,955 are specifically incorporated herein by reference for purposes of further describing the operative attachment of coagulants to form coaguligands.

A construct, receptorbody or betabody of the invention may be directly linked to the coagulant or coagulation factor, or may be linked to a second binding region that binds and then releases the coagulant or coagulation factor. As used herein, the terms "coagulant" and "coagulation factor" are each used to refer to a component that is capable of directly or indirectly stimulating coagulation under appropriate conditions, preferably when provided to a specific in vivo environment, such as the tumor vasculature.

Preferred coagulation factors are Tissue Factor compositions, such as truncated TF (tTF), dimeric, multimeric and mutant TF molecules. "Truncated TF" (tTF) refers to TF constructs that are rendered membrane-binding deficient by removal of sufficient amino acid sequences to effect this change in property. A "sufficient amount" in this context is an amount of transmembrane amino acid sequence originally sufficient to enter the TF molecule in the membrane, or otherwise mediate functional membrane binding of the TF protein. The removal of such a "sufficient amount of transmembrane spanning sequence" therefore creates a truncated Tissue Factor protein or polypeptide deficient in phospholipid membrane binding capacity, such that the protein is substantially a soluble protein that does not significantly bind to phospholipid membranes. Truncated TF thus substantially fails to convert Factor VII to Factor VIa in a standard TF assay, and yet retains so-called catalytic activity including activating Factor X in the presence of Factor VIIa.

U.S. Pat. Nos. 5,504,067, 6,156,321, 6,132,729 and 6,132,730 are specifically incorporated herein by reference for the purposes of further describing such truncated Tissue Factor proteins. Preferably, the Tissue Factors for use in these aspects of the present invention will generally lack the transmembrane and cytosolic regions (amino acids 220-263) of the protein. However, there is no need for the truncated TF molecules to be limited to molecules of the exact length of 219 amino acids.

Tissue Factor compositions may also be useful as dimers. Any of the truncated, mutated or other Tissue Factor constructs may be prepared in a dimeric form for use in the present invention. As will be known to those of ordinary skill in the art, such TF dimers may be prepared by employing the standard techniques of molecular biology and recombinant expression, in which two coding regions are prepared in-frame and expressed from an expression vector. Equally, various chemical conjugation technologies may be employed in connection with the preparation of TF dimers. The individual TF monomers may be derivatized prior to conjugation. All such techniques would be readily known to those of skill in the art.

If desired, the Tissue Factor dimers or multimers may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metalloproteinase, such as collagenase, gelatinase or stromelysin.

In certain embodiments, the Tissue Factor dimers may further comprise a hindered hydrophobic membrane insertion moiety, to later encourage the functional association of the Tissue Factor with the phospholipid membrane, but only under certain defined conditions. As described in the context of the truncated Tissue Factors, hydrophobic membrane-association sequences are generally stretches of amino acids that promote association with the phospholipid environment due to their hydrophobic nature. Equally, fatty acids may be used to provide the potential membrane insertion moiety.

Such membrane insertion sequences may be located either at the N-terminus or the C-terminus of the TF molecule, or generally appended at any other point of the molecule so long as their attachment thereto does not hinder the functional properties of the TF construct. The intent of the hindered insertion moiety is that it remains non-functional until the TF construct localizes within the tumor environment, and allows the hydrophobic appendage to become accessible and even further promote physical association with the membrane. Again, it is contemplated that biologically-releasable bonds and selectively-cleavable sequences will be particularly useful in this regard, with the bond or sequence only being cleaved or otherwise modified upon localization within the tumor environment and exposure to particular enzymes or other bioactive molecules.

In other embodiments, the tTF constructs may be multimeric or polymeric. In this context a "polymeric construct" contains 3 or more Tissue Factor constructs. A "multimeric or polymeric TF construct" is a construct that comprises a first TF molecule or derivative operatively attached to at least a second and a third TF molecule or derivative. The multimers may comprise between about 3 and about 20 such TF molecules. The individual TF units within the multimers or polymers may also be linked by selectively-cleavable peptide linkers or other biological-releasable bonds as desired. Again, as with the TF dimers discussed above, the constructs may be readily made using either recombinant manipulation and expression or using standard synthetic chemistry.

Even further TF constructs useful in context of the present invention are those mutants deficient in the ability to activate Factor VII. Such "Factor VII activation mutants" are generally defined herein as TF mutants that bind functional Factor VII/VIIa, proteolytically activate Factor X, but are substantially free from the ability to proteolytically activate Factor VII. Accordingly, such constructs are TF mutants that lack Factor VII activation activity.

The ability of such Factor VII activation mutants to function in promoting tumor-specific coagulation is based upon their specific delivery to the tumor vasculature, and the presence of Factor VIIa at low levels in plasma. Upon administration of such a Factor VII activation mutant conjugate, the mutant will be localized within the vasculature of a vascularized tumor. Prior to localization, the TF mutant would be generally unable to promote coagulation in any other body sites, on the basis of its inability to convert Factor VII to Factor VIIa. However, upon localization and accumulation within the tumor region, the mutant will then encounter sufficient Factor VIIa from the plasma in order to initiate the extrinsic coagulation pathway, leading to tumor-specific thrombosis. Exogenous Factor VIIa could also be administered to the patient.

Any one or more of a variety of Factor VII activation mutants may be prepared and used in connection with the present invention. There is a significant amount of scientific knowledge concerning the recognition sites on the TF molecule for Factor VII/VIIa. It will thus be understood that the Factor VII activation region generally lies between about amino acid 157 and about amino acid 167 of the TF molecule. However, it is contemplated that residues outside this region may also prove to be relevant to the Factor VII activating activity, and one may therefore consider introducing mutations into any one or more of the residues generally located between about amino acid 106 and about amino acid 209 of the TF sequence (WO 94/07515; WO 94/28017; each incorporated herein by reference).

As detailed in U.S. Pat. Nos. 6,093,399, 6,004,555, 5,877,289 and 6,036,955, a variety of other coagulation factors may be used in connection with the present invention, as exemplified by the agents set forth below. Thrombin, Factor V/Va and derivatives, Factor VIII/VIIIa and derivatives, Factor IX/IXa and derivatives, Factor X/Xa and derivatives, Factor XI/XIa and derivatives, Factor XII/XIIa and derivatives, Factor XIII/XIIIa and derivatives, Factor X activator and Factor V activator may be used in the present invention.

Russell's viper venom Factor X activator is contemplated for use in this invention. Monoclonal antibodies specific for the Factor X activator present in Russell's viper venom have also been produced, and could be used to specifically deliver the agent as part of a bispecific binding ligand.

Thromboxane $A_2$ is formed from endoperoxides by the sequential actions of the enzymes cyclooxygenase and thromboxane synthetase in platelet microsomes. Thromboxane $A_2$ is readily generated by platelets and is a potent vasoconstrictor, by virtue of its capacity to produce platelet aggregation. Both thromboxane $A_2$ and active analogues thereof are contemplated for use in the present invention.

Thromboxane synthase, and other enzymes that synthesize platelet-activating prostaglandins, may also be used as "coagulants" in the present context. Monoclonal antibodies to, and immunoaffinity purification of, thromboxane synthase are known; as is the cDNA for human thromboxane synthase.

$\alpha$2-antiplasmin, or $\alpha$2-plasmin inhibitor, is a proteinase inhibitor naturally present in human plasma that functions to efficiently inhibit the lysis of fibrin clots induced by plasminogen activator. $\alpha$2-antiplasmin is a particularly potent inhibitor, and is contemplated for use in the present invention.

As the cDNA sequence for $\alpha$2-antiplasmin is available, recombinant expression and/or fusion proteins are preferred. Monoclonal antibodies against $\alpha$2-antiplasmin are also available that may be used in the bispecific binding ligand embodiments of the invention. These antibodies could both be used to deliver exogenous $\alpha$2-antiplasmin to the target site or to garner endogenous $\alpha$2-antiplasmin and concentrate it within the targeted region.

E4. Anti-Tubulin Drugs

A range of drugs exert their effects via interfering with tubulin activity. As tubulin functions are essential to mitosis and cell viability, certain "anti-tubulin drugs" are powerful chemotherapeutic agents. "Anti-tubulin drug(s)", as used herein, means any agent, drug, prodrug or combination thereof that inhibits cell mitosis, preferably by directly or indirectly inhibiting tubulin activities necessary for cell mitosis, preferably tubulin polymerization or depolymerization.

Some of the more well known and currently preferred anti-tubulin drugs for use with the present invention are colchicine; taxanes, such as taxol; vinca alkaloids, such as vinblastine, vincristine and vindescine; and combretastatins. Other suitable anti-tubulin drugs are cytochalasins (including B, J, E), dolastatin, auristatin PE, paclitaxel, ustiloxin D, rhizoxin, 1069C85, colcemid, albendazole, azatoxin and nocodazole.

As described in U.S. Pat. Nos. 5,892,069, 5,504,074 and 5,661,143, each specifically incorporated herein by reference, combretastatins are estradiol derivatives that generally inhibit cell mitosis. Exemplary combretastatins that may be used in conjunction with the invention include those based upon combretastatin A, B and/or D and those described in U.S. Pat. No. 5,892,069, 5,504,074 and 5,661,143. Combretastatins A-1, A-2, A-3, A-4, A-5, A-6, B-1, B-2, B-3 and B-4 are exemplary of the foregoing types.

U.S. Pat. Nos. 5,569,786 and 5,409,953, are incorporated herein by reference for purposes of describing the isolation, structural characterization and synthesis of each of combretastatin A-1, A2, A-3, B-1, B-2, B-3 and B-4 and formulations and methods of using such combretastatins to treat neoplastic growth. Any one or more of such combretastatins may be used in conjunction with the present invention.

Combretastatin A-4, as described in U.S. Pat. Nos. 5,892,069, 5,504,074, 5,661,143 and 4,996,237, each specifically incorporated herein by reference, may also be used herewith. U.S. Pat. No. 5,561,122 is further incorporated herein by reference for describing suitable combretastatin A-4 prodrugs, which are contemplated for combined use with the present invention.

U.S. Pat. No. 4,940,726, specifically incorporated herein by reference, particularly describes macrocyclic lactones denominated combretastatin D-1 and 'Combretastatin D-2', each of which may be used in combination with the compositions and methods of the present invention. U.S. Pat. No. 5,430,062, specifically incorporated herein by reference, concerns stilbene derivatives and combretastatin analogues with anti-cancer activity that may be used in combination with the present invention.

E5. Anti-Angiogenic Agents

Anti-angiogenic agents are useful for attachment to a construct, receptorbody or betabody of the invention. Many anticancer agents have an anti-angiogenic effect as part of their mechanism of action. Any one or more of such agents described for use in combination therapies, including those in Table E, may also be conjugated to a construct, receptorbody or betabody of the invention, as described herein. Certain other agents have been discovered, designed or selected to have an anti-angiogenic effect as a primary mechanism of action. Examples of such agents are described below, any of which may also be used to prepare a conjugate or used separately in combination therapy with the invention.

Numerous tyrosine kinase inhibitors useful for the treatment of angiogenesis, as manifest in various diseases states, are now known. These include, for example, the 4-aminopyrrolo[2,3-d]pyrimidines of U.S. Pat. No. 5,639,757, specifically incorporated herein by reference, which may also be used in combination with the present invention. Further examples of organic molecules capable of modulating tyrosine kinase signal transduction via the VEGFR2 receptor are the quinazoline compounds and compositions of U.S. Pat. No. 5,792,771, which is specifically incorporated herein by reference for the purpose of describing further combinations for use with the present invention in the treatment of angiogenic diseases.

Compounds of other chemical classes have also been shown to inhibit angiogenesis and may be used in combination with the present invention. For example, steroids such as the angiostatic 4,9(11)-steroids and C21-oxygenated steroids, as described in U.S. Pat. No. 5,972,922, specifically incorporated herein by reference, may be employed in combined therapy. U.S. Pat. Nos. 5,712,291 and 5,593,990, each specifically incorporated herein by reference, describe thalidomide and related compounds, precursors, analogs, metabolites and hydrolysis products, which may also be used in combination with the present invention to inhibit angiogenesis. The compounds in U.S. Pat. Nos. 5,712,291 and 5,593,990 can be administered orally. Further exemplary anti-angiogenic agents that are useful in connection with combined therapy are listed in Table B. Each of the agents listed therein are exemplary and by no means limiting.

TABLE B

Inhibitors and Negative Regulators of Angiogenesis

| Substances | References |
|---|---|
| Angiostatin | O'Reilly et al., 1994 |
| Endostatin | O'Reilly et al., 1997 |
| 16 kDa prolactin fragment | Ferrara et al., 1991; Clapp et al., 1993; D'Angelo et al., 1995; Lee et al., 1998 |
| Laminin peptides | Kleinman et al., 1993; Yamamura et al., 1993; Iwamoto et al., 1996; Tryggvason, 1993 |
| Fibronectin peptides | Grant et al., 1998; Sheu et al., 1997 |
| Tissue metalloproteinase inhibitors (TIMP 1, 2, 3, 4) | Sang, 1998 |
| Plasminogen activator inhibitors (PAI-1, -2) | Soff et al., 1995 |
| Tumor necrosis factor α (high dose, in vitro) | Frater-Schroder et al., 1987 |
| TGF-β1 | RayChadhury and D'Amore, 1991; Tada et al., 1994 |
| Interferons (IFN-α, -β, γ) | Moore et al., 1998; Lingen et al., 1998 |
| ELR-CXC Chemokines: IL-12; SDF-1; MIG; Platelet factor 4 (PF-4); IP-10 | Moore et al., 1998; Hiscox and Jiang, 1997; Coughlin et al., 1998; Tanaka et al., 1997 |
| Thrombospondin (TSP) | Good et al., 1990; Frazier, 1991; Bornstein, 1992; Tolsma et al., 1993; Sheibani and Frazier, 1995; Volpert et al., 1998 |
| SPARC | Hasselaar and Sage, 1992; Lane et al., 1992; Jendraschak and Sage, 1996 |
| 2-Methoxyoestradiol | Fotsis et al., 1994 |
| Proliferin-related protein | Jackson et al., 1994 |
| Suramin | Gagliardi et al., 1992; Takano et al., 1994; Waltenberger et al., 1996; Gagliardi et al., 1998; Manetti et al., 1998 |
| Thalidomide | D'Amato et al., 1994; Kenyon et al., 1997 Wells, 1998 |
| Cortisone | Thorpe et al., 1993 Folkman et al., 1983 Sakamoto et al., 1986 |
| Linomide | Vukanovic et al., 1993; Ziche et al., 1998; Nagler et al., 1998 |
| Fumagillin (AGM-1470; TNP-470) | Sipos et al., 1994; Yoshida et al., 1998 |
| Tamoxifen | Gagliardi and Collins, 1993; Linder and Borden, 1997; Haran et al., 1994 |
| Korean mistletoe extract (*Viscum album coloratum*) | Yoon et al., 1995 |
| Retinoids | Oikawa et al., 1989; Lingen et al., 1996; Majewski et al. 1996 |
| CM101 | Hellerqvist et al., 1993; Quinn et al., 1995; Wamil et al., 1997; DeVore et al., 1997 |
| Dexamethasone | Hori et al., 1996; Wolff et al., 1997 |
| Leukemia inhibitory factor (LIF) | Pepper et al., 1995 |

Certain preferred components for use in inhibiting angiogenesis are angiostatin, endostatin, vasculostatin, canstatin and maspin. The protein named "angiostatin" is disclosed in U.S. Pat. Nos. 5,776,704; 5,639,725 and 5,733,876, each incorporated herein by reference. Angiostatin is a protein having a molecular weight of between about 38 kD and about 45 kD, as determined by reducing polyacrylamide gel electrophoresis, which contains approximately Kringle regions 1 through 4 of a plasminogen molecule. Angiostatin generally has an amino acid sequence substantially similar to that of a fragment of murine plasminogen beginning at amino acid number 98 of an intact murine plasminogen molecule.

The amino acid sequence of angiostatin varies slightly between species. For example, in human angiostatin, the amino acid sequence is substantially similar to the sequence of the above described murine plasminogen fragment, although an active human angiostatin sequence may start at either amino acid number 97 or 99 of an intact human plasminogen amino acid sequence. Further, human plasminogen may be used, as it has similar anti-angiogenic activity, as shown in a mouse tumor model.

Certain anti-angiogenic therapies have already been shown to cause tumor regressions, and angiostatin is one such agent. Endostatin, a 20 kDa COOH-terminal fragment of collagen XVIII, the bacterial polysaccharide CM101, and the antibody LM609 also have angiostatic activity. However, in light of their other properties, they are referred to as anti-vascular therapies or tumor vessel toxins, as they not only inhibit angiogenesis but also initiate the destruction of tumor vessels through mostly undefined mechanisms.

Angiostatin and endostatin have become the focus of intense study, as they are the first angiogenesis inhibitors that have demonstrated the ability to not only inhibit tumor growth but also cause tumor regressions in mice. There are multiple proteases that have been shown to produce angiostatin from plasminogen including elastase, macrophage metalloelastase (MME), matrilysin (MMP-7), and 92 kDa gelatinase B/type IV collagenase (MMP-9).

MME can produce angiostatin from plasminogen in tumors and granulocyte-macrophage colony-stimulating factor (GMCSF) upregulates the expression of MME by macrophages inducing the production of angiostatin. The role of MME in angiostatin generation is supported by the finding that MME is in fact expressed in clinical samples of hepatocellular carcinomas from patients. Another protease thought to be capable of producing angiostatin is stromelysin-1 (MMP-3). MMP-3 has been shown to produce angiostatin-like fragments from plasminogen in vitro. The mechanism of action for angiostatin is currently unclear, it is hypothesized that it binds to an unidentified cell surface receptor on endothelial cells inducing endothelial cell to undergo programmed cell death or mitotic arrest.

Endostatin appears to be an even more powerful anti-angiogenesis and anti-tumor agent although its biology is less clear. Endostatin is effective at causing regressions in a number of tumor models in mice. Tumors do not develop resistance to endostatin and, after multiple cycles of treatment, tumors enter a dormant state during which they do not increase in volume. In this dormant state, the percentage of tumor cells undergoing apoptosis was increased, yielding a population that essentially stays the same size. Endostatin is thought to bind an unidentified endothelial cell surface receptor that mediates its effect.

U.S. Pat. No. 5,854,205, to Folkman and O'Reilly, specifically incorporated herein by reference, concerns endostatin and its use as an inhibitor of endothelial cell proliferation and angiogenesis. The endostatin protein corresponds to a C-terminal fragment of collagen type XVIII, and the protein can be isolated from a variety of sources. U.S. Pat. No. 5,854,205 also teaches that endostatin can have an amino acid sequence of a fragment of collagen type XVIII, a collasen type XV, or BOVMPE 1 pregastric esterase. Combinations of endostatin with other anti-angiogenic proteins, particularly angiostatin, are also described by U.S. Pat. No. 5,854,205, such that the combined compositions are capable of effectively regressing the mass of an angiogenesis-dependent tumor.

CM101 is a bacterial polysaccharide that has been well characterized in its ability to induce neovascular inflammation in tumors. CM101 binds to and cross-links receptors expressed on dedifferentiated endothelium that stimulates the activation of the complement system. It also initiates a cytokine-driven inflammatory response that selectively targets the tumor. It is a uniquely antipathoangiogenic agent that down-regulates the expression VEGF and its receptors. CM101 is currently in clinical trials as an anti-cancer drug, and can be used in combination with this invention.

Thrombospondin (TSP-1) and platelet factor 4 (PF4) may also be used in the present invention. These are both angiogenesis inhibitors that associate with heparin and are found in platelet α-granules. TSP-1 is a large 450 kDa multi-domain glycoprotein that is constituent of the extracellular matrix. TSP-1 binds to many of the proteoglycan molecules found in the extracellular matrix including, HSPGs, fibronectin, laminin, and different types of collagen. TSP-1 inhibits endothelial cell migration and proliferation in vitro and angiogenesis in vivo. TSP-1 can also suppress the malignant phenotype and tumorigenesis of transformed endothelial cells. The tumor suppressor gene p53 has been shown to directly regulate the expression of TSP-1 such that, loss of p53 activity causes a dramatic reduction in TSP-1 production and a concomitant increase in tumor initiated angiogenesis.

PF4 is a 70aa protein that is member of the CXC ELR-family of chemokines that is able to potently inhibit endothelial cell proliferation in vitro and angiogenesis in vivo. PF4 administered intratumorally or delivered by an adenoviral vector is able to cause an inhibition of tumor growth.

Interferons and metalloproteinase inhibitors are two other classes of naturally occurring angiogenic inhibitors that can be delivered according to the present invention. The anti-endothelial activity of the interferons has been known since the early 1980s, however, the mechanism of inhibition is still unclear. It is known that they can inhibit endothelial cell migration and that they do have some anti-angiogenic activity in vivo that is possibly mediated by an ability to inhibit the production of angiogenic promoters by tumor cells. Vascular tumors in particular are sensitive to interferon, for example, proliferating hemangiomas can be successfully treated with IFNα.

Tissue inhibitors of metalloproteinases (TIMPs) are a family of naturally occurring inhibitors of matrix metalloproteases (MMPs) that can also inhibit angiogenesis and can be used in the treatment protocols of the present invention. MMPs play a key role in the angiogenic process as they degrade the matrix through which endothelial cells and fibroblasts migrate when extending or remodeling the vascular network. In fact, one member of the MMPs, MMP-2, has been shown to associate with activated endothelium through the integrin αvβ3 presumably for this purpose. If this interaction is disrupted by a fragment of MMP-2, then angiogenesis is downregulated and in tumors growth is inhibited.

There are a number of pharmacological agents that inhibit angiogenesis, any one or more of which may be used as part of the present invention. These include AGM-1470/TNP-470, thalidomide, and carboxyamidotriazole (CAI). Fumagillin was found to be a potent inhibitor of angiogenesis in 1990, and since then the synthetic analogues of fumagillin, AGM-1470 and TNP-470 have been developed. Both of these drugs inhibit endothelial cell proliferation in vitro and angiogenesis in vivo. TNP-470 has been studied extensively in human clinical trials with data suggesting that long-term administration is optimal.

Thalidomide was originally used as a sedative but was found to be a potent teratogen and was discontinued. In 1994 it was found that thalidomide is an angiogenesis inhibitor. Thalidomide is currently in clinical trials as an anti-cancer agent as well as a treatment of vascular eye diseases.

CAI is a small molecular weight synthetic inhibitor of angiogenesis that acts as a calcium channel blocker that prevents actin reorganization, endothelial cell migration and spreading on collagen IV. CAI inhibits neovascularization at physiological attainable concentrations and is well tolerated orally by cancer patients. Clinical trials with CAI have yielded disease stabilization in 49% of cancer patients having progressive disease before treatment.

Cortisone in the presence of heparin or heparin fragments was shown to inhibit tumor growth in mice by blocking endothelial cell proliferation. The mechanism involved in the additive inhibitory effect of the steroid and heparin is unclear although it is thought that the heparin may increase the uptake of the steroid by endothelial cells. The mixture has been shown to increase the dissolution of the basement membrane underneath newly formed capillaries and this is also a possible explanation for the additive angiostatic effect. Heparin-cortisol conjugates also have potent angiostatic and anti-tumor effects activity in vivo.

Further specific angiogenesis inhibitors may be delivered to tumors using the tumor targeting methods of the present invention. These include, but are not limited to, Anti-Invasive Factor, retinoic acids and paclitaxel (U.S. Pat. No. 5,716,981; incorporated herein by reference); AGM-1470 (Ingber et al., 1990; incorporated herein by reference); shark cartilage extract (U.S. Pat. No. 5,618,925; incorporated herein by reference); anionic polyamide or polyurea oligomers (U.S. Pat. No. 5,593,664; incorporated herein by reference); oxindole derivatives (U.S. Pat. No. 5,576,330; incorporated herein by reference); estradiol derivatives (U.S. Pat. No. 5,504,074; incorporated herein by reference); and thiazolopyrimidine derivatives (U.S. Pat. No. 5,599,813; incorporated herein by reference) are also contemplated for use as anti-angiogenic compositions for the combined uses of the present invention.

Compositions comprising an antagonist of an $\alpha_v\beta_3$ integrin may also be used to inhibit angiogenesis as part of the present invention. As disclosed in U.S. Pat. No. 5,766,591 (incorporated herein by reference), RGD-containing polypeptides and salts thereof, including cyclic polypeptides, are suitable examples of $\alpha_v\beta_3$ integrin antagonists.

As angiopoietins are ligands for Tie2, other methods of therapeutic intervention based upon altering signaling through the Tie2 receptor can also be used in combination herewith. For example, a soluble Tie2 receptor capable of blocking Tie2 activation (Lin et al., 1998a) can be employed. Delivery of such a construct using recombinant adenoviral gene therapy has been shown to be effective in treating cancer and reducing metastases (Lin et al., 1998a).

The angiopoietins, in common with the members of the VEGF family, are growth factors specific for vascular endothelium (Davis and Yancopoulos, 1999; Holash et al., 1999; incorporated herein by reference). The angiopoietins first described were a naturally occurring receptor activator or agonist, angiopoietin-1 (Ang-1), and a naturally occurring receptor antagonist, angiopoietin-2 (Ang-2), both of which act by means of the endothelial cell tyrosine kinase receptor, Tie2.

Two new angiopoietins, angiopoietin-3 (mouse) and angiopoietin-4 (human) have also been identified (Valenzuela et al., 1999). Angiopoietin-3 appears to act as an antagonist (like Ang-2), whereas angiopoietin-4 appears to function as an agonist (like Ang-1) (Valenzuela et al., 1999). A protein termed angiopoietin-3 was also cloned from human heart and reported not to have mitogenic effects on endothelial cells (Kim et al., 1999).

Whereas VEGF is necessary for the early stages of vascular development, angiopoietin-1 is generally required for the later stages of vascularization. VEGF thus acts to promote endothelial cell differentiation, proliferation and primitive vessel formation. Angiopoietin-1 acts, via the Tie2 receptor, to promote maintenance and stabilization of mature vessels. Angiopoietin-1 is thus a maturation or stabilization factor, thought to convert immature vessels to immature vessels by promoting interactions between endothelial cells and surrounding support cells (Holash et al., 1999).

E6. Apoptosis-Inducing Agents

The present invention may also be used to deliver agents that induce apoptosis in any cell, including tumor cells, tumor vascular endothelial cells and virally infected cells. Many anti-cancer agents have, as part of their mechanism of action, an apoptosis-inducing effect. Any one or more of such agents described for use in combination therapies, including those in Table F, may also be conjugated to a construct, receptorbody or betabody of the invention, as described herein. Certain other agents have been discovered, designed or selected to have an apoptosis-inducing effect as a primary mechanism. Examples of such agents are described below, any of which may also be used to prepare a conjugate or used separately in combination therapy with the invention.

Many forms of cancer have reports of mutations in tumor suppressor genes, such as p53. Inactivation of p53 results in a failure to promote apoptosis. With this failure, cancer cells progress in tumorigenesis, rather than become destined for cell death. Thus, delivery of tumor suppressors is also contemplated for use in the present invention to stimulate cell death. Exemplary tumor suppressors include, but are not limited to, p53, Retinoblastoma gene (Rb), Wilm's tumor (WT1), bax alpha, interleukin-1b-converting enzyme and family, MEN-1 gene, neurofibromatosis, type 1 (NF1), cdk inhibitor p16, colorectal cancer gene (DCC), familial adenomatosis polyposis gene (FAP), multiple tumor suppressor gene (MTS-1), BRCA1 and BRCA2.

Preferred for use are the p53 (U.S. Pat. Nos. 5,747,469; 5,677,178; and 5,756,455; each incorporated herein by reference), Retinoblastoma, BRCA1 (U.S. Pat. Nos. 5,750,400; 5,654,155; 5,710,001; 5,756,294; 5,709,999; 5,693,473; 5,753,441; 5,622,829; and 5,747,282; each incorporated herein by reference), MEN-1 (GenBank accession number U93236) and adenovirus E1A (U.S. Pat. No. 5,776,743; incorporated herein by reference) genes.

Other oncogenes that inhibit apoptosis or programmed cell death include, but are not limited to, bcr-ab1, bcl-2 (distinct from bcl-1, cyclin D1; GenBank accession numbers M14745, X06487; U.S. Pat. Nos. 5,650,491; and 5,539,094; each incorporated herein by reference) and family members including Bcl-x1, Mcl-1, Bak, A1, A20. Overexpression of bcl-2 was first discovered in T cell lymphomas. bcl-2 functions as an oncogene by binding and inactivating Bax, a protein in the apoptotic pathway. Inhibition of bcl-2 function prevents inactivation of Bax, and allows the apoptotic pathway to proceed. Thus, inhibition of this class of oncogenes, e.g., using antisense nucleotide sequences, is contemplated for use in the present invention in aspects wherein enhancement of apoptosis is desired (U.S. Pat. Nos. 5,650,491; 5,539,094; and 5,583,034; each incorporated herein by reference).

Other compositions that may be delivered by a construct, receptorbody or betabody of the present invention include genes encoding the tumor necrosis factor related apoptosis inducing ligand termed TRAIL, and the TRAIL polypeptide (U.S. Pat. No. 5,763,223; incorporated herein by reference); the 24 kD apoptosis-associated protease of U.S. Pat. No. 5,605,826 (incorporated herein by reference); Fas-associated factor 1, FAF1 (U.S. Pat. No. 5,750,653; incorporated herein by reference). Also contemplated for use in these aspects of the present invention is the provision of interleukin-1β-converting enzyme and family members, which are also reported to stimulate apoptosis.

Compounds such as carbostyril derivatives (U.S. Pat. Nos. 5,672,603; and 5,464,833; each incorporated herein by reference); branched apogenic peptides (U.S. Pat. No. 5,591,717; incorporated herein by reference); phosphotyrosine inhibitors and non-hydrolyzable phosphotyrosine analogs (U.S. Pat. Nos. 5,565,491; and 5,693,627; each incorporated herein by reference); agonists of RXR retinoid receptors (U.S. Pat. No. 5,399,586; incorporated herein by reference); and even antioxidants (U.S. Pat. No. 5,571,523; incorporated herein by reference) may also be used. Tyrosine kinase inhibitors, such as genistein, may also be linked to the antibodies of the present invention (as supported by U.S. Pat. No. 5,587,459; incorporated herein by reference).

E7. Anti-Viral Agents

As PS and other anionic phospholipids become exposed on virally infected cells, a construct, receptorbody or betabody of the invention may also be linked to any one or more anti-viral agents. Exemplary anti-viral agents for linking to a construct, receptorbody or betabody include those in Table G. Such anti-viral agents may also be used separately in the combination anti-viral therapies of the invention.

In addition to so-called classic anti-viral agents, other DNA/RNA inhibitors may also be attached to form an anti-viral therapeutic. Exemplary anti-viral agents are listed in Table G, any one or more of which may be attached to prepare an anti-viral conjugate of the invention, or can be used separately in the anti-viral combination therapies of the invention.

TABLE G

Common Disease-Causing Viruses and Anti-Viral Drugs

| Disease-Causing Viruses | Drug Categories | Exemplary Anti-Viral Drugs |
|---|---|---|
| Herpes virus | | Cidofovir, acyclovir, penciclovir (famciclovir), gancyclovir (ganciclovir), deoxyguanosine, foscarnet, idoxuridine, trifluorothymidine, vidarabine, sorivudine |
| Retroviruses | Nucleoside reverse transcriptase (RT) inhibitors | Zidovudine, didanosine, zalcitabine, lamivudine, stavudine, abacavir, multinucleoside resistance A, multinucleoside resistance B |
| | Non-nucleoside RT inhibitors | Nevirapine, delavirdine, efavirenz, Adefovir Dipivoxil |
| | Protease Inhibitors | Indinavir, ritonavir, saquinavir, nelfinavir, amprenavir |
| | Cell cycle phase specific antineoplastic | Hydroxyurea (Hydrea ™, Bristol Myers-Squibb) |
| Hepatitis B | | Deoxycytosine iphosphate, lamivudine triphosphate, emticitabine triphosphate, adefovir diphosphate, penciclovir triphosphate, lobucavir triphosphate |
| Hepatitis C | | Interferon alpha, ribavirin |
| Influenza A and B | | Amantadine, rimantadine, zanamivir, oseltamivir |

Within the range of anti-viral agents and drugs, AZT and cidofovir are currently preferred. Irrespective of the chosen anti-viral drug, the anti-viral conjugate will bind to macrophages in the lungs, to virally infected cells and may also bind to virus particles. Depending on the linker or conjugation technology used, the anti-viral drug may be released at the surface of the target cell and then be taken up into the cell. Preferably, the conjugate itself is taken up into the cell, such as a macrophage or virally infected cell. Uptake can either occur naturally or can be virus-mediated. Once inside the cell, as with an antibody conjugate, hydrolysis of the linker releases the active anti-viral agent.

Other linkages containing biologically labile bonds can be used, such as, e.g., disulfide, acid labile, enzymatically cleavable or hydrolysable. Accordingly, any biologically-releasable or selectively hydrolyzable bond described for use in linking to therapeutic agents can be used in connection with the anti-virals of the present invention.

F. Biologically Functional Equivalents

Equivalents, or even improvements, of a construct, receptorbody or betabody can now be made, generally using the materials provided above as a starting point. Modifications and changes may be made in the structure of such a construct, receptorbody or betabody and still obtain a molecule having like or otherwise desirable characteristics. For example, certain amino acids may substituted for other amino acids in a protein structure without appreciable loss of interactive binding capacity. These considerations also apply to toxins, anti-angiogenic agents, apoptosis-inducing agents, coagulants and the like.

Since it is the interactive capacity and nature of a protein that defines that protein's biological functional activity, certain amino acid sequence substitutions can be made in a protein sequence (or of course, the underlying DNA sequence) and nevertheless obtain a protein with like (agonistic) properties. It is thus contemplated that various changes may be made in the sequence of the antibodies or therapeutic agents (or underlying DNA sequences) without appreciable loss of their biological utility or activity. Biological functional equivalents made from mutating an underlying DNA sequence can be made using the codon information provided herein in Table A, and the supporting technical details on site-specific mutagenesis.

TABLE A

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |

TABLE A-continued

| Amino Acids | | | Codons |
|---|---|---|---|
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It also is well understood by the skilled artisan that, inherent in the definition of a "biologically functional equivalent" protein or peptide, is the concept that there is a limit to the number of changes that may be made within a defined portion of the molecule and still result in a molecule with an acceptable level of equivalent biological activity. Biologically functional equivalent proteins and peptides are thus defined herein as those proteins and peptides in which certain, not most or all, of the amino acids may be substituted. Of course, a plurality of distinct proteins/peptides with different substitutions may easily be made and used in accordance with the invention.

Amino acid substitutions are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making more quantitative changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte and Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 is preferred, those which are within ±1 are particularly preferred, and those within ±0.5 are even more particularly preferred.

It is thus understood that an amino acid can be substituted for another having a similar hydrophilicity value and still obtain a biologically equivalent protein. As detailed in U.S. Pat. No. 4,554,101 (incorporated herein by reference), the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threoni (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon hydrophilicity values, the substitution of amino acids whose hydrophilicity values are within ±2 is preferred, those which are within ±1 are particularly preferred, and those within ±0.5 are even more particularly preferred.

G. Conjugation

An antibody Fc region is operatively attached, associated with or conjugated to at least a first phosphatidylserine binding protein to provide a construct, receptorbody or betabody of the invention. Such a construct, receptorbody or betabody may be further conjugated or attached to, e.g., anti-cellular and cytotoxic agents, coagulants and anti-viral agents.

Although covalent linkages are preferred, other means of operative attachment may also be used. For example, any linked construct may be generated using avidin:biotin bridges. In addition to the knowledge available to those of ordinary skill in the art, co-owned U.S. Pat. No. 6,093,399 is specifically incorporated herein by reference for purposes of even further describing and enabling the use of avidin:biotin in the operative attachment of targeting agents to biological and therapeutic agents.

Any two or tree agents may also be joined by a second binding region, preferably an antibody or antigen binding region thereof. This is exemplified by coaguligands wherein the targeting agent is linked to the coagulant via a second binding region (U.S. Pat. Nos. 6,093,399, 6,004,555, 5,877,289, and 6,036,955, each specifically incorporated herein by reference), which have been made and used successfully in the treatment of cancer.

Immunoconjugate technology is now generally known in the art. However, certain advantages may be achieved through the application of certain preferred technology, both in the preparation and purification for subsequent clinical administration. Additionally, while numerous types of disulfide-bond containing linkers are known that can be successfully employed in conjugation, certain linkers will generally be preferred over other linkers, based on differing pharmacological characteristics and capabilities. For example, linkers that contain a disulfide bond that is sterically "hindered" may be preferred, due to their greater stability in vivo, thus preventing release prior to binding at the site of action.

Each type of cross-linker, as well as how the cross-linking is performed, will tend to vary the pharmacodynamics of the resultant conjugate. One may desire to have a conjugate that will remain intact under conditions found everywhere in the body except the intended site of action, at which point it is desirable that the conjugate have good "release" characteristics. Therefore, the particular cross-linking scheme, including the cross-linking reagent used and the structures that are cross-linked, will be of some significance.

Depending on the specific agents to be conjugated, it may be necessary or desirable to provide a peptide spacer operatively attaching the agents. Certain peptide spacers are capable of folding into a disulfide-bonded loop structure. Proteolytic cleavage within the loop would then yield a heterodimeric polypeptide wherein the agents are linked by only a single disulfide bond. An example of such a toxin is a Ricin A-chain toxin.

When certain other toxin compounds are utilized, a non-cleavable peptide spacer may be provided to operatively attach the toxin compound of the fusion protein. Toxins which may be used in conjunction with non-cleavable peptide spacers are those which may, themselves, be converted by proteolytic cleavage, into a cytotoxic disulfide-bonded form. An example of such a toxin compound is a *Pseudonomas* exotoxin compound.

maintains biological activity and/or recovers biological activity when released from the construct.

Attachment of biological agents via carbohydrate moieties on Fc regions is also contemplated. Glycosylation, both O-linked and N-linked, naturally occurs in antibodies. Recombinant antibodies can be modified to recreate or create additional glycosylation sites if desired, which is simply achieved by engineering the appropriate amino acid sequences (such as Asn-X-Ser, Asn-X-Thr, Ser, or Thr) into the primary sequence of the antibody.

G1. Biochemical Cross-Linkers

In additional to the general information provided above, certain preferred biochemical cross-linkers may be used. Cross-linking reagents are used to form molecular bridges that tie together functional groups of two different molecules. To link two different proteins in a step-wise manner, hetero-bifunctional cross-linkers can be used that eliminate unwanted homopolymer formation. Exemplary hetero-bifunctional cross-linkers are referenced in Table C.

TABLE C

HETERO-BIFUNCTIONAL CROSS-LINKERS

| Linker | Reactive Toward | Advantages and Applications | Spacer Arm Length after cross-linking |
|---|---|---|---|
| SMPT | Primary amines<br>Sulfhydryls | Greater stability | 11.2 A |
| SPDP | Primary amines<br>Sulfhydryls | Thiolation<br>Cleavable cross-linking | 6.8 A |
| LC-SPDP | Primary amines<br>Sulfhydryls | Extended spacer arm | 15.6 A |
| Sulfo-LC-SPDP | Primary amines<br>Sulfhydryls | Extended spacer arm<br>Water-soluble | 15.6 A |
| SMCC | Primary amines<br>Sulfhydryls | Stable maleimide reactive group<br>Enzyme-antibody conjugation<br>Hapten-carrier protein conjugation | 11.6 A |
| Sulfo-SMCC | Primary amines<br>Sulfhydryls | Stable maleimide reactive group<br>Water-soluble<br>Enzyme-antibody conjugation | 11.6 A |
| MBS | Primary amines<br>Sulfhydryls | Enzyme-antibody conjugation<br>Hapten-carrier protein conjugation | 9.9 A |
| Sulfo-MBS | Primary amines<br>Sulfhydryls | Water-soluble | 9.9 A |
| SIAB | Primary amines<br>Sulfhydryls | Enzyme-antibody conjugation | 10.6 A |
| Sulfo-SIAB | Primary amines<br>Sulfhydryls | Water-soluble | 10.6 A |
| SMPB | Primary amines<br>Sulfhydryls | Extended spacer arm<br>Enzyme-antibody conjugation | 14.5 A |
| Sulfo-SMPB | Primary amines<br>Sulfhydryls | Extended spacer arm<br>Water-soluble | 14.5 A |
| EDC/Sulfo-NHS | Primary amines<br>Carboxyl groups | Hapten-Carrier conjugation | 0 |
| ABH | Carbohydrates<br>Nonselective | Reacts with sugar groups | 11.9 A |

A variety of chemotherapeutic and other pharmacological agents have now been successfully conjugated and shown to function pharmacologically. Exemplary antineoplastic agents that have been investigated include doxorubicin, daunomycin, methotrexate, vinblastine, and various others. Moreover, the attachment of other agents such as neocarzinostatin, macromycin, trenimon and α-amanitin has been described. These attachment methods can be adapted for use herewith.

Any covalent linkage should ideally be made at a site distinct from the functional site(s). The compositions are thus "linked" in any operative manner that allows each region to perform its intended function without significant impairment, in particular, so that the resultant construct still binds to the intended PS and so that the attached agent(s) substantially Hetero-bifunctional cross-linkers contain two reactive groups: one generally reacting with primary amine group (e.g., N-hydroxy succinimide) and the other generally reacting with a thiol group (e.g., pyridyl disulfide, maleimides, halogens, etc.). Through the primary amine reactive group, the cross-linker may react with the lysine residue(s) of one protein and through the thiol reactive group, the cross-linker, already tied up to the first protein, reacts with the cysteine residue (free sulfhlydryl group) of the other protein.

Compositions therefore generally have, or are derivatized to have, a functional group available for cross-linking purposes. This requirement is not considered to be limiting in that a wide variety of groups can be used in this manner. For example, primary or secondary amine groups, hydrazide or hydrazine groups, carboxyl alcohol, phosphate, carbamate, or alkylating groups may be used for binding or cross-linking.

The spacer arm between the two reactive groups of a cross-linkers may have various length and chemical compositions. A longer spacer arm allows a better flexibility of the conjugate components while some particular components in the bridge (e.g., benzene group) may lend extra stability to the reactive group or an increased resistance of the chemical link to the action of various aspects (e.g., disulfide bond resistant to reducing agents). The use of peptide spacers, such as L-Leu-L-Ala-L-Leu-L-Ala, is also contemplated.

It is preferred that a cross-linker having reasonable stability in blood will be employed. Numerous types of disulfide-bond containing linkers are known that can be successfully employed in conjugation. Linkers that contain a disulfide bond that is sterically hindered may prove to give greater stability in vivo, preventing release of the agent prior to binding at the site of action. These linkers are thus one preferred group of linking agents.

One of the most preferred cross-linking reagents is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the tumor site. It is contemplated that the SMPT agent may also be used in connection with the conjugates of this invention.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxysuccinimidyl group reacts with primary amino groups and the phenylazide (upon photolysis) reacts non-selectively with any amino acid residue.

In addition to hindered cross-linkers, non-hindered linkers can also be employed in accordance herewith. Other useful cross-linkers, not considered to contain or generate a protected disulfide, include SATA, SPDP and 2-iminothiolane. The use of such cross-linkers is well understood in the art.

Once conjugated, the conjugate is separated from unconjugated agents and from other contaminants. A large a number of purification techniques are available for use in providing conjugates of a sufficient degree of purity to render them clinically useful. Purification methods based upon size separation, such as gel filtration, gel permeation or high performance liquid chromatography, will generally be of most use. Other chromatographic techniques, such as Blue-Sepharose separation, may also be used.

G2. Biologically Releasable Linkers

Although it is preferred that any linking moiety will have reasonable stability in blood, to prevent substantial release of the attached therapeutic agent before targeting to the disease, e.g., tumor site, in certain aspects, the use of biologically-releasable bonds and/or selectively cleavable spacers or linkers is contemplated. "Biologically-releasable bonds" and "selectively cleavable spacers or linkers" still have reasonable stability in the circulation.

A construct, receptorbody or betabody of the invention may thus be linked to one or more therapeutic or second agents via a biologically-releasable bond. "Biologically-releasable bonds" or "selectively hydrolyzable bonds" include all linkages that are releasable, cleavable or hydrolyzable only or preferentially under certain conditions. This includes disulfide and trisulfide bonds and acid-labile bonds, as described in U.S. Pat. Nos. 5,474,765 and 5,762,918, each specifically incorporated herein by reference.

The use of an acid sensitive spacer for attachment of a therapeutic agent to a construct, receptorbody or betabody of the invention is particularly contemplated. In such embodiments, the therapeutic agents are released within the acidic compartments inside a cell. It is contemplated that acid-sensitive release may occur extracellularly, but still after specific targeting, preferably to the tumor site or virally infected cell. Certain currently preferred examples include antibodies linked to colchicine or doxorubicin via an acid sensitive spacer. Attachment via carbohydrate moieties of antibodies is also contemplated. In such embodiments, the therapeutic agent are released within the acidic compartments inside a cell.

A construct, receptorbody or betabody may also be derivatized to introduce functional groups permitting the attachment of the therapeutic agents through a biologically releasable bond. A construct, receptorbody or betabody may thus be derivatized to introduce side chains terminating in hydrazide, hydrazine, primary amine or secondary amine groups. Therapeutic agents may be conjugated through a Schiffs base linkage, a hydrazone or acyl hydrazone bond or a hydrazide linker (U.S. Pat. Nos. 5,474,765 and 5,762,918, each specifically incorporated herein by reference).

Also as described in U.S. Pat. Nos. 5,474,765 and 5,762,918, each specifically incorporated herein by reference, a construct, receptorbody or betabody may be operatively attached to a therapeutic agent through one or more biologically releasable bonds that are enzyme-sensitive bonds, including peptide bonds, esters, amides, phosphodiesters and glycosides.

Certain aspects of the invention concern the use of peptide linkers that include at least a first cleavage site for a peptidase and/or proteinase that is preferentially located within a disease site, particularly within the tumor environment. The delivery of the attached therapeutic agent thus results in cleavage specifically within the disease site or tumor environment, resulting in the specific release of the active therapeutic agent. Certain peptide linkers will include a cleavage site that is recognized by one or more enzymes involved in remodeling.

Peptide linkers that include a cleavage site for urokinase, pro-urokinase, plasmin, plasminogen, TGFβ, staphylokinase, Thrombin, Factor IXa, Factor Xa or a metalloproteinase, such as an interstitial collagenase, a gelatinase or a stromelysin, are particularly preferred. U.S. Pat. Nos. 6,004,555, 5,877,289, and 6,093,399 are specifically incorporated herein by reference for the purpose of further describing and enabling how to make and use immunoconjugates comprising biologically-releasable bonds and selectively-cleavable linkers and peptides. U.S. Pat. No. 5,877,289 is particularly incorporated herein by reference for the purpose of further describing and enabling how to make and use immunoconjugates that comprise a selectively-cleavable peptide linker that is cleaved by urokinase, plasmin, Thrombin, Factor Ixa, Factor Xa or a metalloproteinase, such as an interstitial collagenase, a gelatinase or a stromelysin, within a tumor environment.

Currently preferred selectively-cleavable peptide linkers are those that include a cleavage site for plasmin or a metalloproteinase (also known as "matrix metalloproteases" or "MMPs"), such as an interstitial collagenase, a gelatinase or a stromelysin. Additional peptide linkers that may be advantageously used in connection with the present invention include, for example, plasmin cleavable sequences, such as those cleavable by pro-urokinase, TGFβ, plasminogen and staphylokinase; Factor Xa cleavable sequences; MMP cleavable sequences, such as those cleavable by gelatinase A; collagenase cleavable sequences, such as those cleavable by calf skin collagen (α1(I) chain), calf skin collagen (α2(I) chain), bovine cartilage collagen (α1(II)chain), human liver collagen (α1(III) chain), human $\alpha_2$M, human PZP, rat $\alpha_1$M, rat $\alpha_2$M, rat $\alpha_1I_3$(2J), rat $\alpha_1I_3$(27J), and the human fibroblast collagenase autolytic cleavage sites. In addition to the knowledge available to those of ordinary skill in the art, the text and sequences from Table B2 in co-owned U.S. Pat. Nos. 6,342,219, 6,524,583, 6,342,221 and 6,416,758, are specifically incorporated herein by reference for purposes of even further describing and enabling the use of such cleavable sequences.

G3. Fusion Proteins and Recombinant Expression

A construct, receptor body or betabody can be prepared as a fusion protein using molecular biological techniques. Any fusion protein may be designed and made using any construct, receptor body or betabody and second therapeutic agents disclosed herein and those known in the art. The fusion protein technology is readily adaptable to prepare fusion proteins with other modifications, such as linkage via a selectively cleavable peptide sequence, and such like.

The use of recombinant DNA techniques to achieve such ends is now standard practice to those of skill in the art. These methods include, for example, in vitro recombinant DNA techniques, synthetic techniques and in vivo recombination/genetic recombination. DNA and RNA synthesis may, additionally, be performed using an automated synthesizers (see, for example, the techniques described in Sambrook et al., 1989).

The preparation of such a fusion protein generally entails the preparation of a first and second DNA coding region and the functional ligation or joining of such regions, in frame, to prepare a single coding region that encodes the desired fusion protein. Once the desired coding region has been produced, an expression vector is created. Expression vectors contain one or more promoters upstream of the inserted DNA regions that act to promote transcription of the DNA and to thus promote expression of the encoded recombinant protein. This is the meaning of "recombinant expression".

To obtain a so-called "recombinant" version of a construct, receptor body or betabody, the vector is expressed in a recombinant cell. The engineering of DNA segment(s) for expression in a prokaryotic or eukaryotic system may be performed by techniques generally known to those of skill in recombinant expression. It is believed that virtually any expression system may be employed in expression.

A construct, receptor body or betabody of the invention may be successfully expressed in eukaryotic expression systems, e.g., CHO cells, however, it is envisioned that bacterial expression systems, such as *E. coli* pQE-60 will be particularly useful for the large-scale preparation and subsequent purification of the constructs. cDNAs may also be expressed in bacterial systems, with the encoded proteins being expressed as fusions with β-galactosidase, ubiquitin, *Schistosoma japonicum* glutathione S-transferase, and the like. It is believed that bacterial expression will have advantages over eukaryotic expression in terms of ease of use and quantity of materials obtained thereby.

In terms of microbial expression, U.S. Pat. Nos. 5,583,013; 5,221,619; 4,785,420; 4,704,362; and 4,366,246 are incorporated herein by reference for the purposes of even further supplementing the present disclosure in connection with the expression of genes in recombinant host cells.

A recombinantly produced construct, receptorbody or betabody may be purified and formulated for human administration. Alternatively, nucleic acids encoding a construct, receptorbody or betabody may be delivered via gene therapy. Although naked recombinant DNA or plasmids may be employed, the use of liposomes or vectors is preferred. The ability of certain viruses to enter cells via receptor-mediated endocytosis and to integrate into the host cell genome and express viral genes stably and efficiently have made them attractive candidates for the transfer of foreign genes into mammalian cells. Preferred gene therapy vectors for use in the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines. Other viruses, such as adenovirus, herpes simplex viruses (HSV), cytomegalovirus (CMV), and adeno-associated virus (AAV), such as those described by U.S. Pat. No. 5,139,941 (incorporated herein by reference), may also be engineered to serve as vectors for gene transfer.

Although some viruses that can accept foreign genetic material are limited in the number of nucleotides they can accommodate and in the range of cells they infect, these viruses have been demonstrated to successfully effect gene expression. However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (e.g., temporal, strength) makes it possible to control expression to a greater extent than in other systems. It also is an advantage that the virus has relatively few spliced messages, further easing genetic manipulations. HSV also is relatively easy to manipulate and can be grown to high titers.

Of course, in using viral delivery systems, one will desire to purify the virion sufficiently to render it essentially free of undesirable contaminants, such as defective interfering viral particles or pyrogens such that it will not cause any untoward reactions in the cell, animal or individual receiving the vector construct. A preferred means of purifying the vector involves the use of buoyant density gradients, such as cesium chloride gradient centrifugation.

H. Pharmaceutical Compositions

The therapeutic agents of the present invention will generally be formulated as pharmaceutical compositions. The pharmaceutical compositions will comprise a biologically or therapeutically effective amount of at least a first therapeutic agent of the invention, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

H1. Injectable Formulations

The therapeutic agents of the invention will often be formulated for parenteral administration, particularly for tumor treatment, e.g., formulated for injection via the intravenous, intramuscular, sub-cutaneous, transdermal, or other such routes, including peristaltic administration and direct instillation into a tumor or disease site (intracavity administration). The preparation of an aqueous composition that contains an antibody, immunoconjugate or peptide conjugate as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

The therapeutic agents can be formulated into a sterile aqueous composition in a neutral or salt form. Solutions of therapeutic agents as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Suitable carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the therapeutic agents should be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Suitable pharmaceutical compositions in accordance with the invention will generally include an amount of the therapeutic agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. For human administration, preparations should meet sterility, pyrogenicity, general safety and purity standards as required by FDA Office of Biological Standards. Upon formulation, the therapeutic agents will be administered in a manner compatible with the dosage formulation and in such amount as is therapeutically effective.

H2. Sustained Release Formulations

Formulations are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may also be used. Slow release formulations are generally designed to give a constant drug level over an extended period and may be used to deliver therapeutic agents in accordance with the present invention. The slow release formulations are typically implanted in the vicinity of the disease site, for example, at the site of a tumor or viral infection.

Suitable examples of sustained-release preparations include semipermeable matrices of solid hydrophobic polymers containing therapeutic agents, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919;

copolymers of L-glutamic acid and γ ethyl-L-glutamate; non-degradable ethylene-vinyl acetate; degradable lactic acid-glycolic acid copolymers, such as the Lupron Depot™ (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

H3. Liposomes and Nanocapsules

In certain embodiments, liposomes and/or nanoparticles may also be employed with the therapeutic agents. The formation and use of liposomes is generally known to those of skill in the art, as summarized below. The present invention provides particular combinations of antibodies, liposomes and chemotherapeutic agents, which are described below. In addition, a liposomal formulation may be used as a routine component of any of the therapeutic agents of the overall invention.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 Å, containing an aqueous solution in the core.

Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

H4. Ophthalmic Formulations

Many diseases of the eye, particularly those having an angiogenic component, can be treated by the present invention. For example ocular neovascular disease, age-related macular degeneration, diabetic retinopathy, retinopathy of prematurity, comeal graft rejection, neovascular glaucoma, retrolental fibroplasias and other diseases associated with corneal neovascularization or retinal/choroidal neovascularization, as described hereinbelow.

The therapeutic agents of the present invention may thus be advantageously employed in the preparation of pharmaceutical compositions suitable for use as ophthalmic solutions, including those for intravitreal and/or intracameral administration. For the treatment of any of the foregoing or other disorders the therapeutic agents are administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparations will contain a therapeutic agent in a concentration from about 0.01 to about 1% by weight, preferably from about 0.05 to about 0.5% in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Suitable preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Suitable antioxidants and stabilizers include sodium bisulfite, sodium metabisulfite, sodium thiosulfite, thiourea and the like. Suitable wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

H5. Topical Formulations

In the broadest sense, formulations for topical administration include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of therapeutic agents for topical use, such as in creams, ointments and gels, includes the preparation of oleaginous or water-soluble ointment bases, will be well known to those in the art in light of the present disclosure. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

H6. Nasal Formulations

Local delivery via the nasal and respiratory routes is contemplated for treating various conditions, particularly for use in the anti-viral treatment methods of the present invention. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Suitable formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. Thus, the aqueous nasal solutions usually are isotonic and slightly buffered to maintain a pH of 5.5 to 6.5. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 μm. Fine mists are produced by pressurized aerosols and hence their use in considered advantageous.

I. Binding, Functional and Screening Assays

Although the present invention has significant utility in animal and human treatment regimens, it also has many other specific and credible uses, including practical uses in many in vitro embodiments. Certain of these uses are related to the specific binding properties of a construct, receptorbody or betabody. In that each of the constructs of the invention include at least one protein that binds to PS or an anionic phospholipid, they may be used in a variety of binding embodiments, including useful binding assays.

The presence of an Fc region or an attached agent, where relevant, although providing advantageous properties, does not negate the utility of the first region in any binding assay. Suitably useful binding assays thus include those commonly employed in the art, such as in immunoblots, Western blots, dot blots, RIAs, ELISAs, immunohistochemistry, fluorescent activated cell sorting (FACS), immunoprecipitation, affinity chromatography, and the like, as further described herein.

Certain standard binding assays are those in which an antigen is immobilized onto a solid support matrix, e.g., nitrocellulose, nylon or a combination thereof, such as in immunoblots, Western blots, ELISAs and related assays. Other important assays are those using cells, wherein the components of the present invention can be used to assay for cells with PS or anionic phospholipids at the cell surface. Such assays can be applied in pre-clinical testing, e.g., regarding the design of drugs, testing the mechanism of action and/or selecting therapeutic agents for combined use.

Further in vitro assays are useful in the diagnosis of diseases connected with aberrant cell activation and/or apoptosis, wherein testing for the presence of PS or anionic phospholipids at the cell surface would be particularly useful. The constructs of the invention may thus be used in conjunction with both fresh-frozen and formalin-fixed, paraffin-embedded tissue blocks in immunohistochemistry; in fluorescent activated cell sorting, flow cytometry or flow microfluorometry.

They constructs of the invention have further practical uses in immunoprecipitation, antigen purification embodiments, such as affinity chromatography, and in many other binding assays that will be known to those of skill in the art given the information presented herein.

Yet further practical uses of the present constructs are as controls in functional assays, including many in vitro and ex vivo assays and systems. As the binding and functional properties of a construct, receptorbody or betabody of the invention are particularly specific, as disclosed herein, such "control" uses are actually extremely valuable. The assays that benefit from such a practical application of the present invention include, for example, assays concerning detection of PS or anionic phospholipids at the cell surface.

These assays systems can also be developed into in vitro or ex vivo drug screening assays, wherein the present provision of biological materials with well defined properties is particularly important. For example, in using the constructs of the present invention as positive controls in the selection of small molecules that have similar, equivalent or improved binding properties, e.g., in drug screening and development.

The binding assays and systems of the invention can also be developed into in vitro or ex vivo drug screening assays, wherein the present provision of biological materials with well defined properties, is particularly important. For example, in using the constructs of the present invention as positive controls in the selection of small molecules that have similar, equivalent or improved binding properties, e.g., in drug screening and development.

J. Diagnostic and Therapeutic Kits

This invention also provides diagnostic and therapeutic kits comprising at least a first construct, receptorbody or betabody of the present invention, for use in treatment methods, combined treatment methods and/or in imaging and treatment embodiments. Such kits will generally contain, in at least a first suitable container (or container means), a pharmaceutically acceptable formulation of at least one construct, receptorbody or betabody of the invention. The kits may include written or electronic instructions for use, e.g. in preclinical, clinical and/or veterinary embodiments.

The kits may also contain other compositions, pharmaceutically acceptable formulations and second biological and therapeutic agents, including those for combined therapy and/or for diagnostic and imaging. For example, such kits may contain any one or more of a range of chemotherapeutic, radiotherapeutic or anti-angiogenic agents, anti-tumor cell, anti-tumor vasculature or anti-tumor stroma antibodies, immunotoxins or coaguligands, anti-viral agents and/or diagnostic components or agents. Written or electronic instructions for use in combined therapy and/or for diagnosis and imaging may also be included.

The kits may have a single container that contains the first construct, receptorbody or betabody, with or without any additional components, or they may have distinct containers for each desired agent. Where combined therapeutics are provided, a single solution may be premixed, either in a molar equivalent combination, or with one component in excess of the other. Alternatively, the primary therapeutic agent of the invention and the second biological or therapeutic agent, such as a second anti-cancer or anti-viral agent, kit may be maintained separately within distinct containers of the kit prior to administration to a patient.

Diagnostic components will most often be maintained in at least a second container, distinct from the other or first container that comprises the one or more therapeutic agents. The diagnostic kits may include labeled antibodies or peptides that bind to PS, or any other agent suitable for diagnosing the disease to be treated. The kits may include diagnostic agents for use in vitro, for use in vivo, or both such agent. The kits may include written or electronic instructions for use, e.g. in pre-clinical, clinical and/or veterinary diagnostic embodiments.

For immunodetection in vitro, a construct, receptorbody or betabody may be bound to a solid support, such as a well of a microtitre plate. The immunodetection kits preferably comprise at least a first immunodetection reagent. The immunodetection reagents of the kit may take any one of a variety of forms, including those detectable labels that are associated with or linked to the given antibody, such as used in vivo. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. A number of exemplary labels are known in the art and all such labels may be employed in connection with the present invention. These kits may contain antibody-label conjugates either in fully conjugated form, in the form of intermediates, or as separate moieties to be conjugated by the user of the kit. The imaging kits will preferably comprise a targeting agent or antibody that is already attached to an in vivo detectable label. However, the label and attachment means could be separately supplied.

Either form of diagnostic kit may further comprise control agents, such as suitably aliquoted biological compositions, whether labeled or unlabeled, as may be used to prepare a standard curve for a detection assay. The components of the kits may be packaged either in aqueous media or in lyophilized form.

When the components of the kit are provided in one or more liquid solutions, the liquid solution is preferably an aqueous solution, with a sterile aqueous solution being particularly preferred. However, the components of the kit may be provided as dried powder(s). When reagents or components are provided as a dry powder, the powder can be reconstituted by the addition of a suitable solvent. The solvent may also be provided in another container within the kit.

The containers of the therapeutic and diagnostic kits will generally include at least one vial, test tube, flask, bottle, syringe or other container or container means, into which the therapeutic and any other desired agent are placed and, preferably, suitably aliquoted. As at least two separate components are preferred, the kits will preferably include at least two such containers. The kits may also comprise a third or fourth container for containing a sterile, pharmaceutically acceptable buffer or other diluent.

The kits may also contain a means by which to administer the therapeutic agents to an animal or patient, e.g., one or more needles or syringes, or even an eye dropper, pipette, or other such like apparatus, from which the formulations may be injected into the animal or applied to a diseased area of the body. The kits of the present invention will also typically include a means for containing the vials, or such like, and other component, in close confinement for commercial sale, such as, e.g., injection or blow-molded plastic containers into which the desired vials and other apparatus are placed and retained.

K. Immunodetection and Imaging

The present invention further provides in vitro and in vivo diagnostic and imaging methods. Such methods are applicable for use in generating diagnostic, prognostic and/or imaging information, e.g., related to angiogenic diseases and viral infections, and preferably related to tumor treatment and imaging methods. The methods of the invention include in vitro diagnostic tests, e.g., wherein the samples can be obtained non-invasively and preferably tested in high throughput assays and/or where the clinical diagnosis in ambiguous and confirmation is desired. In the field of in vivo diagnostics and imaging, a construct, receptorbody or betabody of the invention is linked to one or more detectable agents and used to form an image of an angiogenic site or tumor, optionally as a first step prior to treatment.

K1. Immunodetection Methods and Kits

The invention thus concerns immunodetection methods for binding, purifying, quantifying or otherwise generally detecting PS and anionic phospholipids, e.g., for use in diagnosing activated and apoptotic cells and associated diseases. A construct, receptorbody or betabody of the present invention may be employed to detect PS and anionic phospholipids in vivo (see below), in isolated issue samples, biopsies or swabs and/or in homogenized tissue samples. Such immunodetection methods have evident diagnostic utility, but also have applications to non-clinical samples, such as in the titering of antigen samples, and the like.

The steps of various useful immunodetection methods have been described in the scientific literature, such as, e.g., Nakamura et al., 1987, specifically incorporated herein by reference. In general, the immunobinding methods include obtaining a sample suspected of containing PS or anionic phospholipids, preferably cells suspected of having PS at the cell surface, and contacting the sample with a construct, receptorbody or betabody of the invention, under conditions effective to allow the formation of immune complexes. Any immune complexes formed during the binding process are then detected and preferably quantified.

The sample analyzed may be a cell sample, such as cells exposed to certain test conditions in the laboratory. The sample may also be a biological sample from an animal or patient, e.g., one suspected of having a disease associated with activation or apoptosis of one or more cell types. Such a sample may be a tissue section or specimen, a biopsy, a swab or smear test sample, a homogenized tissue extract or separated or purified forms of such.

Contacting the chosen biological sample with a construct, receptorbody or betabody under conditions effective and for a period of time sufficient to allow the formation of immune complexes (primary immune complexes) is generally a matter of simply adding a construct, receptorbody or betabody to the sample and incubating the mixture for a period of time long enough for the construct, receptorbody or betabody to form immune complexes with, i.e., to bind to, any PS or anionic phospholipids present. After this time, the sample composition, such as a tissue section or ELISA plate, will generally be washed to remove any non-specifically bound species, allowing only those specifically bound within the primary immune complexes to be detected.

The detection of immunocomplex formation is well known in the art and may be achieved through the application of numerous approaches. These methods are generally based upon the detection of a label or marker, such as any radioactive, fluorescent, biological or enzymatic tags or labels known in the art. U.S. patents concerning the use of such labels include U.S. Pat. Nos. 3,817,837; 3,850,752; 3,939,350; 3,996,345; 4,277,437; 4,275,149 and 4,366,241, each incorporated herein by reference. The use of enzymes that generate a colored product upon contact with a chromogenic substrate are generally preferred. Secondary binding ligands, such as a second antibody or a biotin/avidin ligand binding arrangement, may also be used, as is known in the art.

A construct, receptorbody or betabody employed in the detection may themselves be linked to a detectable label, wherein one would then simply detect this label, thereby allowing the amount of the primary immune complexes in the composition to be determined.

Preferably, the primary immune complexes are detected by means of a second binding ligand that has binding affinity for a construct, receptorbody or betabody of the invention. In such cases, the second binding ligand may be linked to a detectable label. The second binding ligand is itself often an antibody, and may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two step approach. A second binding ligand, such as an antibody, that has binding affinity for the first antibody is used to form secondary immune complexes, as described above. After washing, the secondary immune complexes are contacted with a third binding ligand or antibody that has binding affinity for the second antibody, again under conditions effective and for a period of time sufficient to allow the formation of immune complexes (tertiary immune complexes). The third ligand or antibody is linked to a detectable label, allowing detection of the tertiary immune complexes thus formed. This system may provide for signal amplification if desired.

Clinical diagnosis or monitoring may be applied to patients with a variety of diseases, particularly those associated with increased PS or anionic phospholipid exposure at the cell surface. The detection of PS or anionic phospholipid, or an increase in the levels of PS or anionic phospholipid, in comparison to the levels in a corresponding biological sample from a normal subject, is indicative of a patient with such a disease.

However, as is known to those of skill in the art, such a clinical diagnosis would not likely be made on the basis of this method in isolation. Those of skill in the art are very familiar with differentiating between significant expression of a biomarker, which represents a positive identification, and low level or background expression of a biomarker. Indeed, background expression levels are often used to form a "cut-off" above which increased staining will be scored as significant or positive.

K2. In Vivo Imaging

The present invention provides a variety of in vivo diagnostic and imaging embodiments. Certain aspects of the invention concern new and surprisingly effective compositions for in vivo diagnosis and imaging. For example, a construct, receptorbody or betabody of the invention is linked to an in vivo detectable agent to form an immunodiagnostic conjugate of the invention. The resultant immunodiagnostics may now be used in any previously described diagnostic or imaging embodiment connected with the detection of PS or an anionic phospholipid.

In this regard, immunodiagnostics comprising a construct, receptorbody or betabody of the invention, may be used in imaging vascular thromboses, particularly in or near the heart, such as in deep vein thrombosis, pulmonary embolism, myocardial infarction, atrial fibrillation, problems with prosthetic cardiovascular materials, stroke, and the like. Such compositions of the invention may also be used in imaging activated platelets, e.g., in conditions such as abscesses, restenosis, inflammation of joints and in hemostatic disorders, such as arterial, coronary, venous and cerebral thrombosis and the like. The immunodiagnostic compositions of the invention may also be used in detecting apoptotic cells, as may be used in the diagnosis and imaging of a variety of diseases in which increased or inappropriate apoptosis occurs.

The in vivo imaging compositions and methods of the invention can be used in imaging per se, or in pre-imaging a site in the body to form a reliable image prior to treatment. Preferably, the imaging is tumor imaging. These compositions and methods can also be applied to imaging and diagnosis of other diseases or conditions associated with PS and anionic phospholipids, such those involving cell activation and/or apoptosis, including angiogenic diseases, atherosclerosis, viral infections, and other such conditions in which an internal image is desired for diagnostic or prognostic purposes or to design treatment.

In these embodiments, a construct, receptorbody or betabody of the invention is operatively attached, linked or conjugated to a detectable label. “Detectable labels” are compounds or elements that can be detected due to their specific functional properties, or chemical characteristics, the use of which allows the component to which they are attached to be detected, and further quantified if desired. In conjugates for in vivo diagnostic protocols or “imaging methods”, the labels can be detected using non-invasive methods.

Many appropriate imaging agents are known in the art, as are methods for their attachment to binding ligands (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the antibody (U.S. Pat. No. 4,472,509). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

An example of detectable labels are the paramagnetic ions. In this case, suitable ions include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred.

Ions useful in other contexts, such as X-ray imaging, include but are not limited to lanthanum (III), gold (III), lead (II), and especially bismuth (III). Fluorescent labels include rhodamine, fluorescein and renographin. Rhodamine and fluorescein are often linked via an isothiocyanate intermediate.

In the case of radioactive isotopes for diagnostic applications, suitable examples include $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technetium$^{99m}$ and yttrium$^{90}$. $^{125}$I is often being preferred for use in certain embodiments, and technicium$^{99m}$ and indium$^{111}$ are also often preferred due to their low energy and suitability for long range detection.

A radioactively labeled construct, receptorbody or betabody for use in the present invention may be produced according to well-known methods in the art. For instance, intermediary functional groups that are often used to bind radioisotopic metallic ions to antibodies are diethylenetriaminepentaacetic acid (DTPA) and ethylene diaminetetracetic acid (EDTA).

A construct, receptorbody or betabody can also be iodinated by contact with sodium or potassium iodide and a chemical oxidizing agent such as sodium hypochlorite, or an enzymatic oxidizing agent, such as lactoperoxidase. A construct, receptorbody or betabody according to the invention may be labeled with technetium-$^{99}$ by a ligand exchange process, for example, by reducing pertechnate with stannous solution, chelating the reduced technetium onto a Sephadex column and applying the antibody to this column. Direct labeling techniques are also suitable, e.g., by incubating pertechnate, a reducing agent such as $SNCl_2$, a buffer solution such as sodium-potassium phthalate solution, and the antibody.

Any of the foregoing type of detectably labeled binding ligands may be used in the imaging aspects of the invention, either for imaging alone or to form an image of a disease site or tumor prior to treatment. Either way, the methods generally comprise administering to an animal or patient a diagnostically effective amount of a construct, receptorbody or betabody that is conjugated to a marker that is detectable by non-invasive methods. The binding ligand-marker conjugate is allowed sufficient time to localize and bind to cells expressing PS or anionic phospholipids in the disease site, such as the tumor or tumor vasculature. The patient is then exposed to a detection device to identify the detectable marker, thus forming an image of the disease site or tumor.

The nuclear magnetic spin-resonance isotopes, such as gadolinium, are detected using a nuclear magnetic imaging device; and radioactive substances, such as technicium$^{99m}$ or indium$^{111}$, are detected using a gamma scintillation camera or detector. U.S. Pat. No. 5,627,036 is also specifically incorporated herein by reference for purposes of providing even further guidance regarding the safe and effective introduction of detectably labeled constructs into the blood of an individual, and means for determining the distribution of the detectably labeled agent extracorporally, e.g., using a gamma scintillation camera or by magnetic resonance measurement.

Dosages for imaging embodiments are generally less than for therapy, but are also dependent upon the age and weight of a patient. A one time dose of between about 0.1, 0.5 or about 1 mg and about 9 or 10 mgs, and more preferably, of between about 1 mg and about 5-10 mgs of antibody- or binding ligand-conjugate per patient is contemplated to be useful.

K3. Surrogate Marker for Cancer Therapy

In regard to the in vivo diagnostic and imaging, the present invention further provides compositions and methods for use as a surrogate marker for cancer therapy. Such embodiments concern the use of a construct, receptorbody or betabody of the invention linked to an in vivo detectable agent.

Many anti-cancer therapies in current use induce apoptosis and necrosis. Anionic phospholipids, particularly PS, are markers of pre-apoptotic and apoptotic cells. Therefore, imaging with a suitable construct, receptorbody or betabody can be used to identify pre-apoptotic and apoptotic cells and thus provide information regarding the progress of the therapy. This is what is meant by a “surrogate marker for cancer therapy”, as used herein.

The use of a construct, receptorbody or betabody of the invention provides particular advantages as a surrogate marker for cancer therapy. For example, the ability to identify pre-apoptotic cells is a particular advantage. The specificity will also provide more meaningful imaging data for the physician. Also, the safety profile is impressive and provides advantages over annexin, for example, as annexin suffers from drawbacks associated with coagulation.

Accordingly, any of the in vivo diagnostic and imaging methods described above may be adapted for prognostic use as a surrogate marker for cancer therapy simply by use in a patient undergoing cancer therapy.

L. Tumor Treatment

Important aspects of the present invention concern the treatment of malignancies, tumors and vascularized tumors. This includes tumors in which angiogenesis is more or less important and tumors having prothrombotic blood vessels.

The treatment of benign tumors is included in the invention, such as acoustic neuroma, neurofibroma, trachoma, pyogenic granulomas and BPH. The treatment of blood-born tumors, such as leukemias, and various acute or chronic neoplastic diseases of the bone marrow is also encompassed.

The present invention is broadly applicable to the treatment of any malignant tumor, whether having a vascular component or not. Tumors for treatment include solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like.

The present invention is contemplated for use in the treatment of any patient that presents with a solid tumor. In general, the invention can be used to treat tumors of all sizes, including those about 0.3-0.5 cm and upwards, tumors of greater than 0.5 cm in size and patients presenting with tumors of between about 1.0 and about 2.0 cm in size, although tumors up to and including the largest tumors found in humans may also be treated.

Although the present invention is not generally intended as a preventative or prophylactic treatment, use of the invention is certainly not confined to the treatment of patients having tumors of only moderate or large sizes. There are many reasons underlying these aspects of the invention. For example, a patient presenting with a primary tumor of moderate size or above may also have various other metastatic tumors that are considered to be small-sized or even in the earlier stages of metastatic tumor seeding. Given that a construct, receptorbody or betabody of the invention is generally administered into the systemic circulation of a patient, they will naturally have effects on the secondary, smaller and metastatic tumors, although this may not be the primary intent of the treatment. Furthermore, even in situations where the tumor mass as a whole is a single small tumor, certain beneficial anti-tumor effects will result from the use of the present treatments.

The guidance provided herein regarding the suitable patients for use in connection with the present invention is intended as teaching that certain patient's profiles may assist with the selection of patients for treatment by the present invention. The pre-selection of certain patients, or categories of patients, does not in any way negate the basic usefulness of the present invention in connection with the treatment of all patients having cancer. A further consideration is the fact that the assault on the tumor provided by the antibody therapy of the invention may predispose the tumor to further therapeutic treatment, such that the subsequent treatment results in an overall synergistic effect or even leads to total remission or cure.

It is not believed that any particular type of tumor should be excluded from treatment using the present invention. However, the type of tumor cells may be relevant to the use of the invention in combination with tertiary therapeutic agents, particularly chemotherapeutics and anti-tumor cell immunotoxins. As the present invention includes within its modes of action the targeting and destruction of tumor vasculature, and as the vasculature is substantially or entirely the same in all solid tumors, it will be understood that the present methodology is widely or entirely applicable to the treatment of all solid tumors, irrespective of the particular phenotype or genotype of the tumor cells themselves. The data presented herein is compelling as it shows impressive results in a wide range of different tumor models.

Therapeutically effective doses are readily determinable using data from an animal model, as shown in the studies detailed herein, and from clinical data using a range of therapeutic agents. Experimental animals bearing solid tumors are frequently used to optimize appropriate therapeutic doses prior to translating to a clinical environment. Such models are known to be very reliable in predicting effective anti-cancer strategies. For example, mice bearing solid tumors, such as used in the Examples, are widely used in pre-clinical testing. The inventors have used such art-accepted mouse models to determine working ranges of therapeutic agents that give beneficial anti-tumor effects with minimal toxicity.

In terms of tumor therapy, bearing in mind the attendant safety benefits associated with the overall invention, one may refer to the scientific and patent literature on the success of using other anti-vascular therapies. By way of example, U.S. Pat. Nos. 5,855,866; 5,877,289; 5,965,132; 6,051,230; 6,004,555; 5,776,427; 6,004,554; 6,036,955; and 6,093,399 are incorporated herein by reference for the purpose of further describing the use of such agents as may be applied to those of the present invention. U.S. Pat. Nos. 6,312,694, 6,783,760, 6,818,213 and 6,406,693 are further specifically incorporated herein by reference for guidance on dosing and treatment using unconjugated antibodies to PS and related immunoconjugates.

As is known in the art, there are realistic objectives that may be used as a guideline in connection with pre-clinical testing before proceeding to clinical treatment. However, due to the safety already demonstrated in accepted models, pre-clinical testing of the present invention will be more a matter of optimization, rather than to confirm effectiveness. Thus, pre-clinical testing may be employed to select the most advantageous agents, doses or combinations.

Any dose, combined method or medicament that results in any consistently detectable anti-tumor effect, including detectable tumor vasculature regression, thrombosis and/or destruction and tumor necrosis, will still define a useful invention. Regressive, thrombotic, destructive and necrotic effects should preferably be observed in between about 10% and about 40-50% of the tumor blood vessels and tumor tissues, upwards to between about 50% and about 99% of such effects being observed. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-tumor effects of the therapy are towards the low end of this range, it may be that this therapy is still equally or even more effective than all other known therapies in the context of the particular tumor. It is unfortunately evident to a clinician that certain tumors cannot be effectively treated in the intermediate or long term, but that does not negate the usefulness of the present therapy, particularly where it is at least about as effective as the other strategies generally proposed.

In designing appropriate doses of a construct, receptorbody or betabody for the treatment of vascularized tumors, one may readily extrapolate from the animal studies described herein in order to arrive at appropriate doses for clinical administration. To achieve this conversion, one would account for the mass of the agents administered per unit mass of the experimental animal and, preferably, account for the differences in the body surface area between the experimental animal and the human patient. All such calculations are well known and routine to those of ordinary skill in the art.

For example, in taking the successful doses of therapeutics used in the mouse studies, and applying standard calculations based upon mass and surface area, effective doses of agents for use in human patients would be between about 1 mg and about 500 mgs antibody per patient, and preferably, between about 10 mgs and about 100 mgs antibody per patient.

Accordingly, using this information, the inventors contemplate that useful low doses for human administration will be about 1, 2, 3, 4, 5, 6, 7, 8, 9, 10, 15, 20, 25 or about 30 mgs or so per patient; and useful high doses for human administration will be about 250, 275, 300, 325, 350, 375, 400, 425, 450, 475 or about 500 mgs or so per patient. Useful intermediate doses for human administration are contemplated to be about 35, 40, 50, 60, 70, 80, 90, 100, 125, 150, 175, 200 or about 225 mgs or so per patient. In general, dosage ranges of between about 5-100 mgs, about 10-80 mgs, about 20-70 mgs, about 25-60 mgs, or about 30-50 mgs per patient will be preferred. However, any particular range using any of the foregoing recited exemplary doses or any value intermediate between the particular stated ranges is contemplated.

Notwithstanding the stated ranges, it will be understood that, given the parameters and detailed guidance presented herein, further variations in the active or optimal ranges will be encompassed within the present invention. It will thus be understood that lower doses may be more appropriate in combination with certain agents, and that high doses can still be tolerated, particularly given the enhanced safety of the present constructs. The use of human constructs and human effectors renders the present invention even safer for clinical use, further reducing the chances of significant toxicity or side effects in healthy tissues.

The intention of the therapeutic regimens of the present invention is generally to produce significant anti-tumor effects whilst still keeping the dose below the levels associated with unacceptable toxicity. In addition to varying the dose itself, the administration regimen can also be adapted to optimize the treatment strategy. A currently preferred treatment strategy is to administer between about 1-500 mgs, and preferably, between about 10-100 mgs of the antibody, or therapeutic cocktail containing such, about 3 times within about a 7 day period. For example, doses would be given on about day 1, day 3 or 4 and day 6 or 7.

In administering the particular doses themselves, one would preferably provide a pharmaceutically acceptable composition (according to FDA standards of sterility, pyrogenicity, purity and general safety) to the patient systemically. Intravenous injection is generally preferred, and the most preferred method is to employ a continuous infusion over a time period of about 1 or 2 hours or so. Although it is not required to determine such parameters prior to treatment using the present invention, it should be noted that the studies detailed herein result in at least some thrombosis being observed specifically in the blood vessels of a solid tumor within about 12-24 hours of injection, and that the tumor cells themselves begin to die within about 24 to 72 hours. Widespread tumor necrosis is generally observed in the next about 48-96 hours, up to and including greater than 60% necrosis being observed.

Naturally, before wide-spread use, clinical trials will be conducted. The various elements of conducting a clinical trial, including patient treatment and monitoring, will be known to those of skill in the art in light of the present disclosure. The following information is being presented as a general guideline for use in establishing such trials.

Patients chosen for the first treatment studies will have failed to respond to at least one course of conventional therapy, and will have objectively measurable disease as determined by physical examination, laboratory techniques, and/or radiographic procedures. Any chemotherapy should be stopped at least 2 weeks before entry into the study. Where murine monoclonal antibodies or antibody portions are employed, the patients should have no history of allergy to mouse immunoglobulin.

Certain advantages will be found in the use of an indwelling central venous catheter with a triple lumen port. The therapeutics should be filtered, for example, using a 0.22μ filter, and diluted appropriately, such as with saline, to a final volume of 100 ml. Before use, the test sample should also be filtered in a similar manner, and its concentration assessed before and after filtration by determining the $A_{280}$. The expected recovery should be within the range of 87% to 99%, and adjustments for protein loss can then be accounted for.

The constructs may be administered over a period of approximately 4-24 hours, with each patient receiving 2-4 infusions at 2-7 day intervals. Administration can also be performed by a steady rate of infusion over a 7 day period. The infusion given at any dose level should be dependent upon any toxicity observed. Hence, if Grade II toxicity was reached after any single infusion, or at a particular period of time for a steady rate infusion, further doses should be withheld or the steady rate infusion stopped unless toxicity improved. Increasing doses should be administered to groups of patients until approximately 60% of patients showed unacceptable Grade III or IV toxicity in any category. Doses that are ⅔ of this value are defined as the safe dose.

Physical examination, tumor measurements, and laboratory tests should, of course, be performed before treatment and at intervals up to 1 month later. Laboratory tests should include complete blood counts, serum creatinine, creatine kinase, electrolytes, urea, nitrogen, SGOT, bilirubin, albumin, and total serum protein. Serum samples taken up to 60 days after treatment should be evaluated by radioimmunoassay for the presence of the administered construct, and antibodies against any portions thereof. Immunological analyses of sera, using any standard assay such as, for example, an ELISA or RIA, will allow the pharmacokinetics and clearance of the therapeutics to be evaluated.

To evaluate the anti-tumor responses, the patients should be examined at 48 hours to 1 week and again at 30 days after the last infusion. When palpable disease was present, two perpendicular diameters of all masses should be measured daily during treatment, within 1 week after completion of therapy, and at 30 days. To measure nonpalpable disease, serial CT scans could be performed at 1-cm intervals throughout the chest, abdomen, and pelvis at 48 hours to 1 week and again at 30 days. Tissue samples should also be evaluated histologically, and/or by flow cytometry, using biopsies from the disease sites or even blood or fluid samples if appropriate.

Clinical responses may be defined by acceptable measure. For example, a complete response may be defined by the disappearance of all measurable tumor 1 month after treatment. Whereas a partial response may be defined by a 50% or greater reduction of the sum of the products of perpendicular diameters of all evaluable tumor nodules 1 month after treatment, with no tumor sites showing enlargement. Similarly, a mixed response may be defined by a reduction of the product of perpendicular diameters of all measurable lesions by 50% or greater 1 month after treatment, with progression in one or more sites.

In light of results from clinical trials, such as those described above, an even more precise treatment regimen may be formulated. Even so, some variation in dosage may later be necessary depending on the condition of the subject being treated. The physician responsible for administration will, in light of the present disclosure, be able to determine the appropriate dose for the individual subject. Such optimization and adjustment is routinely carried out in the art, and by no means reflects an undue amount of experimentation.

M. Combination Tumor Therapies

The treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the treatment of the invention, its combination with the present invention is contemplated.

Combination therapy for non malignant diseases is also contemplated. A particular example of such is benign prostatic hyperplasia (BPH), which may be treated in combination other treatments currently practiced in the art. For example, targeting of immunotoxins to markers localized within BPH, such as PSA.

In connection solid tumor treatment, the present invention may be used in combination with classical approaches, such as surgery, chemotherapy, radiotherapy, cytokine therapy, anti-angiogenesis and the like. The invention therefore provides combined therapies in which a construct, receptorbody or betabody is used simultaneously with, before, or after surgery or radiation treatment; or is administered to patients with, before, or after conventional chemotherapeutic or radiotherapeutic agents, cytokines, anti-angiogenic agents, apoptosis-inducing agents, targeted immunotoxins or coaguligands or such like. Many examples of suitable therapeutic agents have been described above in connection with the conjugate aspects of the present invention. Any of the agents initially described for use as one part of a therapeutic conjugate may also be used separately, in the combination therapies of the present invention.

In terms of surgery, any surgical intervention may be practiced in combination with the present invention. In connection with radiotherapy, any mechanism for inducing DNA damage locally within tumor cells is contemplated, such as γ-irradiation, X-rays, UV-irradiation, microwaves and even electronic emissions and the like. The directed delivery of radioisotopes to tumor cells is also contemplated, and this may be used in connection with a targeting antibody or other targeting means.

The general use of combinations of substances in cancer treatment is well known. For example, U.S. Pat. No. 5,710,134 (incorporated herein by reference) discloses components that induce necrosis in tumors in combination with non-toxic substances or "prodrugs". The enzymes set free by necrotic processes cleave the non-toxic "prodrug" into the toxic "drug", which leads to tumor cell death. Also, U.S. Pat. No. 5,747,469 (incorporated herein by reference) discloses the combined use of viral vectors encoding p53 and DNA damaging agents. Any such similar approaches can be used with the present invention.

When one or more agents are used in combination with a construct, receptorbody or betabody of the present invention, there is no requirement for the combined results to be additive of the effects observed when each treatment is conducted separately. Although at least additive effects are generally desirable, any increased anti-tumor effect above one of the single therapies would be of benefit. Also, there is no particular requirement for the combined treatment to exhibit synergistic effects, although this is certainly possible and advantageous.

M1. Selection of Second Anti-Cancer Agents

The "primary therapeutic agent" of the present invention, as used herein, is a construct, receptorbody or betabody or conjugate thereof. The "secondary therapeutic agents", as used herein, are second, distinct therapeutic agents or anti-cancer agents, i.e., therapeutic agents or anti-cancer agents "other than" the primary therapeutic agent. Any secondary therapeutic agent may be used in the combination therapies of the present invention. Also, secondary therapeutic agents or "second anti-cancer agents" may be selected with a view to achieving additive, greater than additive and potentially synergistic effects, according to the following guidance.

To practice combined anti-tumor therapy, one would simply administer to an animal or patient a construct, receptorbody or betabody of the present invention in combination with another, i.e., a second, distinct anti-cancer agent in a manner effective to result in their combined anti-tumor actions within the animal or patient. The agents would therefore be provided in amounts effective and for periods of time effective to result in their combined presence within the tumor or tumor vasculature and their combined actions in the tumor environment. To achieve this goal, the primary therapeutics of the present invention and the second, distinct anti-cancer agents may be administered to the animal substantially simultaneously, either in a single composition, or as two distinct compositions using different administration routes.

Alternatively, a construct, receptorbody or betabody of the present invention may precede, or follow, the second, distinct anti-cancer agent by, e.g., intervals ranging from minutes to weeks. In certain embodiments where the primary therapeutics of the present invention and the second, distinct anti-cancer agents are applied separately to the animal, one would ensure that a significant period of time did not expire between the time of each delivery, such that each agent would still be able to exert an advantageously combined effect on the tumor. In such instances, it is contemplated that one would contact the tumor with both agents within about 5 minutes to about one week of each other and, more preferably, within about 12-72 hours of each other, with a delay time of only about 12-48 hours being most preferred.

The secondary therapeutic agents for separately timed combination therapies may be selected based upon certain criteria, including those discussed below. However, a preference for selecting one or more second, distinct anti-cancer agents for prior or subsequent administration does not preclude their use in substantially simultaneous administration if desired.

Second, distinct anti-cancer agents selected for administration "prior to" the primary therapeutic agents of the present invention, and designed to achieve increased and potentially synergistic effects, include agents that induce the expression of aminophospholipids or anionic phospholipids within the tumor vasculature. For example, agents that stimulate localized calcium production, activate membrane transporters that move PS and other phospholipids to the outer surface of the plasma membrane, injure the tumor endothelium, cause preapoptotic changes and/or induce apoptosis in the tumor endothelium will generally result in increased aminophospholipid and anionic phospholipid expression. Examples of such agents are docetaxel and paclitaxol. The aminophospholipids and anionic phospholipids can then be targeted using a construct, receptorbody or betabody of the invention, thus amplifying the overall therapeutic effect, and also giving increased attack via host effectors (complement, ADCC, antibody-mediated phagocytosis, CDC).

Drugs that have selectivity for angiogenic, remodeling or activated endothelial cells, such as are present in tumor blood vessels, but not in normal resting blood vessels, can also be used to selectively causes exposure of PS and other phospholipids on the surface of tumor endothelial cells. Examples of such agents are combretastatins and docetaxel. This again would lead to increased antibody binding and enhanced initiation of host effector mechanisms.

Second, distinct anti-cancer agents selected for administration "subsequent to" the primary therapeutic agents of the present invention, and designed to achieve increased and potentially synergistic effects, include agents that benefit from the effects of the primary therapeutic agent. The construct, receptorbody or betabody of the present invention will cause tumor destruction. Accordingly, effective second, distinct anti-cancer agents for subsequent administration include anti-angiogenic agents, which inhibit metastasis; agents targeting necrotic tumor cells, such as antibodies specific for intracellular antigens that become accessible from malignant cells in vivo (U.S. Pat. Nos. 5,019,368, 4,861,581 and 5,882,626, each specifically incorporated herein by reference); and chemotherapeutic agents and anti-tumor cell immunoconjugates, which attack any tumor cells that may survive at the periphery.

In some situations, it may be desirable to extend the time period for treatment significantly, where several days (2, 3, 4, 5, 6 or 7), several weeks (1, 2, 3, 4, 5, 6, 7 or 8) or even several months (1, 2, 3, 4, 5, 6, 7 or 8) lapse between the respective administrations. This would be advantageous in circumstances where one treatment was intended to substantially destroy the tumor, such as the primary therapeutic agent of the present invention, and another treatment was intended to prevent micrometastasis or tumor re-growth, such as the administration of an anti-angiogenic agent. Anti-angiogenics should be administered at a careful time after surgery, however, to allow effective wound healing. Anti-angiogenic agents may then be administered for the lifetime of the patient.

It is also envisioned that more than one administration of either the primary therapeutic agent or the second, distinct anti-cancer agent will be utilized. The primary therapeutic agent and the second, distinct anti-cancer agent may be administered interchangeably, on alternate days or weeks; or a sequence of one agent treatment may be given, followed by a sequence of the other treatment. In any event, to achieve tumor regression using a combined therapy, all that is required is to deliver both agents in a combined amount effective to exert an anti-tumor effect, irrespective of the times for administration.

Whether administered substantially simultaneously or sequentially, the construct, receptorbody or betabody and therapeutics of the present invention may be administered in combination with one or more chemotherapeutic agents or drugs. Chemotherapeutic drugs can kill proliferating tumor cells, enhancing the necrotic areas created by the overall treatment. The drugs can thus enhance the thrombotic action of the primary therapeutic agents of the invention.

Most cancer chemotherapeutic drugs are selective for dividing, oxygenated cells. These have advantages in combined therapy as the chemotherapeutic drug acts on different targets from the primary therapeutic agents of the invention, leading to a more complete anti-vascular or anti-tumor effect. For example, chemotherapeutic drugs are selectively active against the rapidly dividing, oxygenated tumor cells in the tumor periphery, whereas the agents of the invention act primarily on vessels or tumor cells in the 'stressed' tumor core, where activating reactive oxygen species are abundant. Anti-angiogenic drugs that are selective for well-oxygenated, angiogenic vessels in the tumor periphery would also be effective in combination, as the agents of the invention act on the relatively hypoxic, quiescent vessels in the tumor core.

By inducing the formation of thrombi in tumor vessels, the primary therapeutic agents of the present invention can also enhance the action of the chemotherapeutic drugs by retaining or trapping the drugs within the tumor. The chemotherapeutics are thus retained within the tumor, while the rest of the drug is cleared from the body. Tumor cells are thus exposed to a higher concentration of drug for a longer period of time. This entrapment of drug within the tumor makes it possible to reduce the dose of drug, making the treatment safer as well as more effective.

Further drugs for combined use in the present invention are those that act on cells that are "sensitized" to the drug by the action of the primary therapeutic agent, such that reduced doses of the second drug are needed to achieve its anti-tumor effect. For example, this could occur where a major component of the second drug's action is exerted on tumor vessels and the agents of the invention sensitize the cells to the drug. The same is true where the primary therapeutic agent of the invention sensitizes tumor cells to a second drug, either directly or through stimulation of cytokine release.

Other suitable second anti-cancer agents for combination therapy are those that further enhance the activity of host effector cells, e.g., by selectively inhibiting the activity of immunosuppressive components of the immune system. Such agents enable the primary therapeutic agents of the invention, which stimulate attack by effector cells as part of their mechanism, to work more aggressively. An example of such an agent is docetaxel.

Although an understanding of the precise mechanism(s) of action of the primary therapeutic agents is not necessary to practice the treatment of the invention, data and reasoned deductions concerning such mechanisms can be used to select particular second anti-cancer agents for combined use in the present invention. The effectiveness of the chosen combination therapy, in turn, supports the original data and proposed mechanisms of action, and also leads to preferred categories of second anti-cancer agents for practicing combination therapy.

Drugs that induce apoptosis are preferred for use in the combination therapies. Docetaxel, for example, induces apoptosis and therefore PS exposure by binding to microtubules and disrupting cell mitosis (Hotchkiss et al., 2002). Treatment of endothelial cells, which line tumor blood vessels, and tumor cells with docetaxel at subclinical concentrations is herein shown to induce PS expression at the cell surface, as demonstrated by strong binding of the 3G4 antibody in vitro.

The present inventors have also determined that the anti-tumor effects of the invention include Fc domain-mediated augmentation of immune effector functions, as shown by increased antibody-mediated phagocytosis. Therefore, other Fc domain-mediated functions will occur, such as ADCC, CDC, stimulation of cytokine production, and such mechanisms in combination. This is also relevant to docetaxel, as other studies have shown that the treatment of breast cancer patients with docetaxel leads to increases in serum IFN-γ, IL-2, IL-6 and GM-CSF cytokine levels, augmenting the anti-tumor immune responses in these patients by enhancing the activity of natural killer (NK) and lymphokine activated killer (LAK) cells (Tsavaris et al., 2002).

Therefore, the inventors reasoned that docetaxel will both induce PS expression and binding of the administered construct, receptorbody or betabody, and also enhances the activities of immune effectors, which mediate anti-tumor effects. Based upon the foregoing considerations, the inventors have shown that combination of the 3G4 antibody with docetaxel was significantly superior to either docetaxel or 3G4 alone in mice bearing orthotopic MDA-MB-435 human breast cancer xenografts (Example XX).

Accordingly, docetaxel and other chemotherapeutic agents that induce apoptosis are preferred agents for use in the combination treatments of the present invention. Combinations of a construct, receptorbody or betabody with chemotherapeutics or drugs that induce apoptosis, such as docetaxel, should synergistically attack tumor vasculature endothelial cell and tumor cell compartments, leading to not only significantly enhanced treatment efficacy but also lower toxicity. These combinations are contemplated for use in breast cancer treatment, particularly the combination of metronomic chemotherapy using docetaxel with an antibody of the present invention.

M2. Endotoxin

Endotoxin and detoxified endotoxin derivatives may be used in the combination treatment, preferably at low doses (PCT Publication No. WO 03/028840, specifically incorporated herein by reference). Various detoxified endotoxins are available, which are preferred for use in animals and particularly for use in humans. Detoxified and refined endotoxins, and combinations thereof, are described in U.S. Pat. Nos. 4,866,034; 4,435,386; 4,505,899; 4,436,727; 4,436,728; 4,505,900, each specifically incorporated herein by reference.

The non-toxic derivative monophosphoryl lipid A (MPL) is one example of a detoxified endotoxin that may be used in the present invention. MPL is known to be safe for humans; clinical trials using MPL as an adjuvant have shown 100 $\mu g/m^2$ to be safe for human use, even on an outpatient basis.

M3. Cytokines

Cytokine therapy has proven to be an effective partner for combined therapeutic regimens. Various cytokines may be employed in the combined approaches of the present invention. Examples of cytokines include IL-1α IL-1β, IL-2, IL-3, IL-4, IL-5, IL-6, IL-7, IL-8, IL-9, IL-10, IL-11, IL-12, IL-13, TGF-β, GM-CSF, M-CSF, G-CSF, TNFα, TNFβ, LAF, TCGF, BCGF, TRF, BAF, BDG, MP, LIF, OSM, TMF, PDGF, IFN-α, IFN-β, IFN-γ. Cytokines are administered according to standard regimens, consistent with clinical indications such as the condition of the patient and relative toxicity of the cytokine. Uteroglobins may also be used to prevent or inhibit metastases (U.S. Pat. No. 5,696,092; incorporated herein by reference).

M4. TNFα and Inducers of TNFα

TNFα and inducers of TNFα may also be used in combination with the present invention. TNFα increases vascular permeability, and is therefore useful in facilitating the penetration of anti-cancer agents into the tumor. Although localization is by no means a problem when targeting PS and anionic phospholipids, as in the present invention, the combined use of TNFα can facilitate access of other chemotherapeutics and immunoconjugates to the tumor, and even increase binding of the antibodies of the invention to far distant tumor cells.

Low levels of endotoxin, Rac1 antagonists, such as an attenuated or engineered adenovirus, DMXAA (and FAA), CM11 and thalidomide may also be used. Rac1 antagonists may be used in the combined treatment of the present invention, as about 5000 DNA particles per cell cause TNF upregulation independent of CD14 (Sanlioglu et al., 2001). CM101, thalidomide and DMXAA can also be used in combination herewith, at standard or reduced doses.

M5. Chemotherapeutics

Irrespective of the underlying mechanism(s), a variety of chemotherapeutic agents may be used in the combined treatment methods disclosed herein. Chemotherapeutic agents contemplated for combined use include, e.g., tamoxifen, taxol, vinblastine, etoposide (VP-16), adriamycin, 5-fluorouracil (5FU), camptothecin, actinomycin-D, mitomycin C, combretastatin(s), more particularly docetaxel (taxotere), cisplatin (CDDP), cyclophosphamide, doxorubicin, methotrexate, paclitaxel and vincristine, and derivatives and prodrugs thereof.

As will be understood by those of ordinary skill in the art, appropriate doses of chemotherapeutic agents include those already employed in clinical therapies wherein the chemotherapeutics are administered alone or in combination with other chemotherapeutics. However, lower doses are now possible due to the advantages provided by the present invention. By way of example only, agents such as cisplatin, and other DNA alkylating may be used. Cisplatin has been widely used to treat cancer, with efficacious doses used in clinical applications of 20 $mg/m^2$ for 5 days every three weeks for a total of three courses. Cisplatin is not absorbed orally and must therefore be delivered via injection intravenously, subcutaneously, intratumorally or intraperitoneally.

Further useful agents include compounds that interfere with DNA replication, mitosis, chromosomal segregation and/or tubulin activity. Such chemotherapeutic compounds include adriamycin, also known as doxorubicin, etoposide, verapamil, podophyllotoxin(s), combretastatin(s) and the like. Widely used in a clinical setting for the treatment of neoplasms, these compounds are administered through bolus injections intravenously at doses ranging from 25-75 $mg/m^2$ at 21 day intervals for adriamycin, to 35-50 $mg/m^2$ for etoposide intravenously or double the intravenous dose orally.

Agents that disrupt the synthesis and fidelity of polynucleotide precursors may also be used. Particularly useful are agents that have undergone extensive testing and are readily available. As such, agents such as 5-fluorouracil (5-FU) are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Exemplary chemotherapeutic agents that are useful in connection with combined therapy are listed in Table D. Each of the agents listed therein are exemplary and by no means limiting. The skilled artisan is directed to "Remington's Pharmaceutical Sciences" 15th Edition, chapter 33, in particular pages 624-652. Some variation in dosage will necessarily occur depending on the condition of the subject being treated. The physician responsible for administration will be able to determine the appropriate dose for the individual subject.

TABLE D

| CHEMOTHERAPEUTIC AGENTS USEFUL IN NEOPLASTIC DISEASE | | | |
|---|---|---|---|
| CLASS | TYPE OF AGENT | NONPROPRIETARY NAMES (OTHER NAMES) | DISEASE |
| Alkylating Agents | Nitrogen Mustards | Mechlorethamine ($HN_2$) | Hodgkin's disease, non-Hodgkin's lymphomas |
| | | Cyclophosphamide<br>Ifosfamide | Acute and chronic lymphocytic leukemias, Hodgkin's disease, non-Hodgkin's lymphomas, multiple myeloma, neuroblastoma, breast, ovary, lung, Wilms' tumor, cervix, testis, soft-tissue sarcomas |
| | | Melphalan (L-sarcolysin) | Multiple myeloma, breast, ovary |
| | | Chlorambucil | Chronic lymphocytic leukemia, primary macroglobulinemia, Hodgkin's disease, non-Hodgkin's lymphomas |
| | Ethylenimenes and Methylmelamines | Hexamethylmelamine | Ovary |
| | | Thiotepa | Bladder, breast, ovary |
| | Alkyl Sulfonates | Busulfan | Chronic granulocytic leukemia |
| | Nitrosoureas | Carmustine (BCNU) | Hodgkin's disease, non-Hodgkin's lymphomas, primary brain tumors, multiple myeloma, malignant melanoma |
| | | Lomustine (CCNU) | Hodgkin's disease, non-Hodgkin's lymphomas, primary brain tumors, small-cell lung |
| | | Semustine (methyl-CCNU) | Primary brain tumors, stomach, colon |
| | | Streptozocin (streptozotocin) | Malignant pancreatic insulinoma, malignant carcinoid |
| | Triazines | Dacarbazine (DTIC; dimethyltriazenoimidazolecarboxamide) | Malignant melanoma, Hodgkin's disease, soft-tissue sarcomas |
| Antimetabolites | Folic Acid Analogs | Methotrexate (amethopterin) | Acute lymphocytic leukemia, choriocarcinoma, mycosis fungoides, breast, head and neck, lung, osteogenic sarcoma |
| | Pyrimidine Analogs | Fluouracil (5-fluorouracil; 5-FU)<br>Floxuridine (fluorodeoxyuridine; FUdR) | Breast, colon, stomach, pancreas, ovary, head and neck, urinary bladder, premalignant skin lesions (topical) |
| | | Cytarabine (cytosine arabinoside) | Acute granulocytic and acute lymphocytic leukemias |
| | | Mercaptopurine (6-mercaptopurine; 6-MP) | Acute lymphocytic, acute granulocytic and chronic granulocytic leukemias |
| | Purine Analogs and Related Inhibitors | Thioguanine (6-thioguanine; TG) | Acute granulocytic, acute lymphocytic and chronic granulocytic leukemias |
| | | Pentostatin (2-deoxycoformycin) | Hairy cell leukemia, mycosis fungoides, chronic lymphocytic leukemia |
| Natural Products | Vinca Alkaloids | Vinblastine (VLB) | Hodgkin's disease, non-Hodgkin's lymphomas, breast, testis |
| | | Vincristine | Acute lymphocytic leukemia, neuroblastoma, Wilms' tumor, rhabdomyosarcoma, Hodgkin's disease, non-Hodgkin's lymphomas, small-cell lung |
| | Epipodophyllotoxins | Etoposide<br>Tertiposide | Testis, small-cell lung and other lung, breast, Hodgkin's disease, non-Hodgkin's lymphomas, acute granulocytic leukemia, Kaposi's sarcoma |
| | Antibiotics | Dactinomycin (actinomycin D) | Choriocarcinoma, Wilms' tumor, rhabdomyosarcoma, testis, Kaposi's sarcoma |
| | | Daunorubicin (daunomycin; rubidomycin) | Acute granulocytic and acute lymphocytic leukemias |
| | | Doxorubicin | Soft-tissue, osteogenic and other sarcomas; Hodgkin's disease, non-Hodgkin's lymphomas, acute leukemias, breast, genitourinary, thyroid, lung, stomach, neuroblastoma |
| | | Bleomycin | Testis, head and neck, skin, esophagus, lung and genitourinary tract; Hodgkin's disease, non-Hodgkin's lymphomas |

TABLE D-continued

CHEMOTHERAPEUTIC AGENTS USEFUL IN NEOPLASTIC DISEASE

| CLASS | TYPE OF AGENT | NONPROPRIETARY NAMES (OTHER NAMES) | DISEASE |
|---|---|---|---|
| | | Plicamycin (mithramycin) | Testis, malignant hypercalcemia |
| | | Mitomycin (mitomycin C) | Stomach, cervix, colon, breast, pancreas, bladder, head and neck |
| | Enzymes | L-Asparaginase | Acute lymphocytic leukemia |
| | Biological Response Modifiers | Interferon alfa | Hairy cell leukemia., Kaposi's sarcoma, melanoma, carcinoid, renal cell, ovary, bladder, non-Hodgkin's lymphomas, mycosis fungoides, multiple myeloma, chronic granulocytic leukemia |
| Miscellaneous Agents | Platinum Coordination Complexes | Cisplatin (cis-DDP) Carboplatin | Testis, ovary, bladder, head and neck, lung, thyroid, cervix, endometrium, neuroblastoma, osteogenic sarcoma |
| | Anthracenedione | Mitoxantrone | Acute granulocytic leukemia, breast |
| | Substituted Urea | Hydroxyurea | Chronic granulocytic leukemia, polycythemia vera, essental thrombocytosis, malignant melanoma |
| | Methyl Hydrazine Derivative | Procarbazine (N-methylhydrazine, MIH) | Hodgkin's disease |
| | Adrenocortical Suppressant | Mitotane (o, p'-DDD) | Adrenal cortex |
| | | Aminoglutethimide | Breast |
| Hormones and Antagonists | Adrenocorticosteroids | Prednisone (several other equivalent preparations available) | Acute and chronic lymphocytic leukemias, non-Hodgkin's lymphomas, Hodgkin's disease, breast |
| | Progestins | Hydroxyprogesterone caproate Medroxyprogesterone acetate Megestrol acetate | Endometrium, breast |
| | Estrogens | Diethylstilbestrol Ethinyl estradiol (other preparations available) | Breast, prostate |
| | Antiestrogen | Tamoxifen | Breast |
| | Androgens | Testosterone propionate Fluoxymesterone (other preparations available) | Breast |
| | Antiandrogen | Flutamide | Prostate |
| | Gonadotropin-releasing hormone analog | Leuprolide | Prostate |

M6. Anti-Angiogenics

The term "angiogenesis" refers to the generation of new blood vessels, generally into a tissue or organ. Under normal physiological conditions, humans or animals undergo angiogenesis only in specific restricted situations. For example, angiogenesis is normally observed in wound healing, fetal and embryonic development and formation of the corpus luteum, endometrium and placenta. New evidence, however, shows that angiogenesis is important in certain normal situations, such as in adrenal tissue, prostate and ovary. The therapeutic agents of the present invention, in which anti-angiogenesis is not the only mode of action, thus have advantages over prominent anti-angiogenic therapies, such as antibody A4.6.1 (Brem, 1998; Baca et al., 1997; Presta et al., 1997), in that desirable or "physiological" angiogenesis will not be inhibited when using the present invention.

Uncontrolled (persistent and/or unregulated) angiogenesis is related to various disease states, and occurs during tumor development and metastasis. Both controlled and uncontrolled angiogenesis are thought to proceed in a similar manner. Endothelial cells and pericytes, surrounded by a basement membrane, form capillary blood vessels. Angiogenesis begins with the erosion of the basement membrane by enzymes released by endothelial cells and leukocytes. The endothelial cells, which line the lumen of blood vessels, then protrude through the basement membrane. Angiogenic stimulants induce the endothelial cells to migrate through the eroded basement membrane. The migrating cells form a "sprout" off the parent blood vessel, where the endothelial cells undergo mitosis and proliferate. The endothelial sprouts merge with each other to form capillary loops, creating the new blood vessel.

Despite the new evidence that angiogenesis is required in some normal tissues, anti-angiogenic therapies are still important in the treatment of tumors and other diseases. Anti-angiogenic therapies are therefore intended for use in the combination treatments of the present invention. The combination of a low, relatively frequent dose of a therapeutic agent of the present invention in combination with an agent that inhibits angiogenesis is particularly contemplated. Exemplary anti-angiogenic agents that are useful in connection with combined therapy are listed above (in connection with immunoconjugates). Any one or more of such agents, including those in Table B, may be used in combination therapy with the invention. Angiostatin, endostatin, vasculostatin, canstatin and maspin are currently preferred.

Many known anti-cancer agents also have an anti-angiogenic effect as part of their mechanism of action. These agents, as exemplified by those in Table E, are particularly contemplated for use in the combination therapy aspects of the present invention (they may also be conjugated to a construct, receptorbody or betabody of the invention, as described above).

TABLE E

| Anti-Cancer Agents with Anti-Angiogenic Activity | |
|---|---|
| Class or Type of Agent | Examples |
| Alkylators | Cyclophosphamide, edelfosine, estramustine, melphalan |
| Antimetabolites | Fluorouracil, methotrexate, mercaptopurine, UFT, tegafur, uracil, cytarabine |
| Anti-Tumor Antibiotics | Bleomycin, daunorubicin, doxorubicin, epirubicin, mitomycin, mitoxantrone |
| Topoisomerase Inhibitors | Camptothecin, irinotecan, etoposide, topotecan |
| Taxanes | Docetaxel, paclitxael |
| Vinca Alkaloids | Vinblastine, vincristine |
| Miscellaneous | Cisplatin, octreotide |

In addition, the antibody LM609 against the $\alpha_v\beta_3$ integrin also induces tumor regressions and may be used in combination therapies. Integrin $\alpha_v\beta_3$ antagonists, such as LM609, induce apoptosis of angiogenic endothelial cells leaving the quiescent blood vessels unaffected. LM609 or other $\alpha_v\beta_3$ antagonists may also work by inhibiting the interaction of $\alpha_v\beta_3$ and MMP-2, a proteolytic enzyme thought to play an important role in migration of endothelial cells and fibroblasts.

Apoptosis of the angiogenic endothelium by LM609 may have a cascade effect on the rest of the vascular network. Inhibiting the tumor vascular network from completely responding to the tumor's signal to expand may, in fact, initiate the partial or full collapse of the network resulting in tumor cell death and loss of tumor volume. It is possible that endostatin and angiostatin function in a similar fashion. The fact that LM609 does not affect quiescent vessels but is able to cause tumor regressions suggests strongly that not all blood vessels in a tumor need to be targeted for treatment in order to obtain an anti-tumor effect.

Antibodies to angiogenin may also be employed, as described in U.S. Pat. No. 5,520,914, specifically incorporated herein by reference. As FGF is connected with angiogenesis, FGF inhibitors may also be used. Certain examples are the compounds having N-acetylglucosamine alternating in sequence with 2-O-sulfated uronic acid as their major repeating units, including glycosaminoglycans, such as archaran sulfate. Such compounds are described in U.S. Pat. No. 6,028,061, specifically incorporated herein by reference, and may be used in combination herewith.

M7. VEGF Inhibitors

VEGF is a multifunctional cytokine that is induced by hypoxia and oncogenic mutations. VEGF is a primary stimulant of the development and maintenance of a vascular network in embryogenesis. It functions as a potent permeability-inducing agent, an endothelial cell chemotactic agent, an endothelial survival factor, and endothelial cell proliferation factor. Its activity is required for normal embryonic development, as targeted disruption of one or both alleles of VEGF results in embryonic lethality.

The use of one or more VEGF inhibition methods is a preferred aspect of the combination therapies of the present invention. The recognition of VEGF as a primary stimulus of angiogenesis in pathological conditions has led to various methods to block VEGF activity. Any of the VEGF inhibitors developed may now be advantageously employed herewith. Accordingly, any one or more of the following neutralizing anti-VEGF antibodies, soluble receptor constructs, antisense strategies, RNA aptamers and tyrosine kinase inhibitors designed to interfere with VEGF signaling may thus be used.

Suitable agents include neutralizing antibodies (Kim et al., 1992; Presta et al., 1997; Sioussat et al., 1993; Kondo et al., 1993; Asano et al., 1995), soluble receptor constructs (Kendall and Thomas, 1993; Aiello et al., 1995; Lin et al., 1998; Millauer et al., 1996), tyrosine kinase inhibitors (Siemeister et al., 1998), antisense strategies, RNA aptamers and ribozymes against VEGF or VEGF receptors (Saleh et al., 1996; Cheng et al., 1996). Variants of VEGF with antagonistic properties may also be employed, as described in WO 98/16551. Each of the foregoing references are specifically incorporated herein by reference.

Blocking antibodies against VEGF will be preferred in certain embodiments, particularly for simplicity. Monoclonal antibodies against VEGF have been shown to inhibit human tumor xenograft growth and ascites formation in mice (Kim et al., 1993; Mesiano et al., 1998; Luo et al., 1998a; 1998b; Borgstrom et al., 1996; 1998; each incorporated herein by reference). The antibody A4.6.1 is a high affinity anti-VEGF antibody capable of blocking VEGF binding to both VEGFR1 and VEGFR2 (Kim et al., 1992; Wiesmann et al., 1997; Muller et al., 1998; Keyt et al., 1996; each incorporated herein by reference). A4.6.1 has recently been humanized by monovalent phage display techniques and is currently in Phase I clinical trials as an anti-cancer agent (Brem, 1998; Baca et al., 1997; Presta et al., 1997; each incorporated herein by reference).

Alanine scanning mutagenesis and X-ray crystallography of VEGF bound by the Fab fragment of A4.6.1 showed that the epitope on VEGF that A4.6.1 binds is centered around amino acids 89-94. This structural data demonstrates that A4.6.1 competitively inhibits VEGF from binding to VEGFR2, but inhibits VEGF from binding to VEGFR1 most likely by steric hindrance (Muller et al., 1998; Keyt et al., 1996; each incorporated herein by reference)

A4.6.1 may be used in combination with the present invention. However, a new antibody termed 2C3 (4545) is currently preferred, which selectively blocks the interaction of VEGF with only one of the two VEGF receptors. 2C3 inhibits VEGF-mediated growth of endothelial cells, has potent anti-tumor activity and selectively blocks the interaction of VEGF with VEGFR2 (KDR/Flk-1), but not VEGFR1 (FLT-1). In contrast to A4.6.1, 2C3 allows specific inhibition of VEGFR2-induced angiogenesis, without concomitant inhibition of macrophage chemotaxis (mediated by VEGFR1), and is thus contemplated to be a safer therapeutic. U.S. Pat. Nos. 6,342,219, 6,342,221, 6,416,758 and 6,416,758, are specifically incorporated herein by reference for the purposes of even further describing the 2C3 antibody and its uses in anti-angiogenic therapy and VEGF inhibition.

M8. Apoptosis-Inducing Agents

The therapeutic agents of the present invention are also preferably combined with treatment methods that induce apoptosis in any cells within the tumor, including tumor cells and tumor vascular endothelial cells. Exemplary agents that induce apoptosis are listed above (in connection with immunoconjugates). Any one or more of such apoptosis-inducing agents may be used in the combination therapies of the present invention, without being linked to an antibody of the invention.

Many known anti-cancer agents also have an apoptosis-inducing effect as part of their mechanism of action. These agents, as exemplified by those in Table F, are particularly contemplated for use in the combination therapy aspects of the present invention (they may also be conjugated to an antibody of the invention, as described above).

TABLE F

| Anti-Cancer Agents that Induce Apoptosis | |
|---|---|
| Class or Type of Agent | Examples |
| Antimetabolites | Cytarabine, fludarabine, 5-fluoro-29-deoxyuridine, gemcitabine, hydroxyurea, methotrexate |
| DNA Cross-Linking Agents | Chlorambucil, cisplatin, cyclophosphamide, nitrogen mustard |
| Intercalating Agents | Adriamycin (doxorubicin), mitixantrone |
| Topoisomerase II Poisons | Etoposide, teniposide |
| Microtubule-Directed Agents | Colcemid, colchicine, docetaxel, vincristine |
| Kinase Inhibitors | Flavopiridol, staurosporine, STI571 (CPG 57148B), UCN-01 (7-hydroxystaurosporine) |
| Farnesyl Transferase Inhibitors | L-739749, L-744832 |
| Hormones | Glucocorticoids, fenretinide |
| DNA Fragmenting Agents | Bleomycin |
| Hormone Antagonists | Tamoxifen, finasteride, LHRH antagonists |
| Biologicals | TNF-α, TRAIL, anti-CD20 |
| Protein Synthesis Inhibitors | L-asparaginase, cycloheximide, puromycin, diphtheria toxin |
| Topoisomerase II Poisons | Camptothecin, toptecan |

M9. Immunotoxins and Coaguligands

The present invention may also be used in combination with other immunotoxins or coaguligands in which the targeting portion is directed to a marker of tumor cells, tumor vasculature or tumor stroma. Any targeting agent for use in targeting to a tumor cell, tumor vasculature or tumor stroma may be used in these embodiments. In the immunotoxins, the attached agents include anti-cellular or cytotoxic agents, cytokines, radiotherapeutic agents, anti-angiogenic agents, apoptosis-inducing agents and anti-tubulin drugs. In the coaguligands, the attached agents are coagulants. U.S. Pat. Nos. 5,855,866, 5,965,132, 6,261,535, 6,051,230, 6,451,312 (immunotoxins), U.S. Pat. Nos. 6,093,399, 6,004,555, 5,877,289, and 6,036,955 (coaguligands) are specifically incorporated herein by reference to exemplify such constructs.

M10. ADEPT and Prodrug Therapy

A construct, receptorbody or betabody of the present invention may also be used in conjunction with prodrugs, wherein the construct, receptorbody or betabody is operatively associated with a prodrug-activating component, such as a prodrug-activating enzyme, which converts a prodrug to the more active form only upon contact with the antibody. This technology is generally termed "ADEPT", and is described in, e.g., WO 95/13095; WO 97/26918, WO 97/24143, and U.S. Pat. Nos. 4,975,278 and 5,658,568, each specifically incorporated herein by reference.

The term "prodrug", as used herein, refers to a precursor or derivative form of a biologically or pharmaceutically active substance that exerts reduced cytotoxic or otherwise anticellular effects on targets cells, including tumor vascular endothelial cells, in comparison to the parent drug upon which it is based. Preferably, the prodrug or precursor form exerts significantly reduced, or more preferably, negligible, cytotoxic or anticellular effects in comparison to the "native" or parent form. "Prodrugs" are capable of being activated or converted to yield the more active, parent form of the drug.

The technical capability to make and use prodrugs exists within the skill of the ordinary artisan. Willman et al. (1986) and Stella et al. (1985) are each specifically incorporated herein by reference for purposes of further supplementing the description and teaching concerning how to make and use various prodrugs. Exemplary prodrug constructs that may be used in the context of the present invention include, but are not limited to, phosphate-containing prodrugs (U.S. Pat. No.

4,975,278), thiophosphate-containing prodrugs, sulfate-containing prodrugs, peptide-based prodrugs (U.S. Pat. Nos. 5,660,829; 5,587,161; 5,405,990; WO 97/07118), D-amino acid-modified prodrugs, glycosylated prodrugs (U.S. Pat. Nos. 5,561,119; 5,646,298; 4,904,768, 5,041,424), β-lactam-containing prodrugs, optionally substituted phenoxyacetamide-containing prodrugs (U.S. Pat. No. 4,975,278), optionally substituted phenylacetamide-containing prodrugs, and even 5-fluorocytosine (U.S. Pat. No. 4,975,278) and 5-fluorouridine prodrugs and the like, wherein each of the patents are specifically incorporated herein by reference.

The type of therapeutic agent or cytotoxic drug that can be used in prodrug form is virtually limitless. The more cytotoxic agents will be preferred for such a form of delivery, over, e.g., the delivery of coagulants, which are less preferred for use as prodrugs. All that is required in forming the prodrug is to design the construct so that the prodrug is substantially inactive and the "released" or activated drug has substantial, or at least sufficient, activity for the intended purpose.

Various improvements on the original prodrugs are also known and contemplated for use herewith, as disclosed in WO 95/03830; EP 751,144 (anthracyclines); WO 97/07097 (cyclopropylindoles); and WO 96/20169. For example, prodrugs with reduced Km are described in U.S. Pat. No. 5,621,002, specifically incorporated herein by reference, which may be used in the context of the present invention. Prodrug therapy that be conducted intracellularly is also known, as exemplified by WO 96/03151, specifically incorporated herein by reference, and can be practiced herewith.

For use in ADEPT, the agent that activates or converts the prodrug into the more active drug is operatively attached to an antibody of the invention. The antibody thus localizes the prodrug converting capability within the angiogenic or tumor site, so that active drug is only produced in such regions and not in circulation or in healthy tissues.

Enzymes that may be attached to the antibodies of the invention to function in prodrug activation include, but are not limited to, alkaline phosphatase for use in combination with phosphate-containing prodrugs (U.S. Pat. No. 4,975,278); arylsulfatase for use in combination with sulfate-containing prodrugs (U.S. Pat. No. 5,270,196); peptidases and proteases, such as serratia protease, thermolysin, subtilisin, carboxypeptidase (U.S. Pat. Nos. 5,660,829; 5,587,161; 5,405,990) and cathepsins (including cathepsin B and L), for use in combination with peptide-based prodrugs; D-alanylcarboxypeptidases for use in combination with D-amino acid-modified prodrugs; carbohydrate-cleaving enzymes such as β-galactosidase and neuraminidase for use in combination with glycosylated prodrugs (U.S. Pat. Nos. 5,561,119; 5,646,298); β-lactamase for use in combination with β-lactam-containing prodrugs; penicillin amidases, such as penicillin V amidase (U.S. Pat. No. 4,975,278) or penicillin G amidase, for use in combination with drugs derivatized at their amino nitrogens with phenoxyacetamide or phenylacetamide groups; and cytosine deaminase (U.S. Pat. Nos. 5,338,678; 5,545,548) for use in combination with 5-fluorocytosine-based prodrugs (U.S. Pat. No. 4,975,278), wherein each of the patents are specifically incorporated herein by reference.

N. Antibody-Coated Liposomes and Therapeutics

Liposomal formulations are often used in therapeutics and pharmaceuticals. However, the biodistribution of liposomes in initial studies meant that such formulations were not widely applicable for use in humans. Liposomes are rapidly taken up by the phagocytic cells of the reticuloendothelial system (RES), including the circulating mononuclear phagocytic cells and those located in the liver and spleen. Thus, the blood circulation half-lives can be as short as a few minutes.

The technology of "stealth or stealthed" liposomes and formulations was thus developed, which allows liposomes to evade uptake by the RES and circulate for longer (Hristova and Needham, 1993). A preferred agent for use in stealthing liposomes is polyethylene glycol (PEG), and the resultant liposomes are also termed PEGylated liposomes. Other stealthing agents include poly(2-methyl-2-oxazoline) and poly(2-ethyl-2-oxazoline) conjugates (Woodle et al., 1994). A range of improved stealthed liposomes are described in U.S. Pat. No. 6,284,267, specifically incorporated herein by reference, which may be used in combination with the present invention.

Liposomes smaller in diameter than the average diameter of the fenestrae in capillaries leak out from the circulation. The average diameter of the fenestrae in rapidly growing tumors is larger than in normal tissues and therefore liposomes smaller than about 100 nm in diameter migrate into tumors. Stealth liposomes have thus been proposed for use in delivering cytotoxic agents to tumors in cancer patients. A range of drugs have been incorporated into stealth liposomes, including cisplatin (Rosenthal et al., 2002), TNFα (Kim et al., 2002), doxorubicin (Symon et al., 1999) and adriamycin (Singh et al., 1999), each reference being specifically incorporated herein by reference. However, recent reports have indicated unexpected low efficacy of stealth liposomal doxorubicin and vinorelbine in the treatment of metastatic breast cancer (Rimassa et al., 2003).

The present invention provides improved stealthed liposome formulations, overcoming various of the drawbacks in the art, in which the stealthed liposomes are functionally associated or "coated" with a construct, receptorbody or betabody of the invention. A divalent construct is not required in these aspects of the invention.

Any stealthed liposome may form the basis of the new liposomal formulations, and preferably a PEGylated liposome will be employed. The stealthed liposomes are "coated", i.e., operatively or functionally associated with a construct, receptorbody or betabody. The operative or functional association is made such that the construct, receptorbody or betabody retains the ability to specifically bind to the target PS or anionic phospholipid, thereby delivering or targeting the stealthed liposome and any contents thereof to PS-positive cells, such as tumor cells and tumor vascular endothelial cells.

The coated stealthed liposomes of the invention may be used alone. Preferably, however, such liposomes will also contain one or more second therapeutic agents, such as anticancer or chemotherapeutic agents (the first therapeutic agent being the antibody itself). The second therapeutic agents are generally described as being within the "core" of the liposome. Any one or more of the second, anti-cancer or chemotherapeutic agents known in the art and/or described herein for conjugation, or for combination therapies, may be used in the antibody-coated stealthed liposomes of the invention. For example, any chemotherapeutic or radiotherapeutic agent, cytokine, anti-angiogenic agent or apoptosis-inducing agent. Currently preferred within the chemotherapeutic agents are anti-tubulin drugs, docetaxel and paclitaxel.

Moreover, the antibody-coated stealthed liposomes of the invention may also be loaded with one or more anti-viral drugs for use in treating viral infections and diseases. As with the anti-cancer agents, any one or more of the second, antiviral drugs known in the art and/or described herein for conjugation to antibodies, or for combination therapies, may be used in the antibody-coated stealthed liposomes of the invention. Cidofovir and AZT are currently preferred examples.

O. Anti-Vascular, Anti-Angiogenic and Other Therapies

The present invention may also be used in the treatment of other diseases in which aberrant vasculature is involved, including diseases and disorders having prothrombotic blood vessels. Although not the only therapeutic mechanism, the construct, receptorbody or betabody of the present invention may also be used to treat animals and patients with aberrant angiogenesis, such as that contributing to a variety of diseases and disorders.

Whether based upon anti-angiogenesis, prothrombotic vasculature or other anti-vascular, mechanisms, the present invention may thus be used to treat prevalent and/or clinically important diseases outside the field of cancer, including arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such disorders, are set forth below.

One prominent disease in which aberrant vasculature and angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint. Various factors, including VEGF, have been shown to be involved in the pathogenesis of rheumatoid arthritis and osteoarthritis.

Another important example of a disease involving aberrant vasculature and angiogenesis is ocular neovascular disease. This disease is characterized by invasion of new blood vessels into the structures of the eye, such as the retina or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization that can be treated according to the present invention include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and comeal graph rejection.

Diseases associated with retinal/choroidal neovascularization that can be treated according to the present invention include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases that can be treated according to the present invention include, but are not limited to, diseases associated with rubeosis (neovascularization of the angle) and diseases caused by the abnormal proliferation of fibrovascular or fibrous tissue including all forms of proliferative vitreoretinopathy, whether or not associated with diabetes.

Chronic inflammation also involves aberrant vasculature and pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with aberrant vasculature and angiogenesis is found in atherosclerosis. The plaques formed within the lumen of blood vessels have been shown to have angiogenic stimulatory activity. There is particular evidence of the pathophysiological significance of angiogenic markers, such as VEGF, in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate. Therapy-resistant hemangiomas exist that cannot be treated with therapeutics currently in use, but are addressed by the invention.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis according to the present invention could be used to induce amenorrhea, to block ovulation or to prevent implantation by the blastula. In wound healing, excessive repair or fibroplasia can be a detrimental side effect of surgical procedures and may be caused or exacerbated by angiogenesis. Adhesions are a frequent complication of surgery and lead to problems such as small bowel obstruction. This can also be treated by the invention.

Each of the foregoing diseases and disorders, along with all types of tumors, are also contemplated for treatment according to the present invention. U.S. Pat. No. 5,712,291 is specifically incorporated herein by reference to further demonstrate the knowledge in the art that once the inhibition of angiogenesis has been shown using a particular agent, the treatment of an extensive range of diseases associated with aberrant angiogenesis using that and like agents can reasonably be carried out. U.S. Pat. No. 6,524,583 is also specifically incorporated herein by reference for similar purposes and to particularly demonstrate that this principle applies to the inhibition of angiogenesis and the treatment of angiogenic diseases using targeted therapeutics.

The invention further provides compositions and methods for use in treating other diseases in which PS or anionic phospholipids play a role. For example, as PS is involved in cell adhesion, inflammatory responses and septic shock, a construct, receptorbody or betabody can be used in the treatment of inflammation and septic shock.

Anionic phospholipids, particularly PS, are also involved in sickle cell anaemia, in particular, as part of the clearance mechanism. A construct, receptorbody or betabody can therefore be used to treat or ameliorate sickle cell anaemia. A construct, receptorbody or betabody of the invention can also be used to treat a parasitic disease and to treat malaria.

P. Anti-Viral Treatment Methods

The present invention further provides a range of constructs, optionally conjugated to anti-viral agents, for use in treating viral infections. The treatment regimens, and particularly the doses, are generally as described above for the cancer treatment aspects of the present invention, which adaptability is an advantage of the invention overall. Although an understanding of the particular mechanism(s) of action is not necessary to practice the anti-viral treatment of the invention, certain of the reasons underlying the viral treatment, as supported by the working examples herein, are as follows.

The most important mechanisms are believed to be connected with viral replication and activation of the host cell. During viral infection, the virus activates the cell during its replication process inside the cell. This process of cell activation is necessary for viral replication, as shown for herpes viruses, hepatitis C and HIV-1. Viral progression activates gene expression, both viral and host. For example, the replication of Pichinde virus and Machupo virus is inhibited by actinomycin D late in the replication cycle, indicating that host cell gene transcription is needed for completion of viral replication.

The activation of the host cell by the virus causes the cell to externalize anionic phospholipids, such PS. In particular, the inventors reason that viral activation causes $Ca^{2+}$ fluxes into the cell, which activate scramblase, externalizing anionic phospholipids, particularly PS. Constructs and conjugates that bind anionic phospholipids, preferably PS, then bind and interfere with the activation process, preventing the virus from being able to replicate properly.

The present examples show that the invention acts late in the process of viral infection, blocking viral maturation or egress. The inventors' studies show that the inhibitory effect of the agents of the invention is widely applicable, as it has been shown to operate on viruses that use different egression mechanisms. For example, the present examples demonstrate block of herpes virus (CMV), which escapes from Golgi-derived exocytotic vesicles, and block of arenavirus (Pichinde virus) and paramyxovirus (RSV), which bud out directly from the plasma membrane.

Virally infected cells externalize anionic phospholipids, particularly PS, which are normally intracellular, i.e., confined to the inner surface of plasma membrane. During escape of the virus, phospholipids redistribute at the site of escape, accommodating membrane bending during viral budding or exocytosis from the plasma membrane, and anionic phospholipids and aminophospholipids are externalized during this process. The constructs and conjugates of the invention can thus bind to the externalized anionic phospholipids, particularly PS, and block the escape of the virus from the infected cell. Binding of the constructs of the invention to virally infected cells is also shown in the present examples.

The constructs and conjugates of the invention may further bind to the externalized anionic phospholipids, particularly PS, and interfere with one or more signaling pathways necessary for viral gene expression and/or replication.

Moreover, enveloped virions themselves likely have anionic phospholipids, such as PS, on their external surface. Since viruses lack a translocase to maintain or restore phospholipid asymmetry, continued exposure of phospholipids such as PS is expected. The constructs and conjugates of the invention may thus cause opsonization, complement binding, phagocytosis by host cells such as macrophages and clearance of free virus particles.

In a further aspect of the invention, viruses likely need anionic phospholipids for infection and/or syncitia formation. The constructs and conjugates of the invention may further block these aspects of the viral life cycle by binding to anionic phospholipids.

According to the foregoing insights, and in light of the present examples, the spectrum of viral treatment for the present invention extends to any virus, whether enveloped or not, DNA or RNA. As the anionic phospholipid- and PS-binding constructs and conjugates of the invention at least in part block viral replication inside the cell, and/or prevent escape of virus from cells, the invention is not limited to the treatment of enveloped viruses alone, nor to any particular virus, which is an important advantage. For example, work published subsequent to the invention reports that annexin V and PS vesicles can inhibit HIV-1 infection of macrophages, but cannot inhibit HIV-1 infection of T cells or inhibit other viruses, such as vesicular stomatitis virus G and amphotropic murine leukemia virus (Callahan et al., 2003).

Naturally, the constructs and conjugates of the invention do act on enveloped viruses, particularly those viruses that have anionic phospholipids, particularly PS, on the outer surface of the envelope, wherein the constructs and conjugates cause viral clearance and/or inhibiting viral entry of target cells.

An important aspect of the present invention is therefore that it is universally applicable, being suitable for the treatment of recombinant, engineered and synthetic viruses, e.g., created as part of bio-terrorism. Indeed, the invention is not limited to the treatment of animals and humans. As the categories of hosts found in the virus taxa include algae, archaea, bacteria, fungi, invertebrates, mycoplasma, plants, protozoa, spiroplasma and vertebrates, the invention can be used to inhibit viral infection and replication in any such setting, including in viruses of agricultural importance. The treatment of viral infection and associated diseases in vertebrates is currently preferred, and any one or more of the viruses in Table H, which infect vertebrate animals, may be inhibited, and the resultant infection treated, using the present invention.

TABLE H

Viruses of Vertebrates

| Family | Genus | Type Species |
|---|---|---|
| Adenoviridae | Mastadenovirus | Human adenovirus 2 |
| | Aviadenovirus | Fowl adenovirus 1 |
| | African Swine Fever-like Viruses | African swine fever virus |
| Arenaviridae | Arenavirus | Lymphocytic choriomeningitis virus |
| | Arterivirus | Equine arteritis virus |
| Astroviridae | Astrovirus | Human astrovirus 1 |
| Birnaviridae | Aquabirnavirus | Infectious pancreatic necrosis virus |
| | Avibirnavirus | Infectious bursal disease virus |
| Bunyaviridae | Bunyavirus | Bunyamwera virus |
| | Hantavirus | Hantaan virus |
| | Nairovirus | Nabrobi sheep disease virus |
| | Phlebovirus | Sandfly fever Sicilian virus |
| Caliciviridae | Calicivirus | Vesicular exanthema of swine virus |
| Circoviridae | Circovirus | Chicken anemia virus |
| Coronaviridae | Coronavirus | Avian infectious bronchitis virus |
| | Torovirus | Berne virus |
| | Deltavirus | Hepatitis delta virus |
| Filoviridae | Filovirus | Marburg virus |
| Flaviviridae | Flavivirus | Yellow fever virus |
| | Pestivirus | Bovine diarrhea virus |
| | Hepatitis C - like viruses | Hepatitis C virus |
| Hepadnaviridae | Orthophepadnavirus | Hepatitis B virus |
| | Avihepadnavirus | Duck hepatitis B virus |
| Herpesviridae Subfamily | | |
| Alphaherpesvirinae | Simplexvirus | Human herpesvirus 1 |
| | Varicellovirus | Human herpesvirus 3 |
| Subfamily: | | |
| Betaherpesvirinae | Cytomegalovirus | Human herpesvirus 5 |
| | Muromegalovirus | Mouse cytomegalovirus 1 |
| Subfamily | | |
| Gammaherpesvirinae | Roseolovirus | Human herpesvirus 6 |
| | Lymphocryptovirus | Human herpesvirus 4 |
| | Rhadinovirus | Ateline herpesvirus 2 |

TABLE H-continued

| Viruses of Vertebrates | | |
|---|---|---|
| Family | Genus | Type Species |
| Iridoviridae | Ranavirus | Frog virus 3 |
| | Lymphocystivirus | Flounder virus |
| | Goldfish virus - like viruses | Goldfish virus 1 |
| Orthomyxoviridae | Influenzavirus A, B | Influenza A virus |
| | Influenzavirus C | Influenza C virus |
| | Thogoto-Like viruses | Thogoto virus |
| Papovaviridae | Polyomavirus | Murine polyomavirus |
| | Papillomavirus | Cottontail rabbit papillomavirus (Shope) |
| Paramyxoviridae Subfamily | | |
| Paramyxovirinae | Parayxovirus | Human parainfluenza virus 1 |
| | Morbillivirus | Measles virus |
| | Rubulavirus | Mumps virus |
| Subfamily | | |
| Pneumovirinae | Pneumovirus | Human respiratory syncytial virus |
| Parvoviridae Subfamily | | |
| Parovirinae | Parvovirus | Mice minute virus |
| | Erythovirus | B19 virus |
| | Dependovirus | Adeno-associated virus 2 |
| Picornaviridae | Enterovirus | Poliovirus 1 |
| | Rhinovirus | Human rhinovirus 1A |
| | Hepatovirus | Hepatitis A virus |
| | Cardiovirus | Encephalomyocarditis virus |
| | Aphthovirus | Foot-and-mouth disease virus O |
| Poxviridae Subfamily | | |
| Chordopoxvirinae | Orthopoxvirus | Vaccinia virus |
| | Parapoxyvirus | Orf virus |
| | Avipoxvirus | Fowlpox virus |
| | Capripoxvirus | Sheeppox virus |
| | Leporipoxvirus | Myxoma virus |
| | Suipoxvirus | Swinepox virus |
| | Molluscipoxvirus | Molluscum contagiosum virus |
| | Yatapoxvirus | Yaba monkey tumor virus |
| Reoviridae | Orthoreovirus | Reovirus 3 |
| | Orbivirus | Bluetongue virus 1 |
| | Rotavirus | Simian rotavirus SA11 |
| | Coltivirus | Colorado tick fever virus |
| | Aquareovirus | Golden shiner virus |
| Retroviridae | Mammalian type B retroviruses | Mouse mammary tumor virus |
| | Mammalian type C retroviruses | Murine leukemia virus |
| | Avian type C retroviruses | Avian leukosis virus |
| | Type D retroviruses | Mason-Pfizer monkey virus |
| | Blv-htlv retroviruses | Bovine leukemia virus |
| | Lentivirus | Human immunodeficiency virus 1 |
| | Spumavirus | Human spumavirus |
| Rhabdoviridae | Vesiculovirus | Vesicular stomatitis Indiana virus |
| | Lyssavirus | Rabies virus |
| | Ephemerovirus | Bovine ephemeral fever |
| Togaviridae | Alphavirus | Sindbis virus |
| | Rubivirus | Rubella virus |

The use of the invention in treating viral infections and associated diseases in mammals is preferred, particularly in terms of valuable or valued animals, such as racehorses and domestic pets, and animals and birds used to directly produce (e.g., meat) or indirectly produce (e.g., milk and eggs) food for human consumption. In addition to human treatment, exemplary embodiments of the invention include the treatment of horses, dogs, cats and the like; the treatment of cows, pigs, boar, sheep, goat, buffalo, bison, llama, deer, elk, and other large animals, as well as their young, including calves and lambs.

The treatment of humans is particularly preferred, whether for naturally occurring viruses or for those created by bioterrorism. In terms of naturally occurring viruses and the resultant diseases, the invention is again unlimited in its applications. Accordingly, any one or more of the viruses in Table J may be inhibited using the present invention, and the resultant infections and diseases thus treated.

TABLE J

| Viral Diseases in Humans | | |
|---|---|---|
| Disease | Virus | Type of Virus |
| AIDS | Human Immunodeficiency Virus (HIV) | Retrovirus |
| Bronchiolitis and viral pneumonia | Respiratory syncytial virus | Paramyxovirus |
| Bronchiolitis | Parainfluenza virus | Paramyxovirus |
| Cervical cancer | Human papilloma virus | Papovavirus |
| Chicken pox | Varicella Zoster virus | Herpesvirus |
| Dengue | Dengue virus | Flavivirus |
| Ebola hemorrhagic fever | Ebola virus | Filovirus |
| Genital Herpes | Herpes Simplex virus-2 | Herpesvirus |
| Hantavirus hemorrhagic fever | Hantavirus | Bunyavirus |
| Hepatitis | Hepatitis A | Picornavirus |
| | Hepatitis B | Hepadavirus |
| | Hepatitis C | Flavivirus |
| | Hepatitis D | Deltavirus |
| | Hepatitis E | Calcivirus |
| Influenza | Influenza viruses A, B and C | Orthomyxovirus |
| Junin Argentinian Hemorrhagic Fever | Junin virus | Arenavirus |
| Lassa hemorrhagic fever | Lassa virus | Arenavirus |
| Machupo hemorrhagic fever | Machupo virus | Arenavirus |
| Measles | Rubeola virus | Paramyxovirus |
| Mononucleosis | Epstein Barr virus | Herpesvirus |
| CMV disease (viral pneumonia, mononucleosis like syndrome) | Cytomegalovirus | Herpesvirus |
| Severe Acute Respiratory Syndrome (SARS) | Human coronavirus | Coronavirus |
| Shingles | Varicella zoster virus | Herpesvirus |
| Smallpox | Variola virus | Poxvirus |
| Yellow fever | Yellow fever virus | Flavivirus |
| West Nile Disease | West Nile virus | |
| Western equine encephalitis | Western EE virus | Togavirus |
| Pneumonia, Hepatitis, acute respiratory disease | Adenovirus | Adenovirus |
| Gastroenteritis | Rotavirus | Rotavirus |
| Encephalitis | Semliki Forest virus | Alphavirus |
| Cowpox | Vaccima virus | Poxvirus |
| Encephalitis | Venezuelan EE | Alphavirus |
| Meningitis, encephalitis, meningoencephalitis | Lymphocytic choriomeningitis | Arenavirus |
| Venezuelan hemorrhagic fever | Guanarito virus | Arenavirus |
| Rift valley fever (hemorrhagic fever, encephalitis) | Rift valley fever virus | Bunyavirus |
| Marburg Hemorrhagic fever | Marburg virus | Filovirus |
| Tick borne encephalitis | Tick borne encephalitis virus (TBEV) | Flavivirus |
| Encephalitis | Hendra virus | Paramyxovirus |
| Encephalitis | Nipah virus | Paramyxovirus |
| Crimean-Congo hemorrhagic fever | Crimean-Congo hemorrhagic fever virus | Bunyavirus |
| Brazilian hemorrhagic fever | Sabia virus | Arenavirus |

The invention is particularly contemplated for use in the treatment of CMV related diseases such as viral pneumonia, mononucleosis like syndrome, and associated congenital malformations (deafness and mental retardation); respiratory diseases, such as those caused by RSV, including bronchiolitis and viral pneumonia, influenza, the common cold and SARS; AIDS; hepatitis; cancers associated with viral infections; mononucleosis; and smallpox.

In other embodiments, the inventors particularly contemplate the inhibition of arenaviruses, which are pathogenic in man. The arenaviruses include the Old World viruses responsible for Lassa fever (Lassa virus) and lymphocytic choriomeningitis (LCMV). Lassa fever is endemic in West Africa, affecting up to 300,000 people annually and causing up to 3000 deaths. Infection with Lassa fever leads to fever and malaise within about 10 days. Abdominal pain, nausea, vomiting and diarrhea are common. Pharyngitis and cough may develop. Neurological symptoms are usually mild. Vascular leak syndromes, such as edema and pleural effusions, are present in more severe cases. Bleeding is seen about one quarter of patients. The disease can cause changes in the cardiovascular system that culminate in shock and death.

Arenaviruses also include and the antigenically-distinct New World viruses responsible for Argentine hemorrhagic fever (Junin virus), Bolivian hemorrhagic fever (Machupo virus) and Venezuelan hemorrhagic fever (Guanarito virus). All of these viruses are on the CDC Category A list of potential bioterrorism weapons.

The doses that are suitable for the anti-tumor embodiments are also suitable for the anti-viral treatments. Similarly, multiple administration may be used for chronic infections, and high doses may be used for acute infections. Any suitable route of administration may be employed, again as disclosed for the cancer treatment aspects, including IV, IM, SC, as an aerosol to lungs or airways and such like.

The therapeutics provided by the invention are valuable agents having broad-spectrum anti-viral activity. In addition to being effective against a large number of potentially lethal viruses, the agents can also be administered after exposure to the virus, even in settings where the exact nature of the virus is not known. Thus, the anti-viral therapeutics of the present invention do not require a prolonged period of time between identification of the pathogen and delivery of the therapy, in marked contrast with the time and expense entailed by the development, production or delivery of specific vaccines.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

Tumor Treatment with Anti-VCAM-1-tTF Coaguligand

The present example shows the specific coagulation of tumor vasculature in vivo that results following the administration of a tumor vasculature-targeted coagulant ("coaguligand") to tumor-bearing animals and the resultant anti-tumor effects. In this coaguligand, an antibody directed to VCAM-1 (vascular endothelial adhesion molecule-1, VCAM-1) is used as a targeting agent to deliver truncated Tissue Factor (tTF), a modified form of a human coagulant, to tumor vasculature.

The MK2.7 hybridoma, secreting a rat $IgG_1$ antibody against murine VCAM-1, was obtained from the American Type Culture Collection (ATCC, Rockville, Md.; ATCC CRL 1909). The R187 hybridoma, secreting a rat $IgG_1$ antibody against murine viral protein p30 gag, was also obtained from the ATCC, and was used as an isotype matched control for the anti-VCAM-1 antibody.

The blood vessels of the major organs and a tumor from mice bearing subcutaneous L540 human Hodgkin's tumors were examined immunohistochemically for VCAM-1 expression using an anti-VCAM-1 antibody. Overall, VCAM-1 expression was observed on 20-30% of total tumor blood vessels stained by the anti-endoglin antibody, MJ 7/18, used as a positive control. Constitutive vascular expression of VCAM-1 was found in heart and lungs in both tumor-bearing and normal animals. Strong stromal staining was observed in testis where VCAM-1 expression was strictly extravascular.

Mice bearing subcutaneous L540 tumors were injected intravenously with anti-VCAM-1 antibody and, two hours later, the mice were exsanguinated. The tumor and normal organs were removed and frozen sections were prepared and examined immunohistochemically to determine the location of the antibody. Anti-VCAM-1 antibody was detected on endothelium of tumor, heart and lung. Staining was specific as no staining of endothelium was observed in the tumor and organs of mice injected with a species isotype matched antibody of irrelevant specificity, R187. No localization of anti-VCAM-1 antibody was found in testis or any normal organ except heart and lung.

An anti-VCAM-1•tTF conjugate or "coaguligand" was prepared using truncated tissue factor (tTF). Intravenous administration of the anti-VCAM-1•tTF coaguligand induces selective thrombosis of tumor blood vessels, as opposed to vessels in normal tissues, in tumor-bearing mice.

The anti-VCAM-1•tTF coaguligand was administered to mice bearing subcutaneous L540 tumors of 0.4 to 0.6 cm in diameter. Before coaguligand injection, tumors were healthy, having a uniform morphology lacking regions of necrosis. The tumors were well vascularized and had a complete absence of spontaneously thrombosed vessels or hemorrhages. Within four hours of coaguligand injection, 40-70% of blood vessels were thrombosed, despite the initial staining of only 20-30% of tumor blood vessels. The thrombosed vessels contained occlusive platelet aggregates, packed erythrocytes and fibrin. In several regions, the blood vessels had ruptured, spilling erythrocytes into the tumor interstitium.

By 24 h after coaguligand injection, the blood vessels were still occluded and extensive hemorrhage had spread throughout the tumor. Tumor cells had separated from one another, had pyknotic nuclei and were undergoing cytolysis. By 72 h, advanced necrosis was evident throughout the tumor. It is likely that the initial coaguligand-induced thrombin deposition results in increased induction of the VCAM-1 target antigen on central vessels, thus amplifying targeting and tumor destruction.

The thrombotic action of anti-VCAM-1•tTF on tumor vessels was antigen specific. None of the control reagents administered at equivalent quantities (tTF alone, anti-VCAM-1 antibody alone, tTF plus anti-VCAM-1 antibody or the control coaguligand of irrelevant specificity) caused thrombosis.

In addition to the thrombosis of tumor blood vessels, this study also shows that intravenous administration of the anti-VCAM-1•tTF coaguligand does not induce thrombosis of blood vessels in normal organs. Despite expression of VCAM-1 on vessels in the heart and lung of normal or L540 tumor-bearing mice, thrombosis did not occur after anti-VCAM-1•tTF coaguligand administration. No signs of thrombosis, tissue damage or altered morphology were seen in 25 mice injected with 5 to 45 μg of coaguligand 4 or 24 h earlier. There was a normal histological appearance of the heart and lung from the same mouse that had major tumor thrombosis. All other major organs (brain, liver, kidney, spleen, pancreas, intestine, testis) also had unaltered morphology.

Frozen sections of organs and tumors from coaguligand-treated mice gave coincident staining patterns when developed with either the anti-TF antibody, 10H10, or an anti-rat IgG antibody and confirmed that the coaguligand had localized to vessels in the heart, lung and tumor. The intensity of staining was equal to that seen when coaguligand was applied directly to the sections at high concentrations followed by development with anti-TF or anti-rat IgG, indicating that saturation of binding had been attained in vivo.

These studies show that binding of coaguligand to VCAM-1 on normal vasculature in heart and lung is not sufficient to induce thrombosis, and that tumor vasculature provides additional factors to support coagulation.

The anti-tumor activity of anti-VCAM-1•tTF coaguligand was determined in SCID mice bearing 0.3-0.4 $cm^3$ L540 tumors. The drug was administered i.v. 3 times at intervals of 4 days. Mean tumor volume of anti-VCAM-1•tTF treated mice was significantly reduced at 21 days of treatment ($P<0.001$) in comparison to all other groups. Nine of a total of 15 mice treated with the specific coaguligand showed more than 50% reduction in tumor volume. This effect was specific since unconjugated tTF, control IgG coaguligand and mixture of free anti-VCAM-1 antibody and tTF did not affect tumor growth.

EXAMPLE II

Phosphatidylserine Expression on Tumor Blood Vessels

To explain the lack of thrombotic effect of anti-VCAM-1•tTF on VCAM-1 positive vasculature in heart and lungs, certain of the inventors developed a concept of differential aminophospholipid and anionic phospholipid, e.g. PS and PE, localization between normal and tumor blood vessels. Specifically, they hypothesized that endothelial cells in normal tissues segregate aminophospholipids and anionic phospholipids, e.g. PS and PE, to the inner surface of the plasma membrane phospholipid bilayer, where PS is unable to participate in thrombotic reactions; whereas endothelial cells in tumors translocate aminophospholipids and anionic phospholipids to the external surface of the plasma membrane, where PS can support the coagulation action of the coaguligand. PS expression on the cell surface allows coagulation because it enables the attachment of coagulation factors to the membrane and coordinates the assembly of coagulation initiation complexes.

The inventors' model of aminophospholipid and anionic phospholipid translocation to the surface of tumor blood vessel endothelial cells, as developed herein, is surprising in that PS expression does not occur after, and does not inevitably trigger, cell death. Aminophospholipid and anionic phospholipid expression at the tumor endothelial cell surface is thus sufficiently stable to allow aminophospholipids and anionic phospholipids, e.g. PS and PE, to serve as targetable entities for therapeutic intervention.

To confirm the hypothesis that tumor blood vessel endothelium expresses PS on the luminal surface of the plasma membrane, the inventors used the following immunohistochemical study to determine the distribution of anti-PS antibody after intravenous injection into L540 tumor bearing mice.

A. Methods

Anti-PS and anti-cardiolipin antibodies, both mouse monoclonal IgM antibodies, were produced and characterized by Rote et al. (1993, incorporated herein by reference) as described in Example IV. The major reactivity of 3SB is with PS, but it also has reactivity with the anionic phospholipid, phosphatidic acid, a relatively minor component of the plasma membrane also tightly segregated to the internal leaflet in normal cells.

L540 tumor-bearing mice were injected i.v. with 20 μg of either anti-PS or anti-cardiolipin mouse IgM antibodies. After 10 min., mice were anesthetized and their blood circulations were perfused with heparinized saline. Tumors and normal tissues were removed and snap-frozen. Serial sections of organs and tumors were stained with either HRP-labeled anti-mouse IgM for detection of anti-PS antibody or with anti-VCAM-1 antibody followed by HRP-labeled anti-rat Ig.

To preserve membrane phospholipids on frozen sections, the following protocol was developed. Animals were perfused with DPBS containing 2.5 mM $Ca^{2+}$. Tissues were mounted on 3-aminopropyltriethoxysilane-coated slides and were stained within 24 h. No organic solvents, formaldehyde or detergents were used for fixation or washing of the slides. Slides were re-hydrated by DPBS containing 2.5 mM $Ca^{2+}$ and 0.2% gelatin. The same solution was also used to wash sections to remove the excess of reagents. Sections were incubated with HRP-labeled anti-mouse IgM for 3.5 h at room temperature to detect anti-PS B. Results This immunohistochemical study showed that anti-PS antibody localized within 10 min. to the majority of tumor blood vessels, including vessels in the central region of the tumor that can lack VCAM-1. Vessels that were positive for VCAM-1 were also positive for PS. Thus, there is coincident expression of PS on VCAM-1-expressing vessels in tumors.

In the in vivo localization studies, none of the vessels in normal organs, including VCAM-1-positive vasculature of heart and lung, were stained, indicating that PS is absent from the external surface of the endothelial cells. In contrast, when sections of normal tissues and tumors were directly stained with anti-PS antibody in vitro, no differences were visible between normal and tumor, endothelial or other cell types, showing that PS is present within these cells but only becomes expressed on the surface of endothelial cells in tumors.

The specificity of PS detection was confirmed by two independent studies. First, a mouse IgM monoclonal antibody directed against a different negatively charged lipid, cardiolipin, did not home to tumor or any organs in vivo. Second, pretreatment of frozen sections with acetone abolished staining with anti-PS antibody, presumably because it extracted the lipids together with the bound anti-PS antibody.

EXAMPLE III

Annexin V Blocks Coaguligand Activity

The present example provides further evidence of the role of surface PS expression in coaguligand activity from studies using the high affinity PS binding ligand, annexin V, to block PS function in vitro and in vivo.

A. Annexin V Blocks Coaguligand Activation of Factor X In Vitro

The ability of Annexin V to affect Factor Xa formation induced by coaguligand was determined by a chromogenic assay. IL-1α-stimulated bEnd.3 cells were incubated with anti-VCAM-•tTF and permeabilized by saponin. Annexin V was added at concentrations ranging from 0.1 to 10 μg/ml and cells were incubated for 30 min. before addition of diluted Proplex T. The amount of Factor Xa generated in the presence or absence of Annexin V was determined. Each treatment was performed in duplicate and repeated at least twice.

The need for surface PS expression in coaguligand action is further indicated by the inventors' finding that annexin V, which binds to PS with high affinity, blocks the ability of anti-VCAM-2•tTF bound to bEnd.3 cells to generate factor Xa in vitro.

Annexin V added to permeabilized cells preincubated with anti-VCAM-1•tTF inhibited the formation of factor Xa in a dose-dependent manner. In the absence of Annexin V, cell-bound coaguligand produced 95 ng of factor Xa per 10,000 cells per 60 min. The addition of increasing amounts of Annexin V (in the μg per ml range) inhibited factor Xa production. At 10 μg per ml, Annexin V inhibited factor Xa production by 58%. No further inhibition was observed by increasing the concentration of Annexin V during the assay, indicating that annexin V saturated all available binding sites at 10 μg per ml.

B. Annexin V Blocks Coaguligand Activity In Vivo

The ability of Annexin V to inhibit coaguligand-induced thrombosis in vivo was examined in L540 Hodgkin-bearing SCID mice. Tumors were grown in mice and two mice per group (tumor size 0.5 cm in diameter) were injected intravenously via the tail vein with one of the following reagents: a) saline; b) 100 μg of Annexin V; c) 40 μg of anti-VCAM-1•tTF; d) 100 μg of Annexin V followed 2 hours later by 40 μg of anti-VCAM-1•tTF.

Four hours after the last injection mice were anesthetized and perfused with heparinized saline. Tumors were removed, fixed with 4% formalin, paraffin-embedded and stained with hematoxylene-eosin. The number of thrombosed and non-thrombosed blood vessels was counted and the percentage of thrombosis was calculated.

Annexin V also blocks the activity of the anti-VCAM-1•tTF coaguligand in vivo. Groups of tumor-bearing mice were treated with one of the control or test reagents. The mice were given (a) saline; (b) 100 μg of Annexin V; (c) 40 μg of anti-VCAM-1•tTF coaguligand; or (d) 100 μg of Annexin V followed 2 hours later by 40 μg of anti-VCAM-1•tTF coaguligand. Identical results were obtained in both mice per group.

No spontaneous thrombosis, hemorrhages or necrosis were observed in tumors derived from saline-injected mice. Treatment with Annexin V alone did not alter tumor morphology.

In accordance with other data presented herein, 40 μg of anti-VCAM-1•tTF coaguligand caused thrombosis in 70% of total tumor blood vessels. The majority of blood vessels were occluded with packed erythrocytes and clots, and tumor cells were separated from one another. Both coaguligand-induced anti-tumor effects, i.e., intravascular thrombosis and changes in tumor cell morphology, were completely abolished by pre-treating the mice with Annexin V.

These findings confirm that the anti-tumor effects of coaguligands are mediated through the blockage of tumor vasculature. These data also demonstrate that PS is essential for coaguligand-induced thrombosis in vivo.

EXAMPLE IV

Generating Antibodies to Aminophospholipids, Anionic Phospholipids and Complexes This example describes an immunization protocol designed by the inventors in light of their observations on aminophospholipid and anionic phospholipid translocation in tumor vascular endothelial cells, and discovered to function well in the generation of antibodies against aminophospholipids and anionic phospholipids. A number of antibodies reactive with aminophospholipids and anionic phospholipids, such as PS and PE, were obtained. In the present and following examples, for simplicity, antibodies reactive with PS can be termed "anti-PS antibodies", although the binding of certain of these antibodies is not restricted to PS but extends to certain other aminophospholipids and anionic phospholipids as shown herein.

A. Immunization Protocol

To present aminophospholipids and anionic phospholipids to the immune system as stronger immunogens, the aminophospholipids and anionic phospholipids were formulated as aminophospholipid-positive and anionic phospholipid-positive cells. The membrane-inserted aminophospholipids and anionic phospholipids, surrounded by other membrane components, have a better conformation and clearance rate for raising antibodies.

The intent is to immunize immunocompetent animals with autologous cells expressing aminophospholipids and anionic phospholipids, as exemplified in this instance by PS, wherein the animals would not produce antibodies against all self surface antigens, but would recognize membrane-exposed phospholipids, e.g. PS, as a foreign element. The procedure is applicable to the use of any standard laboratory animals, such as immunocompetent BALB/c mice and Lewis rats, with any aminophospholipid-positive or anionic phospholipid-positive cells.

BALB/c mice and mouse endothelioma cells, bEnd.3 (immortalized mouse (BALB/c strain) endothelial cells), were first chosen. bEnd.3 were cultured in 10% DMEM with 9 ml/500 ml HEPES Buffer, in 10% $CO_2$ incubator. The bEnd.3 cells were expanded in T175 TC flasks until the desired number of cells were obtained. Typically, each flask at ~70-80% confluency has about $3\times10^6$ cells, and each mouse should receive from $1\times10^6$ to $20\times10^6$ cells, up to $1\times10^7$ cells.

bEnd.3 cells are treated with 50 μM to 200 μM of hydrogen peroxide for 1 or 2 hours at 37° C. to expose anionic phospholipids, such as PS, before immunization. The stock of $H_2O_2$ is [9.8M]; 30% (v/v). This is diluted 1:1000, then 0.4 ml is add into the T175 TC flask with 40 ml media to a final concentration of 100 μM $H_2O_2$. The cells were maintained for 1 hour at 37° C. To harvest, the cells were washed 3× with warm PBS, +10 mM EDTA, to remove all BSA or serum protein in the medium. The cells were removed with gentle trypsin treatment, washed and centrifuged for 5 minutes at 1000 rpm. The supernatant was aspirated and the cells resuspended in DMEM without additives to the appropriate volume (each mouse receives about $1\times10^7$ cells in 200 μl) and kept on ice.

Cells treated in this manner were injected (200 μl of cell suspension) into each mouse IP using 1 ml syringe and 23 gauge needle. Mice were immunized from three to seven times at intervals of 3 to 4 weeks. Immune sera were collected by bleeding the mice ten days after each boost, starting from the second boost. The serum titer for anti-PS was tested by ELISA.

These immunizations with autologous PS-positive cells did not result in unrestricted production of autoantibodies, but were limited to the production of antibodies reactive with PS, reactive with PS in combination with other aminophospholipids and anionic phospholipids and/or reactive with PS in combination with serum proteins.

In another study, female Lewis rats were immunized with bEnd.3 endothelial cells that had been treated with 200 μM of hydrogen peroxide for 2 h. The treatment caused translocation of anionic phospholipids to the external surface in 70-90% of cells as detected by $^{125}$I-labeled annexin V. Treated cells were washed, detached and counted. Two million cells were suspended in sterile PBS and injected 5 times ip., with the interval of 3 wk between injections. The titer of polyclonal antibodies to anionic phospholipids was determined 2 days after each immunization.

B. High Titer Antisera

Mice with extremely high titers of antibodies reactive with anionic phospholipids such as PS were obtained (Table 1). The mice did not show any signs of toxicity. Although this immunization protocol was more effective in mice than rats overall, immunization of rats was effective and produced the 9D2 antibody (see below).

TABLE 1

Anti-PS IgG Antibody Generation

| Titer Range | Number of Mice per Group (% of total) |
|---|---|
| 1:100–1:1,000 | 2/30 (6.66%) |
| 1:1000–1:10,000 | 5/30 (16.6%) |
| 1:10,000–1:100,000 | 18/30 (60%) |
| 1:100,000–1,000,000 | 5/30 (16.6%) |

In further immunizations, various mice were immunized three times with hydrogen peroxide-treated bEnd.3 cells and the serum was tested 54 days after the first immunization. IgG antibodies reactive with PS within serum were detected with an anti-mouse IgG, Fc specific secondary antibody, and IgM antibodies within serum were detected with an anti-mouse IgG mu specific secondary antibody. A number of effective antisera with IgG and IgM antibodies reactive with PS were obtained using this immunization protocol, of which the antisera with IgG antibodies were generally more effective.

These methods can now be used to generate further particular anti-PS antibodies, e.g., including those screened for effectively competition with the 3G4 antibody described below. Typically, when the IgG titer of the desired antisera for PS reaches >200,000, but PC titer is <50,000, fusion can be performed to generate the monoclonal antibody.

Also, these methods are not limited to initial cell treatment with $H_2O_2$, as other methods to induce expression of aminophospholipids and anionic phospholipids can be used. For example, treatment with TNF and actinomycin D is another useful method. In one case, subconfluent (~85% confluence) bEnd. 3 cells were treated with 10 ng/ml mouse TNF and 1 μg/ml actinomycin D for 16 hrs at 37° C. in the incubator. The cells were then taken through the immunization procedure as outlined above. Treatment with the membrane disrupting agent, lysophosphatidylcholine (LPC) may also be used to induce PS exposure.

C. IgG and IgM Monoclonal Antibodies

Hybridomas were obtained by fusing splenocytes from immunized animals with myeloma partner P3×63AG8.653 cells (ATCC, Rockville, Md.).

An important aspect of the inventors' technique to prepare monoclonal antibodies useful in tumor treatment is the selection strategy, which involves screening to select antibodies that bind to aminophospholipids or anionic phospholipids, but not to neutral phospholipids. Another important aspect is to select antibodies that do not cause or significantly contribute to anti-phospholipid syndrome.

The strategy to isolate monoclonal antibodies reactive with PS, for example, involved screening hybridoma supernatants on PS-coated plates using an anti-mouse IgG, Fc gamma specific secondary antibody. Screening was first conducted against four phospholipids (PS, phosphatidylserine; PE, phosphatidylethanolamine; CL, cardiolipin; and PC, phosphatidylcholine), as well as bEnd3 cells. Clones reactive with the neutral phospholipid, PC were discarded, as were clones non-reactive with bEnd3 cells. High binding anti-PS clones were selected. The wells that had PS only reactivity, or strong preference for PS were sub-cloned first, and wells that exhibited PS reactivity in combination with binding to other anionic phospholipids were sub-cloned second.

In certain in the following studies, mouse monoclonal IgM antibodies termed 3SB, D11 and BA3, produced as described by Rote et al. (1993), were also included. The 3SB antibody is described in the literature as an anti-PS antibody and the D11 antibody is described in the literature as an anti-cardiolipin (anti-CL) antibody. Details of the generation and characterization of these antibodies were reported by Rote et al. (1993, incorporated herein by reference).

The isotype of each selected hybridoma generated by the inventors was determined. As antibodies of IgG class have numerous advantages over IgM, including typically higher affinity, lower clearance rate in vivo and simplicity of purification, modification and handling, their generation was particularly desired. To focus on wells with homogeneous IgG isotype, wells containing IgM or a mixture of different Igs were discarded or re-cloned. Sub-cloning of highly positive clones was repeated three to four times.

The isotype of representative IgG and IgM antibodies, as determined by ELISA, is shown in Table 2. The inventors initially termed the 3G4 antibody "F3-G4", before changing the designation to 3G4. This does not reflect any change in biological material. The serum dependence or independence of the antibodies is also set forth in Table 2 (see also, Example XXX).

TABLE 2

Isotype and Serum-Dependence of Anti-PS Antibodies

| Name | Origin | Species/Isotype | Serum cofactor? |
|---|---|---|---|
| 3SB | Rote et al., 1993 | Mouse IgM kappa | No |
| D11 | N. Rote | Mouse IgM kappa | |
| BA3 | Rote et al., 1993 | Mouse IgM kappa | |
| 3G4 | This study | Mouse $IgG_3$ kappa | Yes, β2-glycoprotein I |
| 2aG4 | This study | Mouse $IgG_{2a}$ | Yes |
| Ch3G4 | This study | Human chimeric $IgG_1$ | Yes |
| 9D2 | This study | Rat IgM kappa | No |
| P2D9 | This study | Mouse $IgG_3$ | |
| 1B12 | This study | Mouse $IgG_1$ kappa | |
| 1B9 | This study | Mouse $IgG_1$ kappa | Yes |
| 3B10 | This study | Mouse $IgG_3$ kappa | Yes, at least β2-glycoprotein I |
| 2G7 | This study | Mouse $IgG_1$ kappa | Yes |
| 7C5 | This study | Mouse $IgG_1$ kappa | Yes |
| 3F8 | This study | Mouse $IgG_3$ | |
| Annexin V | | | No |

D. ELISA Protocol and Initial Antibody Characterization

The antibodies were studied further by ELISA and compared to 3 SB and D11. The anti-PS ELISA used in the present studies example is conducted as follows. Unless particular differences are specified, this is the format of the ELISA used throughout the studies of the present application. Other types of ELISA were later developed and results from those studies are set forth in Example XXX.

The ELISA of the present example is exemplified using the antigen PS (P-6641 25 mg 10 mg/ml (solvent is Chloroform: MeOH 95:5) in 2.5 ml bottle). Other phospholipids can be used using the same protocol. The PS (or other phospholipids) stock solution should be aliquoted and stored in an airtight container at −30° C. The preferred 96 well plates are Dynatech U bottom Immulon 1 (from Dynatech Labs, Cat#011-010-3550).

The standard blocking buffer used in the present example is 10% bovine serum dissolved in PBS. Other blocking solutions are suitable, but any detergents should be excluded from block and wash solutions. The primary antibody is the test sample or admixture. The preferred secondary antibody is goat, anti-mouse IgG-HRP. The developing solutions are: 10 ml of 0.2M $Na_2PO_4$, 10 ml of 0.1M citric acid, one 10 mg tablet of OPD, and 10 μl of hydrogen peroxide. The stop solution is 0.18 M $H_2SO_4$.

The protocol of the present example entails coating 96-well plate with PS as follows: dilute the PS stock solution in n-hexane to 10 μg/ml and mix well. Add 50 μl to each well and allow this to evaporate for one hour. Add 200 μl of 10% serum (or other blocking buffer) to each well, cover and maintain at room temperature for 2 hours or overnight at 4° C. Wash the plate three times with PBS. Add the primary antibody (dilute in blocking buffer) and incubate for 2 hours at 37° C. Wash three times with PBS. Add 100 μl/well of secondary antibody (typically goat, anti-mouse IgG-HRP or other appropriate secondary antibody) and incubate for 1 hour at 37° C. Wash the plate three times with PBS. Develop the ELISA by adding 100 μl of developing solution to each of the wells, develop for 10 minutes, then add 100 μl of stop solution to each plate and read the O.D. at 490 nm.

The following results are presented for 9D2, 1B12, 3G4 and 1B9. The affinity of these antibodies for PS was determined and compared to 3SB. Certain of the relative affinities of the new antibodies are much improved compared to 3SB (Table 3).

TABLE 3

| Relative Affinity of Anti-PS Antibodies | | | | |
|---|---|---|---|---|
| Name | $EC_{50}$ (μg/ml)[1] | Binding vs. 3SB (-fold increased) | $EC_{50}$ (nM)[2] | Affinity vs. 3SB (-fold increased) |
| 3SB | 0.468 | 1 | 0.518 | 1 |
| D11 | >40.0 | 0.011 | >44.4 | 0.011 |
| 9D2 | 0.104 | 4.50 | 0.115 | 4.50 |
| 1B12 | 0.312 | 1.50 | 2.07 | 0.25 |
| 3G4 | 0.040 | 11.7 | 0.266 | 1.94 |
| 1B9 | 0.019 | 24.6 | 0.126 | 4.11 |
| Annexin V[3] | 0.100 | 4.68 | 2.77 | 0.18 |

[1]Based on dilutions of Tissue Culture supernatants; concentration of IgG and IgM were determined by sandwich ELISA using either anti-mouse or rat Igs as capturing Antibodies. All clones secrete in average 10 to 15 μg/ml of Ig.
[2]MW used for conversion: IgM - 900 kDa, IgG - 150 kDa, Annexin V - 36 kDa
[3]Affinity of Annexin V to PS is in the range of 0.1 nM to 1 nM. The value in this table represents binding of commercial biotinylated Annexin V detected by streptavidin-HRP using the same ELISA conditions as for anti-PS antibodies.

The specificity of the antibodies was determined by ELISA using plates coated with the following phospholipids: PS, phosphatidylserine; PE, phosphatidylethanolamine; PI, phosphatidylinositol; PA, phosphatidic acid; PG, phosphatidylglycerol; PC, phosphatidylcholine; CL, cardiolipin; and SM, sphingomyelin. The specificity profiles of 9D2, 1B12, 3G4 and 1B9, as compared to 3SB and D11, are shown in Table 4.

TABLE 4

| Phospholipid Specificity of Anti-PS Antibodies | |
|---|---|
| Name | Relative Strength of Reactivity on ELISA[1,2] |
| 3SB | PS = PA >> CL, PI, PE, PG |
| D11 | CL = PA >> PS, PI, PE, PG |
| 3G4 | PS = PA = PI = PG = CL >> PE |
| 2aG4 | PS = PA = PI = PG = CL >> PE |
| Ch3G4 | PS = PA = PI = PG = CL >> PE |
| 9D2 | PA > PS = CL > PG = PI >> PE |
| P2D9 | PS > PE = CL (No PC) |
| 1B12 | PS = PA > CL > PE = PI, PG |
| 3B10 | PS = PA = PI >> PE |
| 1B9 | PS only |
| 2G7 | PS only |
| 7C5 | PS only |
| 3F8 | PS > PE > CL (little or no PC) |
| Annexin V | PS = PE = PI = PA > CL > PG |

[1]The symbol > indicates at least 2-fold difference in binding to various phospholipids tested at identical antibody concentration.
[2]The symbol >> indicates at least 10-fold difference in binding to various phospholipids tested at identical antibody concentration.

The 1B9, 2G7 and 7C5 antibodies behave essentially the same. These antibodies recognize only PS and require serum or serum proteins for binding to PS. The binding of 1B9, 2G7 and 7C5 to various phospholipids in the present example was assayed only in the presence of 10% bovine serum, whereas binding of the other antibodies was tested either in the absence or in the presence of serum. 3SB is essentially devoid of reactivity with phosphatidylethanolamine and phosphatidylinositol, as well as phosphatidylcholine and sphingomyelin (Table 4).

E. Further Antibody Characterization

The reactivity of the 3G4 antibody with plastic-immobilized phospholipids was further tested. Phospholipids were dissolved in n-hexane to a concentration of 50 μg/ml. 100 μl of this solution was added to wells of 96-well microtiter plates. After evaporation of the solvent in air, the plates were blocked for 2 h with 10% FBS diluted in DPBS containing 2 mM $Ca^{2+}$ (binding buffer). The 3G4 antibody was diluted in the binding buffer in the presence of 10% bovine serum at an initial concentration of 33 nM. Serial two-fold dilutions were prepared in the plates (100 μl per well). The plates were then incubated for 2 hr. at room temperature. After washing, HRP goat anti-mouse IgG (diluted 1:1000) was used to detect 3G4. Secondary reagents were detected by using chromogenic substrate OPD followed by reading plates at 490 nm using a microplate reader (Molecular Devices, Palo Alto, Calif.).

Specificity of phospholipid recognition was further confirmed by competition assays with various liposomes. Liposomes were prepared from solutions of 5 mg of a single phospholipid (PS, PI, PC, CL, PA) in chloroform. The solutions were dried under nitrogen to form a thin layer in a round-bottomed glass flask. 10 ml of Tris buffer (0.1 M, pH 7.4) were then added and the flask was sonicated five times for 2 min. 3G4 (6.6 nM) was pre-incubated with 200 μg/ml of liposome solution for 1 h at room temperature. The mixture was added to phospholipid-coated plates. The ability of 3G4 to bind to an immobilized phospholipid in the presence or absence of the different liposomes was determined as described above.

Figure 3:
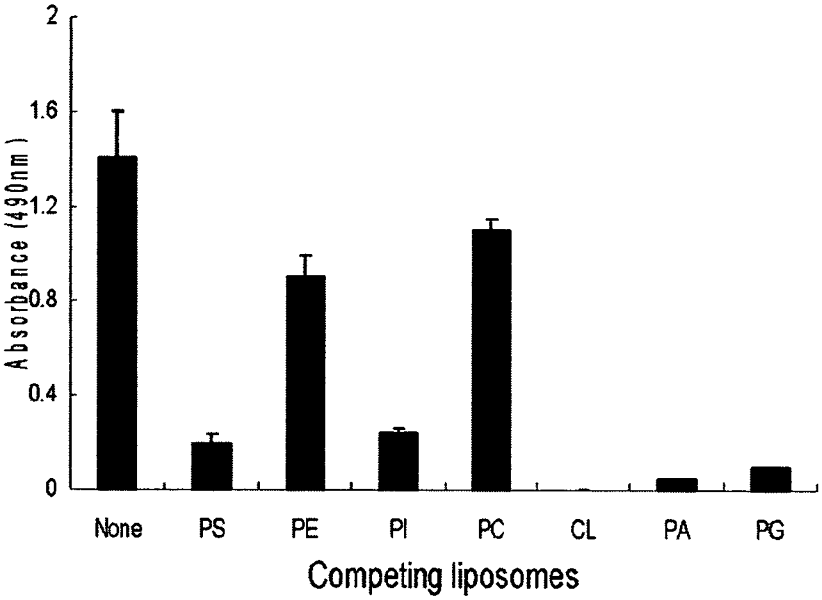
FIG. 3. Inhibition of binding of 3G4 antibody to immobilized PS using competing phospholipid liposomes. Phospholipid-coated microtiter plates were treated with 3G4 at concentrations ranging from 0.016 to 33 nM in 10% bovine serum. The bound antibody was detected using goat anti-mouse IgG-HRP. Competition assays with liposomes prepared from various phospholipids demonstrate that anionic phospholipids can compete with 3G4 (6.7 nM) binding to PS. Bars represent SD of triplicate measurements.

The ongoing studies showed that 3G4 is a mouse IgG3 κ monoclonal antibody that specifically recognizes anionic phospholipids. It binds strongly to ELISA plates coated with anionic phospholipids (PS, PA, CL, PI) in the presence of 5% bovine serum (FIG. 4) or human serum. Half-maximal binding was observed with 3G4 at concentrations of 0.2 to 0.4 nM (FIG. 4). 3G4 does not bind neutral phospholipids (PE, PC and SM) in ELISA. Control mouse IgG3 monoclonal antibodies of irrelevant specificity did not bind. Binding was blocked by liposomes prepared from anionic phospholipids, but not from liposomes prepared from neutral phospholipids (FIG. 3).

3G4 bound to ELISA plates coated with synthetic PS, PA and CL having saturated (non-oxidizable) dipalmitoyl side chains and to lysophosphatidic acid having a single fatty acid side chain. Binding was unaffected by the presence of 5 mM EDTA, showing that binding is not dependent on $Ca^{2+}$.

In the studies of the present example, in the absence of serum, binding to ELISA plates coated with anionic phospholipids was reduced by 90%. Full binding was restored in the presence of 1 mg/ml human β2-glycoprotein I. Binding was unaffected by prothrombin, protein protein C, protein S, oxidized LDL, HMW kininogen, LMW kininogen, factor XII, tissue plasminogen activator or annexin A5. Thus, the 3G4 antibody has now been discovered to recognize anionic phospholipids in the presence of serum or β2-glycoprotein I. Results from further studies relating to this characterization are presented herein in Example XXX.

PS is the most abundant anionic phospholipid of the plasma membrane and is tightly segregated to the internal leaflet of the plasma membrane in normal cells under normal conditions. PS is an aminophospholipid. PE is also an aminophospholipid, but PE is neutral, not anionic. Other than being a neutral aminophospholipid, PE behaves similarly to PS and is normally tightly segregated to the internal leaflet of the plasma membrane.

PI is another major anionic phospholipid of the plasma membrane, which is further tightly segregated to the internal leaflet in normal cells under normal conditions. PA and PG are minor anionic phospholipids of the plasma membrane (Hinkovska-Galcheva et al., 1989), which are also normally segregated to the internal leaflet. CL is an anionic phospholipid present in mitochondrial membranes, and typically absent from the plasma membrane.

PC and SM are choline-containing, neutral phospholipids of the plasma membrane. Each of PC and SM are predominantly located on the external leaflet under normal conditions.

In keeping with the inventors' model for differential aminophospholipid and anionic phospholipid expression between normal and tumor blood vessels, none of the antibodies developed using the selected protocol reacted with the neutral phospholipids, PC and SM. The 1B9 antibody was specific for PS, whereas 9D2, 1B12 and 3G4 bound to anionic phospholipids and aminophospholipids with the preferences shown in Table 4. The 9D2 antibody is also described in Example VI.

EXAMPLE V

Externalized Phosphatidylserine is a Global Marker of Tumor Blood Vessels

The present example shows that the exposure of PS occurs on endothelial cells in each of ten different solid tumors growing in mice and is not limited to the L540 tumor model described in Example II.

Externalized PS in vivo was detected by injecting a monoclonal antibody directed against PS intravenously into mice bearing various types of human or murine tumors. Anti-PS antibodies are shown to bind specifically to vascular endothelium in all ten different tumor models. Vascular endothelium in normal organs derived from the same mice were unstained. An isotype-matched control monoclonal antibody did not localize to either tumor or normal cells. Apoptotic cells were also identified immunohistochemically, wherein very few endothelial cells in tumors expressed markers of apoptosis.

The present example therefore shows that vascular endothelial cells in tumors but not in normal vessels externalize PS. Most of the tumor endothelial cells having exposed PS were not apoptotic. PS is thus an abundant and accessible marker of tumor vasculature that can be used for tumor vessel imaging and therapy.

A. L540, H358 and HT29 Tumors

The anti-PS antibody used in these studies was the mouse monoclonal IgM antibody termed 3SB (Example IV, Rote et al., 1993). 3SB mainly binds to PS, but also reacts with PA, a relatively minor anionic phospholipid with a distribution like PS. The anti-CL antibody used was the mouse monoclonal IgM antibody termed D11 (Example IV, Rote et al., 1993).

PS exposure on tumor and normal vascular endothelium was first examined in three animal tumor models: L540 human Hodgkin's lymphomas, NCI H358 human non-small cell lung carcinoma (NSCLC) and HT29 human colorectal carcinomas. To grow the tumors in vivo, $2\times10^6$ cells were injected into the right flank of SCID mice and tumors allowed to reach 0.8-1.2 cm in diameter.

Mice bearing large tumors (volume above 800 $mm^3$) were injected intravenously via the tail vein with 20 μg of either anti-PS or anti-CL antibodies. One hour after injection, mice were anesthetized and their blood circulation was perfused with heparinized saline. Tumors and normal organs were removed and snap-frozen for preparation of cryosections. Mouse IgM was detected using goat anti mouse IgM (μ specific)—HRP conjugate followed by development with carbazole. At least 10 random fields per section were examined at ×40 magnification and the average percentage of positive vessels was calculated.

The anti-PS antibodies specifically homed to the vasculature of all three tumors (HT 29, L540 and NCI-H358) in vivo, as indicated by detection of the mouse IgM. In this first study, the average percentages of vessels stained in the tumors were 80% for HT 29, 30% for L540 and 50% for NCI-H358. Vessels in all regions of the tumors were stained and there was staining both of small capillaries and larger vessels.

No vessel staining was observed with anti-PS antibodies in any normal tissues. In the kidney, tubules were stained in both anti-PS and anti-CL recipients, and this relates to the secretion of IgM through this organ. Anti-CL antibodies were not detected in any tumors or normal tissues, except kidney. These findings indicate that only tumor endothelium exposes PS to the outer site of the plasma membrane.

B. Small and Large L540 Tumors

To estimate the time at which tumor vasculature loses the ability to segregate PS to the inner side of the membrane, anti-PS localization was examined in L540 tumors ranging in volume from 140 to 1,600 $mm^3$.

Mice were divided into 3 groups according to their tumor size: 140-300, 350-800 and 800-1,600 $mm^3$. Anti-PS Ab was not detected in three mice bearing small L540 tumors (up to 300 $mm^3$). Anti-PS Ab localized in 3 animals of 5 in the group of intermediate size L540 tumors and in all mice (4 out of 4) bearing large L540 tumors (Table 5). Percent of PS-positive blood vessels from total (identified by pan endothelial marker Meca 32) was 10-20% in the L540 intermediate group and 20-40% in the group of large L540 tumors (Table 5).

TABLE 5

PS Externalization Detected in Mid and Large Sized Tumors

| Tumor Size ($mm^3$) | No. Positive Tumors/Total* | % PS-Positive Vessels/Total† |
|---|---|---|
| 350-800 | 3/5 | 10-20 |
| 850-1,600 | 4/4 | 20-40 |

*Mice bearing L540 Cy tumors were divided into three groups according to tumor size. 20 μg of anti-PS antibodies were injected i.v. and allowed to circulate for 1 hour. Mouse antibodies were detected on frozen sections using anti-mouse IgM-peroxidase conjugate.
†Total number of blood vessels was determined using pan-endothelial Ab Meca 32. PS-positive and Meca-positive vessels were counted in 4 fields per cross section of tumor. Range of % PS-positive vessels within the same group is shown.

C. L540, H358, HT29, Colo26, B16 and 3LL Tumors

Using the same anti-PS (3 SB) and anti-CL (D11) antibodies, PS exposure on tumor and normal vascular endothelium was examined in further studies using an additional three animal tumor models (six in total): L540 human Hodgkin's lymphomas, NCI H358 human non-small cell lung carcinoma (NSCLC), HT29 human colorectal carcinomas, Colo26 mouse colon carcinomas, B16 mouse melanomas and 3LL mouse lung tumors.

In these studies, tumors were grown subcutaneously in SCID mice and allowed to reach a volume of 0.4-0.7 $cm^3$. Three or more mice were used per group. Anti-PS or anti-CL mouse IgM antibodies (30 μg/mouse) were injected intravenously in 200 μl of saline. Thirty minutes later, the mice were sacrificed, exsanguinated and their blood circulation perfused with heparinized saline. Major organs and tumors were harvested and snap-frozen for preparation of cryosections. Mouse IgM was detected using goat anti mouse IgM (μ specific)-HRP conjugate followed by development with carbazole.

Serial sections of tumor were stained with a monoclonal antibody, MECA 32, directed against a pan-endothelial marker of mouse vessels. PS-positive vessels were identified morphologically and by their coincident staining with anti-mouse IgM and MECA 32. At least 10 random fields per section (0.317 $mm^2$/field) were examined in blinded fashion by two independent observers. The percentage of MECA 32-positive vessels that stained positively for PS was calculated. Three tumors of each type were examined in each of two separate studies. The mean values and standard errors (SE) were calculated. Inter-tumor variation in the number of total and PS-positive vessels in each group was approximately 10%.

All six tumors in this study contained PS-positive vessels (Table 6A). Detection of PS by 3SB was specific since no staining of tumor endothelium was observed with the anti-CL antibody (Table 6A). No vascular localization of anti-PS or anti-CL antibodies was observed in normal organs other than the kidneys (tubule staining in both anti-PS and anti-CL recipients reflects secretion of IgM through this organ).

TABLE 6A

Specific Localization of Anti-PS Antibodies to Tumor Vessels

| Tissue | Anti-PS* | Anti-CL |
|---|---|---|
| L540 tumor | 19.3 ± 3.3 | 0 |
| H358 tumor | 15.6 ± 4.1 | 0 |
| HT29 tumor | 4.2 ± 1.6 | 0 |
| B16 tumor | 40.6 ± 5.4 | 0 |
| 3LL tumor | 5.3 ± 3.7 | 0 |
| Colo 26 tumor | 12.4 ± 2.4 | 0 |
| Adrenal | 0 | 0 |
| Brain | 0 | 0 |
| Heart | 0 | 0 |
| Kidney | 0† | 0† |
| Intestine | 0 | 0 |
| Liver | 0 | 0 |
| Lung | 0 | 0 |
| Pancreas | 0 | 0 |
| Spleen | 0 | 0 |
| Testis | 0 | 0 |

*The results are presented as the mean (±SE) percentage of PS-positive vessels of MECA 32-stained vessels per field of 0.317 $mm^2$. Six tumor of each type were analyzed. The average number of MECA 32-positive vessels per 0.317 $mm^2$ field was 25, 21, 17, 18, 27and 22 ± 10% vessels for L540, H358, HT29, B16, 3LL and Colo 26 tumors, respectively
†Non-antigen specific tubular staining was visible in both anti-PS and anti-CL recipients.

In these studies, the percentage of PS-positive vessels ranged from 10% in Colo 26 tumors to 40% in B16 tumors. Anti-PS IgM was present on the luminal surface of capillaries and venules in all regions of the tumors. PS-positive vessels appeared to be particularly prevalent in and around regions of necrosis. Positive vessels usually did not show morphological abnormalities that were apparent by light microscopy. Occasional vessels located in necrotic areas showed morphological signs of deterioration. Anti-PS antibody (but not anti-CL antibody) also localized to necrotic and apoptotic tumor cells.

These controlled studies demonstrate that PS is consistently exposed on the luminal surface of vascular endothelial in various tumors, but not in normal tissues, and that the tumor vasculature expression is not model-specific.

D. The Majority of PS-Positive Tumor Vessels are Not Apoptotic

A double labeling technique was used to identify apoptotic endothelial cells in tumor sections. Endothelial cells were identified with the pan-endothelial cell marker, MECA 32. Apoptotic cells were identified immunohistochemically using two independent markers: an active form of caspase-3, which identifies cytosolic changes in dying cells (Krajewska et al., 1997), and fragmented DNA, which identifies cells having nuclear alterations (Gavrieli et al., 1992).

Active caspase-3 was detected by a rabbit anti-caspase-3 specific antibody (R&D, Minneapolis, Minn.) followed by incubation with anti-rabbit IgG conjugated to alkaline phosphatase (AP, Pierce, Rockford, Ill.). Other tumor sections were analyzed by Tunel assay (ApopTag™ kit, Oncor, Md.) using anti-digoxigenin-alkaline phosphatase conjugate as a detecting reagent. Sections were double stained for apoptosis markers (pink) and the endothelial cell marker, MECA 32 (brown). Both colors were clearly visible on the same cells, if markers of endothelial cells and apoptotic cells coincided.

Endothelial cells in five out of six types of tumors (HT29, H358, B16, Colo 26, L540) did not display either of the apoptosis markers (Table 7). The sixth type of tumor, 3LL, displayed a few apoptotic endothelial cells that were located in necrotic areas. In contrast, apoptotic malignant cells were common in all types of tumors. The percentage of apoptotic tumor cells ranged from 1-2% in L540 tumors to 12.6-19.6% in 3LL tumors.

TABLE 7

Expression of Apoptotic Markers in Tumors

| | Active caspase-3 | | Tunel assay | |
|---|---|---|---|---|
| Tumor type | Tumor cells (% of total)* | Tumor vessels | Tumor cells (% of total) | Tumor vessels |
| 3LL | 19.8 ± 4.3 | <1.0† | 12.6 ± 3.6 | 0 |
| HT29 | 13.7 ± 2.3 | 0 | 7.8 ± 2.5 | 0 |
| H358 | 5.8 ± 2.0 | 0 | 4.3 ± 1.6 | 0 |
| Colo 26 | 5.3 ± 1.5 | 0 | 4.1 ± 1.5 | 0 |
| B16 | 4.2 ± 1.8 | 0 | 3.5 ± 1.6 | 0 |
| L540 | 2.3 ± 1.0 | 0 | 1.6 ± 0.5 | 0 |

*The percentage of tumor cells or tumor blood vessels that were positive for either caspase-3 Tunel was determined in ten high power fields per section. The fields were randomly selected along two perpendicular directions from the edges through the center of the tumor. The mean (±SE) of the percentage of positive cells or vessels in tumors from 6 mice is, presented.
†Occasional vessels (1 of >100) in the necrotic area of 3LL tumor displayed both markers of apoptosis.

E. MDA-MB-231 and Meth A Tumors

PS exposure on tumor vascular endothelium was also examined in MDA-MB-231 human breast tumors growing in mice and in mouse Meth A fibrosarcoma growing subcutaneously. The antibody used in these studies was the 9D2 antibody, generated as described in Example IV, which is reactive with anionic phospholipids.

As described in detail in Example VI, 9D2 localized to tumor vessels in L540, NCI-H358 and B16 tumors, as well as in models of MDA-MB-231 breast tumor growing orthotopically in the mammary fat pads of SCID mice and mouse Meth A fibrosarcoma growing subcutaneously. 9D2 localized to tumor vessels in all of five tumors. Vascular endothelium in the tumors showed distinct membrane staining. 9D2 antibody also localized to the membrane and cytosol of necrotic and apoptotic tumor cells. No vascular localization of 9D2 antibody was observed in 9 of the 10 normal organs that were examined, with non-specific staining of the tubules in the kidney being observed.

Double-staining studies were also performed in which mice bearing orthotopic MDA-MB-231 breast tumors were injected i.v. with biotinylated 9D2 antibody and frozen sections later stained with FITC-conjugated MECA32 (Example VI). About 40% of MECA 32-positive vessels bound 9D2.

F. MD-MBA-435 Tumors

In a further breast cancer model, PS exposure on tumor vascular endothelium was examined in MDA-MB-435 human breast cancer cells growing in mice. The antibody used in these studies is a chimeric version of the 3G4 antibody (ch3G4). The 3G4 antibody generation is described in Example IV, and the production of the chimeric 3G4 antibody is detailed in Example XIX. The localization of ch3G4 to tumor vascular endothelium in the MDA-MB-435 model is described in more detail in Example XIX.

Briefly, tumors were established using MD-MBA-435s cells and biotinylated versions of the chimeric 3G4 antibody and a control IgG of irrelevant specificity were administered. Tumor sections were stained with Cy3-conjugated streptavidin to detect the biotinylated proteins. Double staining with the MECA 32 antibody followed by FITC-tagged anti-rat IgG secondary antibody was conducted to detect vascular endothelium. This detection method labeled the biotinylated proteins and the vascular endothelium using red and green, so that biotinylated proteins bound to the endothelium appear yellow in a converged image. This study showed specific localization of the chimeric 3G4 antibody to tumor vascular endothelium.

In similar studies, the ability of 3G4 to localize selectively to tumor blood vessels in vivo was determined by injecting the antibody i.p. or i.v. and exsanguinating the mice 1 h, 6 h or 24 h later. Frozen sections of tumor and normal tissues were stained for the presence of mouse immunoglobulin. SCID mice that had been confirmed as having no detectable circulatory immunoglobulin were used to avoid background staining. In these studies, sections were counterstained with anti-mouse CD31 to detect vascular endothelium and the images were merged. Coincidence of staining between localized 3G4 and CD31 was taken as evidence of specific localization. Coincident staining appeared yellow, unless dominated by a particularly intense green or red fluorescence in that region. The antigen specificity of vessel localization was confirmed by the lack of endothelial staining in tumors from mice injected with the isotype-matched control antibodies, BBG3.

In these studies, 3G4 localized to an average of 40±10% of tumor blood vessels after i.p. or i.v. injection into mice bearing orthotopic MDA-MB-435 breast tumors, as determined by the merged images. Localization to tumor vessels after i.p. injection of 3G4 was visible 1 hr. after injection and was maximal by 6 hr. after injection, whereas i.v. injected 3G4 gave maximal staining within 1 hr. after injection. Labeled vessels were visible in all regions of the tumors, but were particularly abundant in and around regions of necrosis. In the larger vessels, heterogeneity of PS exposure within a single vessel was sometimes observed. Regions where 3G4 had leaked into the tumor interstitium were also visible around the endothelium of some vessels. Tumor cells in and around regions of tumor necrosis were stained. No staining of necrotic tumor cells was observed in tumors from mice injected with the control antibody, BBG3, indicating that the localization to necrotic tumor cells in mice injected with 3G4 was antigen-specific.

Localization of 3G4 to vascular endothelium in normal tissues was not observed in mice injected i.v. with 3G4 or control antibody (BBG3) 4 hr. earlier. Normal tissues examined were: heart, lung, liver, gallbladder, esophagus, stomach, pancreas, duodenum, cecum, rectum, kidney, adrenal gland, spleen, brain, eye, salivary gland and ovary. Non-vascular components of these normal tissues were also unstained.

G. RIP-Tag Tumors

For the tenth model, PS exposure on tumor vascular endothelium was examined in a "RIP-Tag" transgenic mouse model (RIP1-Tag 2) of multistage carcinogenesis. In this transgenic mouse model, every mouse develops islet tumors of the pancreas by 12-14 weeks of age as a result of expression of the SV40 T antigen (Tag) oncogene in insulin-producing beta-cells. Tumors develop in multiple stages from hyperproliferative islets, and require an angiogenic switch in order to progress towards malignancy. Matrix metalloprotinase-9 controls the angiogenic switch (REF).

9D2 localization studies were conducted in the RIP1-Tag2 model in collaboration with Dr. Donald McDonald, Professor of Pathology at UCSF. 9D2 was injected intravenously into RIP1-Tag2 mice starting at 10 weeks of age, when all mice have small, highly vascularized, solid tumors. Double staining of thick (80 μm) tumor sections was performed to identify localized 9D2 and CD31 in tumors and normal pancreas. Approximately 50% of vessels (CD31 positive) in pancreatic tumors had localized 9D2, whereas vessels in normal islets were unstained. Mice injected with control rat IgM had weak and infrequent staining of tumor vessels. Some leakage of 9D2 and control rat IgM into extravascular tissues beyond the endothelium was also apparent.

H. Summary of Tumor Localization Studies

The inventors have now studied the localization of various anti-PS antibodies to tumor blood vessels in mice bearing many different tumors. The combined results from such studies are summarized below in Table 6B. Anti-PS antibodies localize to tumor blood vessels in all tumors, whereas no vascular localization is observed in normal organs (Table 6B).

TABLE 6B

Localization of Anti-PS Antibodies to Tumor and Normal Vessels

| Tissues | Localization |
|---|---|
| Tumor Tissues | |
| L540 Hodgkin's | ++ |
| H358 NSCLC | ++ |
| HT29 colon | +++ |
| Colo 26 colon | ++ |
| B16 melanoma | +++ |
| 3LL lung | +++ |
| MDA-MB-231 | +++ |
| MDA-MB-435 | +++ |
| Rip-Tag | +++ |
| Normal Tissues | |
| Adrenal | − |
| Brain | − |
| Heart | − |
| Kidney | − |
| Intestine | − |
| Liver | − |
| Lung | − |
| Pancreas | − |
| Spleen | − |
| Testis | − |

The present example therefore confirms that vascular endothelial cells in tumors externalize PS and anionic phospholipids to their luminal surface, where they can be bound by anti-PS antibodies in vivo. PS is absent from the external surface of vascular endothelial cells in normal tissues, indicating that PS-recognizing antibodies, annexin V and other ligands can be used for delivering cytotoxic drugs, coagulants and radionuclides for the selective imaging or destruction of vessels in solid tumors.

PS-positive tumor endothelium appeared, for the most part, to be viable in the tumors used in this study. It does not display markers of apoptosis, it is morphologically intact and metabolically active, as indicated by its expression of VCAM-1, E-selectin and other rapidly turned-over proteins. Although often regarded as an indicator of apoptosis, PS exposure has been observed in several types of viable cells, including malignant cells (Rao et al., 1992), (Utsugi et al., 1991) activated platelets (Rote et al., 1993), and embryonic trophoblasts at various stages of migration, matrix invasion and fusion (Adler et al., 1995).

Lack of correlation between PS exposure and commitment to cell death has been also shown on pre-apoptotic B lymphoma cells that restore PS asymmetry and grow normally after removal of the pro-apoptotic stimulus (Hammill et al., 1999). In normal viable cells, PS exposure is probably triggered by surface events, such as ligand-receptor interactions, that induce $Ca^{2+}$ fluxes into the cells (Dillon et al., 2000).

$Ca^{2+}$ fluxes activate scramblase (Zhao et al., 1998) and simultaneously inhibit aminophospholipid translocase (Comfurius et al., 1990).

PS on tumor vessels is attractive as a target for cancer imaging or therapy for several reasons: it is abundant (approximately $3\times10^6$ molecules per cell); it is on the luminal surface of tumor endothelium, which is directly accessible for binding by vascular targeting agents in the blood; it is present on a high percentage of tumor endothelial cells in diverse solid tumors, and it is absent from endothelium in all normal tissues examined to date. Unconjugated antibodies, vascular targeting agents and imaging agents directed against PS on tumor vasculature can therefore be used for the detection and treatment of cancer in man.

EXAMPLE VI

Anionic Phospholipids are Exposed on the Surface of Tumor Blood Vessels

Anionic phospholipids are largely absent from the external leaflet of the plasma membrane of mammalian cells under normal conditions. Exposure of phosphatidylserine, for example, on the cell surface occurs during apoptosis, necrosis, cell injury, cell activation and malignant transformation. The present example shows that anionic phospholipids are upregulated on tumor vasculature in vivo, as demonstrated by localization of both a specific antibody and a natural ligand that binds to anionic phospholipids.

A. monoclonal antibody, 9D2, which specifically recognizes anionic phospholipids, was injected into mice bearing a variety of orthotopic or ectopic tumors. Other mice received annexin V, a natural ligand that binds to anionic phospholipids. Both 9D2 and annexin V specifically localized to vascular endothelium in all tumors and also to tumor cells in and around regions of necrosis. Between 15 and 40% of endothelial cells in tumor vessels were stained. No localization was detected on normal endothelium.

Various factors and tumor-associated conditions known to be present in the tumor microenvironment were examined for their ability to cause exposure of anionic phospholipids in cultured endothelial cells, as judged by 9D2 and annexin V binding. Hypoxia/reoxygenation, acidity, thrombin and inflammatory cytokines all induced exposure of anionic phospholipids. Hydrogen peroxide was also a strong inducer. Combined treatment with inflammatory cytokines and hypoxia/reoxygenation had greater than additive effects. The demonstrated exposure of anionic phospholipids on tumor endothelium in vivo is thus likely to be caused by injury and activation by cytokines and reactive oxygen species. Irrespective of the mechanism, anionic phospholipids are markers of tumor vessels that can now be used for tumor vessel targeting, imaging and therapy.

A. Materials and Methods

1. Materials $Na^{125}I$ was obtained from Amersham (Arlington Heights, Ill.). Dulbecco's modified Eagle's tissue culture medium and Dulbecco PBS containing $Ca^{2+}$ and $Mg^{2+}$ were obtained from Gibco (Grand Island, N.Y.). Fetal calf serum was obtained from Hyclone (Logan, Utah). L-α-phosphatidylserine, L-α-phosphatidylcholine, cardiolipin, L-α-phosphatidylethanolamine, L-α-phosphatidylinositol, sphingomyelin, phosphatidic acid, phosphatidylglycerol, O-phenylenediamine, hydrogen peroxide and thrombin were from Sigma (St. Louis, Mo.). Flat bottom plates with 24 wells were obtained from Falcon (Becton Dickinson and Co., Lincoln Park, N.J.).

Recombinant hepatocyte growth factor (HGF or scatter factor) and actinomycin D was from Calbiochem (San Diego, Calif.). Recombinant murine interleukin-1 alpha, beta and tumor necrosis factor alpha (TNFα) were purchased from R&D Systems (Minneapolis, Minn.). Interferon of Universal Type I (hybrid protein that substitutes for all types of interferons) was purchased from PBL Biomedical Laboratories (New Brunswick, N.J.). Recombinant human vascular endothelial growth factor 121 (VEGF), human platelet-derived growth factor-BB, interleukin-6 (IL-6), interleukin-8 (IL-8), interleukin-10 (IL-10) and human fibroblast growth factor-2 (FGF-2) were purchased from PeproTech (Rocky Hill, N.J.).

2. Antibodies

MECA 32, a pan mouse endothelial cell antibody, was obtained from Dr. E. Butcher (Stanford University, CA) and served as a positive control for immunohistochemical studies. Details of this antibody have been published (Leppink et al., 1989). Rabbit anti-rat immunoglobulin, rat-anti mouse immunoglobulin and goat-anti mouse and anti-rat secondary antibodies conjugated to horseradish peroxidase (HRP) were purchased either from Daco (Carpinteria, Calif.) or from Jackson Immunoresearch Labs (West Grove, Pa.).

The 9D2 antibody used in these studies was generated as described in Example IV. 9D2 is a rat monoclonal antibody reactive with anionic phospholipids. Further characterization of the phospholipid specificity of 9D2 is given in the results section of this example.

3. Cells

L540Cy Hodgkin lymphoma cells, derived from a patient with end-stage disease, were provided by Prof. V. Diehl (Köln, Germany). NCI-H358 human non-small cell lung carcinoma was provided by Dr. Adi Gazdar (Southwestern Medical Center, Dallas, Tex.). Meth A mouse fibrosarcoma and MDA-MB-231 human breast carcinoma were obtained from American Type Cell Collection (Rockville, Md.). The mouse brain endothelioma line, bEnd.3, was provided by Prof. Werner Risau (Max Plank Institution, Munich, Germany) and was maintained in DMEM with 10% FBS. Adult bovine aortic endothelial (ABAE) cells were purchased from Clonetics (San Diego, Calif.; Walkerville, Md.). ABAE cells were maintained in DMEM with 10% serum and 2 ng/ml of bFGF.

4. Tissue Culture bEnd.3, ABAE cells and all tumor cells except L540Cy lymphoma were maintained in DMEM supplemented with 10% fetal calf serum, 2 mM L-glutamine, 2 units/ml penicillin G and 2 μg/ml streptomycin. L540Cy cells were maintained in RPMI 1640 containing the same additives. Cells were sub-cultured once a wk. Trypsinization of bEnd.3 cells was performed using 0.125% trypsin in PBS containing 0.2% EDTA. For in vitro studies, endothelial cells were seeded at a density of $10\times10^3$ cells/ml in 1 ml of culture medium in 24 well plates and incubated 48-96 h before being used in the assays. Medium was refreshed 24 h before each study.

5. Reactivity with Plastic-Immobilized Phospholipids

Phospholipids were dissolved in n-hexane to a concentration of 50 μg/ml. 100 μl of this solution was added to wells of 96-well microtiter plates. After evaporation of the solvent in air, the plates were blocked for 2 h with 10% fetal bovine serum diluted in DPBS containing 2 mM $Ca^{2+}$ (binding buffer).

9D2 antibody or annexin V were diluted in the binding buffer in the presence of 10% serum at an initial concentration of 6.7 nM. Serial two-fold dilutions were prepared in the plates (100 μl per well). The plates were then incubated for 2 h at room temperature. The plates were washed and the 9D2 and annexin V were detected by goat anti-rat IgM conjugated to HRP and rabbit anti-human annexin V followed by goat anti-rabbit IgG conjugated to HRP (all diluted 1:1000), respectively. Secondary reagents were detected by using chromogenic substrate OPD followed by reading plates at 490 nm using a microplate reader (Molecular Devices, Palo Alto, Calif.).

The specificity of the 9D2 antibody binding was validated by using control rat IgM of irrelevant specificity (Pharmingen, San Diego, Calif.). The specificity of annexin V binding to phospholipids, which is $Ca^{2+}$-dependent, was determined by diluting the reagent in the DPBS containing 5 mM EDTA. Additional negative controls consisted of washing the plates with the binding buffer containing 0.2% of a detergent Tween 20. This treatment extracts lipids, thus removing the phospholipid that was absorbed to plastic. Neither 9D2 antibody nor annexin V bound to detergent-washed plates.

6. Detection of Anionic Phospholipids on the Surface of Cultured Endothelial Cells Endothelial cells were grown until they reached approximately 70% confluence. To induce PS exposure, cells were treated with $H_2O_2$ (200 μM) for 1 h at 37° C. Control and treated slides were washed with DPBS containing $Ca^{2+}$ and $Mg^{2+}$ and fixed with 0.25% of glutaraldehyde diluted in the same buffer. Excess aldehyde groups were quenched by incubation with 50 mM of $NH_4Cl$ for 5 min. To examine the effect of detergents and organic solvents on detection of phospholipids, some slides were pre-incubated with acetone (5 min) or with PBS containing 1% (v/v) Triton™ X-100.

Cells were washed with DPBS (containing $Ca^{2+}$, $Mg^{2+}$ and 0.2% (w/v)gelatin) and incubated with 1 μg/ml of biotinylated annexin V (Pharmingen, San Diego, Calif.) or with 1 μg/ml of 9D2 antibody. After 2 h of incubation, cells were washed with 0.2% gelatin buffer and were incubated with streptavidin-HRP (1:500 dilution). Rat IgM of irrelevant specificity and streptavidin alone were used as negative controls in these studies. All steps were performed at room temperature. HRP activity was measured by adding O-phenylenediamine (0.5 mg/ml) and hydrogen peroxide (0.03% w/v) in citrate-phosphate buffer, pH 5.5. After 15 min, 100 μl of supernatant were transferred to 96 well plates, 100 μl of 0.18 M $H_2SO_4$ were added and the absorbance was measured at 490 nm. Alternatively, PS-positive cells were detected by addition of carbazole substrate, resulting in insoluble red-brownish precipitate. Each study was performed in duplicate and repeated at least twice.

7. Inhibition of 9D2 and Annexin V Binding to Phospholipids by Liposomes

The specificity of phospholipid recognition was further confirmed by competition assays with various liposomes. Liposomes were prepared from solutions of 5 mg of a single phospholipid in chloroform. The solutions were dried under nitrogen to form a thin layer in a round-bottomed glass flask. Ten ml of Tris buffer (0.1 M, pH 7.4) were then added and the flask was sonicated five times for 2 min. 9D2 or annexin V (6.66 nM) were pre-incubated with 200 μg/ml of liposomal solution for 1 h at room temperature. The mixture was added to phospholipid-coated plates or endothelial cell monolayers. The ability of 9D2 to bind to an immobilized phospholipid or cell surface in the presence or absence of the different liposomes was determined as described above.

8. Competition of 9D2 and Annexin V for Binding to Immobilized PS

Biotinylated 9D2 antibody and annexin V were prepared by incubating purified proteins with a 10-fold molar excess of N-hydroxysuccinimide biotin (Sigma, MO) for 1 h at room temperature. Free biotin was removed by dialysis against PBS. The biotinylation procedure did not impair the PS-binding capacity of either protein. For competition studies, unmodified and biotinylated proteins were premixed with a 10-fold molar excess of unmodified proteins. The mixtures were then added to PS-coated plates. Bound reagents were detected by streptavidin-HRP conjugate diluted 1:1000. The binding to PS of each reagent in the absence of a competitor was taken as the 100% value.

9. Growth of Subcutaneously Implanted Tumors

For localization studies, $2\times10^7$ L540 human Hodgkin's lymphoma cells or $1\times10^7$ cells of other tumor types were injected subcutaneously into the right flank of SCID mice (Charles River, Wilmington, Mass.). Tumors were allowed to reach a volume of 0.4-0.7 $cm^3$. A minimum of three animals per group was used. Studies were replicated at least three times.

10. Orthotopic Model of Human MDA-MB-231 Breast Carcinoma

Female nu/nu or SCID mice were purchased from Charles River. MDA-MB-231 human mammary carcinoma cells were implanted into the mammary fat pad according to a published protocol (Price, 1996). Briefly, mice were anesthetized and a 5-mm incision was made in the skin over the lateral thorax. The mammary pad was exposed to ensure the correct site for injection of $1\times10^7$ MDA-MB-231 cells re-suspended in 0.1 ml of saline.

11. Detection of Anionic Phospholipids in Tumor Bearing Mice In Vivo

Immunohistochemical techniques, in which 9D2 or annexin V are applied directly to sections of frozen tissues, do not discriminate between anionic phospholipids on the inner leaflet and the outer leaflet of the plasma membrane. To detect externally-positioned phospholipids, methods were performed essentially as previously described (Example V; Ran et al., 1998). Tumor-bearing SCID mice were injected intravenously with either 50 μg of 9D2 or biotinylated 9D2 antibody or 100 μg of biotinylated annexin V. Sixty min later mice were sacrificed and their blood circulation was exsanguinated and perfused with heparinized saline as previously described (Burrows et al., 1992). All major organs and tumor were harvested and snap-frozen for preparation of cryosections.

Sections were blocked with PBS containing 10% serum. To prevent loss of phospholipids during slide processing, detergents and organic solvents were omitted from blocking and washing buffers. Rat IgM was detected using goat anti rat IgM (μ specific)-HRP conjugate followed by development with carbazole or DAB (Fries et al., 1993). Biotinylated reagents were detected by streptavidin conjugated to HRP.

Tumor sections derived from mice injected with saline or rat IgM of irrelevant specificity served as negative controls. Additional controls consisted of incubating the slides in 1% Triton solution or in acetone for 10 min. These treatments extract phospholipids. No signal was detected under these conditions. The number of positive vessels per high power field was determined at magnification of ×100. At least 10 fields per section were examined and the average percentage of positive vessels was calculated. Staining of the sections by this method for the presence of 9D2 or annexin V detects cells having externalized anionic phospholipids that were accessible for binding by the reagents in vivo.

12. Identification and Quantification of PS-Positive Tumor Vessels

Structures with localized 9D2 antibody or annexin V were identified as blood vessels by morphological appearance on DAB-stained sections and by co-incident staining with the pan-endothelial cell marker, MECA 32 on serial sections of frozen tissues. Quantification on DAB-stained sections was done by counting vessels stained by MECA 32, 9D2 or annexin V in serial sections of a tumor. Six slides of each tumor type derived from 6 mice injected with 9D2 antibody, control rat IgM or annexin V were examined. At least 10 random fields per section (0.317 $mm^2$/field) were scored in blinded fashion by two independent observers. The mean numbers and standard errors of vessels stained by 9D2, annexin V or MECA 32 were calculated. The mean number of 9D2 or annexin V-positive vessels determined in each tumor type group was compared to the mean number of MECA 32-positive vessels in the same tumor group. The percentage of 9D2 or annexin V-positive vessels was calculated.

In further studies, mice bearing MDA-MB-231 tumors (0.3-0.7 $cm^3$ in volume) were injected intravenously with 50 µg of biotinylated 9D2, control IgM or annexin V (six mice per group). Biotinylated reagents were first incubated with streptavidin-Cy3 conjugate, washed in PBS, then incubated with MECA 32 antibody followed by FITC-tagged anti-rat IgG secondary antibody. Single images, taken with appropriate filters for Cy3 (red) and FITC (green) fluorescence respectively, were captured by digital camera and transferred to a computer. Images of 10 random fields (0.317 $mm^2$/field) demonstrating yellow color (a product of merged green and red fluorescence) were superimposed with the aid of Metaview software. The same method was used to analyze tumors from mice injected with control rat IgM or saline. The percentage of vessels with localized 9D2 or annexin V was calculated as follows: mean number of yellow vessels per field divided by mean number of green (total) vessels multiplied by 100.

B. Results

1. Phospholipid Specificity of 9D2 Antibody and Annexin V

The 9D2 antibody specifically recognized anionic phospholipids (PS, PA, CL, PI, PG) and had no significant reactivity with neutral phospholipids (PE, PC and SM) in ELISA (Table 8). The order of strength of binding of 9D2 to phospholipids in ELISA was PA>PS=CL>PG=PI. The binding was antigen-specific since no binding was observed with several control rat IgM of irrelevant specificity. Binding of 9D2 to any of the anionic phospholipids adsorbed to ELISA plates was blocked by liposomes prepared from any of the anionic phospholipids, but not by liposomes prepared from any of the neutral phospholipids.

TABLE 8

Phospholipid Specificity of 9D2 and Annexin V

| Phospholipid Name | Phospholipid Type | Abundance and location in the plasma membrane under normal conditions[a] | $EC_{50}$ of binding (pM) 9D2 | $EC_{50}$ of binding (pM) Annexin V |
|---|---|---|---|---|
| PS | Anionic inner amino-PL | Major PL (15%), located on side | 12 | 100 |
| PA | Anionic PL | Minor PL (less than 1%) | 2 | 100 |
| PG | Anionic PL | Minor PL (less than 1%) | 100 | 250 |
| PI | Anionic PL | Major PL (7%), mainly located on the inner side | 100 | 50 |
| CL | Anionic PL | Absent from the plasma membrane | 15 | 130 |
| PE | Neutral amino-PL | Major PL (22%), mainly located on inner side | >8000 | 100 |
| SM | Neutral choline-PL | Major PL (9%), located on the outer side | >8000 | >8000 |
| PC | Neutral choline-PL | Major PL (46%), located on the outer side | >8000 | >8000 |

[a]Percentage of total phospholipids, taken from Fridrikkson, et al., 1999. Percentages may vary for different cell types.

Annexin V also bound to anionic phospholipids, but its binding was less specific than that of 9D2 in that it also bound strongly to the neutral phospholipid, PE. The order of strength of binding of annexin V to phospholipids in ELISA was PI>PS=PE=PA=CL>PG (Table 8). These findings for annexin V are consistent with earlier data (Andree et al., 1990).

The binding of 9D2 was unaffected by the presence of 5 mM EDTA, showing it did not require $Ca^{2+}$ for binding to anionic phospholipids. In contrast, the binding of annexin V to anionic phospholipids was abolished in the presence of 5 mM EDTA, as expected from its known dependence on $Ca^{2+}$ for binding to anionic phospholipids or PE (Schlaepfer et al., 1987; Blackwood and Ernst, 1990).

Neither 9D2 nor annexin V bound to ELISA plates that had been coated with phospholipids but then washed with 0.2% Tween in saline, confirming that their binding was to the absorbed phospholipids. 9D2 and annexin V did not bind detectably to heparin, heparan sulfate or to double or single stranded DNA.

2. 9D2 Antibody and Annexin V Do Not Cross-Block Each Other's Binding to PS

To examine whether 9D2 antibody and annexin V compete for binding to PS, cross-blocking studies were performed using biotinylated proteins on PS-coated plates. Binding of biotinylated 9D2 antibody and annexin V was blocked by a 10-fold molar excess of unmodified 9D2 and annexin V, respectively (Table 9). However, unmodified annexin V did not affect the ability of biotinylated 9D2 to bind to the PS plate. Likewise, addition of unmodified 9D2 antibody did not alter the ability of biotinylated annexin V to bind to the PS plate (Table 9).

TABLE 9

9D2 and Annexin V Do Not Cross-Block Binding to PS

| PS-binding protein | Competitor[a] | Binding (% Control)[b] |
|---|---|---|
| Biotinylated annexin V | Annexin V | 8% |
| Biotinylated 9D2 | Annexin V | 93% |
| Biotinylated annexin V | 9D2 | 95% |
| Biotinylated 9D2 | 9D2 | 5% |

[a]Annexin V or 9D2 antibody were pre-mixed in 10-fold molar excess over the biotinylated reagents. Binding of biotinylated reagents to PS on microtiter plates was detected by streptavidin-HRP.
[b]Reactivity of biotinylated reagents in the absence of a competitor was taken as 100%. The mean values of triplicate determinations are presented. SD was less than 10% of the mean value.

These results indicate that 9D2 antibody and annexin V do not cross-block each other binding to PS-coated plates, either because they recognize different epitopes on the PS molecule or different conformations of PS adsorbed on plastic.

3. Binding to Externalized Anionic Phospholipids on Cell Surfaces

The binding of 9D2 antibody and annexin V to cell surfaces was examined using mouse bEnd.3 endothelioma cells or bovine ABAE cells. Neither 9D2 nor annexin V bound to non-permeabilized monolayers of either cell type under quiescent conditions. This indicates that the majority of anionic phospholipids of the plasma membrane are normally sequestered to the cytosolic domain. In contrast, strong staining was observed when cells were pre-incubated with TNFα and actinomycin D under conditions that caused apoptosis in 90-100% of the endothelial cells.

To confirm that 9D2 and annexin V were binding to phospholipids on cell surfaces, $H_2O_2$-treated bEnd.3 cells were incubated with 9D2 antibody or annexin V in the presence or absence of various competing liposomes. Anionic phospholipids become exposed on non-apoptotic, viable bEnd.3 cells when they are pre-treated with a sub-toxic concentration (100-200 μM) of $H_2O_2$ (Ran et al., 2002a).

The binding of 9D2 antibody to $H_2O_2$-treated bend.3 cells was inhibited by liposomes containing anionic phospholipids but not by liposomes containing neutral phospholipids. The magnitude of inhibition of 9D2 binding to cells varied in the order PA>PS>CL>PG>PI, in close agreement with the results obtained using plastic-immobilized phospholipids. Similarly, the binding of annexin V to $H_2O_2$-treated cells was blocked by liposomes containing PS, PA, PE, CL and, to a lesser extent, PI and PG. Liposomes containing SM or PC did not block annexin V binding to cells, all in agreement with the results obtained using plastic-immobilized phospholipids.

These results confirm that 9D2 binds to anionic phospholipids in the $H_2O_2$-treated endothelial cells, whereas annexin V binds to PE in addition of anionic phospholipids.

4. Detection of Externalized Anionic Phospholipids on Cells In Vivo

Direct immunohistochemical techniques, in which 9D2 or annexin V are applied directly to sections of frozen tissues, do not discriminate between anionic phospholipids on the inner leaflet and the outer leaflet of the plasma membrane. To detect externally-positioned phospholipids, 9D2 and annexin V were injected intravenously into tumor-bearing mice and localization to tumor vessels was determined by indirect immunohistochemistry.

Mice bearing various types of solid tumors were injected intravenously with 9D2 antibody or biotinylated annexin V, and one hour later, were exsanguinated and the tumors and normal tissues were removed and frozen sections were prepared. Frozen sections of tissues were cut and stained with HRP-labeled anti-rat IgM or with HRP-labeled streptavidin to determine to which cells the 9D2 and annexin V had bound after injection. Blood vessels were identified morphologically, and from their positive staining by the pan-endothelial cell antibody, MECA 32, on serial sections.

5. Biodistribution of 9D2 Antibody and Annexin V in Tumor Bearing Mice

9D2 antibody and annexin V localized to tumor vessels in all of five tumors included in this study (Table 10). The tumors were: human MDA-MB-231 breast tumor growing orthotopically in the mammary fat pads of SCID mice; human L540 Hodgkin's tumor growing subcutaneously; human NCI-H358 NSCLC growing subcutaneously; mouse B16 melanoma growing subcutaneously and mouse Meth A fibrosarcoma growing subcutaneously.

TABLE 10

Specific Localization of 9D2 and Annexin V to Tumor Vessels

| Tissue | 9D2 Antibody[a] | Rat IgM control | Annexin V[b] |
|---|---|---|---|
| Tumors | | | |
| MDA-MB-231 | 40.6 ± 5.4 | — | 45.3 ± 5.6 |
| L540cy | 19.3 ± 3.3 | — | 16.7 ± 3.9 |
| NCI-H358 | 15.6 ± 4.1 | — | ND |
| B16 | 23.4 ± 4.5 | — | 21.3 ± 6.6 |
| Meth A | 25.7 ± 6.8 | — | ND |
| Normal | | | |
| Adrenal | — | — | — |
| Brain | — | — | — |
| Heart | — | — | — |
| Kidney | —[c] | —[c] | — |
| Intestine | — | — | — |
| Liver | — | — | — |
| Lung | — | — | — |
| Pancreas | — | — | — |
| Spleen | — | — | — |
| Testis | — | — | — |

[a]Localization of 9D2 antibody and rat IgM control in tumor bearing mice was determined by injecting the antibody (50 μg), perfusing the blood circulation of the mice with saline and detecting the antibody on sections of the tissues by using an anti-mouse IgM - peroxidase conjugate. Theresults are presented as the mean (±SE) percentage of PS-positive vessels of MECA 32-stained vessels per field of 0.317 mm². Six samples of each type were analyzed. The mean number of MECA 32-positive vessels per 0.317 mm² field was 23, 25, 21, 18 and 19 ± 10 vessels for MDA-MB-231, L540cy, H358, B16 andMeth A tumors, respectively

[b]Localization of annexin V was determined by injecting biotinylated annexin V followed by detection on frozen sections using streptavidin-peroxidase conjugate.

[c]Non-antigen specific tubular staining was visible in both 9D2 and control antibody recipients.

9D2 and annexin V gave essentially the same patterns of staining. Localization of the 9D2 antibody to tumor vessels was specific since no staining of tumor endothelium was observed with rat IgM of irrelevant specificity. Presumably, leakage of the control rat IgM out of tumor vessels occurred to some extent, but the staining of extravascular IgM was too diffuse or too weak to discern by indirect immunohistochemistry.

No vascular localization of 9D2 antibody or annexin V was observed in nine of the ten normal organs that were examined (Table 10). In the kidney, staining of tubules was observed that appeared not to be antigen specific. Tubules were stained in both 9D2 and control rat IgM recipients, presumably because of secretion of IgM or its metabolites through this organ. The ovaries, a site of physiological angiogenesis, were not examined.

The percentage of 9D2 and annexin V positive vessels ranged from 40% in MDA-MB-231 tumors to 15% in H358 tumors. Anionic phospholipid-positive vessels were present on the luminal surface of capillaries and vessels in all regions of the tumors, but were particularly prevalent in and around regions of necrosis. Most anionic phospholipid-positive vessels did not show morphological abnormalities that were apparent by light microscopy. Occasional vessels, particularly those located in necrotic areas, showed morphological signs of deterioration. 9D2 antibody and annexin V also localized to necrotic and apoptotic tumor cells, whereas localization of the control IgM was not detectable.

These findings demonstrate that anionic phospholipids are present on the luminal surface of vascular endothelial cells in various tumors but not in normal tissues.

6. Double Staining Studies

Double staining studies were also performed in which mice bearing orthotopic MDA-MB-231 breast tumors were injected intravenously with biotinylated 9D2 antibody, biotinylated control IgM or biotinylated annexin V. One hour later, the mice were exsanguinated, and their tumors were removed and frozen sections were cut. The tumor sections were then stained with Cy3-conjugated streptavidin to detect the biotinylated proteins and with FITC-conjugated MECA32 to detect vascular endothelium. This detection method labeled the biotinylated proteins and the vascular endothelium by red and green. Where the biotinylated proteins are bound to the endothelium, the converged image appears yellow.

In these studies, the biotinylated 9D2 and annexin V appeared mostly to be bound to the vascular endothelium, because their staining patterns converged with that of MECA 32. About 40% of MECA 32 positive vessels bound 9D2 and annexin V, in close agreement with the results obtained by indirect immunohistochemistry. However, leakage of the biotinylated proteins into the tumor interstitium was detected by double staining, whereas it was not apparent by indirect immunohistochemistry.

Biotinylated proteins were visible outside the vascular endothelium around a minority (about 5%) of vessels. In tumors from mice that had been injected with biotinylated rat IgM of irrelevant specificity, the biotinylated IgM had also leaked into the tumor interstitium around a similar percentage (about 5%) of vessels, but mostly appeared not to be bound by the vascular endothelium. Presumably, the detection of extravasated 9D2 and annexin V by the double staining technique, but not by the indirect immunohistochemistry technique, reflects the greater sensitivity of the former technique and the greater precision with which two staining patterns can be compared. Non-injected control tumors were completely unstained by streptavidin-Cy3, indicating that red fluorescence corresponds to a localized protein.

EXAMPLE VII

Anionic Phospholipid Membrane Translocation in a Tumor Environment

The discovery of aminophospholipids and anionic phospholipids as in vivo surface markers unique to tumor vascular endothelial cells prompted the inventors to further investigate the effect of a tumor microenvironment on the translocation and outer membrane expression of such molecules. The present example shows that exposing endothelial cells in vitro to certain conditions that mimic those in a tumor duplicates the earlier observed aminophospholipid and anionic phospholipid surface expression in intact, viable cells.

A. Materials and Methods

1. Iodination of Annexin V

Recombinant human annexin V was purified from *E. coli* transformed with ET12a-Panionic phospholipid1 plasmid (obtained from Dr. J. Tait, University of Washington, Seattle). The purity of the protein and the binding to PS were confirmed on SDS-PAGE and on PS-coated plastic, respectively. Rabbit polyclonal, affinity-purified anti-annexin V antibodies were used to detect annexin V bound to PS. Annexin V was radiolabeled with $^{125}I$ using Chloramine T as described by Bocci (1964). The specific activity was approximately $1\times10^6$ cpm per μg of protein, as measured by a Bradford assay (1976).

2. Endothelial Cell Treatment

Endothelial cells were treated with cytokines or growth factors at the concentrations listed in Table 11. All reagents were diluted in medium containing 10% serum and incubated with the cells at 37° C. for 24 h.

To study the effect of hypoxia, cells were seeded on 24 well plates and were incubated in a humidified normoxic atmosphere (21% $O_2$, 5% $CO_2$) for 48 h before being transferred to a humidified hypoxic atmosphere (1% $O_2$, 5% $CO_2$, 94% $N_2$) in a sealed chamber (Billups Rothenberg Inc., Del Mar, Calif.). Cells were incubated in a hypoxic chamber for 24 h at 37° C. and were then returned to a normoxic environment for 4 h at 37° C. The cells were compared to a parallel culture from an identical passage, seeded on the same day and maintained entirely under normoxic conditions. In some studies, IL-1α (10 ng/ml) and TNFα (20 ng/ml) were added to the medium before transfer to the hypoxic chamber.

To examine the effect of an acidic microenvironment, cells were exposed to the growth medium lacking bicarbonate, which was adjusted to different pHs (ranging between 7.3 and 6.2) with the required amount of HCl. Cells were incubated at 37° C. in the absence of $CO_2$. It was confirmed that culture media held the assigned pH during the 24 h period of culture. These experimental conditions were not toxic to either bovine or mouse endothelial cells and had no effect on cell morphology or viability of the attached monolayer.

3. Detection of PS on Cultured Endothelial Cells by $^{125}I$-Labeled Annexin V

After treatment with the reagents described above, treated and control cells were incubated with 7.1 pmoles of $^{125}I$-labeled annexin V (200 μl/well) in the binding buffer. After 2 h incubation at room temperature, cells were washed extensively and dissolved in 0.5 M of NaOH. The entire volume of 0.5 ml was transferred to plastic tubes and counted in a gamma counter. Non-specific binding was determined in the presence of 5 mM EDTA and was subtracted from experimental values. The results were expressed as net pmoles of cell-bound annexin V, normalized per $1\times10^6$ cells.

Maximal binding of annexin V was determined on cells simultaneously treated with actinomycin D and TNFα (50 ng/ml of each component). As has been previously reported, these agents cause apoptosis and PS exposure in 90-100% of endothelial cells (Lucas et al., 1998). Basal binding of $^{125}I$-annexin V to untreated cells was determined in the presence of medium with 10% serum. The amount of $^{125}I$-annexin V that bound to the untreated cultures was subtracted from that in the treated cultures. Exposure of PS was calculated according to the following formula: cell-bound annexin V (pmoles) under experimental conditions divided by maximal annexin V binding (pmoles), multiplied by 100. Each study was performed in duplicate and was performed at least three times. Mean values were calculated. The SE of the mean values from three separate experiments was less than 5%.

4. Detection of PS on Cultured Endothelial Cells and MDA-MB-435 tumor cells

HUVEC cells and tumor cells were grown on 8 well chamber slides to approximately 70% confluence. To induce PS exposure, cells were treated with $H_2O_2$ (200 μM) in serum-free media for 1 h at 37° C. Cells were washed with DPBS and incubated with 2 μg/ml 3G4 antibody diluted in serum-free media for 1 h at room temperature. After gentle washing with DPBS, the cells were fixed with 4% (v/v) paraformaldehyde in PBS for 15 min.

To co-stain the cytoskeleton with Texas Red labeled phalloidin (Molecular Probes, Eugene, Oreg.), cells were permeabilized with 0.1% Triton-X100 in PBS for 5 min. Texas Red labeled phalloidin (1:50 diluted in PBS containing 1% BSA) and FITC-labeled goat anti-mouse antibody (1:200 diluted in PBS containing 1% BSA) were incubated for 1 h at room temperature. Cell nuclei were counterstained with DAPI. Mouse $IgG_3$ of irrelevant specificity and secondary antibody alone were used as negative controls in these studies. Each study was performed in duplicate and repeated at least twice.

In other studies, $H_2O_2$-treated cells were detached with 0.25% trypsin, washed, suspended in ice cold DMEM containing 0.05% w/v sodium azide and 2 μg/ml 3G4 for 1 h. The cell pellets were washed with PBS containing 1% BSA and suspended in the same buffer containing FITC-labeled goat anti-mouse antibody (1:200 diluted) for 30 min. After washing three times, the cell pellets were suspended in PBS containing 1% BSA and 0.05% w/v sodium azide. For live/dead discrimination, propidium iodide was added before FACS analysis.

B. Results

1. Induction by $H_2O_2$

Mouse bEnd.3 endothelial cells were seeded at an initial density of 50,000 cells/well. Twenty-fours later cells were incubated with increasing concentrations of $H_2O_2$ (from 10 μM to 500 μM) for 1 hour at 37° C. or left untreated. At the end of the incubation, cells were washed 3 times with PBS containing 0.2% gelatin and fixed with 0.25% glutaraldehyde. Identical wells were either stained with anti-PS IgM or trypsinized and evaluated for viability by the Trypan Blue exclusion test. For the anti-PS staining, after blocking with 2% gelatin for 10 min., cells were incubated with 2 μg/ml of anti-PS antibody, followed by detection with anti-mouse IgM-HRP conjugate.

Exposing endothelial cells to $H_2O_2$ at high concentrations causes PS translocation in ~90% cells. However, this is accompanied by detachment of the cells from the substrate and cell viability decreasing to about 50-60%. The association of surface PS expression with decreasing cell viability is understandable, although it is still interesting to note that 90% PS translocation is observed with only a 50-60% decrease in cell viability.

Using lower concentrations of $H_2O_2$ resulted in significant PS expression without any appreciable reduction in cell viability. For example, PS was detected at the cell surface of about 50% of cells in all $H_2O_2$ treated wells using $H_2O_2$ at concentrations as low as 20 μM. It is important to note that, under these low $H_2O_2$ concentrations, the cells remained firmly attached to the plastic and to each other, showed no morphological changes and had no signs of cytotoxicity. Detailed analyses revealed essentially 100% cell-cell contact, retention of proper cell shape and an intact cytoskeleton.

The 50% PS surface expression induced by low levels of $H_2O_2$ was thus observed in cell populations in which cell viability was identical to the control, untreated cells (i.e., 95%). The PS expression associated with high $H_2O_2$ concentrations was accompanied by cell damage, and the PS-positive cells exposed to high $H_2O_2$ concentrations were detached, floating and had disrupted cytoskeletons.

The maintenance of cell viability in the presence of low concentrations $H_2O_2$ is consistent with data from other laboratories. For example, Schorer et al. (1985) showed that human umbilical vein endothelial cells (HUVEC) treated with 15 μM $H_2O_2$ averaged 90 to 95% viability (reported as 5% to 10% injury), whilst those exposed to 1500 μM $H_2O_2$ were only 0%-50% viable (50% to 100% injured).

The use of $H_2O_2$ to mimic the tumor environment in vitro is also appropriate in that the tumor environment is rich in inflammatory cells, such as macrophages, PMNs and granulocytes, which produce $H_2O_2$ and other reactive oxygen species. Although never before connected with stable tumor vascular markers, inflammatory cells are known to mediate endothelial cell injury by mechanisms involving reactive oxygen species that require the presence of $H_2O_2$ (Weiss et al., 1981; Yamada et al., 1981; Schorer et al., 1985). In fact, studies have shown that stimulation of PMNs in vitro produces concentrations of $H_2O_2$ sufficient to cause sublethal endothelial cell injury without causing cell death (measured by chromium release assays) or cellular detachment; and that these $H_2O_2$ concentrations are attainable locally in vivo (Schorer et al., 1985).

The present in vitro translocation data correlates with the earlier results showing that anti-PS antibodies localize specifically to tumor vascular endothelial cells in vivo, and do not bind to cells in normal tissues. The finding that in vivo-like concentrations of $H_2O_2$ induce PS translocation to the endothelial cell surface without disrupting cell integrity has important implications in addition to validating the original in vivo data and the inventors' therapeutic approaches.

Human, bovine and murine endothelial cells are all known to be PS-negative under normal conditions. Any previously documented PS expression has always been associated with cell damage and/or cell death. This is not the case in the present studies, where normal viability is maintained. This shows that PS translocation in tumor vascular endothelium is mediated by biochemical mechanisms unconnected to cell damage. This is believed to be the first demonstration of PS surface expression in morphologically intact endothelial cells and the first indication that PS expression can be disconnected from the apoptosis pathway(s). Returning to the operability of the present invention, these observations again confirm that PS is a sustainable, rather than transient, marker of tumor blood vessels and a suitable candidate for therapeutic intervention.

2. Induction by Thrombin

Thrombin was also observed to increase PS expression, although not to the same extent as $H_2O_2$. This data is also an integral part of the tumor-induction model of PS expression developed by the present inventors: thrombin-induced PS surface expression in normal tissues would also further coagulation as PS expression coordinates the assembly of coagulation initiation complexes.

The tumor environment is known to be prothrombotic, such that tumor vasculature is predisposed to coagulation (U.S. Pat. No. 5,877,289). As thrombin is a product of the coagulation cascade, it is present in tumor vasculature. In fact, the presence of thrombin induces VCAM expression, contributing to the inventors' ability to exploit VCAM as a targetable marker of tumor vasculature (U.S. Pat. Nos. 5,855,866; 5,877,289). The present data showing that thrombin also induces PS expression is thus both relevant to targeting aminophospholipids with naked antibodies and therapeutic conjugates, and further explains the beneficial effects of the anti-VCAM coaguligand containing Tissue Factor (Example I).

3. Other Agents of Oxidative Stress

Mouse bEnd.3 or bovine ABAE cells in vitro were treated for 24 h with various concentrations of factors and conditions that are present in the microenvironment of many tumors (Lichtenbeld et al., 1996; Harris et al., 1996), such as hypoxia/reoxygenation, thrombin, acidity, inflammatory cytokines and hydrogen peroxide (Table 11).

Externalization of PS and anionic phospholipids was quantified by measuring $^{125}$I-annexin V binding. The amount of annexin V binding was compared with that of cells in which apoptosis of 90-100% of cells had been induced by combined treatment with actinomycin D and TNF-α. Actinomycin D and TNF-α induced the binding of 6.2 pmoles of annexin V per $10^6$ cells ($3.8\times10^6$ molecules of annexin V per cell) on both cell types, in good agreement with literature reports (Rao et al., 1992). This value was taken as the maximal level of externalized anionic phospholipids.

TABLE 11

Induction of PS by Recreating Tumor Environment

| | | $^{125}$I-Annexin V (% of Max binding) | |
|---|---|---|---|
| Treatment | Concentration | ABAE CELLS | bEnd.3 cells |
| Medium with 10% serum | N/A | 0 | 0 |
| Actinomycin D + TNF α | 50 ng/ml each | 100 | 100 |
| VEGF | 20 ng/ml | 0 | 0 |
| FGF-2 | 20 ng/ml | 0 | 0 |
| Scatter factor | 40 ng/ml | 0 | 0 |
| TGF $\beta_1$ | 20 ng/ml | 0 | 0 |
| PDGF-BB | 20 ng/ml | 0 | 0 |
| IL-10 | 20 ng/ml | 0 | 0 |
| IL-8 | 20 nglml | 0 | 0 |
| IL-6 | 20 ng/ml | 0 | 0 |
| IL-1α | 10 ng/ml | 6.4 | 7.5 |
| IL-1β | 10 ng/ml | 5.8 | 5.5 |

TABLE 11-continued

Induction of PS by Recreating Tumor Environment

| Treatment | Concentration | $^{125}$I-Annexin V (% of Max binding) ABAE CELLS | bEnd.3 cells |
|---|---|---|---|
| Interferon | 40 ng/ml | 8.6 | 2.8 |
| TNFα | 20 ng/ml | 7.4 | 13.7 |
| Thrombin | 50 nM | 8.8 | 17.4 |
| Hypoxia | 1% $O_2$ | 15.0 to 17.5 | 22.5 |
| Hypoxia + IL-1α | Same as above | 26.0 | 31.0 |
| Hypoxia + TNFα | Same as above | 33.0 | 36.0 |
| pH 6.6 | N/A | 20.2 | 18.9 |
| Hydrogen peroxide | 200 μM | 95.5 | 98.4 |

In Table 11, the concentrations of cytokines, growth factors and thrombin used were selected from literature values to have maximal stimulatory effect on cultured endothelial cells. These concentrations did not cause toxicity over the period of the test (24 h) as judged by morphological appearance, a lack of detachment, and a lack of uptake of trypan blue. The concentration of $H_2O_2$ employed was the maximal concentration that did not cause cytotoxicity under the chosen conditions.

The basal binding of $^{125}$-annexin V was determined in the presence of growth medium alone. Maximal PS exposure was determined after induction of apoptosis by the combined treatment with actinomycin D and TNF α. Average of duplicates from three separate studies is presented. Standard error was less than 5%.

Untreated cells were largely devoid of externalized PS, as judged by annexin V or anti-PS (9D2) antibody binding (Table 11). The basal binding in the presence of growth medium alone was 0.44 and 0.68 pmoles of $^{125}$I-annexin V for ABAE and bEnd.3 cells, respectively. This corresponds to approximately 7.1% and 10.9% of the maximal binding for ABAE and bEnd.3 cells, respectively, which correlated well with the finding that approximately 10% of cells bound biotinylated annexin V under the same conditions.

VEGF, HGF, FGF, TGF$\beta_1$, PDGF, IL-6, IL-8 and IL-10 did not increase binding of $^{125}$I-annexin V above the basal level for untreated cells (Table 11), neither did GM-CSF. Inflammatory mediators (IL-1α, IL-1β, TNFα and interferon) caused a small but reproducible increase in PS and anionic phospholipid translocation that ranged from 5 to 8% of the maximal level for ABAE cells and from 3 to 14% for bEnd3 cells.

Hypoxia/reoxygenation, thrombin or acidic external conditions (pH 6.8-6.6) induced a moderately high externalization of PS and anionic phospholipid that ranged from 8 to 20% of the maximal level for ABAE cells and from 17 to 22% of the maximal level for bend.3 cells. The largest increase in PS and anionic phospholipid translocation was observed after treatment with 100 to 200 μM of hydrogen peroxide. This treatment caused nearly complete (95%) externalization of PS in both cell types as judged by $^{125}$I-annexin V binding (Table 11). More than 70% of ABAE and bEnd.3 cells bound biotinylated annexin V, as judged immunohistochemically.

Endothelial cells in which PS and anionic phospholipid translocation was generated by treatment with hypoxia/reoxygenation, thrombin, acidity, TNFα, IL-1 or $H_2O_2$ remained attached to the matrix during time period of the assay (24 h), retained cell-cell contact and retained their ability to exclude trypan blue dye. Normal PS and anionic phospholipid orientation was restored 24 to 48 h later in the majority of the cells after the inducing-factor was removed, or the culture conditions were returned to normal. These results indicate that mild oxidative stress, created by direct application of $H_2O_2$ or indirectly by hypoxia/reoxygenation, acidity, thrombin, or inflammatory cytokines, triggers a transient translocation of PS and anionic phospholipids on viable endothelial cells.

4. Combined Effects of Inflammatory Cytokines and Hypoxia/Reoxygenation

Enhanced PS and anionic phospholipid exposure was observed when ABAE and bEnd.3 cells were subjected to hypoxia/re-oxygenation in the presence of IL-1α or TNFα. In the absence of the cytokines, hypoxia/reoxygenation increased PS-exposure by ABAE cells to 15%-17.5% of the maximum level for cells treated with apoptotic concentrations of actinomycin D and TNFα. In the presence of subtoxic concentrations of IL-1α or TNFα, hypoxia/reoxygenation increased anionic phospholipid-exposure to 26% and 33% respectively of the maximum (Table 11). Comparison with the effect of cytokines in the absence of hypoxia/reoxygenation indicates that the combination of cytokines and hypoxia/reoxygenation had a greater than additive effects on PS-exposure. Similar effects were observed on bEnd.3 cells.

Therefore, in the tumor environment, the exposure of PS and anionic phospholipids induced by hypoxia/re-oxygenation may be amplified by inflammatory cytokines and possibly by such other stimuli as acidity and thrombin. Neutrophils could play a role in this process.

These in vitro studies shed light on the mechanism of PS exposure on tumor endothelial cells in vivo. They show that various factors induce PS exposure on endothelial cells without causing cytotoxicity, which mimics the situation in tumors in vivo. Hypoxia followed by reoxygenation, acidity, and thrombin most increased PS exposure on viable endothelial cells. Inflammatory cytokines (TNFα and IL-1α) also caused a weak but definite induction of PS exposure.

These conditions are likely to be the major inducing stimuli in tumors in vivo because:

i) PS positive endothelium is prevalent in and around regions of necrosis where hypoxia, acidity, thrombosed blood vessels, and infiltrating host leukocytes are commonly observed;

ii) the finding that hypoxia/reoxygenation amplifies the weak PS-exposing activity of TNFα and IL-1 on endothelial cells in vitro correlates with the situation in vivo in tumors where hypoxia and cytokine-secreting tumor and host cells co-exist; iii) hypoxia/reoxygenation and thrombin have been reported to generate reactive oxygen species (ROS) in endothelial cells through activation of NADPH oxidase-like membrane enzyme (Zulueta et al., 1995). ROS produced by malignant cells might contribute to endothelial cell injury (Shaughnessy et al., 1989). Hydrogen peroxide was the most powerful inducer of PS exposure on cultured endothelial cells found in the present study, providing indirect support for the involvement of ROS.

Externalized PS provides a negative phospholipid surface upon which coagulation factors concentrate and assemble. This may contribute to the procoagulant status on the tumor endothelium that has long been recognized. PS also provides an attachment site for circulating macrophages (McEvoy et al., 1986), T lymphocytes (Qu et al., 1996) and polymorphonuclear cells that assist in leukocyte infiltration into tumors. Adherence of activated macrophages, polymorphonuclear cells and platelets to PS on tumor endothelium may lead to further secretion of reactive oxygen species and further amplification of PS exposure.

5. Antibody Binding to $H_2O_2$-Treated HUVEC and MDA-MB-435 Cells

Figure 5:
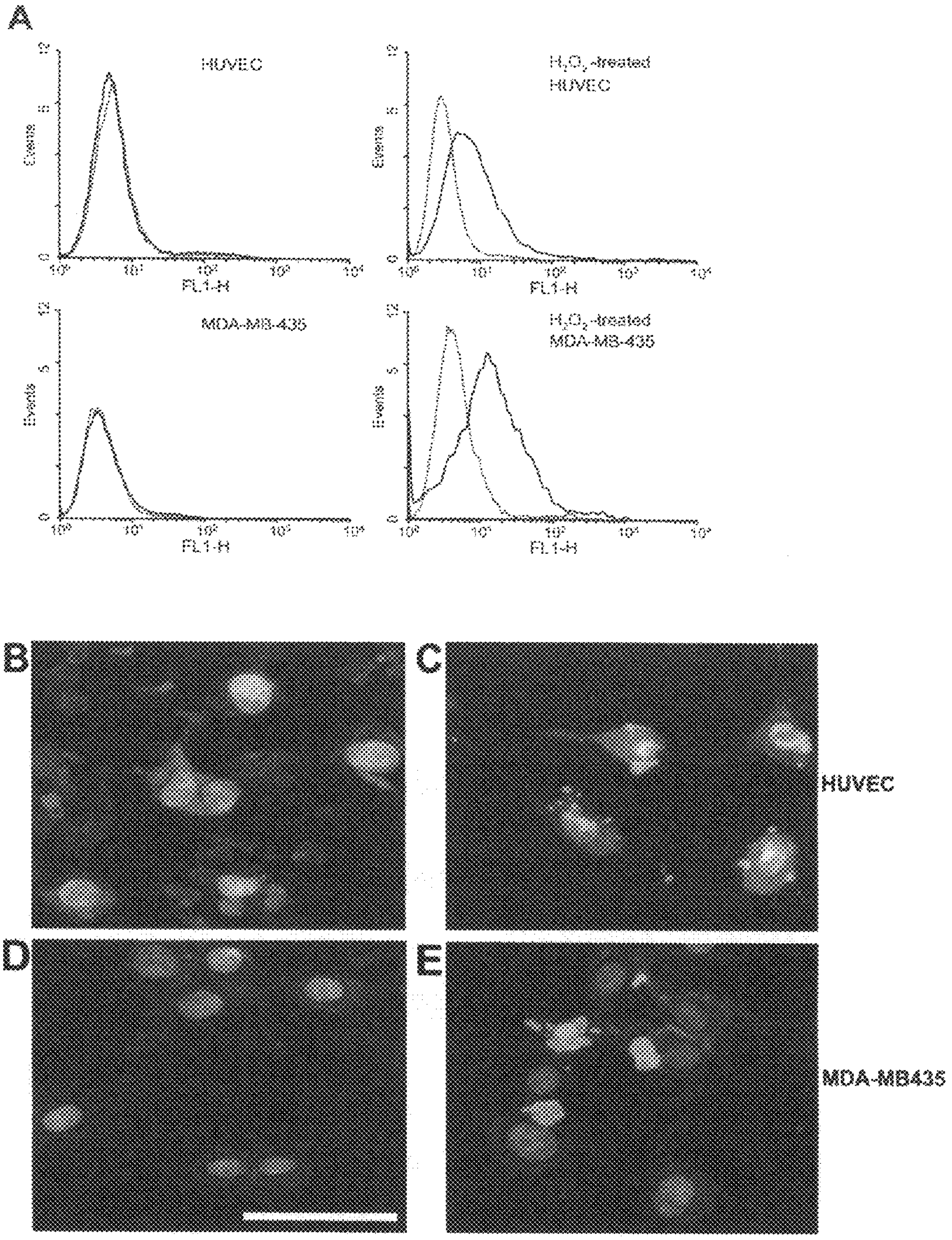
FIG. 5A, FIG. 5B, FIG. 5C, FIG. 5D and FIG. 5E. Induction of 3G4 binding to intact HUVEC and MDA-MB-435 cells by $H_2O_2$ treatment as shown by FACS (FIG. 5A) and immunohistochemistry (FIG. 5B, FIG. 5C, FIG. 5D and FIG. 5E).

The binding of the 3G4 antibody to $H_2O_2$-treated and untreated HUVEC and MDA-MB-435 cells was analyzed by flow cytometry (FIG. 5A). The $H_2O_2$ treatment conditions were established as set forth above to induce exposure of anionic phospholipids on the external surface of the plasma membrane.

Neither cell type bound detectable levels of 3G4 before treatment with $H_2O_2$. After treatment with $H_2O_2$, the mean fluorescence intensity of cells stained with 3G4 followed by FITC-anti-mouse IgG was approximately 10-fold greater than that of cells treated with BBG3 followed by the secondary reagent. $H_2O_2$-treated cells did not stain with propidium iodide, indicating that their outer membranes were intact. 3G4 binding was blocked by liposomes prepared from anionic phospholipids, but not by liposomes prepared from neutral phospholipids, indicating that the 3G4 was binding to cellular anionic phospholipids.

To determine the distribution of the 3G4 antibody on the cell surface, $H_2O_2$-treated HUVEC and MDA-MB-435 cells were stained with 3G4 by indirect immunofluorescence and examined using fluorescence microscopy (FIG. 5B, FIG. 5C, FIG. 5D and FIG. 5E). The 3G4 antibody stained discrete regions of the plasma membrane of $H_2O_2$-treated HUVEC and MDA-MB-435 cells. The stained regions of cell membrane had the appearance of small surface blebs (FIG. 5C, FIG. 5E) similar to the "membrane blebs" observed on endothelial cells treated with $H_2O_2$ (Hastie et al., 1997; van Gorp et al., 2002). The $H_2O_2$-treated cells were not stained by the control antibody, BBG3 (FIG. 5B, FIG. 5D), showing that the binding of 3G4 to the cells was antigen-specific. Identical staining patterns were observed with FITC-labeled annexin A5. The 3G4-positive $H_2O_2$-treated cells did not show morphological signs of nuclear condensation when examined 1 hr. after addition of $H_2O_2$, consistent with reports that peroxide-induced membrane blebbing in endothelial cells is related to glutathione oxidation, not apoptosis, and can be reversible (van Gorp et al., 2000).

These findings therefore indicate that the 3G4 antibody binds to anionic phospholipids that are normally absent from the surface of HUVEC or MDA-MB-435 cells, and that become exposed on the cell surface when the cells are treated with $H_2O_2$.

EXAMPLE VIII

Anti-Tumor Effects of Annexin Conjugates

The surprising finding that aminophospholipids and anionic phospholipids are stable markers of tumor vasculature means that antibody-therapeutic agent constructs can be used in cancer treatment. In addition to using antibodies as targeting agents, annexins, and other specific binding proteins, can also be used to specifically deliver therapeutic agents to tumor vasculature. The following data shows the anti-tumor effects that result from the in vivo administration of annexin-TF constructs.

A. Methods

An annexin V-tTF conjugate was prepared and administered to nu/nu mice with solid tumors. The tumors were formed from human HT29 colorectal carcinoma cells that formed tumors of at least about 1.2 $cm^3$. The annexin V-tTF coaguligand (10 μg) was administered intravenously and allowed to circulate for 24 hours. Saline-treated mice were separately maintained as control animals. After the one day treatment period, the mice were sacrificed and exsanguinated and the tumors and major organs were harvested for analysis.

B. Results

The annexin V-tTF conjugate was found to induce specific tumor blood vessel coagulation in HT29 tumor bearing mice. Approximately 55% of the tumor blood vessels in the annexin V-tTF conjugate treated animals were thrombosed following a single injection. In contrast, there was minimal evidence of thrombosis in the tumor vasculature of the control animals.

EXAMPLE IX

Anti-Tumor Effects of 3SB Anti-PS Antibodies

The present example shows the anti-tumor effects of anti-PS antibodies using syngeneic and xenogeneic tumor models. The 3SB antibody used in this study binds to PS (and PA), but is essentially devoid of reactivity with PE. This anti-PS antibody caused tumor vascular injury, accompanied by thrombosis, and tumor necrosis.

The effects of anti-PS antibodies were first examined in syngeneic and xenogeneic tumor models using the 3SB antibody. For the syngeneic model, $1\times10^7$ cells of murine colorectal carcinoma Colo 26 (obtained from Dr. Ian Hart, ICRF, London) were injected subcutaneously into the right flank of BALB/c mice. In the xenogeneic model, a human Hodgkin's lymphoma L540 xenograft was established by injecting $1\times10^7$ cells subcutaneously into the right flank of male CB17 SCID mice. Tumors were allowed to grow to a size of about 0.6-0.9 $cm^3$ before treatment.

Tumor-bearing mice (4 animals per group) were injected i.p. with 20 μg of 3SB anti-PS antibody (IgM), control mouse IgM or saline. Treatment was repeated 3 times with a 48 hour interval. Animals were monitored daily for tumor measurements and body weight. Tumor volume was calculated as described in Example I. Mice were sacrificed when tumors had reached 2 $cm^3$, or earlier if tumors showed signs of necrosis or ulceration.

The growth of both syngeneic and xenogeneic tumors was effectively inhibited by treatment with 3SB anti-PS antibodies. Anti-PS antibodies caused tumor vascular injury, accompanied by thrombosis, and tumor necrosis. The presence of clots and disintegration of tumor mass surrounding blocked blood vessels was evident.

Quantitatively, the 3SB anti-PS antibody treatment inhibited tumor growth by up to 60% of control tumor volume in mice bearing large Colo 26 and L540 tumors. No retardation of tumor growth was found in mice treated with saline or control IgM. No toxicity was observed in mice treated with anti-PS antibodies, with normal organs preserving unaltered morphology, indistinguishable from untreated or saline-treated mice.

Tumor regression started 24 hours after the first treatment and tumors continue to decline in size for the next 6 days. This was observed in both syngeneic and immunocompromised+ tumor models, indicating that the effect was mediated by immune status-independent mechanism(s). Moreover, the decline in tumor burden was associated with the increase of alertness and generally healthy appearance of the animals, compared to control mice bearing tumors larger than 1500 $mm^3$. Tumor re-growth occurred 7-8 days after the first treatment.

The results obtained with anti-PS treatment of L540 tumors are further compelling for the following reasons. Notably, the tumor necrosis observed in L540 tumor treatment occurred despite the fact that the percentage of vessels that stained positive for PS in L540 tumors was less than in HT 29 and NCI—H358 tumors. This implies that even more rapid necrosis would likely result when treating other tumor types. Furthermore, L540 tumors are generally chosen as an experimental model because they provide clean histological sections and they are, in fact, known to be resistant to necrosis.

EXAMPLE X

Anti-Tumor Effects of Antibody (9D2) Against Anionic Phospholipids

This example demonstrates the effects of the 9D2 antibody, which binds to PS and other anionic phospholipids, in anti-tumor studies in vivo.

A high dose (>150 μg) of the rat antibody that binds to anionic phospholipids, 9D2, was injected into nude mice bearing H358 tumors. Immunolocalization studies shows that it strongly localized to tumor endothelium (4+), although some low level, non-specific binding of 9D2 by normal vessels was observed due to the high dose (as would be observed for a control IgM antibody of irrelevant specificity).

When 9D2 was injected i.p. into a SCID mouse with an L540 tumor for ascites production, the tumor became necrotic and collapsed. Upon injection of a control antibody (MK 2.7, rat IgG) into a SCID mouse with an L540 tumor, no similar effects were observed.

The effect of the 9D2 anti-PS antibody on the growth of L540 tumors in vivo was then determined more precisely. Treatment was started when tumors reached 200-250 μl (day 0). From day 0 to day 7, mice were injected i.p. with ~150 μg of IgM (200 μl supernatant) or 200 μl of 10% DMEM. From day 7 to day 22, mice were injected i.p. with ~300 μg of IgM (400 μl supernatant) or 400 μl of 10% DMEM. Day 22 was the last day of treatment and the mice were sacrificed.

As shown in Table 12, from days 10 to 22, tumor growth is generally inhibited by about 40% to 50%. At the end of the study, only 4 mice in the treated group have tumors larger than 2000 μl in volume, in contrast to 9/9 in the control group.

TABLE 12

Effects of Anti-PS Antibodies on L540 Tumors In Vivo

| Day after start of the treatment | Average Tumor Volume (μl) Control | Treated | % Inhibition | Number of mice with tumor volume >2000 μl Control | Treated |
|---|---|---|---|---|---|
| 0 | 341 | 320 | 6.2 | 0 | 0 |
| 1 | 464 | 325 | 10.8 | 0 | 0 |
| 3 | 412 | 415 | 0 | 0 | 0 |
| 7 | 687 | 455 | 33.8 | 0 | 0 |
| 10 | 904 | 544 | 39.9 | 1/9 | 0 |
| 13 | 945 | 545 | 42.4 | 1/9 | 0 |
| 15 | 1373 | 685 | 50.1 | 4/9 | 1/10 |
| 17 | 1426 | 842 | 41.0 | 4/9 | 4/10 |
| 20 | 1992 | 987 | 50.5 | 6/9 | 4/10 |
| 22 | 2560 | 1365 | 53.3 | 9/9 | 4/10 |

In another in vivo study, the effects of the rat anti-PS antibody on the growth of L540 tumors in CB17 SCID mice were followed for 45 days after tumor cell injections. These tumor bearing mice were treated with 300 μg of anti-PS antibody daily, i.p. or with 300 μl of 10% DMEM daily, i.p., as a control. Various parameters of tumor treatment were markedly better in the treated group in comparison to those of the controls (Table 13).

TABLE 13

Effects of Anti-PS Antibodies on L540 Tumors In Vivo

| Other parameters | Control | Treated |
|---|---|---|
| % Regressed tumors[1] (60 days post treatment) | 0 | 40% |
| % Regressed tumors[1] (90 days post treatment) | 0 | 20% |
| Average volume of secondary tumors (μl)[2] | 537 ± 30 | 366 ± 56 |

[1]Tumors too small to measure in treated mice at indicated times (60 vs. 90 days) after treatment
[2]Metastases in lymph nodes In a further study, the 9D2 antibody was injected intraperitoneally at a dose of 100 μg 3 times per week to mice with L540 tumors. The tumor size was measured with calipers twice a week. The anti-tumor effects in comparison to the control group were marked.

EXAMPLE XI

Anti-Tumor Effects of Anti-PS Antibody 3G4

The present example demonstrates additional anti-tumor effects using the anti-PS antibody 3G4 in syngeneic and xenogeneic tumor models. The 3G4 antibody used in this study is an IgG antibody that binds to PS and other anionic phospholipids (Example IV).

A. Protocols for Animal Tumor Studies

The effects of 3G4 was examined in syngeneic and xenogeneic tumor models. The general protocol for the animal tumor treatment studies is conducted as follows. Unless particular differences are specified, this is the protocol used throughout the studies of the present application.

The animals are obtained from Charles Rivers Laboratories. The mice are 4-5 weeks, female, C.B-17 SCID or Fox Chase SCID mice. Mice are housed in autoclaved caging, sterile food and water, with sterile handling. All procedures performed in laminar flow hoods. Mice are acclimated 1 week and then ear-tagged and a blood sample (approximately 75-100 μl) taken from the tail vein to check for leakiness by ELISA. Any mice that fail the leakiness ELISA test should not be used for test procedures. Mice are injected orthotopically with tumor cells into mammary fat pad (MFP) or subcutaneously into the right flank 2-3 days post ear-tagging and blood sample removal.

In the orthotopic model, $1\times10^7$ cells in 0.1 ml DMEM are typically injected into MFP of anesthetized mice. Mice are anesthetized with 0.075 ml of mouse cocktail injected IP. The mouse cocktail is 5 ml Ketamine (100 mg/ml); 2.5 ml Xylazine (20 mg/ml); 1 ml Acepromazine (10 mg/ml); 11 ml sterile water. Dosage is 0.1 ml per 20-30 grams body weight via the IP route for a duration of 30 minutes.

Once the mouse is anesthetized, as measured by no response to toe/foot pinch, the mouse is laid on its left side and wiped with 70% ethanol just behind the head and around the right forearm/back area. A 2-3 mm incision is made just behind the right forearm (lateral thorax), which reveals a whitish fat pad when the skin flap is raised. 0.1 ml of cells are injected into the fat pad using a 1 ml syringe and a 27-gauge needle, producing a bleb in the fat pad. The incision is closed using a 9 mm sterile wound clip. The mouse is returned to its cage and observed until it has wakened from anesthesia and is mobile. Post-operative health status is determined, and if any signs of distress are observed, the animal is given acetaminophen (0.24 mg/ml)+codeine (0.024 mg/ml) in the drinking water. The wound clip is removed after 1 week. This method is used so that the cells are accurately placed into the selected site and not into the subcutaneous region. Tumors will be approximately 200 μl in volume (L×W×W) in 14-15 days and the take rate is essentially 100%.

In the subcutaneous model, mice are typically injected with $1\times10^7$ cells in 0.2 ml. Mice are not anesthetized, but are restrained using a steady grip of mouse skin exposing the right flank. A 1 ml syringe with a 23 gauge needle is used to inject $1\times10^7$ cells in 200 μl, just under the skin of the mice and a bleb will be seen. It is not unusual to observe a small amount of fluid leak from the injection site. A twisting motion may be used when withdrawing the needle from the subcutaneous injection to reduce this leakage. Tumor volume is measured by L×W×H.

In the perfusion protocol, mice are injected IV with 1000 U of heparin in 0.2 ml saline. Mice are then be sedated by injecting the mouse IP with 0.1 ml mouse cocktail. Once the mouse is sedated enough, as measured by no reflex when toe/foot is pinched, the thoracic cavity is opened to expose the heart and lungs. A 30 gauge needle attached to tubing and perfusion pump is inserted into the left ventricle. The right ventricle is snipped so that blood can drip out. Saline is pumped through for 12 minutes at a speed of 1 ml per minute. At the end of the perfusion, the needle and tubing are removed. Tissues are removed for further studies, either immunohistochemistry or pathology.

B. Tumor Treatment Results

For the syngeneic model, Meth A mouse fibrosarcoma tumor cells were used. In one xenogeneic model, human MDA-MB-231 breast tumor cells were seeded into the mammary fat pad. In another xenogeneic model, a large human Hodgkin's lymphoma L540 xenograft was established by injecting cells and allowing the tumor to grow to a size of over 500 $mm^3$ before treatment. Tumor-bearing mice (10 animals per group) were injected i.p. with 100 μg of 3G4 anti-PS antibody (IgG) as opposed to control. Treatment was repeated 3 times a week. Animals were monitored twice a week for tumor measurements.

The growth of both syngeneic and xenogeneic tumors was effectively inhibited by treatment with 3G4 anti-PS antibodies. The antibodies caused tumor vascular injury, localized thrombosis and tumor necrosis.

The treatment of the syngeneic, Meth A tumor cells was particularly successful, and the treatment of the human MDA-MB-231 breast tumor cells growing in the mammary fat pad also produced tumor regressions. Even in mice bearing large L540 tumors, known to be resistant to necrosis, the 3G4 antibody treatment inhibited tumor growth in comparison to control. No retardation of tumor growth was found in control mice. No toxicity was observed in mice treated with anti-PS antibodies.

Tumors were also established using MD-MBA-435s cells and treated as described above. The growth of these tumors was also effectively inhibited by treatment with the 3G4 antibody. The treatment of large L540 tumors, MDA-MB-231 and MD-MBA-435s tumor cells for 60 days was also effective. The antibodies caused tumor vascular injury, thrombosis and necrosis and retarded tumor growth, with no evidence of toxicity.

MD-MBA-435s lucerifase cells were obtained from Dr. Angels Sierra Jimenez, Barcelona, Spain and were grown in 10% DMEM. Mice were injected with tumor cells as described as above, and at 2 weeks post injection, the tumors were measured and the volume recorded. Treatment of mice with tumors of similar average volumes (200 $mm^3$) was performed using the 3G4 antibody and the chimeric 3G4 antibody, produced as described in Example XIX, versus control. Treatment was initiated by IP injection (800 μg) at day 15 and continued with injections of 200 μg every two to three days until the final injection of 400 μg at day 35. Tumor volumes and mouse body weights were measured on injection days. Mice were sacrificed and perfused with saline for 12 minutes. The organs and tumor were removed, snap-frozen in liquid nitrogen and the tumor sectioned for immunohistochemistical analysis.

This study showed that both the 3G4 antibody and the chimeric 3G4 antibody effectively retarded tumor growth as opposed to control.

EXAMPLE XII

Anti-Viral Effects of Anti-PS Antibodies Against CMV

Surprisingly switching fields from tumor vasculature to viral infections, the inventors next reasoned that antibodies to aminophospholipids and anionic phospholipids would also likely exert an anti-viral effect. The present example indeed shows this to be true, first using the 3G4 antibody in the treatment of cytomegalovirus (CMV) infection.

A. Methods

1. Treatment of CMV-Infected Cells In Vitro

Confluent monolayers of human diploid foreskin fibroblasts (HHF-R2) in 6-well plates were infected with human CMV AD169 expressing green fluorescent protein (GFP) at an MOI=0.01 as previously described (Bresnahan et al., 1996). Briefly, the cells were incubated with virus in a total volume of 1 ml per well at 37° C. for 90 minutes. During the infection, the plates were gently rocked every 30 minutes. Following the infection, the cell supernatant was removed and DMEM/10% FBS/pen-strep (2 ml per well) was added to each well.

Dilutions of 3G4 or the isotype matched control antibody GV39G (100 μg/ml and 50 μg/ml) were added to the wells. The infected cells were incubated at 37° C. for a total of 19 days. The medium and antibody in each well was replaced every 3 days. On day 19, the cells and supernatants from each well were harvested and frozen at −80° C. until the plaque assays were carried out.

2. Fluorescent Microscopy

The recombinant CMV expresses GFP under the control of the SV40 promoter. Hence, infected cells appear green under a fluorescent microscope. In these studies, the antibody treated CMV-infected cells were observed under a fluorescent microscope at days 2, 3 and 9.

3. Plaque Assays

The plaque assays were carried out using standard protocols. Briefly, the frozen cells cell suspensions were thawed quickly at 37° C. and centrifuged to remove debris at 1000 rpm for 1 minute. Different dilutions of the cell supernatants were added to sub-confluent monolayers of HHF-R2 cells in 6-well plates and the cells incubated at 37° C. for 90 minutes (the plates were gently rocked every 30 minutes). Following the infection, the cell supernatants were removed and replaced with 2 ml of DMEM/10% FBS. On day 4, the supernatant in each well was removed and the cells overlayed with 0.01% low melting point agarose/DMEM/10% FBS. The plates were incubated at 37° C. for a total of 14 days post-infection. On day 14, the infected monolayers were fixed with 10% buffered formalin and stained with methylene blue to visualize the plaques.

B. Results 1. 3G4 Inhibits Viral Spread of CMV

To investigate whether 3G4 has an inhibitory effect on CMV infection and replication, confluent human fibroblasts were pretreated with 3G4 before CMV was added at a low m.o.i. The CMV used in these studies expresses green fluorescent protein (GFP). Hence, infected cells appear green when observed under a fluorescence microscope.

On day 3 of treatment, with both 50 μg/ml and 100 μg/ml of antibody, there are single infected cells both in untreated wells and in wells treated with 3G4 or isotype-matched control antibody, GV39G. Thus, treating the fibroblasts with 3G4 does not appear to significantly inhibit the entry of the virus into the cells.

On day 9, however, there is a dramatic difference in the number of infected cells in 3G4-treated vs. control, GV39G-treated wells. While the virus has spread to approximately 80% of the monolayer in the control wells, the virus is restricted to the original singly-infected cell in the 3G4-treated wells. Hence, 3G4 limits the spread of CMV from the original infected cell to the surrounding cells. This inhibition of viral spread is observed when cells are treated with 100 μg/ml and 50 μg/ml.

2. Viral Inhibition is Antibody Concentration-Dependent

In order to determine what concentration of 3G4 is necessary for the anti-viral effect at a low m.o.i., infected cells were treated with different concentrations of 3G4 and the control antibody, GV39G. The complete inhibition of cell-to-cell spread is observed with 3G4 at 100 μg/ml and 50 μg/ml. When the cells were treated with 25, 12.5 and 6.25 μg/ml of 3G4, there are increasing numbers of GFP positive CMV-infected cells. Although 3G4 does not totally prevent viral spread from the primary infected cells at these lower concentrations, it still has a meaningful anti-viral effect, since fewer GFP-positive CMV-infected cells are seen in the 3G4-treated well as compared to GV39G-treated, control wells.

3. Quantification of Viral Load at a Low M.O.I.

The anti-viral effect of 3G4 was quantitated by carrying out plaque assays to determine the viral load following antibody-treatment. The controls included untreated cells, the GV39G antibody and an additional antibody control using the C44 antibody, a mouse IgG2a isotype antibody to colchicine.

Treatment of infected cells (m.o.i.=0.01 pfu/cell) with 100 μg/ml of 3G4 resulted in a dramatic 6 $\log_{10}$ decrease in viral titer as compared to control, GV39G-treated cells. This inhibition translates into an approximately 99.9999% inhibition of viral replication. At a concentration of 50 μg/ml, treatment with 3G4 results in a 3.5 $\log_{10}$ decrease in viral titer as compared to GV39G-treatment. Using 3G4 at 25 μg/ml and 12.5 μg/ml, the results are still dramatic, and even at 6.25 μg/ml an inhibitory effect is still observed.

4. Quantification of Viral Load at a High M.O.I.

3G4 treatment of fibroblasts infected at a high m.o.i. of 3 also results in a dramatic reduction in viral titer. At 100 μg/ml, treatment with 3G4 resulted in a 5 $\log_{10}$ decrease in viral titer as compared to control, GV39G-treated cells. At 50 μg/ml, 3G4 inhibited viral replication by 3 logs when compared to GV39G.

5. Inhibition of Replication at a Late Stage

To determine which stage of the CMV replicative cycle is blocked by 3G4, a timed addition study was performed. For this, 3G4 was added to fibroblasts infected at a high m.o.i. at different time points after the infection. The viral load (in both the cells and supernatant) was quantified using a standard plaque assay.

Addition of 3G4 up to 24 hours after infection resulted in a 5-6 $\log_{10}$ decrease in viral titer. However, when addition of 3G4 was delayed to 48 hours, the inhibitory effect of 3G4 was reduced to 2 $\log_{10}$ and when addition was delayed to 72 to 96 hours, the inhibitory effect was further reduced. This shows that 3G4 interferes with a late stage of CMV replication that occurs between 24-48 hours after infection. Thus, 3G4 does not significantly interfere with infection or with immediate early or early gene expression. It rather acts later in the viral replication cycle, e.g., on late gene expression, viral DNA synthesis, viral packaging or egress.

EXAMPLE XIII

Anti-Viral Effects of Anti-PS Antibodies Against RSV

In addition to the dramatic anti-viral effects against CMV shown in Example XII, the present example demonstrates the use of three different anti-PS antibodies in the inhibition of Respiratory Syncitial Virus (RSV) replication.

A. Methods

1. Treatment of RSV-Infected Cells In Vitro

A-549 cells were grown to 100% confluence in three Costar 12-well tissue culture plates. 200 μL of minimum essential Eagle medium was added to all wells. Anti-phospholipid antibody (Ab) was added (100 μg in 100 μL) to 9 wells of each plate and 30 min. later cells in 6 of those initial 9 wells were infected with an MOI of 1 with RSV long strain in a volume of 100 uL. The three remaining wells were left as non-infected, antibody-treated wells. The three other wells with no antibody were infected with RSV at the same MOI as described above.

Each plate was used to test the three different antibodies: 3G4, 3SB and 1B9 (Example IV). Cells were incubated in 5% $CO_2$ at 40° C. for 2 hours and then 600 μL of medium was added to complete 1 mL volume in each well. An A-549 cell plate was kept in the same conditions, as control. Supernatants were collected at 4, 24 and 72 hours after infection. At each time point, four wells from each plate were sampled: one well with only-Ab treated cells, two wells had Ab-treated/RSV-infected cells and one well had RSV-infected only cells. The samples were frozen at −80 until the plaque assay.

2. Plaque Assays

The plaque assays were carried out as previously described (Kisch et al., 1963; Graham et al., 1988). Briefly, the frozen cells cell suspensions were thawed quickly at 37° C. Three 10-fold dilutions were made from the undiluted cell supernatants: $10^{-1}$, $10^{-2}$, and $10^{-3}$. 100 μL of each dilution plus the undiluted sample were inoculated into 80% confluent Hep-2 cell line plates, all in triplicates. Plates were placed in the 5% $CO_2$, 40° C. incubator for 5 days. On the $5^{th}$ day, the plates were developed and stained with hematoxylin and eosin to reveal the plaques in each well. The plaques were counted using a dissecting microscope to calculate the RSV viral load in pfu (plaque forming units)/mL.

B. Results

Treatment of RSV-infected cells with either 3SB or 1B9 resulted in a log decrease in viral replication. The anti-viral effect was even more pronounced when the infected cells were treated with 3G4. Treatment with 3G4 resulted in a 2 $\log_{10}$ decrease in viral titer. The inhibition was lower than seen with CMV, most likely because the concentration of 3G4 was low (25-50 μg/ml).

EXAMPLE XIV

Single Chain Anti-PS Antibodies

Given the many uses of anti-PS antibodies described herein, including as anti-tumor agents alone, as targeting agents for delivering attached therapeutic agents to tumors, and as anti-viral agents, the present example describes techniques suitable for generating single chain (scFv) anti-PS antibodies, i.e., wherein the $V_H$ and $V_L$ domains are present in a single polypeptide chain, generally joined by a peptide linker.

A. Preparation of the Phage Antibody Library

The secondary stock of the bacterial library (about $1\times10^{10}$ clones) was inoculated into 100 ml 2×TY containing 100 µg/ml ampicillin and 1% glucose. It was grown with shaking at 37° C. until the OD at 600 nm was 0.5.

M13KO7 helper phage was added at $10^{13}$ pfu and incubated without shaking in a 37° C. water bath for 30 min. The infected cells were centrifuged at 3,500 g for 10 min. The pellet was resuspended in 200 ml of 2×TY containing 100 µg/ml ampicillin and 75 µg/ml kanamycin and incubated with shaking at 30° C. overnight.

The culture was centrifuged at 10,800 g for 10 min. ⅕ volume PEG/NaCl was added to the supernatant, mixed well and left for 1 hr at 4° C. It was then centrifuged at 10,800 g for 30 min. The pellet was resuspended in 40 ml PBS and 8 ml PEG/NaCl was added. It was mixed and left for 20 min at 4° C. It was then centrifuged at 10,800 g for 10 min and the supernatant aspirated. The pellet was resuspended in 2 ml 10% human serum and centrifuged at 11,600 g for 10 min in a microcentrifuge to remove most of the remaining bacterial debris.

To pre-pan, the phage antibody library in 10% human serum was added to the PC coated dish and incubated for 60 min at room temperature.

B. Selection on Biotinylated Liposomes

20 µmol phosphatidylinositol and 20 µmol biotinylated phosphatidylserine were dissolved in 10 ml hexane. This solution was dried to a thin layer on the surface of a flask using a rotating evaporator. 2 ml PBS was added and bath sonicated 4° C. for 30 minutes.

100 µl phage scFv and 100 µl biotinylated liposomes were then mixed in the presence of 10% human serum and gently rotated for one hour at room temperature. Blocking was done with 100 µl streptavidin M-280 dynabeads by adding 600 µl 2.5% casein/0.5% BSA for 30 min at room temperature. The beads were separated from the blocking buffer with a MPC-E (Magnetic Particle Concentrator from Dynal) for 4-5 min.

The beads were resuspended in 100 µl PBS. 100 µl of blocked streptavidin Dynabeads was added to the phage bound to the biotinylated antigen and gently rotated for 15 min at room temperature. Separation was achieved with a MPC-E for 5 minutes and the supernatant poured off. It was washed five times with 1 ml PBS. For each wash, the beads were resuspended and brought down with a MPC-E.

Finally, the phage was eluted from the beads by resuspending in 300 µl 100 mM triethalamine for 30 mins. 150 µl 1 M Tris pH=7.4 was added for neutralization. The beads were separated again with the MPC-E.

150 µl of the phage supernatant was used to infect 10 ml TG1 bacteria in log phase. The 10 ml culture was shaken in the presence of 20 µg/ml ampicillin at 37° C. for one hour. Ampicillin was added to the final concentration of 50 µg/ml and shaken for another hour. $10^{13}$ pfu M13 helper phage was added to this culture, transferred to 100 ml 2TY medium containing 100 µg/ml ampicillin and shaken at 37° C. for one hour. Kanamycin was added to the final concentration of 100 µg/ml and shaken at 30° C. overnight.

The phage preparation procedure was repeated and the selection procedure repeated another 3 to 4 times.

C. Monoclonal Single Chain Antibody ELISA

Individual HB2151 colonies from the plates (after 4 rounds of selection) were inoculated into 500 µl 2×TY containing 100 µg/ml ampicillin and 1% glucose in 96-well plates and grown with shaking (300 rpm.) overnight at 37° C. 5 µl from this plate were transferred to a second 96-well plate containing 500 µl 2×TY containing 100 µg/ml ampicillin per well and grown shaking at 37° C. for 3 hr (OD600=0.9).

To each well was added 50 µl 2×TY containing 100 µg/ml ampicillin, 10 mM IPTG (final concentration is 1 mM), which was grown with shaking overnight at 30° C. It was centrifuged at 1,800 g for 10 min and 100 µl of the supernatant used in the following ELISA.

96 well plates (DYNEX IMMULON®1B) were coated with PS dissolved in ethanol at a concentration of 10 µg/ml (P6641 10 mg/ml solvent was Chloroform:MeOH 95:5). 10 µg/ml PC was coated in the same way. These plates were evaporated at 4° C. in the cold room. 250 µl 2.5% casein was added to each well, and the plates were covered and blocked at 37° C. for 1 hour.

Wells were rinsed 3 times with PBS, 100 µl/well 10% human serum and 100 µl/well supernatant containing soluble scFv was added and incubated for 60 min at 37° C. The solution was discarded and washed 6 times with PBS. 100 µl 9E10 in 5% casein/0.5% BSA-PBS (1:5000 dilution) was added to each well, incubated at 37° C. for 1 hour and washed 6 times with PBS. 100 µl HRP-goat-anti-mouse antibody (1:10000 dilution) was added to each well, incubated at 37° C. for 1 hour and washed 5 times with PBS. 100 µl 0.05% OPD was added to each well and developed for 5 minutes. 100 µl 0.18 M $H_2SO_4$ was added to stop the reaction and read at O.D. 490.

Antigen-positive clones were streaked on 2×TYAG plates and grown overnight at 30° C. Positive single colonies were picked into 3 ml 2×TYAG media and grown 12 hours at 37° C. Plasmids were extracted and scFv gene inserts checked by enzyme digestion and PCR. The ones with the correct size inserts were sequenced.

The colonies with the correct size inserts were grown into 100 ml 2×TYAG media and shaken at 37° C. OD 600=0.5. These were transferred into 900 ml 2×TYA and grown until OD 600=0.9. 1 M IPTG was added to a final concentration of 1 mM and shaken at 30° C. overnight. The supernatant was checked using the same ELISA method as previously. The scFv protein was purified from the periplasmic fraction using $Ni^{++}$-agarose affinity chromatography.

D. Results

After 4 rounds of panning, the following clones gave promising ELISA signal on PS plates and have the correct size insert: 3E5, 3A2, G5, C8, E4 and 4D5. These have been subcloned, wherein E4 gave 5 positive subclones and 4D5 gave 5 positive subclones (Table 14).

TABLE 14

| ELISA on PS Plate | | | | | | | | | | | |
|---|---|---|---|---|---|---|---|---|---|---|---|
| 0.099 | 0.107 | 0.118 | 0.115 | 0.100 | 0.094 | 0.084 | 0.086 | 0.166 | 0.164 | 0.102 | 0.191 |
| 0.113 | 0.106 | 0.127 | 0.150 | 0.128 | 0.097 | 0.078 | 0.087 | 0.190 | 0.144 | 0.102 | 0.154 |
| 0.122 | 0.115 | 0.117 | 0.112 | 0.105 | 0.097 | 0.085 | 0.088 | 0.230 | 0.071 | 0.168 | 0.150 |

TABLE 14-continued

| ELISA on PS Plate | | | | | | | | | | | |
|---|---|---|---|---|---|---|---|---|---|---|---|
| 0.107 | 0.108 | 0.121 | 0.123 | 0.107 | 0.101 | 0.083 | 0.085 | 0.191 | 0.246 | 0.186 | 0.150 |
| 0.138 | 0.121 | 0.114 | 0.131 | 0.100 | 0.096 | 0.082 | 0.079 | 0.183 | 0.187 | 0.275 | 0.171 |
| 0.118 | 0.115 | 0.116 | 0.132 | 0.099 | 0.094 | 0.082 | 0.086 | 0.185 | 0.073 | 0.208 | 0.102 |
| 0.111 | 0.176 | 0.126 | 0.118 | 0.096 | 0.087 | 0.123 | 0.087 | 0.144 | 0.226 | 0.112 | 0.126 |
| 0.102 | 0.107 | 0.131 | 0.125 | 0.089 | 0.102 | 0.082 | 0.084 | 0.188 | 0.073 | 0.142 | 0.151 |
| 3E5 | | 3A2 | | G5 | | C8 | | E4 | | 4D5 | |

Once the positive clones were identified, they were sequenced. The ScFv nucleic acid and protein sequence of clone 3A2 is set forth in SEQ ID NO:5 and SEQ ID NO:6, respectively. The positive clones were grown up on a large scale and the scFv purified using Nickel agarose affinity chromatography. The purified scFv has been obtained using Phast-gel electrophoresis.

EXAMPLE XV

Synthesis of PE-Binding Peptide Derivatives

The present example concerns the design and synthesis of exemplary PE-binding peptide derivatives and conjugates for use in treating tumors and viral diseases. The structures for exemplary duramycin derivatives result from the following description.

A. DLB 0.5 mg (0.25 μmole) of duramycin dissolved in 0.387 ml 0.1M $NaHCO_3$ in water was added to 0.113 mg (0.25 μmole) of NHS-LC-Biotin (Sigma). The reaction mixture was incubated at room temperature for 1 hr and then at 4° C. overnight. The sample was loaded onto a silica column, washed with 0.1% trifluoroacetic acid (TFA), eluted with 0.1% TFA and 70% $CH_3CN$. The eluant was collected and concentrated by centrifugation. The total yield was 0.5 mg.

B. DIB 0.5 mg (0.25 μmole) of duramycin dissolved in 0.286 ml of 0.1 M $NaHCO_3$ in water was added to 0.034 mg (0.25 μmole) of 2-iminothiolane hydrochloride (2-IT). The mixture was incubated at room temperature for 1 hr. 0.13 mg (0.26 μmole) of iodoacetyl-LC-Biotin (Pierce) was added and the reaction incubated at room temperature for 1 hr and at 4° C. overnight. The sample was loaded onto a silica column, washed with 0.1% TFA, eluted with 0.1% TFA and 70% $CH_3CN$. The eluant was collected and concentrated by centrifugation. The total yield was 0.5 mg.

C. $(DLB)_4NA$ 1.9 mg (0.94 μmole) duramycin was dissolved in 0.5 ml of 0.1M $NaHCO_3$ in water. To this, 0.4 mg (0.88 μmole) NHS-LC-Biotin (Sigma) in 200 μl dimethylformamide (DMF) was added. The mixture was incubated at room temperature for 4 hr. 10 mg (0.17 μmole) neutravidin (NA) in 1 ml was added to the reaction mixture, which was incubated at room temperature for 2 hr and then at 4° C. overnight. The reaction mixture was then loaded onto a G-25 column (volume 50 ml) in PBS buffer. The fractions were collected and analyzed by SDS PAGE (phast gel). Protein-containing fractions (7-16) were pooled together, sterilized by filtration through a 0.22 μm filter and the concentration determined by measuring absorption at 280 nm. The total yield was 5.1 mg.

The sample was then fractionated by FPLC. Three peaks were collected that corresponded to the following: peak 1: $[(DLB)_4NA]_3$ (fractions 17-23); peak 2: $[(DLB)_4]_2$ (fractions 24 33) and peak 3: $(DLB)_4NA$ (fractions 35-48). All the samples were sterilized by filtration through a 0.22 μm filter. The final yields obtained were: 0.34 mg of $[(DLB)_4NA]_3$; 0.59 mg of $[(DLB)_4]_2$ and 1.41 mg of $(DLB)_4NA$.

D. $(DLB)_4NA$-F 0.61 mg of $(DLB)_4NA$ in PBS buffer was added to 0.005 mg N-hydroxysuccinimidyl fluorescein (NHS-Fluorescein) (Sigma) in DMF. The mixture was incubated at room temperature for 1 hr. The reaction mixture was then fractionated on a PD10 column (10 ml). $(DLB)_4NA$-F was eluted in the protein-containing fractions (3 and 4), which were pooled together and sterilized by filtration through a 0.22 μm filter. The total yield was 0.5 mg.

E. $(DIM)_n$ HIgG

Human IgG (HIgG) was first purified as follows: 1.3 ml HIgG (that included 100 mg/ml HIgG, 22.5 mg/ml glycine and 3 mg/ml albumin in borate buffer with 1 mM EDTA, pH 9) was applied to an FPLC (S200, 250 ml) column. The fractions were collected and analyzed by SDS PAGE on a phast gel. Fractions containing monomeric IgG (21-32) were pooled together and sterilized by filtration through a 0.22 μm filter. The total yield as determined by absorption at 280 nm was 111 mg.

Purified HIgG (55 mg in 13 ml of borate buffer, pH 9) was added to 1.003 mg in 0.5 ml of SMCC (Pierce) in DMF. The mixture was incubated at room temperature for 1 hr. At the same time, another reaction mixture containing 6 mg duramycin (3 μmole; dissolved in 0.5 ml 0.1M $NaHCO_3$) and 0.413 mg 2-IT (3 μmole; in 0.1M $NaCO_3$) was incubated at room temperature for 1 hr. After completion of the reactions, the two reaction mixtures were combined and incubated at room temperature for 2 hr and at 4° C. overnight. The reaction products were analyzed by SDS PAGE on a phast gel. The reaction products were loaded onto an FPLC column in borate buffer, pH 9. The FPLC fractions corresponding to trimer (5-14), dimer (15-24), and monomer (25-37) were pooled and sterilized by filtration through a 0.22 μm filter. The total yield of monomer was 54.6 mg. Five to seven duramycin groups were attached to each molecule of HigG.

F. $(DIM)_n$ HIgG-F 1 mg (0.7 ml) of $(DIM)_n$HIgG was added to 5 μl of NHS-Fluorescein in DMF. The reaction mixture was incubated at room temperature for 1 hr and desalted on a PD-10 column. Protein-containing fractions (2-3) were pooled and sterilized by filtration through a 0.22 μm filter. The total yield was 0.9 mg.

G. $(DIM)_n$HIgG-B and $[(DIM)_n HIgG]_2$-B

To synthesize biotinylated derivatives of $[(DIM)_n HIgG]_2$, 0.66 mg (1 ml) of $[(DIM)_n HIgG]_2$ was added to 8 μl of 1 mg/ml of NHS-LC-Biotin (Pierce) in DMF. The mixture was incubated at room temperature for 1 hr. The reaction mixture was then desalted on a PD-10 column. Protein-containing fractions (3 and 4) were pooled and sterilized by filtration through a 0.22 μm filter. The final yield was 0.46 mg.

The biotinylation of the monomer $(DIM)_n$HIgG was performed in the same manner. Briefly, 1.06 mg (0.75 ml) of $(DIM)_n$HIgG were added to 12 μl of 1 mg/ml NHS-LC-Biotin in DMF. After incubation at room temperature for 1 hr, the reaction product was desalted on a PD-10 column. Protein-containing fractions (3 and 4) were pooled and sterilized by filtration through a 0.22 μm filter. The final yield was 0.62 mg.

H. $(DIB)_4NA$ 2 mg (0.99 μmole) of duramycin were dissolved in 0.5 ml 0.1 M $NaHCO_3$ and added to 0.136 mg (0.99 μmole) of 2-IT. The reaction mixture was incubated at room temperature for 1 hr. Following this, 0.483 mg (0.95 μmole) of iodoacetyl-LC-Biotin (Pierce) was added and the reaction mixture incubated at room temperature for 1 hr. 10 mg (0.17 μmole) of neutravidin in 1 ml of $H_2O$ was added and incubated at 4° C. overnight. The reaction mixture was fractionated by FPLC. Three different peaks were collected and pooled: $[(DIB)_4NA]_3$ (fractions 17-23); $[(DIB)_4NA]_2$ (fractions 24-33); and $(DIB)_4NA$ (fractions 35-48). All the samples were sterilized by filtration through a 0.22 μm filter. The total yields obtained were 0.87 mg of $[(DIB)_4NA]_3$; 1.25 mg of $[(DIB)_4NA]_2$; and 1.83 mg of $(DIB)_4NA$.

I. $(DIB)_4NA$-B 0.023 mg (0.3 μmole) of $(DIB)_4NA$ was added to 0.9 μg of NHS-LC-Biotin (Pierce). The reaction was incubated at room temperature for 1 hr and then desalted on a PD-10 column. The total yield was 0.04 mg.

J. DS-1

5 mg (2.5 μmole) of duramycin dissolved in 0.5 ml of 0.1M $NaHCO_3$ in water was added to 0.319 mg (2.6 μmole) of 1,3 propane sultone. The mixture was incubated at 4° C. overnight. The sample was loaded onto a silica column, washed with 0.1% TFA, eluted with 0.1% TFA and 70% $CH_3CN$. The eluant was collected and concentrated by centrifugation under reduced pressure. The total yield was 5 mg.

K. DS-2

1 mg (0.497 μmole) of duramycin dissolved in 0.3 ml of 0.1 M $NaHCO_3$ in water was added to 0.072 mg (0.523 μmole) of 2-IT. The reaction mixture was incubated at room temperature for 1 hr. 0.125 mg (0.49 μmole) of SBF-Chloride (Pierce) was added. The reaction mixture was incubated at room temperature for 1 hr and 4° C. overnight. The peptide was purified on a silica column. The eluant was collected and concentrated by centrifugation under reduced pressure. The total yield was 1 mg.

L. DS-3

1 mg (0.497 μmole) of duramycin dissolved in 0.4 ml of 0.1M $NaHCO_3$ in water was added to 0.109 mg (0.592 μmole) of 2-sulfobenzoic acid cyclic anhydride. The reaction was incubated at room temperature for 1 hr and 4° C. overnight. The peptide was purified on a silica column. The eluant was collected and concentrated by centrifugation under reduced pressure. The total yield was 1 mg.

M. DS-4

0.25 mg (0.124 μmole) of duramycin dissolved in 0.5 ml of 0.1M $NaHCO_3$ in water was added to 0.017 mg (0.124 μmole) of 2-IT. The reaction mixture was incubated at room temperature for 1 hr. The mixture was then added to 0.049 mg (0.124 μmole) Ellman's reagent. The mixture was incubated at room temperature for 2 hr and overnight at 4° C. 250 μl of 1 mg/ml of 4-Amino-5-hydroxy-2,7-naphthalene disulfonic acid mono-sodium salt hydrate was added to 100 μl of 1 mg/ml 2-IT. The reaction was incubated at room temperature for 1 hr. 50 μl of this reaction mixture was added to the previous reaction and incubated at room temperature for 1 hr. The peptide was purified on a silica column. The eluant was collected and concentrated by centrifugation under reduced pressure.

N. DS-5

5 mg (2.51 μmole) of duramycin dissolved in 0.5 ml of 0.1M $NaHCO_3$ in water was added to 0.356 mg (2.6 μmole) of 1,3 butane sultone. The mixture was incubated at 4° C. overnight. The sample was loaded onto a silica column, washed with 0.1% TFA, eluted with 0.1% TFA and 70% $CH_3CN$. The eluant was collected and concentrated by centrifugation under reduced pressure. The total yield was 5 mg.

O. DC-1

0.25 mg (0.124 μmole) of duramycin dissolved in 0.5 ml of 0.1M $NaHCO_3$ in water was added to 0.017 mg (0.124 μmole) of 2-IT. The reaction mixture was incubated at room temperature for 1 hr. The mixture was then added to 0.049 mg (0.124 μmole) Ellman's reagent. The mixture was incubated at room temperature for 2 hr and overnight at 4° C. The peptide was purified on a silica column. The eluant was collected and concentrated by centrifugation under reduced pressure.

EXAMPLE XVI

Duramycin Derivatives Specifically Bind PE

The present example shows that the duramycin derivatives synthesized in Example XV are specific for PE and can therefore be used as designed, by linking to cell-impermeant, targeting or anti-viral agents and use in the treatment of tumors and viral diseases.

To test the specificity of the duramycin derivatives, particularly the binding to PE in preference to other phospholipids, a series of competition ELISAs were performed. The ability of the duramycin derivatives to compete with either DIB or DLB for binding to PE was tested in the following method.

PE and PC were dissolved separately in ethanol. The final concentration was 5 μg/ml. 100 μl was added to each well of 96 well ELISA plates (DYNEX IMMULON®1B). These plates were evaporated at 4° C. in a cold room. 250 μl 2.5% casein was added to each well, covered and blocked at 37° C. for 1 hour. The blocking buffer was discarded and 100 μl 2.5% casein added to each well. The duramycin compound was added as a serial dilution across the plate, such as (DIM) nHIgG, (DIB)4NA, (DLB)4NA, DS, duramycin and DIB.

The (DIM)nHIgG starting concentration was 1.4 mg/ml, the (DIB)4NA starting concentration was 800 μg/ml, and the (DLB)4NA starting concentration was 800 μg/ml. These were incubated at 37° C. for 1 hour and washed 5 times with PBS. 100 μl HRP-streptavidin (1:5000 dilution) was added to each well, incubated at 37° C. for 1 hour and washed 5 times with PBS. 100 μl 0.05% OPD was added to each well and developed for 5 minutes. 100 μl 0.18 M H2SO4 was added to stop the reaction and read at O.D. 490.

The resultant data was tabulated and then plotted graphically. Increasing concentrations of the duramycin derivatives decrease absorbance at 490 nm, showing that the duramycin derivatives compete with DIB and DLB for binding to phosphatidylethanolamine.

The phospholipid binding profiles of duramycin constructs were confirmed using further ELISAs. The respective test lipids PS, PE, PI, CL, PC, PG, SM, and cholesterol were dissolved separately in ethanol and used to coat ELISA plates. Duramycin compounds were added as serial dilutions across the plates. After incubation and washing steps, a secondary detection reagent was added to each well and reactivity determined using the colorimetric assay as described above.

Representative phospholipid binding profiles for the duramycin biotin derivatives, DIB and DLB were plotted. It was shown that DIB and DLB are specific for PE, with binding to each of PS, PI, CL, PC, PG and SM being negligible or undetectable. $(DIM)_nHIgG$-B and $[(DIM)_nHIgG]_2$-B had essentially the same binding profile as DLB. Although minimal binding to PS was observed at high concentrations of DIB, this is not meaningful in the context of this study, as binding to PS was undetectable at DIB concentrations that were saturating and half maximal for PE binding. Therefore, the duramycin constructs specifically bind to phosphatidylethanolamine.

It was also shown that serum has no significant effect on PE binding by duramycin derivatives. This is exemplified by binding of the duramycin biotin derivative, DLB to PE-coated ELISA plates in the presence and absence of serum (BSA), wherein the binding profiles show no significant differences.

EXAMPLE XVII

Anti-Viral Effects of PE-Binding Peptide Derivatives

In addition to the anti-viral effects mediated by anti-PS antibodies, as shown in Example XII and Example XIII, the present example demonstrates the anti-viral effects of peptide derivatives that specifically bind to the other common aminophospholipid, PE.

A. Methods

1. Treatment of CMV-Infected Cells In Vitro

Confluent monolayers of human diploid foreskin fibroblasts (HHF-R2) in 6-well plates were infected with human CMV AD169 expressing green fluorescent protein (GFP) at an MOI=0.01 as described in Example XII (Bresnahan et al., 1996). The cells were incubated with virus in a total volume of 1.5 ml per well at 37° C. for 90 minutes. During the infection, the plates were gently rocked every 30 minutes. Following the infection, the cell supernatant was removed and DMEM/10% FBS/pen-strep (2 ml per well) was added to each well.

Different dilutions of duramycin derivatives $(DLB)_4NA$, $(DIM)_nHIgG$, DS-1, DS-2, DS-3 and DC-1 were added to the wells before the addition of the virus, and following infection. The infected cells were incubated at 37° C. for a total of 14 days. The medium and duramycin derivative in each well were replaced every 3 days.

2. Fluorescent Microscopy

As in Example XII, the recombinant CMV expresses GFP under the control of the SV40 promoter. Hence, infected cells appear green under a fluorescent microscope. In these studies, the CMV-infected cells treated with the duramycin derivatives were observed under a fluorescent microscope at days 4 and 6.

B. Results

On day 4, there are single infected GFP-positive green cells in untreated wells and wells treated with $(DLB)_4NA$ and $(DIM)_nHIgG$. Thus, treatment of HHF-R2 cells with these duramycin derivatives does not appear to inhibit the entry of the virus into the cells. There is some preliminary evidence that the duramycin derivatives DS-1, DS-2 and DS-3 inhibit viral entry into the cells.

On day 6 after treatment with $(DLB)_4NA$ and $(DIM)_n$-HIgG, there is a marked difference in the number of infected GFP-positive cells in untreated vs. the duramycin derivative treated wells. By day 6, the virus has spread from the single infected cell seen on day 4 surrounding cells in the untreated wells. However, on day 6 in the wells treated with $(DLB)_4NA$ and $(DIM)_nHIgG$, the virus is limited to the original singly infected cell.

Accordingly, $(DLB)_4NA$ and $(DIM)_nHIgG$ limit the spread of CMV from the original infected cell to the surrounding cells. This inhibition of viral spread is observed when cells were treated with different concentrations of $(DLB)_4NA$ (100 μg/ml and 50 μg/ml) and $(DIM)_nHIgG$ (200 μg/ml and 100 μg/ml).

EXAMPLE XVIII

Advantages of 3G4 Antibody

The 3G4 antibody developed by the inventors' unique protocol, as described in Example IV, has many advantages over the anti-PS antibodies in the literature, including the prominent anti-PS antibody, 3SB (Rote et al. (1993). The present example describes certain of those advantages.

A. Class and Specificity

3G4 is an IgG antibody, whereas 3SB is IgM. Antibodies of IgG class have numerous advantages over IgM, including higher affinity, lower clearance rate in vivo and simplicity of purification, modification and handling. A comparison of the PS binding of the IgM antibody, 3SB, with 3G4 and another IgG antibody was plotted.

3G4 reacts strongly with the anionic phospholipids PS, PA, PI, PG and CL with approximately the same intensity, and binds to the aminophospholipid, PE less strongly. It has no reactivity with PC and SM and has the binding specificity profile: PS=PA=PI=PG>CL>>PE (Example IV; Table 4). 3G4 does not bind detectably to heparin, heparan sulfate or to double or single stranded DNA, nor to cellular proteins extracted from bEnd.3 cells on Western blots. The binding of 3G4 is unaffected by the presence of 5 mM EDTA, showing that $Ca^{2+}$ is not require for 3G4 binding to anionic phospholipids. 3G4 did not bind to ELISA plates that had been coated with phospholipids but then washed with 0.2% Tween 20 in saline, confirming that the binding was to the absorbed phospholipid.

The epitope recognized by 3G4 appears to lie within the phosphoglycerol core of the anionic phospholipids, which is the same in phospholipids from all mammalian species. The antibody thus reacts with both mouse and human phospholipids, which is important for pre-clinical and clinical development. 3G4 is more specific for anionic phospholipids than the natural ligand, annexin V. Unlike 3G4, annexin V also binds strongly to neutral phospholipids in physiological concentrations of $Ca^{2+}$.

The specificity of 3G4 for anionic phospholipids was confirmed by assays in which liposomes formed from different phospholipids were used to compete for 3G4 binding to immobilized PS. Liposomes were prepared from solutions of 5 mg of a single phospholipid in chloroform. The solutions were dried under nitrogen to form a thin layer in a round-bottomed glass flask. Ten ml of Tris buffer (0.1 M, pH 7.4) were then added and the flask was sonicated five times for 2 min. The 3G4 antibody (0.1 μg/ml) was added to either buffer or different phospholipid liposomes and pre-incubated for 30 minutes at room temperature. The mixture was added to PS-coated plates (after standard blocking), incubated for 1 hour, washed and the secondary antibody added. After 1 hour, the plates were washed and developed for 5 minutes using OPD.

As shown in Example IV, 3G4 binds to PS, PA, PI, PG and CL when immobilized and binds to immobilized PE to a lesser degree, but does not bind to immobilized PC. The ability of 3G4 to bind to immobilized PS in the presence or absence of the different liposomes is shown in FIG. 3. Results from these liposome competition studies show that binding of 3G4 to PS adsorbed to ELISA plates was blocked by liposomes prepared from PS, PA, PI and CL, but that liposomes prepared from PE and PC did not result in a detectable reduction in 3G4 binding (FIG. 3). Also, SM liposomes were not inhibitory.

B. Inhibition of Cell Proliferation

3G4 binds to activated, dividing, injured, apoptotic and malignant cells that externalize PS and other anionic phospholipids. The 3G4 antibody inhibits the proliferation of endothelial cells in vitro, and shows a marked selective inhibition of dividing endothelial cells as opposed to quiescent cells.

The effect of the anti-PS antibodies 3G4, 9D2, 3B10, 1B9, 2G7, 7C5 and 3SB on the growth of bEnd.3 cells in vitro was determined. bEnd.3 cells (10,000/well) were seeded in 48 well plates and allowed to attach. 20% DMEM alone (control) or 20% DMEM containing the antibodies (20 μg to 40 μg total IgG per well) was added 4 hours after seeding. Each clone was tested on two separate plates in triplicates. Cells were detached 48 and 96 hours later, the cell count was determined in each well and the average cell number per treatment was calculated.

The 3G4 and 9D2 antibodies were particularly effective, followed by 3SB and 3B10, with 1B9, 2G7 and 7C5 having less inhibitory effects. Each of the antibodies show a selective inhibition of dividing (subconfluent) endothelial cells as opposed to quiescent (confluent) cells. In comparative studies, 3G4 showed the greatest inhibitory effect, followed by 9D2, each of which were more inhibitory than 3SB.

C. Anti-Tumor Effects

3G4 binds to the surface of tumor vascular endothelial cells in vivo. When injected intravenously into mice bearing various tumors, 3G4 specifically and consistently localized to the tumor, but not to normal organs. Staining was observed on tumor vascular endothelium, necrotic areas and individual malignant cells. There are multiple binding sites for 3G4 in tumors, which allows simultaneous targeting of both tumor endothelial and tumor cells.

3G4 suppresses angiogenesis and tumor growth in vivo and shows no detectable organ toxicity in tumor-bearing mice. In initial studies, 3G4 has shown impressive anti-tumor effects in syngeneic and xenogeneic tumor models, wherein the antibody causes tumor vascular injury, decrease in vascularity and tumor necrosis (Example XI). Regressions of established tumors have been observed in 30% to 50% of the animals treated.

The anti-angiogenic and vascular targeting effects of the 3G4 antibody have been observed in repeated studies. Analyses of tumor sections from nude mice bearing MDA-MB-231 orthotopic tumors treated with 3G4 revealed anti-angiogenic effects in all treated tumors, as opposed to control antibodies. The control tumor showed no signs of necrosis and is highly vascularized, as demonstrated by the pan-endothelial cell marker, CD31, detected on tumor blood vessels. In contrast, tumors from the mice treated with 3G4 have 80 to 90% necrosis and almost complete disappearance of CD31-positive structures, indicating that the treatment produced a substantial anti-angiogenic effect.

Another component of the anti-cancer activity of 3G4 is the induction of tumor vascular damage. This is illustrated by blood vessels in the control tumors being well perfused, morphologically intact and surrounded by viable dividing tumor cells, whereas the blood vessels in the 3G4-treated animals are frequently observed to have a disintegrating endothelial layer and are blocked by the detached endothelial cells and, likely, by host cells that are attracted to the denuded vessels. The vessels in the 3G4-treated tumor clearly show loss of function, as indicated by the pre-necrotic layer of surrounding tumor cells. These studies also showed that treatment with 3G4 causes leukocyte infiltration into tumors (FIG. 1).

In these studies, the 3G4 treatment of mice bearing orthotopic MDA-MB-231 tumors also decreased the plasma volume and reduced the vascular density in the tumors. A 60% percentage reduction was observed in the total tumor plasma volume of 3G4-treated mice as compared with BBG3-treated mice, as judged by the reduction in plasma marker, FITC-dextran. The mean number of CD-31 positive vessels per square millimeter in tumors from 3G4-treated mice was 50±15 as compared with 160±20 in tumors from BBG3-treated mice, representing a reduction in tumor vascularity of about 70% after 3G4 treatment.

In summary, the histological examination following the treatment of orthotopic MDA-MB-231 tumors using 3G4 shows: 1) disintegration of vascular endothelium in about 50% of vessels in the tumor; 2) attachment of leukocytes to tumor endothelium and infiltration of mononuclear cells into the tumor interstitium; 3) occlusion of tumor vessels by platelet aggregates and red cells; 4) a 70% reduction in microvascular density in tumors from 3G4 treated vs. untreated mice; and 5) central necrosis of the tumors, with survival of a peripheral rim of tumor cells, typical of a VTA. Thus, a primary anti-tumor action of the 3G4 antibody is exerted through effects on tumor vasculature. Other mechanisms, particularly antibody-dependent cellular cytotoxicity directed against the tumor cells themselves, likely contributes to the anti-tumor effect. This is important, and may permit killing of more tumor cells, including those in the peripheral rim.

In follow-up studies, the effect of 3G4 on tumor growth has been examined in other murine models, including syngeneic (mouse Meth A fibrosarcoma), subcutaneous xenografts (L540 human Hodgkin's lymphoma) and orthotopic tumors (human MDA-MB-231 breast cancer and human MDA-MB-435 breast cancer). Treatment of mice with 3G4 antibody resulted in 90%, 65% and 50% and 70% growth retardation of these tumors, respectively. Both small (0.1 cm diameter) and well-established (0.3 cm diameter, 200 $mm^3$) tumors were inhibited alike. Anti-PS treatment induced long-term complete remissions in 50% of Meth A-bearing mice and 30% of mice with MBA-MD-231 tumors. 3G4 has the highest inhibitory effect in immunocompetent mice. The orthotopic models of human breast tumors (MDA-MB-231 and MDA-MB-435), in which human breast tumors are grown in the mammary fat pads of mice, are important as these are practical and realistic models of human breast cancer growing within the breast of humans.

D. Safety Profile

The 3G4 antibody is different to anti-phospholipid antibodies described in the literature. Typically, anti-phospholipid antibodies are regarded as pathogenic antibodies that interfere with the coagulation cascade. They inhibit coagulation reactions in vitro and cause thrombosis in vivo. In contrast, 3G4, 9D2 and like antibodies are therapeutic antibodies without pathogenic effects.

1. Coagulation

An important aspect of the 3G4, 9D2 and like antibodies stems from the inventors' ability to prepare antibodies that are not linked to anti-phospholipid syndrome or associated pathologies.

In studies of blood coagulation in vitro, a weak inhibition of Tissue Factor (TF)-induced coagulation was observed using high doses of 3G4 antibody. In other studies using lower doses, recalcified plasma from 3G4 treated mice coagulated at the same rate as did recalcified plasma from BBG3 treated mice in the presence of tissue factor. Also, the addition of 100

μg/ml of 3G4 to cells plus tissue factor in vitro did not affect the generation rate of coagulation Factor Xa in proplex (extrinsic coagulation pathway).

Despite the weak inhibition of TF-induced coagulation using high antibody levels in vitro, the 3G4 antibody has been tested in vivo and does not cause thrombotic complications in normal or tumor-bearing mice (e.g., see Example XI). The 3G4 antibody has also been tested in monkeys in vivo and no significant side effects have been observed.

2. Other Indicators of Low or No Toxicity

The first evidence that 3G4 has no or low toxicity in mice came from the finding that 3G4 grows as a hybridoma in mice without evidence of toxicity. Also, when 1 mg of purified 3G4 was injected intraperitoneally, no toxicity was observed.

Systematic in vivo studies have now been conducted in which groups of three 8 week old BALB/c mice were injected IP with 100 μg of purified 3G4 or with an isotype-matched control IgG3 (BBG3) three times a week for 2 to 4 weeks. No physical signs of toxicity have been observed, and no histopathological signs of organ toxicity or morphological abnormalities have been detected in sections of major organs removed from 3G4-treated mice. The following parameters were specifically examined.

In terms of bodyweight, 3G4-treated mice gained weight at the same rate as BBG3 treated mice. No weight loss was observed in the earlier studies. There were no physical signs of toxicity, e.g. hair loss, loss of appetite, etc., and physical activity was normal compared with control animals.

No evidence of hematologic toxicity was identified compared with control animals. Peripheral blood composition was normal (based upon measurements of complete blood counts with differentials); evaluation of erythrocyte morphology showed no evidence of intravascular hemolysis (i.e., absence of schistocytes); all blood coagulation parameters (PT, APTT, D-dimer) were normal. There are no changes in blood cell counts, including red cells, platelets, white cells, absolute lymphocyte counts or absolute neutrophil counts.

Bone marrow cellularity and composition were normal. To analyze bone marrow cellularity, paraffin sections of bone marrow derived from 3G4 or BBG3-treated mice (six injections, 100 μg) were examined for total cellularity and cellular composition. Marrows in the treated animals were essentially completely cellular (as would be expected for a young mammal). Erythroid, granulocytic, lymphocytic progenitors and megakaryocytes were present in normal numbers. Other organ toxicity was absent, as assessed by post-mortem histologic examination of the lung, liver, heart, brain, intestine, stomach and kidney.

In summary, no instance of toxicity has been observed in more than 200 mice treated with high doses of 3G4 (0.1 mg) three times a week for 2-4 weeks, or in rats. Even when doses as high as 2 mg were given, no signs of toxicity were seen. Mice retain normal physical signs, bone marrow cellularity, white blood cell counts, histology and coagulation functions. In further studies, groups of five non-tumor bearing mice given a single i.p. injection of 2 mg 3G4, or repeated i.p. injections of 0.5 mg 3G4 daily for 14 days (7 mg total dose), showed no physical signs of toxicity.

Blood clearance kinetic studies have also been conducted in mice. 3G4 was radioiodinated using the Bolton Hunter reagent and was injected intravenously into mice (25 g). Samples of blood were removed via the tail vein at various later time points. The blood clearance rate of 3G4 was typical of a mouse IgG in the mouse. The half-life in the α-phase of clearance was 3 hours while that in the β-phase was 5 days. Volume of distribution was normal (100 ml/kg). These studies indicate that 3G4 does not interact with normal host tissues, leading to its accelerated clearance.

The humanized 3G4 antibody has also been administered to atherosclerotic rabbits and shown to be safe.

3. Monkey Safety Studies

The humanized 3G4 antibody (see Example XIX, below) has also been administered to monkeys in safety studies and no significant side effects have been observed. Humanized 3G4 antibody was administered IV as a single bolus at up to 100 mg/kg to cynomolgus monkeys. This is 100 times the calculated therapeutic dose (1 mg/kg).

No adverse effect level (NOAEL) was approximately 10 mg/kg/week in repeat dosing. There was a transient prolongation in APTT and PT at doses of 10-100 mg/kg. There were no significant changes in blood cell counts, including white blood cells, red blood cells and platelets, or other clinical chemistries.

E. Anti-Viral Effects

The 3G4 antibody also exerts significant anti-viral effects. As shown in seen in Example XIII, the treatment of RSV-infected cells with 3G4 was superior to the effect observed using 3SB. These results therefore highlight another advantage of the 3G4 antibody over the prominent anti-PS antibody in the literature, 3SB (Rote et al. (1993).

The 3G4 antibody is also shown to be very effective in inhibiting CMV, both in vitro (Example XII) and in enhancing the survival of mice infected with mCMV in vivo (Example XXI). In addition, the 3G4 antibody is further shown to inhibit Pichinde virus infection, the infectious agent of Lassa fever (Example XXIV). The cell surface PS exposure herein shown to follow viral infection, and the ability of the 3G4 antibody to bind to cells infected with Vaccinia virus (Example XXIII), shows that the 3G4 antibody has enormous potential as a broad spectrum anti-viral agent.

EXAMPLE XIX

3G4 Antibody, CDR Sequences, Chimera and Related Construct

The 3G4 antibody thus possesses the combined properties of an anti-angiogenic, anti-tumor vascular and anti-viral agent. The inhibitory activities of 3G4 on cell division, angiogenesis, tumor growth and viral infectivity, taken together with lack of apparent toxicity, show broad therapeutic indications for this antibody, including in the treatment of angiogenic disorders, cancer, diabetes and viral infections.

Antibodies recognizing substantially the same epitope as the 3G4 antibody can be generated for use in one or more of the anti-angiogenic, anti-tumor vascular and anti-viral therapies, e.g., by immunization and confirmed by antibody competition studies. Antibodies that bind to essentially the same epitope as the 3G4 antibody can also be generated from a knowledge of the 3G4 antibody sequences provided herein. The present example provides the sequences of the complementarity determining regions (CDRs) of the 3G4 antibody and the use of the sequence information.

A. 3G4 Antibody Sequences

The original sequences of the antibody variable regions were obtained by RACE from the hybridoma that produces the 3G4 antibody and the sequences verified. The nucleic acid and amino acid sequences of the variable region of the heavy chain (Vh) of the 3G4 antibody CDR1-3 are represented by SEQ ID NO:1 and SEQ ID NO:2, respectively.

SEQ ID NO:1 and SEQ ID NO:2 include part of the mouse leader sequence and constant chain sequences, as shown in FIG. 2A. The leader sequence is represented by amino acids 1 through 19 of SEQ ID NO:2, and the mature protein begins as shown by the arrow in FIG. 2A. Sufficient complementarity determining region sequence information is included by the sequence of the mature protein up to the sequence portion concluding VSS, after which the amino acids are not essential for antigen binding. As such, the BstEII site in the nucleic acid sequence can be used as a convenient site to prepare a functional mouse variable region, e.g., for use in grafting onto a human constant region (FIG. 2A).

In practice, the 3G4-2BVH sequence has been grafted onto a human γ1 constant region at the BstEII site using a Lonza pEE vector. The resultant product contains the mouse leader sequence and its VH is joined to the human CH1 sequence in the manner shown in FIG. 2A, wherein ASTLGPSVFPLAPSSKSTSG (SEQ ID NO:7) represents the first part of the human CH1 sequence.

The nucleic acid and amino acid sequences of the variable region of the light chain (Vκ) of the 3G4 antibody CDR1-3 are represented by SEQ ID NO:3 and SEQ ID NO:4, respectively. SEQ ID NO:3 and SEQ ID NO:4 again include part of the mouse leader sequence and constant chain sequences, as shown in FIG. 2B. The leader sequence is amino acids 1 through 22 of SEQ ID NO:4, and the mature protein begins as shown by the arrow in FIG. 2B. Sufficient complementarity determining region sequence information is included by the sequence of the mature protein up to the sequence portion concluding TVF, after which the amino acids are not essential for antigen binding. As such, the BbsI site in the nucleic acid sequence can be used as a convenient site to prepare a functional mouse variable region, e.g., for use in grafting onto a human constant region (FIG. 2B).

In practice, the 3G4-2BVL sequence has been grafted onto a human κ constant region at the BbsI site using a Lonza pEE vector. The resultant product contains the mouse leader sequence and its VL is joined within the human CL1 sequence in the manner shown in FIG. 2B, wherein IFPPSDEQLKSGTAS (SEQ ID NO:8) represents the first part of the human κ constant region sequence.

B. Generation and Characterization of 3G4 Human Chimeric Antibody

The chimeric construct containing the murine complementarity determining regions and the human constant regions has been produced (ch3G4) and shown to behave essentially the same as the original murine antibody.

The murine 3G4 antibody was converted into a human-mouse chimeric antibody (Avanir (Xenerex) Biosciences, San Diego, Calif.). The murine $V_H$ was cloned and grafted onto the human $\gamma_1$ constant region at the BstEII site of the Lonza 2BVH vector. The murine $V_K$ was cloned and grafted onto the human K constant region at the BbsI site of the Lonza 2BVL vector. The sequences were verified. The entire construct was expressed in CHO cells and purified. The human-mouse chimeric ("humanized") antibody has been termed bavituximab.

Figure 4:
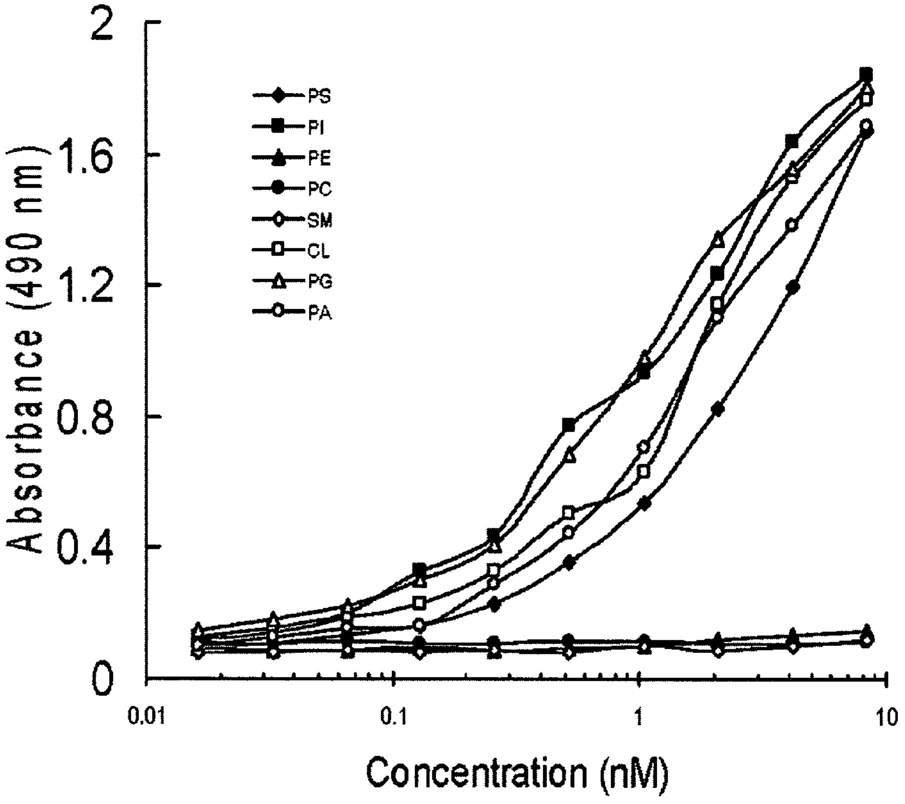
FIG. 4. Binding of 3G4 to phospholipids. Phospholipid-coated microtiter plates were treated with 3G4 at concentrations ranging from 0.016 to 33 nM in 10% bovine serum. The bound antibody was detected using goat anti-mouse IgG-HRP. 3G4 specifically bound to anionic phospholipids including PS, PI, PA and CL, but not to neutral lipids, including PE, PC and SM.

The resultant ch3G4 bound at least as did well as the murine 3G4 to phospholipid-coated ELISA plates. The in vitro binding profile of chimeric 3G4 to the panel of phospholipids is shown in FIG. 4, wherein binding to PS, PA, CL and PI is shown to be similar. The binding was antigen-specific since no binding was observed with control antibodies of irrelevant specificity. In certain studies, an apparently greater binding of chimeric 3G4 vs. the 3G4 antibody was observed; this may be due to superior binding of the secondary antibody.

C. Anti-Tumor Effects of the Humanized Antibody

In vivo, ch3G4 localizes to tumor vascular endothelium and exerts anti-tumor effects. The anti-tumor effects of ch3G4 in MDA-MB-435 human breast cancer cells growing in mice is described in Example XI. Treatment of mice with MDA-MB-435 tumors using the chimeric antibody effectively retarded tumor growth as opposed to control.

Localization of ch3G4 was examined in MDA-MB-435 human breast cancer cells growing in mice. Mice were injected intravenously with biotinylated ch3G4 or control IgG of irrelevant specificity. One hour later, the mice were exsanguinated, and their tumors were removed and frozen sections were cut. Biotinylated reagents were first incubated with streptavidin-Cy3 conjugate, washed in PBS, then incubated with MECA 32 antibody followed by FITC-tagged secondary antibody. Single images, taken with appropriate filters for Cy3 (red) and FITC (green) fluorescence respectively, were captured by digital camera and transferred to a computer. Converged images demonstrating yellow color (a product of merged green and red fluorescence) were superimposed with the aid of Metaview software.

In this double staining method, the biotinylated proteins and the vascular endothelium are labeled by red and green. Where the biotinylated proteins are bound to the endothelium, the converged image appears yellow. Biotinylated ch3G4 binds to the tumor vascular endothelium, because the staining patterns converges with that of MECA 32.

Bavituximab has also been radiolabeled and shown to home to syngeneic prostatic tumors in rats. Reduced tumor perfusion was also observed in tumor-bearing rats treated with bavituximab.

D. Generation and Characterization of Recombinant IgG2a Isotype of 3C4

The human chimera of the murine 3G4 antibody (ch3G4) is a human $IgG_1$ isotype ($hIgG_1$). The murine IgG homolog of ch3G4 requires a mouse $IgG_{2a}$ isotype ($mIgG_{2a}$). This construct was made and tested, and shown to behave essentially the same as the parent antibody.

Lonza expression vectors pEE12.4 & pEE6.4 were obtained from Lonza Biologics via an agreement with Peregrine Pharmaceuticals Inc. Use of the vectors, transfection, and screening of transfected NS0 mouse myeloma cells was conducted according to Lonza Biologics' "Operating Procedures for use with: NS0 Myeloma cells". Briefly, the 3G4 light chain coding sequence was amplified by RT-PCR from total RNA isolated from the 3G4 hybridoma cell line. RT-PCR primers were designed such that the amplified fragment contained XmaI and EcoRI restriction enzyme sites on either end of the amplified product for cloning into the Lonza pEE12.4 vector.

The variable region of the 3G4 heavy chain was amplified by RT-PCR from total RNA isolated from the 3G4 hybridoma cell line. Primers were designed such that the amplified fragment contained HindIII and XmaI restriction enzyme sites on either end of the amplified product for cloning into the Lonza pEE6.4 vector. The murine IgG2a constant region was amplified by PCR from a plasmid vector provided by Dr. Shozo Izui. PCR primers were designed with BstII and EcoRI restriction enzyme sites at either end of the amplification product for cloning into the pEE6.4+3G4VH vector. Importantly, the BstEII site was designed to be in-frame with the 3G4 VH variable region sequence upstream. The heavy and light chain constructs were combined into a single double gene vector (12.4 3G4 IgG2a) by cutting both vectors with SalI and NotI. The heavy and light chain coding regions were verified by sequencing at the UT Southwestern sequencing core facility.

The 12.4 3G4 IgG2a vector was transfected into NS0 cells by electroporation. Following transfection, the NS0 cells were diluted and plated into 96-well plates in media lacking glutamine. Only cells transfected with the construct (which contains the glutamine synthease gene for positive selection) can grow in the absence of glutamine. Over the next two months, various transfectants were identified screened for antibody secretion by PS-ELISA. Those transfectants secreting the highest amounts of antibody were grown in large culture to generate purified antibody. The antibodies were purified using the same purification protocol as used for the 3G4 antibody.

The amino acid sequences of the IgG2a heavy chain and the 3G4 Light Chain ($C_K$) are represented by SEQ ID NO:10 and SEQ ID NO:11, respectively, as shown in FIG. 2C and FIG. 2D.

As expected, purified 2aG4 antibodies migrate on an SDS-PAGE gel as a 150 kDa band, and bind to PS in PS-ELISA with an affinity and specificity essentially the same as for 3G4. 2aG4 thus binds to anionic phospholipids with the same profile as 3G4 (see Table 4, above).

The mouse $IgG_{2a}$ isotype was generated mainly to provide a better model for the human chimera, ch3G4 (bavituximab). The mouse $IgG_{2a}$ isotype is also thought to be more stable than the mouse $IgG_3$, the current isotype of the murine 3G4 antibody. The 2aG4 antibody may generate a stronger anti-tumor effect than the 3G4 $IgG_3$, via enhanced ADCC.

The 2aG4 antibody has been tested in a preliminary study in a mouse WiDr (colon carcinoma) model, along with the 3G4 and ch3G4 antibodies and the C44 antibody as a control. Treatment was started on day 5, when the tumors were small (10 mice per group). 100 μg of each antibody was injected 3×/week and tumor growth monitored. All three of the test antibodies slowed tumor growth to essentially the same degree.

EXAMPLE XX

3G4 Antibody in Combination Therapies, Including Docetaxel

The present example concerns combination therapies for tumor treatment using the 3G4 antibody and the chemotherapeutic drug, docetaxel. These agents are designed to attack tumor vasculature endothelial cell and tumor cell compartments, leading to synergistic treatment with lower toxicity. The results showed that this combination therapy did indeed significantly enhance treatment efficacy.

A. Fc Domain-Mediated Anti-Tumor Effects

The 3G4 antibody was tested for inhibitory effects on tumor cells in vitro. No direct inhibitory effect on tumor cells was observed. Therefore, it is likely that the anti-tumor effects of the 3G4 antibody include Fc domain-mediated augmentation of immune effector functions, such as antibody mediated phagocytosis, ADCC, CDC and stimulation of cytokine production, or these mechanisms combined.

The effects of 3G4 on the phagocytosis of PS-positive cells by macrophages have been evaluated. Fluorescent tumor cells were treated with $H_2O_2$ to induce PS exposure. Treated and untreated cells were then harvested and contacted with the 3G4 antibody or a control antibody (BBG). Mouse bone marrow macrophages were then added, and the ability of the macrophages to phagocytose the fluorescent tumor cells was analyzed using a fluorescent microscope.

It was determined that 3G4 could increase the phagocytosis of PS-positive cells by macrophages by more than three fold. This finding supports the inventors' reasoning that the Fc domain of the 3G4 antibody contributes to the anti-tumor effects of the antibody. That is, the Fc domain activates host immune effector functions, which then exert anti-tumor effects. The 3G4 antibody should therefore enhance the lytic activity of NK cells, leading to more effective ADCC.

B. Docetaxel Induces PS Exposure on Endothelial Cells and Tumor Vessels

The induction of PS exposure on endothelial cells by subclinical concentrations of docetaxel was examined in vitro by FACS analysis. Human umbilical vein endothelial cells (HUVEC) and human microvessel endothelial cells (HMVEC) were treated with 10 nM of docetaxel for 24 hrs and examined by FACS. Both treated HUVEC and HMVEC showed significant increase in 3G4 binding as compared to untreated cells. Docetaxel incubations for 48 and 72 hrs were also conducted.

Treatment of HUVEC cells in vitro with concentrations of docetaxel at 20 pM also caused anionic phospholipids to be externalized without inducing apoptosis.

C. Docetaxel Induces PS Exposure on Tumor Cells

The in vitro induction of PS exposure by subclinical concentrations of docetaxel was also examined by FACS analysis using a panel of tumor cell lines. Mouse lewis lung carcinoma 3LL, mouse colon carcinoma Colo26 and human breast cancer MDA-MB-435 cells were treated with 10 nM of docetaxel for 24 hrs and examined by FACS. All tumor cell lines tested showed significant increase in 3G4 binding as compared with untreated cells. Docetaxel incubations for 48 and 72 hrs were also conducted. Mouse melanoma B16 and mouse firbrosarcoma Meth A tumor cell lines were further examined and also showed significant increase in 3G4 binding as compared with untreated cells.

Human breast cancer MDA-MB-231 cells were treated with 10 nM of docetaxel for 24 hrs and incubated with either the chimeric 3G4 antibody (ch3G4) or control, human IgG and analyzed by FACS. These results show that the significant increase in antibody binding is antigen-specific and that the chimeric antibody behaves like the parent 3G4 antibody.

D. Docetaxel Induces PS Exposure on Tumor Vessels

Results from controlled studies also showed that docetaxel increases PS exposure on tumor vessels. In such studies, docetaxel treatment of mice increased the percentage of tumor vessels that expose anionic phospholipids from 35% to 60%. No induction of PS was observed on vessels in normal tissues even after systemic treatment with docetaxel.

E. Synergistic Tumor Treatment with 3G4 and Docetaxel

The inventors have thus shown that the treatment of endothelial cells and tumor cells with docetaxel at subclinical concentration significantly increases 3G4 binding. They have also shown that the 3G4 antibody facilitates macrophage-mediated phagocytosis of tumor cells on which PS is exposed at the surface. The increased 3G4 binding mediated by docetaxel should therefore augment the phagocytosis of tumor cells and other anti-tumor effects mediated by the Fc domain of the 3G4 antibody, such as increasing the lytic activity of NK cells, leading to more effective ADCC. Studies of others have also shown that treatment of breast cancer patients with docetaxel leads to an increase in serum IFN-γ, IL-2, IL-6 and GM-CSF cytokine levels and enhancement of NK and LAK cell activity (Tsavaris et al., 2002).

The anti-tumor effect of the combined therapy of 3G4 with docetaxel was therefore examined in an orthotopic model in SCID mice bearing human MDA-MB-435 breast carcinoma. Mice bearing orthotopic MDA-MB-435 human breast tumor were treated i.p. with 3G4 alone (100 μg/dose), docetaxel alone (10 mg/kg), or 3G4 in combination with docetaxel (100 μg/dose and 10 mg/kg, respectively), for three weeks, with administration 3 times a week. Treatment started 6 days after tumor cell implantation.

These studies showed that treatment of mice bearing orthotopic MDA-MB-435 human breast tumors with 3G4 plus docetaxel inhibited tumor growth by 93%. Treatment of mice bearing disseminated MDA-MB-435 tumors with 3G4 plus docetaxel reduced the average number of tumor colonies in the lungs by 93% and half the animals did not develop tumors. In both tumor models, the antitumor effect of the combination was statistically superior ($p<0.01$) to that of docetaxel or 3G4 alone. Combination therapy reduced the tumor vessel density and plasma volume in tumors to a greater extent than did the individual drugs. The combination therapy was no more toxic to the mice than was docetaxel alone. These results indicate that, as an adjuvant therapy, 3G4 could enhance the therapeutic efficacy of docetaxel in breast cancer patients.

F. 3G4 Enhances the Activity of Cisplatin Against Drug-Resistant Breast Tumors

The 3G4 antibody also enhances the activity of cisplatin against drug-resistant breast tumors in animals. Mice were inoculated with drug-resistant breast tumors and treated after day 20. Treatment groups were cisplatin alone, the 3G4 antibody alone, an isotype-matched control antibody (BBG3) or cisplatin in combination with the 3G4 antibody.

The tumors in the control animals continued to grow rapidly. In mice treated with either cisplatin alone or the 3G4 antibody alone, tumor growth was slowed. The combination treatment group (cisplatin and 3G4 antibody) showed the best anti-tumor response. Thus, antibodies such as 3G4 enhance the effectiveness of chemotherapeutic drugs, such as cisplatin, even against drug-resistant tumors.

G. Combination Therapy of Pancreatic Cancer

There is an urgent need for improved treatments for pancreatic cancer. In humans, the overall long-term survival for patients with pancreatic cancer is less than 4%. Approximately 70-80% of pancreatic cancer patients fail therapy due to metastases to the liver, and there is currently no effective therapy for metastatic disease.

Pan02 mouse pancreatic adenocarcinoma cells were injected into the pancreas of immunocompetent C57BL/6 mice. Treatment was started on day 5 after tumor cell injection. Treatment groups were PBS as a control, the 3G4 antibody alone (100 μg), gemcitabine alone (3.5 mg), or the 3G4 antibody in combination with gemcitabine (100 μg and 3.5 mg, respectively). Gemcitabine is a pyrimidine anti-metabolite. The animals were sacrificed at day 22 after tumor cell injection, and the tumor weight determined.

In these studies, both gemcitabine and the 3G4 antibody showed a significant anti-tumor effect. Animals treated with gemcitabine in combination with the 3G4 antibody showed a significantly enhanced anti-tumor effect over each agent alone, without adverse effects, e.g., on weight loss. The nodal, peritoneal and liver metastases were also significantly reduced in treatment with either gemcitabine or the 3G4 antibody alone. Again, animals treated with gemcitabine in combination with the 3G4 antibody showed significantly reduced nodal, peritoneal and liver metastases when compared to each agent alone. Importantly, in animals treated with the combination of gemcitabine and the 3G4 antibody, there were no detectable metastases to the liver. This is significant, as in humans, metastases to the liver are the most frequent cause of death following diagnosis of pancreatic cancer.

These studies also showed significant infiltration of macrophages into the tumor in the combination treatment group. Microvessel density was reduced upon treatment with the 3G4 antibody alone and with the 3G4 antibody in combination with gemcitabine.

H. Treatment of Lung Cancer with Radiation and 3G4

In studies of mice with lung cancer, 10 Gy focal irradiation induced PS exposure on tumor blood vessel endothelium, as shown in double-labeling studies. In the treatment phase, both irradiation and the 3G4 antibody alone showed an anti-tumor effect. Again, the combination of treatment modalities, i.e., irradiation and the 3G4 antibody, showed the greatest anti-tumor effect.

I. 3G4-Targeting of Apoptotic Tumor Cells to FcγR on Dendritic Cells

Tumors from mice treated with 3G4 plus docetaxel also contained unusual amount of lymphocytes, as compared to control tumors. Although this phenomenon could represent typical chemoattraction of immune cells by disintegrating tumor cells, it could also reflect activation of the immune system by 3G4 mediated through Fc binding to FcγR on immune effector cells.

To characterize the effects of 3G4 and docetaxel administration on the intratumoral immune cell infiltrate, the types of cells present in these infiltrates can be identified by immunostaining of frozen sections and/or paraffin sections of tumor tissues using antibodies directed against specific markers of macrophages, neutrophils, granulocytes, NK cells and activated lymphocytes (Pharmingen, San Diego, Calif.). The extent, phenotype, and activation status of this infiltrate can be graded. Cytokine production by infiltrating immune cells, including IL-2 and INF, can also be analyzed via immunohistochemical techniques. Serum cytokine levels can be evaluated by ELISA and intracellular staining can be used to identify the specific cellular compartments responsible for cytokine production. The effects of infiltrating immune cells on tumor cell proliferation and apoptosis can thus be systematically evaluated.

In light of the foregoing data, the inventors further contemplate methods enhancing the potency of immunotherapy of breast cancer by 3G4-mediated targeting of apoptotic tumor cells to the Fc gamma receptor (Fc(γ)R) on dendritic cells. Efficient antigen presentation, which induces effective cellular and humoral immune responses, is important for the development of tumor vaccines and immunotherapies. Dendritic cells (DC) are the most potent antigen-presenting cells (APC) that prime cytotoxic T lymphocytes against tumor-associated antigens. Improvement of tumor antigen presentation by dendritic cells (DCs) should lead to develop more potent tumor vaccines.

Antigenic presentation by Fc(γ)R receptor-mediated internalization of DCs can be enhanced up to 1,000-fold compared with fluid phase antigen pinocytosis. Apoptotic tumor cells (ATC) are an excellent source of antigens for dendritic cell loading because multiple tumor specific antigens (both known and unknown) can be efficiently presented to naïve T cells, making the occurrence of immune escape variants less likely due to the lock of certain epitopes. In animal studies, DCs pulsed with ATCs have been shown to produce potent anti-tumor immunity in vitro and in vivo. However, recent data has demonstrated that ATCs alone were somewhat inefficient for activating anti-tumor immunity, possibly because of their insufficient uptake and inability to induce DC maturation.

Recent studies have also demonstrated that ATC-immune complex, formed by binding of anti-tumor antibody to apoptotic tumor cells, can be targeted to Fc(γ)R on DC. Compared with ATCs alone, ATC-immune complexes were more efficiently internalized by DC, more efficient in inducing DC activation and maturation, and more importantly, ATC-immune complexes can significantly enhance both MHC I and II-restricted antigen presentation, therefore induce potent anti-tumor T helper and CTL immunity.

The inventors therefore envision using the anti-PS antibodies of the present invention to enhance both hormonal and cellular anti-tumor immunity, and boost the efficacy of ATC based DC tumor vaccines. As PS is a universal and the most abundant specific marker of apoptotic tumor cells, the panel of antibodies of the invention, particularly 3G4, can bind to PS on ATCs. The inventors have already demonstrated that 3G4 can enhance DC uptake of apoptotic tumor cells by 300% through Fc(γ)R mediated internalization of 3G4-ATC complexes. By enhancing the uptake of ATC by DC mediated through Fc(γ)R, it is therefore reasoned that 3G4 and like antibodies can greatly enhance both MHC I and II restricted antigen presentation, induce both potent hormonal and cellular anti-tumor immunity, and boost the efficacy of ATC based DC tumor vaccines. This can be demonstrated by establishing the efficacy of DC loaded with 3G4-ATC immune complexes in the induction of T h1, CTL and antibody response in vivo, and by determining the potency of anti-tumor immunity induced by immunization of DC loaded with 3G4-ATC immune complexes in vivo.

EXAMPLE XXI

Anti-PS Antibodies Treat CMV Infections In Vivo

Following the anti-viral effects against CMV in vitro shown in Example XII, the present example demonstrates the enhanced survival of mice infected with the murine version of the CMV virus, mCMV.

Balb/C mice (6 week old, five mice per group) were infected i.p. with $5\times10^5$ pfu of mCMV RVG102. The mice were treated i.p. on day 1 with the 3G4 antibody (1 mg/mouse), or the human-mouse chimeric antibody, ch3G4 described above (1 mg/mouse). Untreated mice served as the control. The mice were treated every four days thereafter with 0.5 mg/mouse of antibody or chimeric antibody until day 26. The mice were monitored for survival past 90 days post infection.

Treatment with both the parent and chimeric forms of the 3G4 antibody resulted in increased survival of the mCMV-infected mice. Mice treated with 3G4 or ch3G4 had 100% and 80% survival, respectively, as compared to untreated mice, wherein only 25% of the mice survived the infection.

EXAMPLE XXII

PE-Binding Peptide Derivative Treats CMV Infection In Vivo

In addition to the in vitro anti-viral effects against CMV shown in Example XVII, this example demonstrates that the duramycin-biotin derivative, DLB increased survival of mice infected with mCMV.

Balb/C mice (6 week old, five mice per group) were infected i.p. with $5\times10^5$ pfu of mCMV RVG102. The mice were treated i.p. on day 1 and every four days with 20 μg/mouse of the duramycin derivative, DLB. Untreated mice served as the control. The mice were monitored for survival past 90 days post infection.

Treatment with the duramycin-biotin derivative, DLB enhanced survival of the mCMV-infected mice. Mice treated with DLB had 100% survival, as compared to untreated mice, wherein only 25% of the mice survived the infection.

EXAMPLE XXIII

Anti-PS Antibodies Bind to Virally Infected Cells

The present example shows that viral infection induces PS exposure at the cell surface and that anti-PS antibodies bind to virally infected cells. Cells infected with Vaccinia virus become PS-positive, as shown by increased binding of the chimeric 3G4 antibody to the cell surface demonstrated in FACS analyses.

U937 cells were infected with trypsinized Vaccinia virus at a high m.o.i of 2. Briefly, Vaccinia virus was treated with an equal volume of 0.25 mg/ml trypsin for 30 minutes at 37° C. The virus was added to U937 cells in a total volume of 0.5 ml. After 1.5 hr, fresh medium was added to the cells and the cells were incubated in a T25 flask at 37° C. for 2 days. Uninfected cells served as the controls.

Infected and uninfected U937 cells were stained with a primary antibody, either with the chimeric 3G4 antibody (ch3G4) or with human IgG (HIgG) as a control. The cells were washed, blocked with normal mouse serum and then stained with the primary antibody for 45 minutes on ice. After three washes, the cells were stained with a 1:400 dilution of goat anti-human FITC-conjugated secondary antibody and were analyzed on a FACScan.

Results from the FACS analyses show that there is a significant shift with ch3G4 on U-937 cells infected with Vaccinia virus, as compared to that obtained on uninfected U937 cells. This study therefore shows that infection of cells with Vaccinia virus leads to PS exposure on the cell surface and that the chimeric version of the anti-PS antibody, 3G4 is capable of binding to these virally infected cells.

EXAMPLE XXIV

Anti-Viral Effects of Anti-PS Antibodies Against Pichinde Virus

In addition to the anti-viral effects against CMV and RSV, the present example further shows that anti-PS antibodies inhibit Pichinde virus infection in vitro. Pichinde virus is New World arenavirus, which is non-pathogenic in man, and is used in an animal model for Lassa fever.

Confluent monolayers of Vero cells were treated with the 3G4 antibody or an isotype-matched control antibody, GV39G, after infection with Pichinde virus at a low m.o.i. of 0.01 pfu/cell. Briefly, the cells were incubated with virus in a total volume of 1 ml per well at 37° C. for 90 minutes. During the infection, the plates were gently rocked every 30 minutes. Following the infection, the cell supernatant was removed and DMEM/10% FBS/pen-strep was added to each well (2 ml per well). On day 2, the cells were harvested with trypsin and allowed to adhere to Biocoat chamber slides. They were fixed and stained with polyclonal rabbit anti-PIC serum followed by a biotin-conjugated goat anti-rabbit secondary (secondary antibody alone produced no staining). The number of infected cells per field of 100 cells was counted.

In cells treated with 3G4, the virus is restricted to single cells that stain a dark red, numbering about one in about a hundred cells. These are probably the cells that were originally infected by the virus, as was seen with CMV (Example XII). However, in cells treated with the control, GV39G antibody, the virus has spread and infected all the cells.

This pattern of inhibition of viral replication is similar to that observed when 3G4 was used to treat CMV-infected human fibroblasts. Thus, the anti-PS antibody, 3G4 effectively and quantifiably prevents the spread of Pichinde virus from cell to cell.

EXAMPLE XXV

Tumor Treatment Using PE-Binding Peptide Derivative

Further to the anti-viral effects of duramycin derivatives, both in vitro and in vivo, the present example demonstrates the localization of duramycin derivatives to tumor vasculature and associated anti-tumor effects.

A. Tumor Treatment with Duramycin-HuIgG Conjugate

Human IgG (HIgG) was first purified as described in Example XV. Purified HIgG was linked to duramycin using the SIAB linker, and the resultant $(D\text{-}SIAB)_n$HIgG conjugate purified.

Mouse fibrosarcoma cell-line MethA was grown, harvested at log phase and resuspended in DPBS. Approximately $10^6$ MethA tumor cells were injected subcutaneously in the middle dorsum of 6-8 week old BALB/c male mice. 5 days after implantation, the mice were randomly separated into two groups (n=15). From day 10, one group received 150 μg Duramycin-HuIgG conjugate by intraperitoneal injection for consecutive 2 weeks. The other group received the same amount of HuIgG as a control. Tumor volumes were measured twice a week and were calculated using the formula $\frac{1}{2}ab^2$, (where "a" is the long axis and "b" the short axis of the tumor). Mice were sacrificed when the tumors reached a size of approximately 1400 $mm^3$.

The duramycin-HIgG conjugate inhibited MethA tumor growth in BALB/c mice at the dose of 150 μg/day, as compared to the human IgG control.

B. Duramycin-HuIgG Conjugate Localizes to Tumor Vasculature

Using the same MethA mouse tumor model as above, when the tumor size reach 500 $mm^3$, 100 μg $(D\text{-}SIAB)_n$HIgG in 100 μl PBS was injected through the tail vein. The same amount of human IgG was injected as a control. After 4 hours, mice was euthanized and perfused with normal saline for 5 minutes and 1% parafornadehyde for 10 minutes. The tumor and other major organs were dissected and frozen in liquid nitrogen. After embedding in OCT, tissue was cryosected in 10 μm section and placed on silanized slides. After fixing in cold acetone for 10 minutes, slides were stained with peroxidase labeled goat anti human IgG to detect the biodistribution of duramycin-HuIgG. Meca32 and peroxidase labeled goat anti-rat IgG were used to detect blood vasculature of tissue.

This study showed that the duramycin-HIgG conjugate localized to the tumor vasculature in the treated animals.

EXAMPLE XXVI

Biodistribution and Properties of Duramycin Conjugates

The present example demonstrates the lack of toxicity of cell-impermeant duramycin derivatives in vitro, the biodistribution of duramycin derivatives administered in vivo and the ability of duramycin-antibody conjugates to increase the phagocytosis of apoptotic cells by macrophages.

A. Duramycin-Biotin Conjugates are Not Cytotoxic

The duramycin derivatives and conjugates of the invention are designed to minimize the non-specific toxic effects of the parent duramycin molecule. In many examples, this is achieved by linking duramycin to a cell impermeant group (Example XV).

The biotinylated duramycin construct DLB was prepared as described in Example XV. The unmodified duramycin compound and DLB were tested for cytotoxic effects on HUVEC using an MTT assay. Whilst the unmodified duramycin showed dose-dependent toxicity, DLB was non-toxic, matching the untreated control.

B. Localization of Duramycin-Biotin Conjugate to Macrophages in Lung

The human breast cancer cell line MDA-MB-435 was grown, harvested at log phase, and resuspended in DPBS. Approximately $10^7$ cells were injected into the mammary fat pad of 6-8 week old female ethylic nude mice. 100 μg duramycin-biotin in 100 μl PBS was injected through the tail vein. After 4 hours, mice was euthanized and perfused with normal saline for 5 minutes and 1% paraformadehyde for 10 minutes. Major organs, including heart, lung, liver, kidney, brain, intestine, testes and spleen were dissected and frozen in liquid nitrogen. After embedding in OCT, tissue was cryosected in 10 μm sections and placed on silanized slides. After fixing in cold acetone for 10 minutes, slides were stained with Cy3 labeled streptavidin to detect the biodistribution of the duramycin-biotin construct. Meca32 and FITC labeled goat anti rat IgG were used to detect blood vasculature of tissue.

The intravenous injection of the duramycin-biotin conjugate into nude mice bearing MDA-MB-435 tumors resulted in the deposition of drug in the tumor cells, renal tubules and in the macrophages in the lung. There was minimal deposition in liver and no detectable distribution in brain, intestine, testes. The localization to macrophages in the lung can be exploited in the anti-viral embodiments of the invention.

C. Duramycin-Antibody Conjugate Enhances Phagocytosis of Apoptotic Cells

The ability of a duramycin-antibody conjugate (duramycin-C44, DuC44) to increase the phagocytosis of apoptotic cells was next investigated.

Macrophages were isolated and cultured from mouse bone marrow. The medium used for the isolation, culture, and stimulation of BM macrophages was DMEM containing 2 mM glutamine, 0.37% (w/v) $NaHCO_3$, 10% (v/v) heat-inactivated FCS, and 0.5 ng/ml mouse GM-CSF. Bone marrow cells were flushed acceptically from the dissected femurs with jet of complete medium directed through a 25-gauge needle. The cells were then adjusted to a density of approximately $3\times10^5$ cells/ml of complete medium, and were distributed in 0.5 ml aliquots into 8 well chamber slides.

Cells were incubated for 1 hour at 37° C. in 5% $CO_2$, in a humidified chamber to allow macrophages to adhere and spread. Nonadherent cells were removed by adding 5 ml of warmed PBS to each well, resuspending nonadherent cells by moderately tapping the plate, and flicking the slides to discard the nonadherent cells. This washing was performed a total of three times. The cells were maintained at 37° C. under a 7.5% (v/v) $CO_2$ atmosphere for 5 days. The complete medium was changed every other day until the cells were used.

The following method was used to label HL-60 target cells with a fluorescent cell tracer. A 10 mM CFDA SE stock solution was prepared immediately prior to use by dissolving the contents of one vial dye in 90 μL of the DMSO and diluting in PBS to 10 μM. Centrifugation was used to obtain a HL-60 cell pellet and the supernatant aspirated. The cells were resuspend in CFDA/PBS and incubated at 37° C. for 15 minutes. The samples was centrifuged and the supernatant aspirated. The cells were resuspend in media and incubated for another 30 minutes. The cell viability and fluorescence were confirmed to be over 95%.

In this phagocytosis assay, labeled HL-60 cells were exposed to UV 254 nm for 5 minutes and incubated at 37° C. for one hour to induce apoptosis. $10^4$ apoptotic HL-60 cells were incubated with macrophages for one hour. Duramycin-C44 conjugate was included at the concentration of 10 μg/ml. The same concentration of mouse antibody BBG3 was used as a negative control, and the 3G4 antibody was also included for comparison. Hoechst 33342 was added in media in the last 45 minutes at the concentration of 10 μg/ml.

Slides were washed with PBS 3 times, and fixed in 4% paraformadehyde for 15 minutes. The slides were stained with rat anti-mouse CD11 antibody (CD11 is a macrophage marker), diluted in 0.2% gelatin for one hour, washed and stained with Texas red labeled goat anti-rat secondary antibody.

The cells were analyzed under the fluorescence microscope. Macrophages are identified as red cells, due to the CD11 marker. Macrophages that have phagocytosed apoptotic cells are identified as green cells, due to the fluorescent tracer in the target cells. Red and green cells are counted and the phagocytosis is quantified as the percent phagocytes positive for uptake.

This study shows that the duramycin-antibody conjugate, DuC44 enhanced phagocytosis of apoptotic HL-60 cells by macrophages. Thus, the duramycin portion is binding to the surface of the apoptotic cells, permitting the protruding antibody portion of the conjugate to be recognized by the macrophages. The duramycin-antibody conjugate thus functioned similarly to the 3G4 antibody. As expected, an $(Fab)_2$ fragment of the 3G4 antibody, lacking the Fc region, did not induce phagocytosis above control levels.

As the earlier study showed duramycin-biotin conjugates to localize to macrophages in the lung following administration in vivo, the stimulation of macrophage-mediated phagocytosis of apoptotic cells shown in the present study has important implications for the therapeutic uses of the present invention, such as in treating pulmonary viral infections.

EXAMPLE XXVII

Infiltration of Macrophages During Tumor Treatment

As shown in the foregoing studies, antibodies to aminophospholipids and anionic phospholipids are effective in tumor treatment. For example, the 3G4 antibody specifically localizes to tumor vessels, causes tumor vessel destruction and retards tumor growth in multiple mouse models without causing toxicity (Example XI; Example XVIII). The present example shows that 3G4 treatment of animals with tumors also causes mononuclear leukocytes to bind to the tumor vascular endothelium and induces macrophages to infiltrate into the tumor.

A. Methods

Groups of 8-10 female SCID mice were injected subcutaneously with $2\times10^7$ L540 cells or orthotopically with $1\times10^7$ M DA-MB-435 or MDA-MB-231 cells. BALB/c mice were injected subcutaneously with $1\times10^6$ Meth A cells. Tumors were allowed to grow to an average diameter of 0.8-1 cm (L540), 0.6-0.7 cm (MDA-MB-435), 0.5-0.7 cm (MDA-MB-231), or <0.1 cm (Meth A). The mice were then treated i.p. with 100 μg 3G4 antibody or control antibody (BBG3) three times a week for 2-3 weeks. Animals were monitored three times a week for tumor size and body weight. Mice were sacrificed when tumors in control mice reached a diameter of 1.5-2 cm.

B. Results

3G4 treatment of mice bearing orthotopic MDA-MB-435 and MDA-MB-231 tumors caused mononuclear leukocytes to bind to the tumor vascular endothelium and infiltrate into the tumor interstitium (FIG. 6A, FIG. 6B, FIG. 6C and FIG. 6D). In this figure, the red staining shows endothelium, the green staining shows macrophages, and the blue staining shows nuclei.

Figure 6:
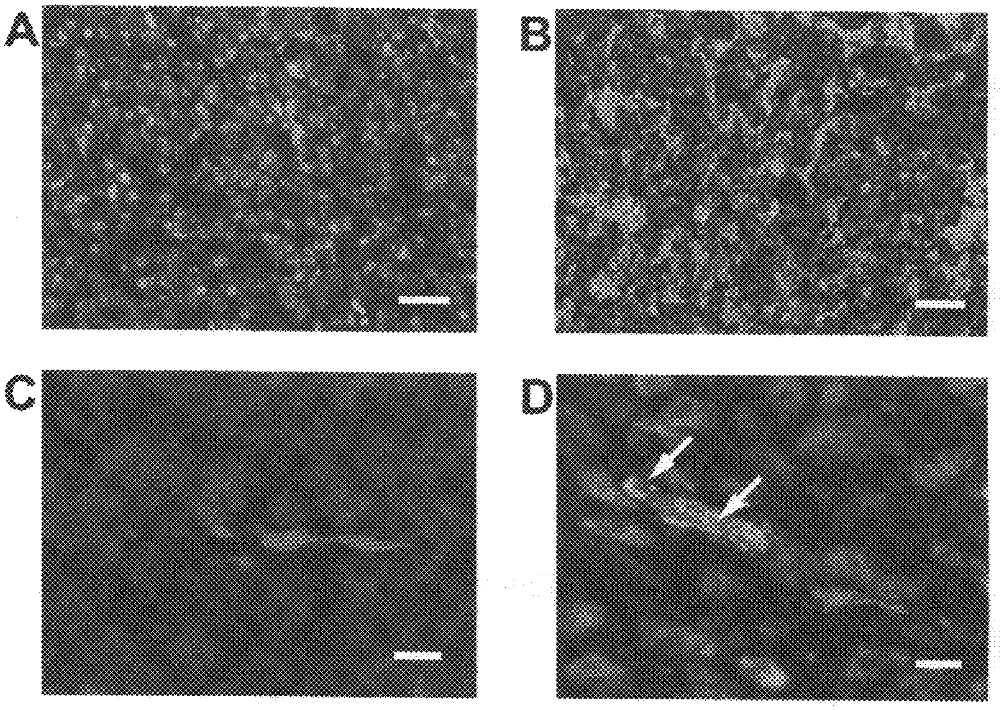
FIG. 6A, FIG. 6B, FIG. 6C and FIG. 6D. Antibodies to phosphatidylserine and anionic phospholipids cause monocytes to bind to tumor blood vessels and macrophages to infiltrate tumors. SCID mice bearing orthotopic human breast tumors were treated i.p. with 100 μg of control antibodies BBG3 (FIG. 6A and FIG. 6C) or 3G4 antibodies (FIG. 6B and FIG. 6D) three times a week for two weeks. Tumors were MDA-MB-435 (FIG. 6A and FIG. 6B) or MDA-MB-231 (FIG. 6C and FIG. 6D). Frozen tumor sections were prepared. Mouse macrophages and monocytes were detected with rat anti-mouse M1/70 (Mac-1) antibody followed by FITC-labeled anti-rat IgG (green). Anti-F4/80 and anti-FcγR antibodies gave coincident staining patterns with anti-M1/70 antibody. Blood vessels were detected with hamster anti-mouse CD31 followed by Texas-red labeled anti-hamster IgG (red). Nuclei were visualized with DAPI (blue).

Often vessels in 3G4-treated tumors were packed with mononuclear leukocytes (FIG. 6D), whereas only occasional leukocytes were seen adhering to vessels in tumors from control, BBG3-treated mice (FIG. 6C). Mononuclear leukocytes infiltrated into the interstitium of tumors from 3G4-treated mice in strikingly greater numbers than they did in BBG3-treated mice (compare FIG. 6B and FIG. 6A).

Almost all (>90%) of the cells that adhered to tumor vessels and infiltrated into the tumors expressed the monocytes/macrophage markers F4/80, M1/70 (CD11b, Mac-1) and FcγR (FIG. 6A, FIG. 6B, FIG. 6C and FIG. 6D). The cells lacked the neutrophil marker, Ly-6G, the NK cell marker, Ly-49, and the dendritic cell marker, CD11c. Lymphocyte markers were absent, as expected of SCID mice. Taken together, the results indicate that the cells that were adhering to tumor vessels and that were infiltrating into the tumor interstitium were monocytes and macrophages respectively.

EXAMPLE XXVIII

$F(ab')_2$ Fragments are Effective in Tumor Treatment

Antibodies to aminophospholipids and anionic phospholipids, such as the 3G4 antibody, are effective in tumor treatment (Example XI; Example XVIII). The present example shows that the $F(ab')_2$ fragment of the 3G4 antibody is as effective as the intact 3G4 antibody in tumor treatment.

Figure 8:
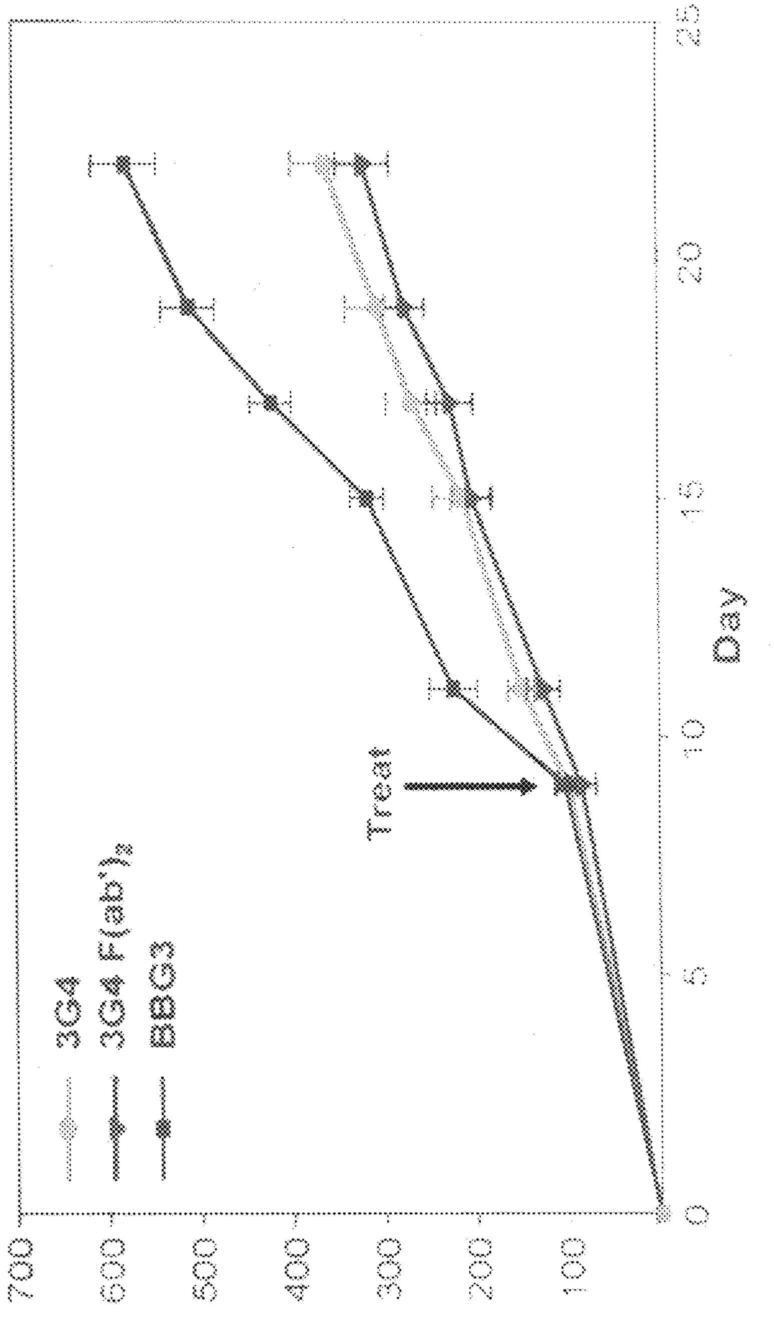
FIG. 8. The $F(ab')_2$ fragment of the 3G4 antibody is as effective as 3G4 as an anti-tumor agent. Mice were inoculated with tumors on day 1, and treated on day 9 with the 3G4 antibody, the $F(ab')_2$ fragment of the 3G4 antibody or an isotype-matched control antibody (BBG3). The tumors in the control animals continued to grow rapidly (■), whereas in mice treated with either the 3G4 antibody (●) or the $F(ab')_2$ fragment of the 3G4 antibody (▼), tumor growth was significantly slowed, with the $F(ab')_2$ fragment being at least as effective as 3G4.

In controlled studies mice with tumors were treated (on day 9) with either the 3G4 antibody, the $F(ab')_2$ fragment of the 3G4 antibody or an isotype-matched control antibody (BBG3). The tumors in the control animals continued to grow rapidly, whereas in mice treated with either the 3G4 antibody or the $F(ab')_2$ fragment of the 3G4 antibody, tumor growth was significantly slowed (FIG. 8). The $F(ab')_2$ fragment was at least as effective as the intact antibody (FIG. 8), and the anti-tumor effect of the $F(ab')_2$ fragment may have been underestimated in these studies.

This supports the proposal that antibodies such as 3G4 enhance the ability of monocytes and macrophages to mount an inflammatory response against PS-expressing tumor vasculature and tumor cells. Antibodies such as 3G4 may prevent PS on tumor vasculature from silencing host inflammatory responses, thereby permitting macrophages to secrete inflammatory cytokines, such as TNF-α, IL-1 and others, directly damaging tumor endothelium and recruiting further host cells into the tumor (FIG. 7).

EXAMPLE XXIX

Annexin V Dimer Localizes to Tumor Vessels Better Than Monomer

Example XXVII and Example XXVIII concern the role of macrophages in tumor treatment using antibodies to aminophospholipids and anionic phospholipids. From such data and other information, the inventors developed the receptor body aspects of the overall invention. As supportive of such embodiments, an annexin V homodimer was generated and found to localize to tumor vessels better than the corresponding annexin V monomer.

EXAMPLE XXX

Co-Binding of 3G4 and β2GPI to PS

The present example demonstrates that the interaction between the 3G4 antibody and PS is dependent on the plasma protein, β2-glycoprotein I (β2GPI). 3G4 binds to β2GPI at domain II, which is not linked to pathogenic antibodies isolated from patients with APS (which commonly recognize β2GPI domain I). The data show that divalent 3G4/β2GPI complexes are required for enhanced PS binding, including to PS-positive cells, since 3G4 Fab' fragments do not have this activity. The divalent 3G4/β2GPI binding to PS-positive cells supports the use of the Fc-β2GPI construct of the invention, which are also dimers, to target PS-positive cells and thus treat diseases such as cancer and viral infections.

A. Materials and Methods

1. Materials

Dulbecco's modified Eagle's medium (DMEM) and trypsin/EDTA were obtained from Mediatech, Inc. (Herndon, Va.). Fetal bovine serum (FBS), normal human serum, normal rat serum and normal mouse serum were obtained from Biomeda (Foster City, Calif.). Fresh human plasma was obtained from Carter Blood Care (Dallas, Tex.). Serum-free Hybridoma Media, Synthechol NS0 supplement, L-α-phosphatidylserine (PS), bovine serum albumin (BSA), and ovalbumin from chicken egg white (OVA) and were obtained from Sigma Chemical Co. (St. Louis, Mo.). DEAE cellulose, heparin-Sepharose, and Hybond-P membranes were obtained from Amersham Biosciences (Buckinghamshire, UK). 1-palmitoyl-2-hydroxy-sn-glycero-3-phosphocholine [lysophosphatidylchloine (LPC)] was obtained from Avanti Polar Lipids (Alabaster, Ala.). Ninety six-well Immulon-1B and -2HB microtiter plates were obtained from Thermo Lab Systems (Franklin, Mass.). Tris-HCl gradient SDS-PAGE gels and an Opti-4CN Substrate kit were obtained from Biorad (Hercules, Calif.). Eight-well glass chamber slides were obtained from BD Biosciences (Bedford, Mass.).

2. Antibodies

The 3G4 mouse monoclonal antibody, which was raised to bind the anionic phospholipid PS, is the antibody described in Example IV and other examples herein (see also, Ran et al., 2005). 3G4 was produced originally in hybridoma supernatant, but was subsequently converted to a mouse IgG2a isotype (Example XIX, D) and is now produced in the NS0 mouse myeloma cell line.

NS0 cells were cultured in DMEM supplemented with 10% FBS or serum-free Hybridoma Media with Synthechol NS0 supplement. A human IgG1 chimeric version of 3G4 (ch3G4) has also been generated (Example XIX, B) and is produced under serum-free conditions by Peregrine Pharmaceuticals, Inc. (Tustin, Calif.). This antibody has been termed bavituximab.

The mouse anti-human β2GPI (anti-β2GPI or α-β2GPI) mAb was obtained from US Biological (Swampscott, Mass.). A hybridoma secreting C44, a colchicine-specific mouse IgG2a mAb, was obtained from the American Type Culture Collection (Rockville, Md.) and used as a control for 3G4 and anti-β2GPI. Rituximab (human IgG1 chimeric mAb) was obtained from the UT Southwestern pharmacy and used as a control for ch3G4. All antibodies produced in culture supernatants were purified as described in the previous examples (see also, Ran et al., 2003, specifically incorporated herein by reference). All secondary antibodies were obtained from Jackson Immunoresearch Labs (West Grove, Pa.).

3. Preparation of Antibody Fragments

3G4 $F(ab')_2$ was generated by incubation with the protease pepsin. 3G4 Fab and control Fab 7H11 (anti-adenovirus) were generated by incubation with the protease papain. All antibody cleavage products were purified by FPLC, and verified by SDS-PAGE.

4. Purification of β2GPI from Human Plasma

Human β2GPI (hβ2GP1) was purified from human plasma essentially as described previously (Polz et al., 1980; Wurm et al., 1984; each specifically incorporated herein by reference). Briefly, perchloric acid (70%) was added to pooled plasma to a final concentration of 1.57% (v/v). The precipitate was discarded and the supernatant was adjusted to pH 7.5 with saturated $Na_2CO_3$, followed by extensive dialysis against 50 mM Tris, pH 8.0. This material was applied to a DEAE cellulose column equilibrated with 50 mM Tris, pH 8.0 to remove contaminants. The DEAE column flow-through was then applied to a heparin-Sepharose affinity column equilibrated with 50 mM Tris, pH 8.0, and bound proteins were eluted using 1.0 M NaCl. Finally, the η2GPI preparation was dialyzed against PBS and purified further by protein A/G to remove contaminating IgG. The final preparation contained a homogeneous band at 50 kDa, as shown by non-reduced SDS/PAGE and commassie staining.

5. Construction and Expression of β2GPI and β2GPI Domains

To generate pure recombinant full-length and deleted forms of β2GPI, the yeast shuttle expression vector pPIC6αA (Invitrogen) and host strain $Mut^+$X-33 (Invitrogen) were used. The expression vector contains the 5' promoter and the 3' transcription termination sequences of the alcohol (methanol) oxidase gene (AOX1). The vector also has a yeast α mating factor signal sequence downstream of the AOX1 promoter to which foreign cDNA can be fused for secretion of recombinant heterologous protein into the culture medium. Expression in *P. pastoris* provides glycosylation and disulfide bond formation similar to that in mammalian cells.

To generate the expression constructs, the following five expression constructs were made using human β2GPI cDNA:

```
(1) The entire coding region of β2GPI cDNA with-
    out its cognate signal peptide (domain 1-5),
                                          (SEQ ID NO:12)
    5' primer; 5'-GGAATTCGGACGGACCTGTCCCAAGC-3';

(2) Domain 1 deleted (domain 2-5),
                                          (SEQ ID NO:13)
    5' primer; 5'-GGAATTCGTATGTCCTTTTGC-3';

(3) Domain 1 & 2 deleted (domain 3-5),
                                          (SEQ ID NO:14)
    5' primer, 5'-GGAATTCGCTCCCATCATCTGC-3';

(4) Domain 1-3 deleted (domain 4-5),
                                          (SEQ ID NO:15)
    5' primer, 5'-GGAATTCGTAAAATGCCCATTC-3';
and

(5) Domain 5 only,
                                          (SEQ ID NO:16)
    5' primer, 5'-GGAATTCGCATCTTGTAAAGTAC-3'.
```

A common 3' primer, 5'-TTCTAGATTAGCATGGCTTTAC-3' (SEQ ID NO:17) was used for PCR of all fragments. PCR amplified fragments were inserted in-frame between the EcoR1 and XbaI restriction sites of pPICαA, directly downstream from the α mating factor signal sequence. A Stop codon was introduced at the end of each fragment to prevent fusion of the recombinant proteins to a c-myc epitope or a His tag at the C-terminus. Plasmid constructs were propagated in *E. coli* in presence of 100 μg/ml blasticidin and verified by restriction analysis and nucleotide sequencing. Recombinant proteins expressed by constructs (1), (2), (3), (4), and (5) encoded proteins of approximately 36, 29, 24, 16, and 9 kDa, respectively, before glycosylation.

For the transformation and screening of expression clones, the recombinant plasmid constructs were linearized with restriction enzyme SacI, purified, and 10 μg was used to transform host strain X-33 by the spheroplasts method (Invitrogen). Transformants for each of these constructs were selected on YPD (Yeast extract Peptone Dextrose Medium) plates containing 400 μg/ml blasticidin for 4 days. Several clones for each of these constructs were restreaked on YPD plates with 400 μg/ml blasticidin to determine the true integrants. Ten clones of each construct were then streaked on Minimal Dextrose (MD) and Minimal Methanol (MM) plates. Five clones of each construct, growing equally well on both MD and MM plates, were then grown in liquid MD and MM medium for 24, 48, 72, 96 and 120 hours. Supernatants and pellets for each clone at each time point were analyzed by Western blot using anti-human β2GPI polyclonal antibody. Clones that showed highest expression of the protein in supernatant were further used for large-scale preparation.

For the large scale purification of the recombinant proteins, recombinant proteins were produced using culture conditions recommended by Invitrogen. A starter culture of each clone was cultured in 5 ml of buffered minimal glycerol-complex medium (BMGY) at 30° C. with vigorous shaking overnight. Cells were collected, used to inoculate 25 ml of BMGY, and grown for 2 days. Cells from the 25 ml culture were then used to inoculate 1 L of buffered minimal methanol-complex (BMMY) medium (1.0% methanol). Culture was continued for 4 days at 30° C. with vigorous shaking and 100% methanol was added every 24 hours (final concentration of 1.0%) to maintain protein expression. Culture medium was clarified by centrifugation (4000×g, 15 min) and supernatant was dialyzed for 2 days at 4° C. in 50 mM Tris buffer before being applied to a DEAE-sephacel column equilibrated with 50 mM Tris buffer. Flow through solution was collected and applied to a heparin-sepharose column. β2GPI was eluted from heparin-sepharose column with 1 M NaCl, dialyzed against 50 mM Tris buffer, concentrated using Amicon concentrator, and analyzed by Western blot. The N-terminus of each protein was sequenced to confirm cleavage of the α-factor leader sequence. Protein yields varied from 10 mg/L (full-length β2GPI) to 25 mg/L (β2GPI domain V).

6. Preparation of "Nicked" hβ2GPI

Nicked hβ2GPI was prepared from intact hβ2GPI purified from human plasma as described above. hβ2GPI was incubated with plasmin-coated beads at 37° C. for 17 hrs. The beads were removed by centrifugation and the supernatant containing the cleaved protein was recovered. Western blotting of the purified product indicated the nicked β2GPI preparations were plasmin-free and did not contain plasmin autoproteolytic products (no reactivity with anti-plasmin or anti-angiostatin antibodies). N-terminal sequence analysis revealed two N-termini that corresponded to the N-terminus of β2GPI and a new sequence generated at the Lys317/Thr318 cleavage site.

7. Anti-PS ELISA

The assay was performed as follows (see also, Ran et al., 2005, specifically incorporated herein by reference). PS-coated Immunlon 1B microtiter plates were blocked overnight in 1% OVA (w/v). The following day, serial 2-fold dilutions of 3G4 purified from serum-containing or serum-free supernatant were prepared from an initial concentration of 13.33 nM. Dilutions were performed in 1% OVA or 10% non-heat inactivated sera from cow, human, rat or mouse. Plates were incubated for 1 hr. at 37° C. and binding of 3G4 was detected. All ELISA studies were performed at least three times.

8. Anti-hβ2GPI ELISA

The assay was performed as described above with the following modifications. hβ2GPI, nicked hβ2GPI, or recombinant hβ2GPI peptides were coated on 96-well Immunlon 2HB microtiter plates overnight at a concentration of 10 μg/ml. Plates were then blocked in 1% OVA for 1 hr. at room temperature. 3G4, ch3G4, or anti-β2GPI were diluted in 1% OVA to an initial concentration of 13.33 nM and serial 2-fold dilutions were prepared. Plates were incubated for 1 hr. at 37° C. and antibody binding was detected. All ELISA studies were performed at least three times.

9. Western Blot

Protein samples were heated to 95° C. for 5 min in non-reducing SDS sample buffer. The samples were then loaded onto a Tris-HCl 4-15% gradient SDS-PAGE gel and separated using a Mini Protean II apparatus (Biorad). Separated proteins were transferred to a PVDF membrane and blocked overnight in 3% BSA (w/v). Membranes were probed with anti-β2GPI, 3G4, or control mouse IgG diluted to 1 μg/ml in 3% BSA, washed thoroughly, and incubated with peroxidase-labeled goat anti-mouse IgG. Membranes were developed using an Opti-4CN Substrate kit.

10. Induction and Detection of PS Exposure on Endothelial Cells

Adult bovine aortic endothelial (ABAE) cells were maintained in DMEM supplemented with 10% FBS and 2 mM L-glutamine. ABAE cells were removed from subconfluent cultures by brief exposure to 0.25% trypsin/0.02% EDTA, and 8-well chamber slides were seeded with $2\times10^4$ cells/well. Following overnight culture, cells were washed gently with PBS and treated with 200 μM lysophosphatidylcholine (LPC) to induce PS exposure. LPC-treatment was performed in the presence of 3G4, ch3G4, or control IgG for 30 min at 37° C. in either 10% FBS or 10% normal mouse serum (MS). If LPC-treatment was performed in 10% MS, hβ2GPI was added as a co-factor because 3G4/ch3G4 cannot bind PS in MS (see Results).

PS exposure was determined by immunofluorescence staining. Cells were washed thoroughly in PBS, fixed in 4% paraformaldehyde (w/v), and incubated with a biotin-conjugated anti-mouse secondary antibody. Next, cells were incubated with FITC-conjugated streptavidin (Jackson Immunoresearch) to detect antibody binding. Cells were then permeablized with 0.1% Triton-X100 in PBS and counterstained with Texas Red-conjugated phalloidin (Molecular Probes, Eugene, Oreg.), and 4',6-diamidino-2-phenylindole (DAPI; Molecular Probes). Images were captured using a Coolsnap digital camera (Photometrics, Tucson, Ariz.) mounted on a Nikon microscope and processed with MetaVue software (Universal Imaging Corporation, Downingtown, Pa.).

11. Quantification of Antibody Binding to ABAE Cells

The area of antibody binding was determined using MetaVue image analysis software, which is able to quantify the number of illuminated pixels in an image. Images of FITC fluorescence were used to quantify antibody binding. Corresponding images of DAPI fluorescence were used to normalize the FITC images for the number of cells present in the field. A small FITC/DAPI ratio indicates a small antibody binding area, whereas a large FITC/DAPI ratio indicates a large binding area. The FITC/DAPI ratios were used to determine increases or decreases in antibody binding area relative to a basal amount of antibody binding under the selected conditions. Five images at 200× magnification were used for each analysis. Data are presented as average relative FITC/DAPI ratios with error bars representing the standard deviation.

B. Results 1. 3G4 Requires a Serum Factor to Bind PS-Coated Microtiter Plates

Figure 9:
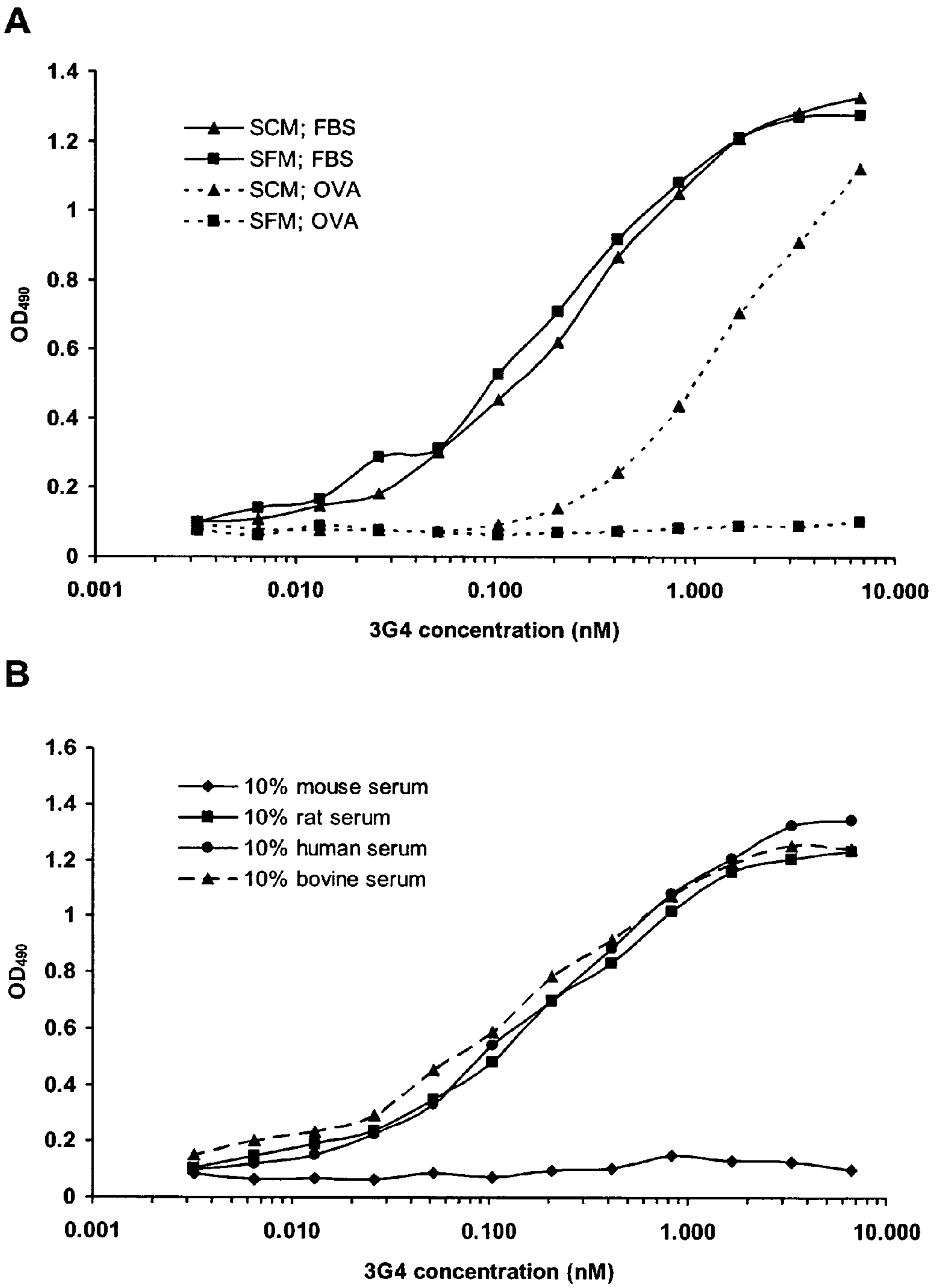
FIG. 9A and FIG. 9B. 3G4 binding to PS-coated microtiter plates is serum-dependent.

The 3G4 antibody purified from serum-containing media (SCM) or serum-free media (SFM) binds to PS-coated microtiter plates when serial dilutions are performed in 10% FBS (FIG. 9A, solid lines). In contrast, when serial dilutions are performed in 1% OVA (which lacks bovine serum proteins) 3G4 purified from SFM no longer binds PS (FIG. 9A, dashed line, ■). This finding indicates a factor present in bovine serum mediates the interaction between 3G4 and PS.

Interestingly, 3G4 purified from SCM binds PS weakly when serial dilutions are performed in 1% OVA (FIG. 9A, dashed line, ▲). This suggests purification of 3G4 grown in SCM does not completely remove the serum protein required to mediate the interaction between 3G4 and PS. Therefore, studies described below were performed using 3G4 purified from SFM.

2. 3G4 Binding to PS in Sera from Different Species

To determine whether sera from other mammalian species can mediate the interaction between 3G4 and PS, serial dilutions of 3G4 were performed in 10% mouse, rat, human or other sera. 3G4 bound PS in the presence of rat and human serum, much like in the presence of bovine serum (FIG. 9B). However, 3G4 did not bind PS in the presence of mouse serum (FIG. 9B). In other studies, 3G4 bound PS in the presence of hamster, ferret, guinea pig, rabbit and monkey serum. Therefore, the serum protein epitope recognized by 3G4 is conserved among all mammalian species tested except mouse.

3. 3G4 Binds the Serum Glycoprotein β2GPI

In the late 1980's, a cohort of patients suffering venous and arterial thromboses, thrombocytopenia and/or recurrent pregnancy loss was shown to have circulating anti-phospholipid (aPL) antibodies (Hughes et al., 1986; Deleze et al., 1989). These patients were described as having the "Anti-phospholipid Syndrome" (APS). In the early 1990s, it was shown that many so-called aPL antibodies do not recognize phospholipids directly, but bind serum proteins with affinity for phospholipids instead (Galli et al., 1990; McNeil et al., 1990). Therefore, a panel of human serum proteins known to interact with anionic phospholipids was screened for 3G4 reactivity.

Figure 10A:
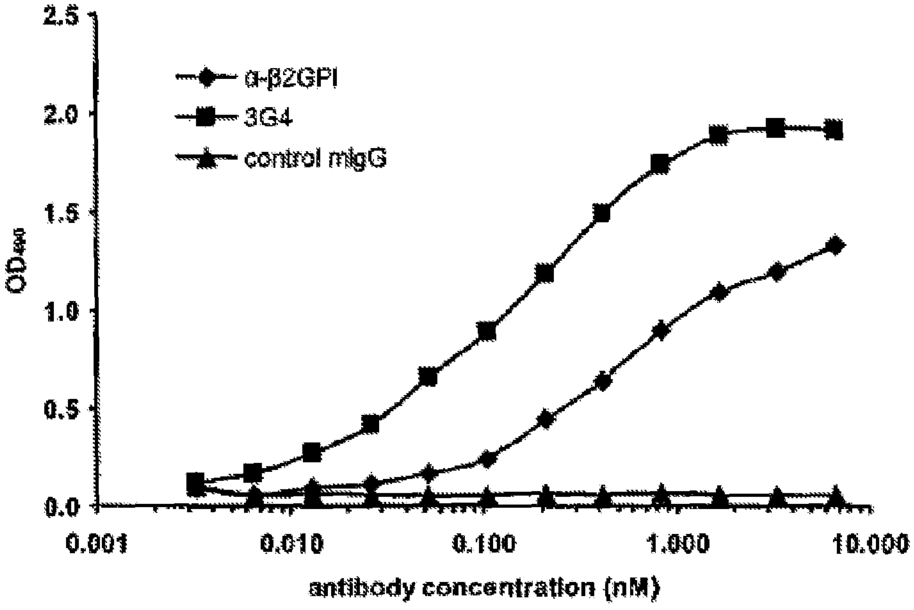
FIG. 10A and FIG. 10B. 3G4 binds the plasma protein β2GPI (FIG. 10A) and binds at β2GPI domain II (FIG. 10B).

In terms of β2GPI, human β2GPI (hβ2GPI) was coated on a microtiter plate and incubated with mouse anti-human β2GPI antibody (anti-β2GPI), 3G4, or a control mouse IgG2a of irrelevant specificity (control mIgG). As expected, anti-β2GPI bound to hβ2GPI, while the control mIgG did not (FIG. 10A). 3G4 also bound strongly to the hβ2GPI coated plate (FIG. 10A).

To determine whether β2GPI is the only serum protein recognized by 3G4, purified hβ2GPI and 10% human serum were run on an SDS-PAGE gel and transferred to a membrane support for immunoblot. 3G4 detected the 50-kDa purified hβ2GPI and a single band of similar size in human serum. Importantly, the 3G4 immunoblot was virtually identical to a blot generated using the anti-β2GPI antibody. The control mIgG antibody did not detect any protein. Together, these data indicate that 3G4 binds serum protein β2GPI.

Other human serum proteins known to interact with anionic phospholipids were tested for 3G4 reactivity in ELISAs. Equal amounts of the particular protein were coated on microtiter plates, blocked in 1% OVA, and incubated with a serial dilution of 3G4. Plates were washed thoroughly and antibody binding was detected with a peroxidase-labeled secondary detection antibody. All studies included positive and negative control antibodies, which worked as expected. The results of the immunoblot and ELISA studies are shown in Table 15, which thus identifies β2GPI as the co-binding factor for 3G4.

TABLE 15

3G4 Reactivity with Serum Proteins that interact with Phospholipids

| Serum Protein | 3G4 Reactivity |
|---|---|
| annexin V | − |
| beta2-glycoprotein I | + |
| factor XII | − |
| kininogen | − |
| oxidized LDL | − |
| protein C | − |
| protein S | − |
| prothrombin | − |
| tPA | − |

4. 3G4 Binds β2GPI at Domain II

β2GPI has five domains, of which the fifth domain is responsible for binding to anionic phospholipids. To determine which domain of β2GPI is recognized by the 3G4 antibody, recombinant human β2GPI constructs were generated with different domain structures and tested alongside recombinant full-length hβ2GPI. These domain constructs were made by serial truncations from the N-terminus, and so lack each of the N-terminal domains in turn, as follows: recombinant full-length hβ2GPI contains domains I-V; hβ2GPI from which domain I has been deleted contains domains II-V; hβ2GPI from which domains I and II have been deleted contains domains III-V; hβ2GPI from which domains I, II and III have been deleted contains domains IV-V; and hβ2GPI from which domains I, II, III and IV have been deleted contains domain V only.

Figure 10B:
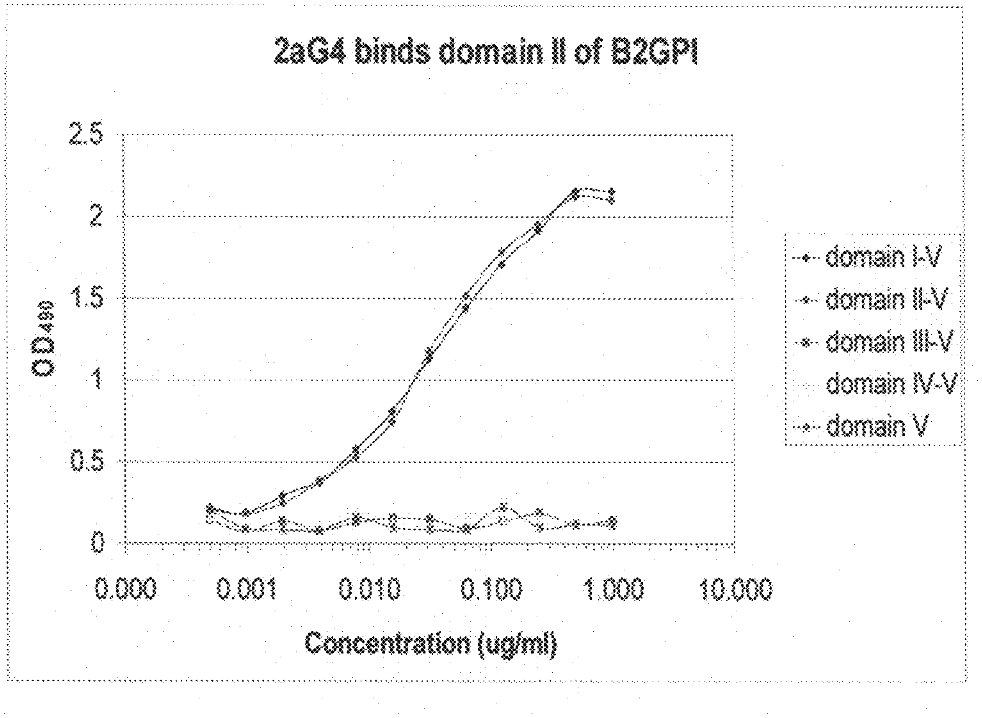

Equal amounts of the full-length hβ2GPI and each of the above hβ2GPI domain constructs were coated on microtiter plates and incubated with a serial dilution of 3G4. This study showed that only hβ2GPI constructs containing domain II of β2GPI (domains I-V and domains II-V) were detected by 3G4 (FIG. 10B). When domain I was deleted, 3G4 bound equally well to domains II-V (FIG. 10B). Thus, 3G4 binds to β2GPI at domain II.

The finding that 3G4 binds to β2GPI at domain II is important in light of the information known about pathogenic antibodies isolated from patients with APS. Pathogenic anti-β2GPI antibodies isolated from patients with APS commonly recognize domain I of β2GPI (de Laat et al., 2005a). Anti-2GPI antibodies from APS patients that recognize domain II are not often pathogenic. This likely explains the lack of toxicity associated with 3G4 following extensive toxicological studies performed in a variety of animal models.

5. Co-Binding of 3G4 and β2GPI to Cells with Exposed PS

Characterizing the binding of anti-β2GPI antibodies using β2GPI-coated microtiter plates has been controversial due to inconsistencies observed depending on the type or even the lot of microtiter plate (de Laat et al., 2004a). To verify the above findings under more physiological conditions, a live-cell binding assay was developed. This assay detects and measures antibody binding to endothelial cell membrane surfaces following treatment with the membrane disrupting agent, lysophosphatidylcholine (LPC) to induce PS exposure.

In this assay, ABAE cells were incubated with 3G4 or control mIgG in DMEM+10% FBS in the presence or absence of 200 μM LPC for 30 min. Cells were then washed, fixed, and stained with fluorescent markers to visualize binding of antibody to the cell surface. The pixel area of 3G4 or mIgG binding was quantified using MetaVue software. All values were relative to the binding of 3G4 to non-LPC treated cells, which was set to one.

When 3G4 is added to ABAE cell culture media under normal conditions, no binding to the cells is observed. However, when ABAE cells are incubated with 3G4 in the presence of LPC, numerous pinpoints of 3G4 binding are readily detectable. LPC is known to induce temporary membrane distortions (Kogure et al., 2003), which likely cause a loss of membrane asymmetry and exposure of PS.

Quantification showed that the area of 3G4 binding increased greater than 500-fold upon LPC-treatment, while binding of a control mIgG remained undetectable. Similar results were obtained previously, when 3G4 and the PS-binding molecule annexin V were shown to bind endothelial cells following induction of PS exposure with $H_2O_2$ (Example VI; Example VII; see also, Ran et al., 2005).

Importantly, LPC-treated ABAE cells were not stained by the membrane impermeant dyes propidium iodide or DAPI, indicating 3G4 bound PS on the cell surface, not the inner leaflet of the plasma membrane.

To determine whether β2GPI is required for binding of 3G4 to endothelial cells with exposed PS, the live-cell binding assay was performed in media containing 10% MS rather than 10% FBS to prevent interference from bovine β2GPI. As demonstrated above, 3G4 does not bind PS in the presence of MS. Furthermore, 3G4 did not detect any protein in 10% MS by immunoblot, indicating that 3G4 does not recognize murine β2GPI.

Figure 11:
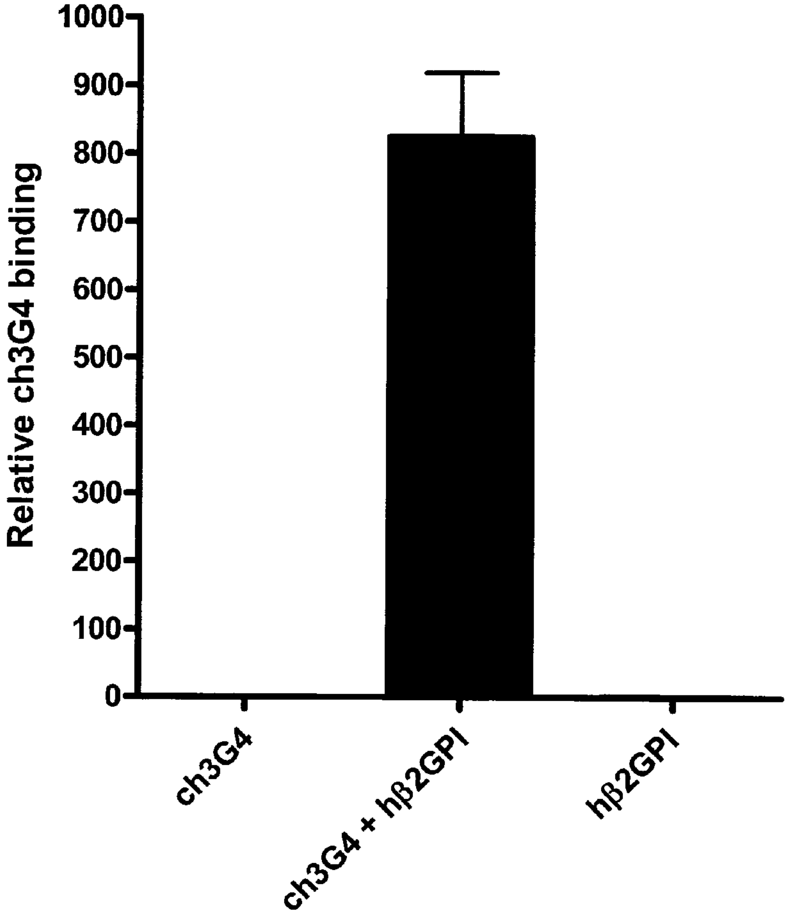
FIG. 11. ch3G4 and β2GPI must be present simultaneously to bind endothelial cells (EC) with exposed PS. ABAE cells were incubated for 30 min with 200 μM lysophosphatidylchloine (LPC) in DMEM+10% normal mouse serum (MS), plus (i) purified hβ2GPI, (ii) ch3G4, or (iii) ch3G4+hβ2GPI simultaneously. Cells were then washed and incubated for 30 min with (i) ch3G4, (ii) hβ2GPI, or (iii) DMEM+10% MS, respectively. Finally, cells were washed, fixed, and stained with fluorescent markers to detect binding of ch3G4. ch3G4 and hβ2GPI were used at a concentration of 2 μg/ml. The pixel area of ch3G4 binding was quantified using MetaVue software. Values are relative to the binding of ch3G4 under condition (i), which was set to one.

For this study, a human chimeric 3G4 (ch3G4) was used to prevent background caused by detection of murine IgG present in MS. When ABAE cells were incubated with ch3G4 in the presence of 10% MS and LPC, no antibody binding was detected (FIG. 11). In contrast, addition of purified hβ2GPI to the binding reaction supported widespread binding of ch3G4 (FIG. 11), demonstrating that ch3G4 binding is dependent upon hβ2GPI. In all situations, ch3G4 binding was dependent upon LPC treatment and no binding was detected using a control human IgG of irrelevant specificity.

Interestingly, when ABAE cells were incubated with hβ2GPI in the presence of 10% MS and LPC, washed thoroughly, then incubated with ch3G4 to detect binding of hβ2GPI, very little ch3G4 binding was detected (FIG. 11). This finding indicates that hβ2GPI does not bind endothelial cells with exposed PS in the absence of ch3G4, and is consistent with reports that β2GPI has a low affinity for anionic phospholipid membrane surfaces under physiological conditions (Willems et al., 1996; Bevers et al., 2005). Together, these data show that ch3G4 and hβ2GPI must be present simultaneously to bind ABAE cells with exposed PS, suggesting ch3G4 enhances the affinity of β2GPI for anionic phospholipids surfaces.

6. The Lipid Binding Region of β2GPI is Required for Co-Binding of 3G4

To confirm that the lipid binding region of β2GPI is required for co-binding of β2GPI and 3G4 (and ch3G4) to endothelial cells with exposed PS and other anionic phospholipids, the live-cell binding assay was performed using "nicked" hβ2GPI. Nicked hβ2GPI is unable to bind PS and other anionic phospholipids due to plasmin-mediated cleavage within the lipid binding region of domain V (Hunt et al., 1993; Hunt and Krilis, 1994).

When ABAE cells are incubated with ch3G4 and hβ2GPI or nicked hβ2GPI in the absence of LPC, no ch3G4 binding is detected (FIG. 12A). In the presence of LPC, hβ2GPI is able to mediate binding of ch3G4 to ABAE cells with exposed PS, while nicked hβ2GPI is not able to mediate binding (FIG. 12A). The lack of binding in the live-cell assay is not due to an inability of ch3G4 to bind nicked hβ2GPI, since ch3G4 binds nicked hβ2GPI as well as hβ2GPI when equal amounts of protein are coated on microtiter plates (FIG. 12B). These findings demonstrate that the ch3G4/hβ2GPI complex detects PS and other anionic phospholipids exposed on ABAE cells following LPC-treatment through the lipid binding region of hβ2GPI domain V.

7. Antibody Divalency is Required for Co-Binding of β2GPI

The data presented above suggest that 3G4 detects PS and anionic phospholipids by enhancing the affinity of β2GPI for anionic phospholipids. Interestingly, anti-β2GPI antibodies isolated from many APS patients are known to increase the affinity of β2GPI for anionic phospholipid surfaces (Bevers et al., 2004). Furthermore, the phenomenon is dependent upon the formation of a divalent antibody-β2GPI complex.

Figure 13:
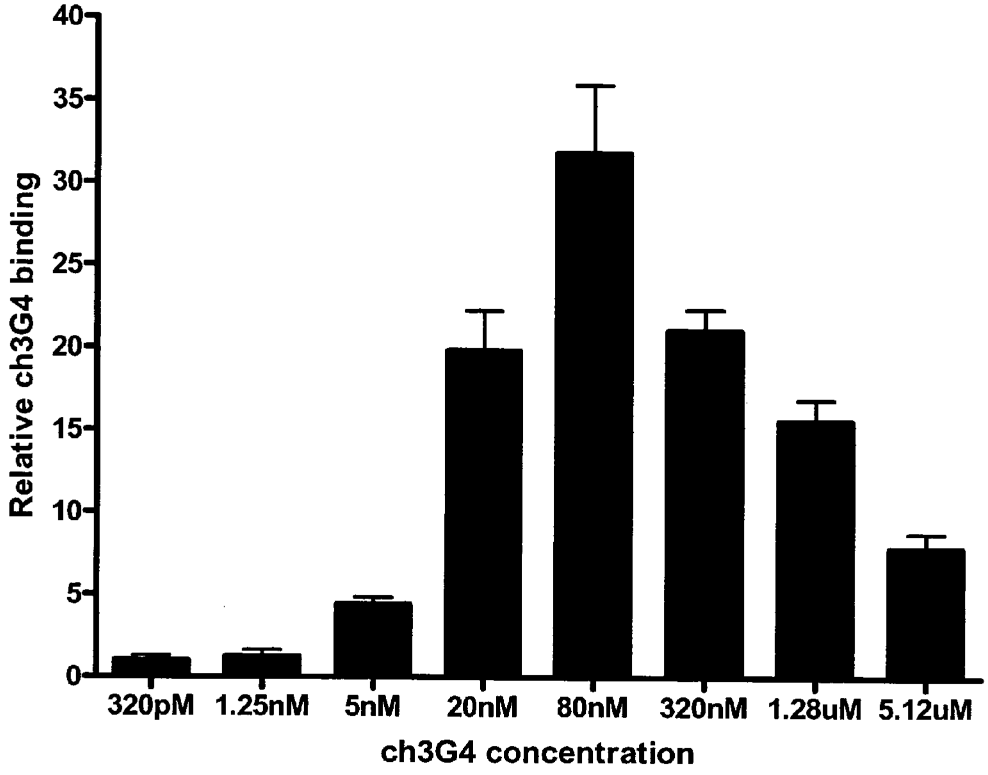
FIG. 13. Excess ch3G4 inhibits binding of ch3G4/β2GPI complexes to endothelial cells with exposed PS. ABAE cells were incubated for 30 min with 200 μM LPC, 40 nM purified hβ2GPI, and a titer of ch3G4 in DMEM+10% MS. Cells were then washed, fixed, and stained with fluorescent markers to detect binding of ch3G4. The pixel area of ch3G4 binding was quantified using MetaVue software. Values are relative to the binding of 320 pM ch3G4, which was set to one.

To determine whether divalency is required for binding of 3G4/β2GPI complexes to PS and anionic phospholipids, LPC-treated ABAE cells were incubated with purified hβ2GPI and varying amounts of ch3G4. The area of ch3G4 binding increased in a concentration-dependent manner to a peak at an antibody to β2GPI ratio of 2:1 (FIG. 13). Further increases in ch3G4 concentration caused a concentration-dependent decrease in binding. The bell shaped relationship between the concentration of ch3G4 and binding to endothelial cells with exposed PS suggests the formation of divalent ch3G4/β2GPI complexes on the membrane surface. At very high antibody concentration, competition between monovalent and divalent complexes causes a decrease in the amount of ch3G4/β2GPI complex bound to the LPC-treated ABAE cells.

Figure 14:
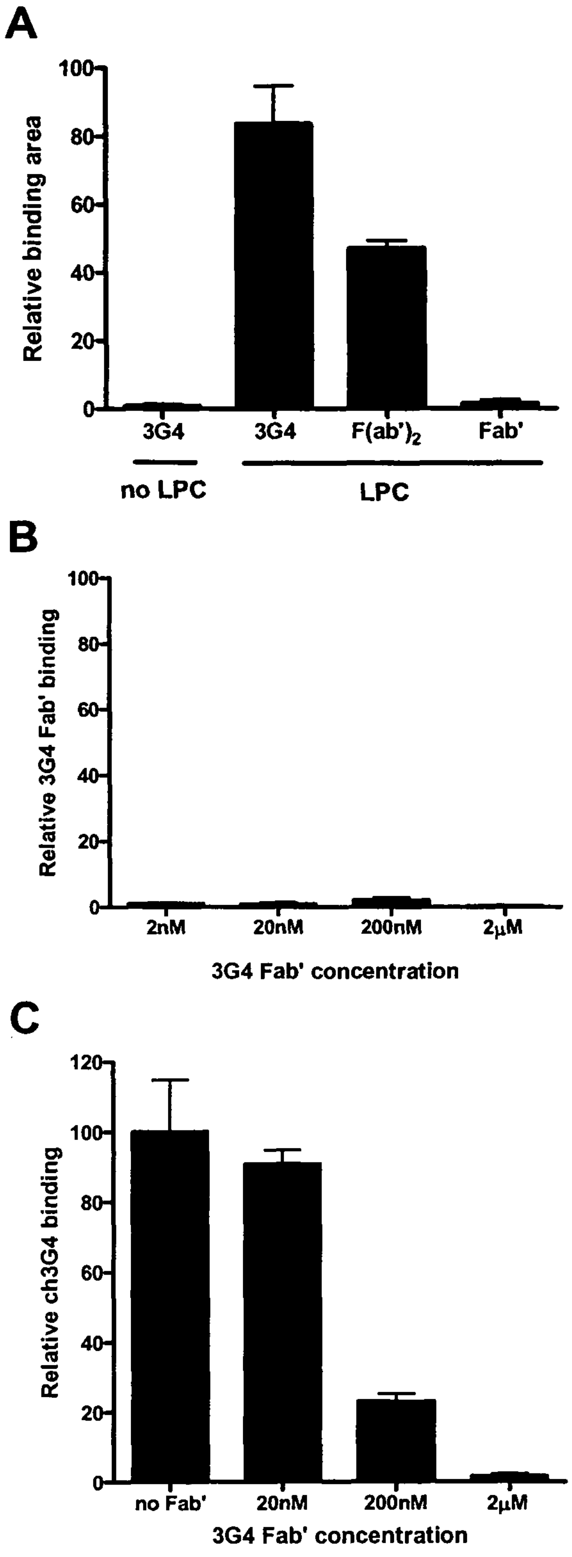
FIG. 14A, FIG. 14B and FIG. 14C. ch3G4 divalency is required for β2GPI-mediated binding to endothelial cells with exposed PS.

To further examine whether divalency is required for binding to endothelial cells with exposed PS, 3G4 $F(ab')_2$ and 3G4 Fab' monomers were generated and used in live-cell binding assays with intact 3G4. As expected, intact 3G4 bound to LPC-treated ABAE cells, but not to untreated cells (FIG. 14A). An equivalent concentration of 3G4 $F(ab')_2$ also bound to LPC-treated ABAE cells, but binding of 3G4 Fab' was negligible (FIG. 14A). The apparent decrease in binding of 3G4 $F(ab')_2$ relative to 3G4 (FIG. 14A) is likely due to lost binding of the polyclonal secondary antibody to Fc epitopes missing on 3G4 $F(ab')_2$. No binding of 3G4 Fab' was detectable on ABAE cells even at a concentration of 2 μM (FIG. 14B), which is 1,000-fold above the concentration required to bind β2GPI coated on microtiter plates.

Moreover, 3G4 Fab' inhibited ch3G4/β2GPI binding to LPC-treated ABAE cells in a concentration-dependent manner (FIG. 14C), while a control Fab' of irrelevant specificity did not. The ability of 3G4 Fab' to inhibit ch3G4 binding confirms that 3G4 Fab' is able to bind β2GPI and that monomeric 3G4 Fab'/β2GPI complexes cannot bind endothelial cells with exposed PS. These data support the hypothesis that divalent 3G4/β2GPI complexes are required to bind anionic phospholipid surfaces.

Figure 15:
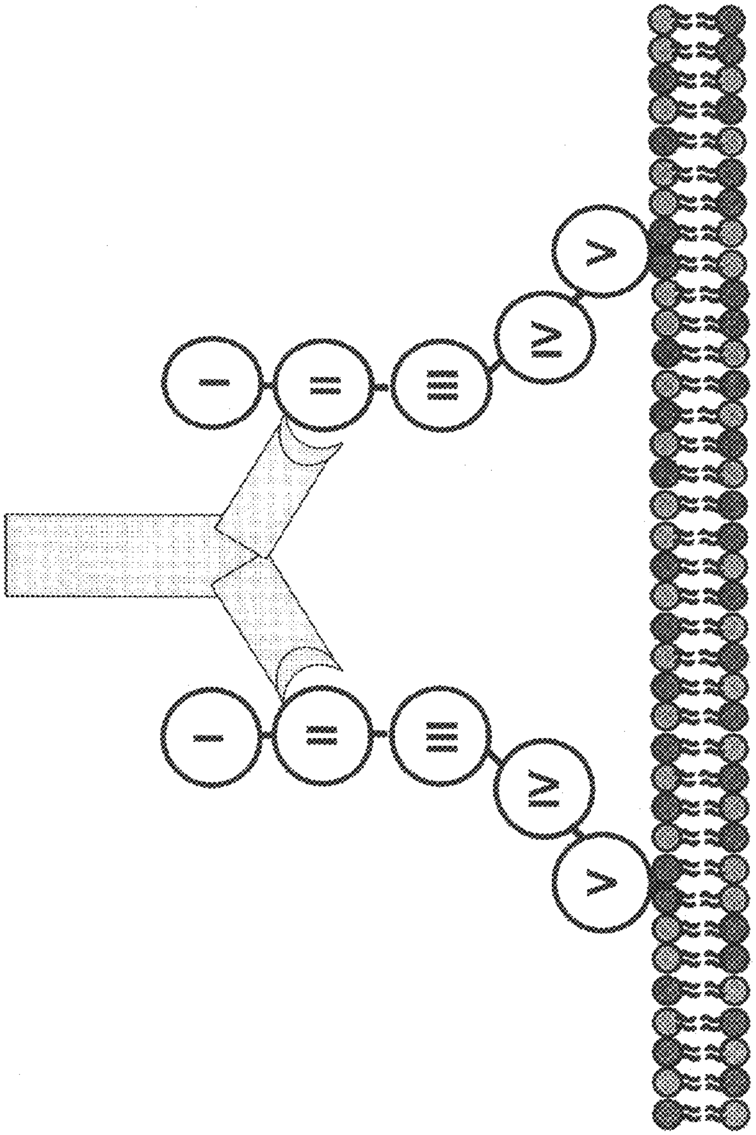
FIG. 15. Schematic representation of the β2GPI-dependent binding of the 3G4 antibody and the human-mouse chimeric antibody counterpart, termed bavituximab, to a PS surface. β2GPI is shown with its five domains (I, II, III, IV and V). Antibody binding to PS surfaces, including PS exposed on cell membranes, is mediated by binding to domain II of β2GPI.

As shown in FIG. 10B, the 3G4 antibody binds to β2GPI at domain II, and as shown in FIG. 12A and FIG. 12B, the lipid binding region of β2GPI domain V is required for co-binding of 3G4 (and ch3G4) and β2GPI to PS exposed on endothelial cells. In addition, as demonstrated here, antibody divalency is required for the co-binding of 3G4 (and ch3G4) and β2GPI to the exposed PS. Accordingly, the inventors have presented a model of antibody and β2GPI co-binding to PS exposed on the outer surfaces of membranes, such as occurs on activated endothelial cells, tumor vascular endothelial cells and tumor cells, as well as on virally infected cells (FIG. 15).

EXAMPLE XXXI

Preparation and Characterization of an Fc-β2GPI

This example concerns the preparation and characterization of an exemplary Fc-β2GPI construct. In this construct, the Fc region of mouse $IgG_2a$ was attached to full length mouse β2GPI (domains I-V) to create murine Fc-β2GPI or Fc-mβ2GPI. The mouse $IgG_{2a}$ Fc is used both as a dimerization domain and to provide effector functions. The resultant dimeric Fc-β2GPI construct has various uses, including targeting tumor blood vessels and virally infected cells, each of which have exposed PS. An advantage of using an Fc region is that the Fc-β2GPI construct can mark the targeted cells for attack by the host immune system.

A. Preparation

Figure 16:
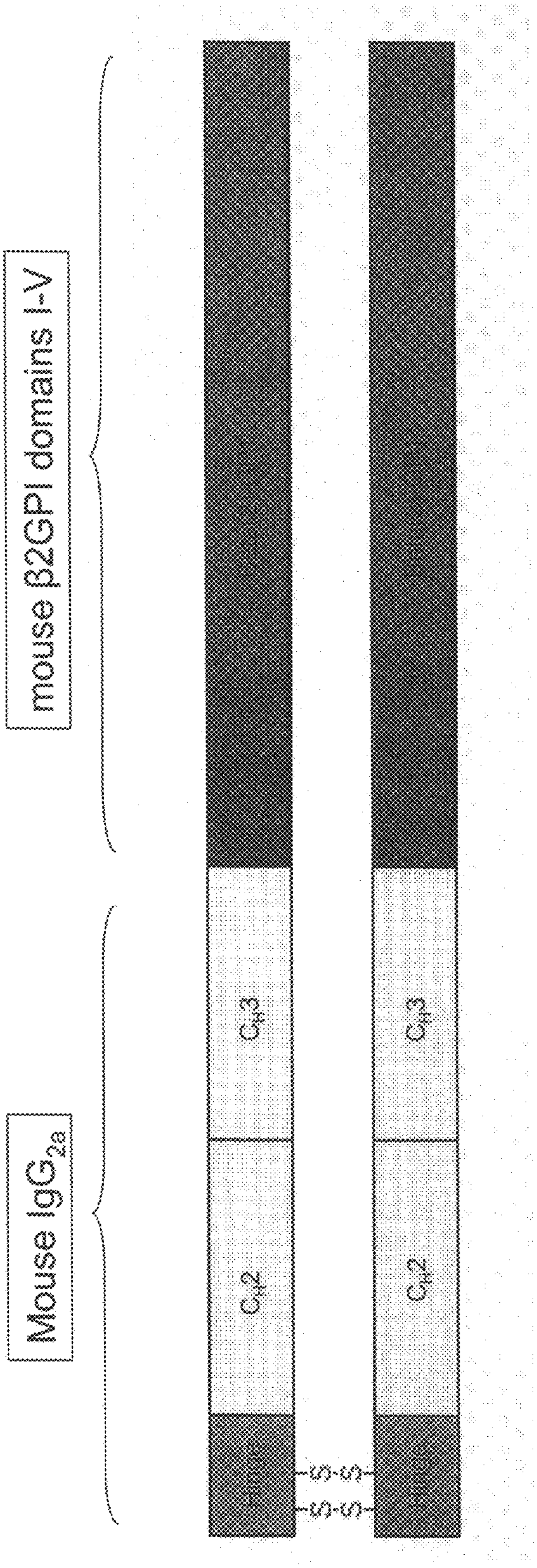
FIG. 16. Schematic representation of an exemplary Fc-β2GPI construct. In this construct, the variable regions of an antibody have been removed, but are not replaced by β2GPI. Rather, β2GPI is attached at the C-terminus of the $C_H3$ domains of the Fc region. The figure shows the disulphide-bonded hinge region, two $C_H2$ and $C_H3$ domains of the Fc region from mouse $IgG_{2a}$ operatively attached to two mouse β2GPI proteins. In the counterpart human construct, the Fc region from human $IgG_1$ would be operatively attached to two human β2GPI proteins. The Fc region from human $IgG_3$ would also be preferred for use with two human β2GPI proteins. In the exemplary Fc-β2GPI construct depicted, mouse β2GPI is shown with all five domains (I-V), although other mouse or human constructs could readily be made without all five domains, so long as the lipid binding region of domain V of β2GPI is maintained.

Although a variety of Fc-β2GPI constructs have been designed, the exemplary Fc-β2GPI (Fc-mβ2GPI) construct of the present example uses a murine Fc region as the N-terminus and domains I-V of murine β2GPI as the C-terminus. The Fc-β2GPI thus contains the disulphide-bonded hinge region and two $C_H2$ and $C_H3$ domains of the Fc region from mouse $IgG_{2a}$, with the C-terminal end of each $C_H3$ domain being linked to the N-terminal end of two full length mouse β2GPI proteins (FIG. 16).

To prepare an expression plasmid, the signal sequence of the 3G4 light chain was amplified by PCR from the 2aG4 construct; a mouse IgG2a Fc region containing the hinge, $C_H2$ and $C_H3$ domains was amplified by PCR from the 2aG4 construct; and mouse β2GPI was amplified by RT-PCR from commercially obtained mouse liver RNA. The resultant Fc-mβ2GPI protein sequence is shown in FIG. 18A. The mIgGκ signal sequence (SEQ ID NO:18) is cleaved, leaving the mature Fc-mβ2GPI as SEQ ID NO:19 (FIG. 18A).

Figure 17:
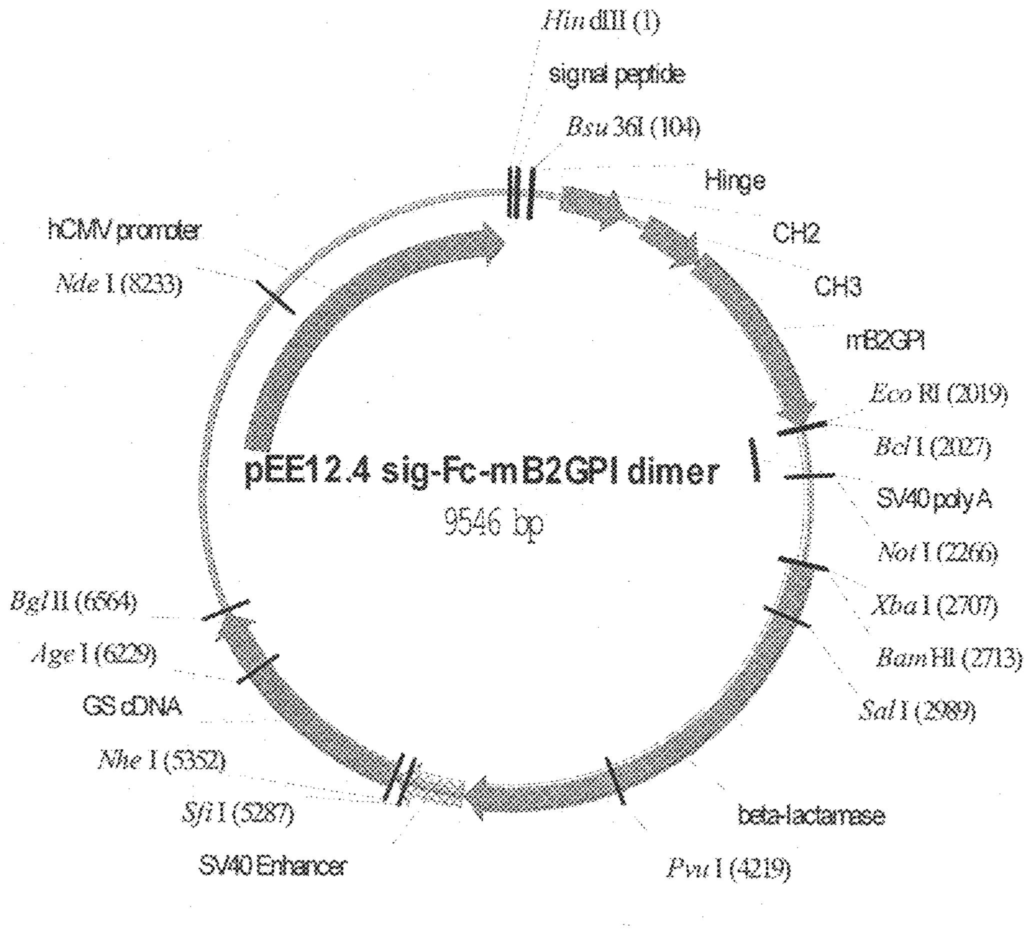
FIG. 17. Plasmid map of the Fc-mβ2GPI construct. The first Fc-β2GPI construct prepared, termed "Fc-mβ2GPI", was generated from three units: (1) the signal sequence of the 3G4 light chain amplified by PCR from 2aG4 construct; (2) a mouse IgG2a Fc region containing the hinge, $C_H2$, $C_H3$, amplified by PCR from 2aG4 construct; and (3) mouse β2GPI amplified by RT-PCR from commercially obtained mouse liver RNA. The plasmid map is shown. The sequence of the plasmid is provided as SEQ ID NO:25.

The plasmid map is shown in FIG. 17 and the entire sequence of the plasmid is provided as SEQ ID NO:25. The Fc-mβ2GPI construct was transfected into CHO cells with FuGENE 6 reagent. Two days later, the supernatant was harvested and used in several assays.

A counterpart human Fc-β2GPI (Fc-hβ2GPI) can be prepared using the sequence information in FIG. 18B, which provides an exemplary amino acid sequence for a human $IgG_1$ heavy chain constant region (Accession number P01857; SEQ ID NO:21) and the entire sequence for human β2GPI (Accession number 1C1ZA; SEQ ID NO:22), including the location of domains I, II, III, IV and V. The human hinge, $C_H2$ and $C_H3$ domains would be attached to domains I, II, III, IV and V of human β2GPI to provide the Fc-hβ2GPI of SEQ ID NO:23.

B. Fc-mβ2GPI is a Dimer

Figure 19:
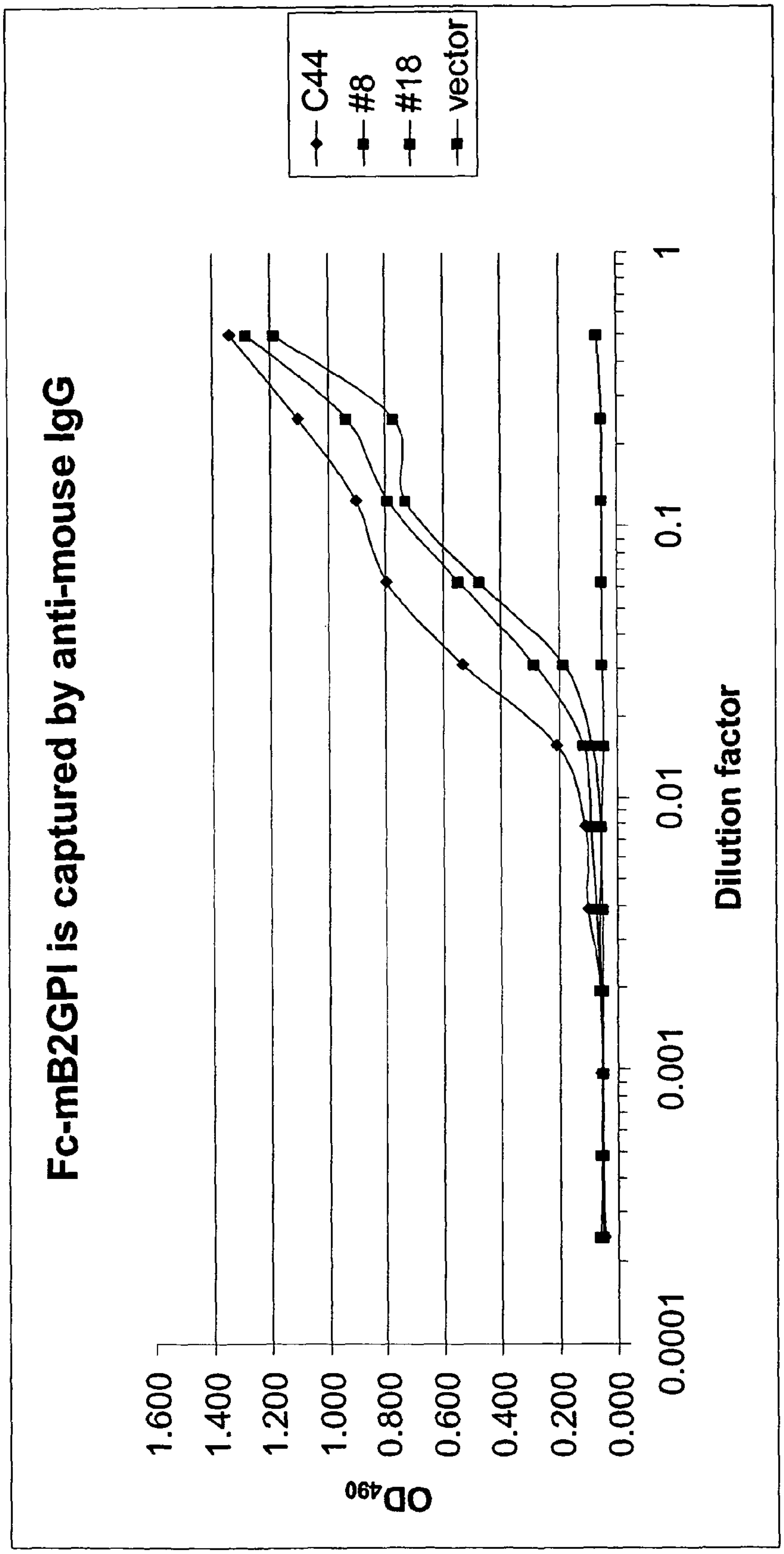
FIG. 19. Expression of Fc-mβ2GPI and capture by anti-mouse IgG. The Fc-mβ2GPI construct was transfected into CHO cells with FuGENE 6 reagent. Two days later, the cell supernatant was harvested and assayed. In the expression assay, a microtiter plate was coated with anti-mouse IgG and blocked with 1% OVA. Serial dilutions of the cell culture supernatants were performed in 1% OVA. #8 and #18 are two different clones of Fc-mβ2GPI. Binding was detected with ch3G4 and anti-human IgG-HRP. The vector is the negative control, which is the baseline.

The chosen system was effective to express Fc-mβ2GPI. FIG. 19 shows results from a capture assay using two different clones of Fc-mβ2GPI (#8 and #18), in which the Fc-mβ2GPI cell culture supernatants bind to anti-mouse IgG.

Samples of the Fc-mβ2GPI protein were subjected to gel electrophoresis. Under non-reducing gel conditions, a band of the expected size for a dimer was detected (apparent Mw on the gel of 150 kDa). Under reducing conditions, bands of a smaller size were detected (apparent Mw on the gel ~90-100 kDa).

C. Fc-mβ2GPI Binds PS and Cells with Exposed PS

Figure 20:
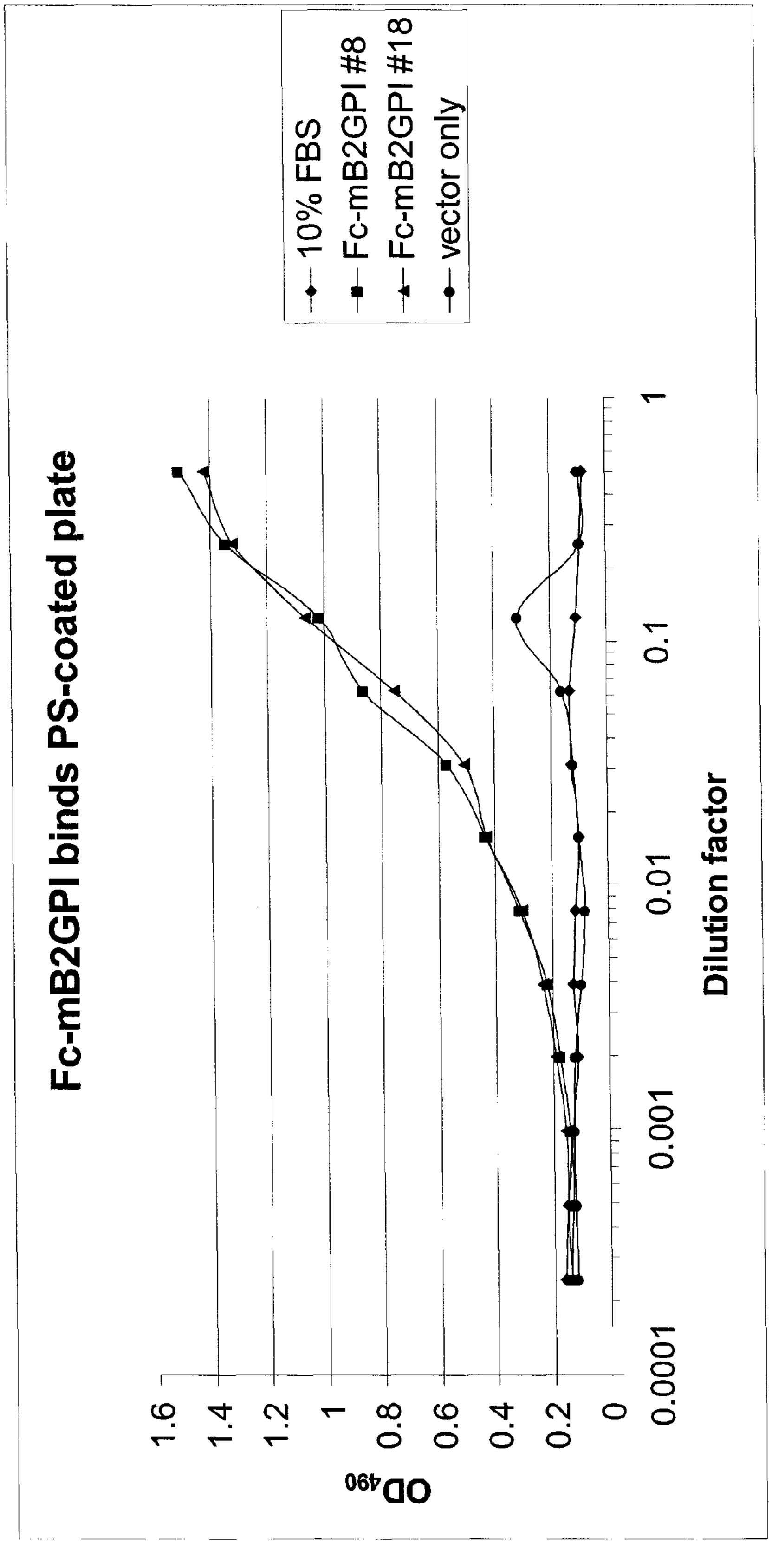
FIG. 20. Fc-mβ2GPI binds PS on PS-coated plates. In this binding assay, a microtiter plate was coated with PS and blocked with 1% OVA. Serial dilutions of Fc-mβ2GPI cell culture supernatants were performed in 1% OVA. #8 and #18 are two different clones of Fc-mβ2GPI. Binding was detected with anti-mouse IgG-HRP.
Figure 21:
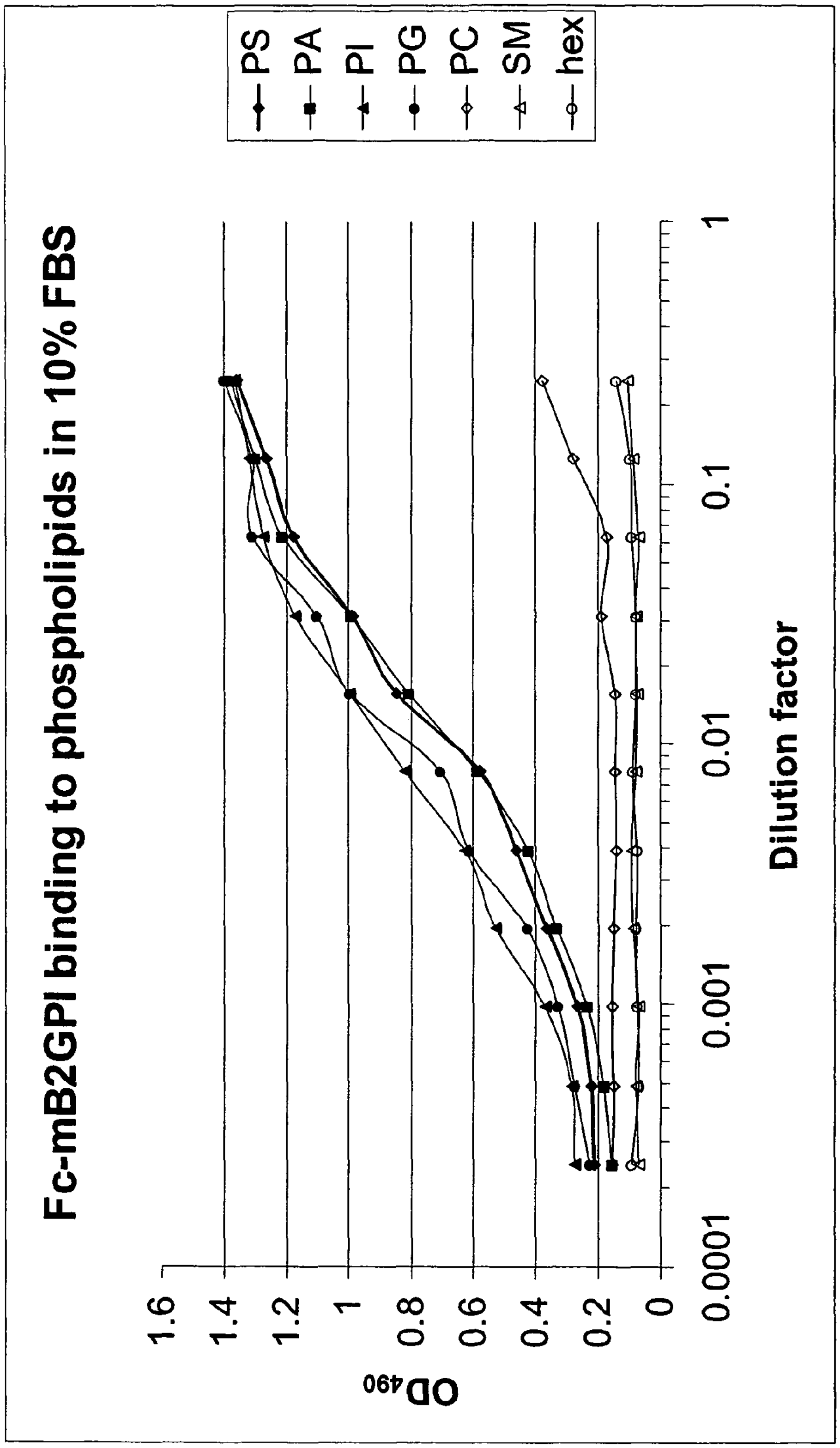
FIG. 21. Fc-mβ2GPI binds anionic phospholipids. This assay measures Fc-mβ2GPI binding to phospholipids in 10% FBS. The microtiter plates were coated with various lipids, as indicated, and blocked with 1% OVA. Serial dilutions of Fc-mβ2GPI cell culture supernatant were performed in 1% OVA. Binding was detected with anti-mouse IgG-HRP. Fc-mβ2GPI binds to the anionic phospholipids PS, PA, PI and PG, but not to the neutral lipids, PC and SM.

Fc-mβ2GPI was able to bind to PS on PS-coated plates. Using a microtiter plate coated with PS, the Fc-mβ2GPI cell culture supernatants (#8 and #18) were determined to bind to PS in a concentration-dependent manner (FIG. 20).

In common with the 3G4 antibody and the chimeric version (ch3G4 or bavituximab), Fc-mβ2GPI binding is not limited to PS, but extends to other anionic phospholipids. Results from phospholipid binding assays (in 10% FBS) show that Fc-mβ2GPI cell culture supernatants bind to the anionic phospholipids PS, PA, PI and PG, but not to the neutral lipids, PC and SM.

Figure 22A:
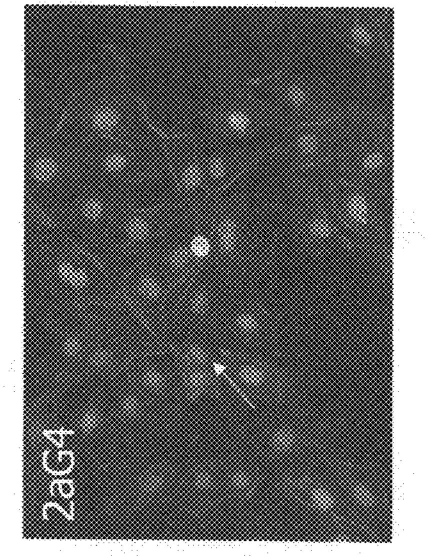
FIG. 22A, FIG. 22B and FIG. 22C. Fc-mβ2GPI detects PS exposed on naturally apoptotic ABAE cells. $2\times10^4$ ABAE cells were seeded onto 8-well glass chamber slides in DMEM+10% FBS overnight at 37° C. The next day, cells were washed and incubated with 2aG4 (FIG. 22A), supernatant from Fc-mβ2GPI transfected CHO cells (FIG. 22B), or mock transfected cells ("control supernatant", FIG. 22C). 2aG4 and Fc-mβ2GPI were detected with a FITC-labeled secondary antibody (green). The cytoskeletons and nuclei were counter-stained with Texas Red-labeled phalloidin and DAPI (blue), respectively. Arrows highlight apoptotic cells.
Figure 22B:
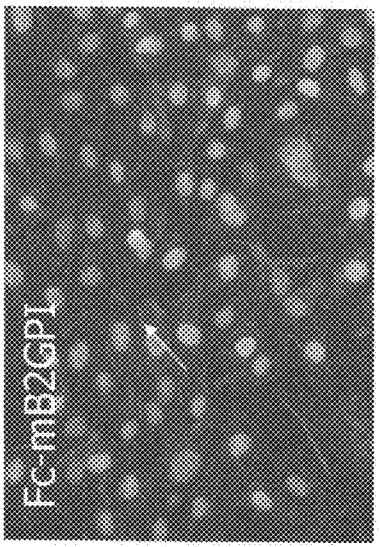
Figure 22C:
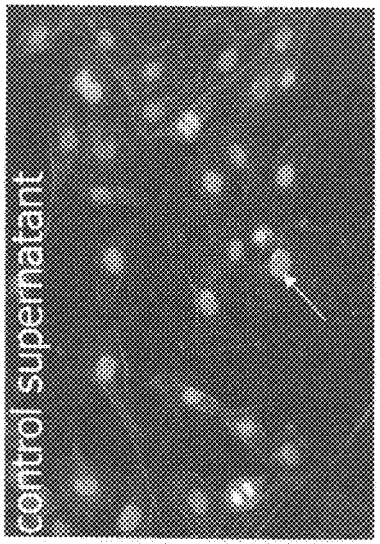

Fc-mβ2GPI is also capable of binding PS exposed at the cell surface. Cells undergoing apoptosis expose PS at the outer surface. In studies using ABAE cells undergoing apoptosis, Fc-mβ2GPI was found to stain the apoptotic cells (FIG. 22A, FIG. 22B and FIG. 22C). The arrows highlight apoptotic cells, which are rounded and have dense nuclei.

Figure 23B:
FIG. 23A and FIG. 23B. Fc-mβ2GPI detects PS exposed on LPC-treated ABAE cells. $2\times10^4$ ABAE cells were seeded onto 8-well glass chamber slides in DMEM+10% FBS overnight at 37° C. The next day, cells were washed and incubated supernatant from Fc-mβ2GPI transfected CHO cells. Fc-mβ2GPI was detected with a FITC-labeled secondary antibody (green). The cytoskeletons and nuclei were counter-stained with Texas Red-labeled phalloidin and DAPI (blue), respectively.
Figure 23A:
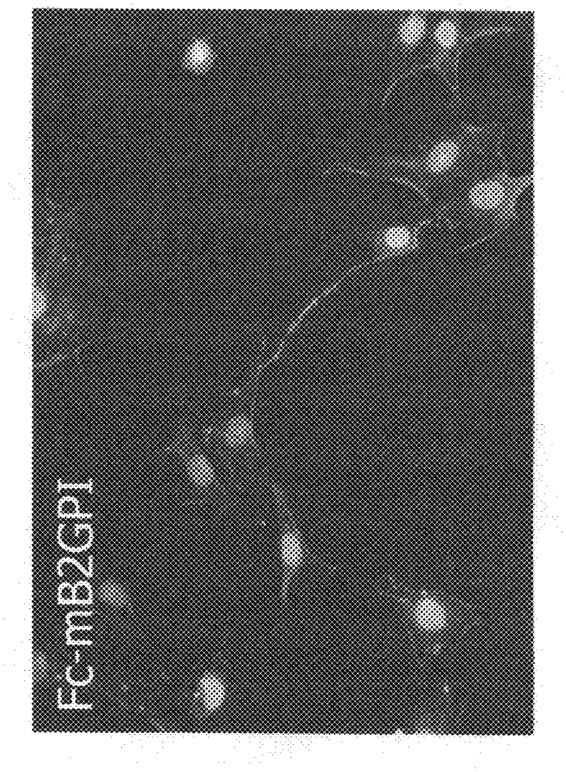

Cells can also be induced to present PS at the cell surface without undergoing apoptosis. When ABAE cells are incubated in the presence of LPC, temporary membrane distortions occur, causing a loss of membrane asymmetry and PS exposure. Using LPC-treated ABAE cells, Fc-mβ2GPI was also found to bind to PS exposed at the cell surface, seen as small pinpoints of green staining (FIG. 23A and FIG. 23B). No pinpoint staining was seen on non-LPC treated cells or using control supernatant.

EXAMPLE XXXII

Dimeric β2GPI Binds to Endothelial Cells with Exposed PS

Following the results described in Example XXX, and to further validate the information set forth in Example XXXI, the present example provides data to show that dimeric β2GPI binds to endothelial cells with exposed PS in the absence of the 3G4 antibody.

In these studies, an artificial β2GPI dimer is used, which was generated by fusing hβ2GPI to the C-terminus of the apple 4 dimerization domain of factor XI (Lutters et al., 2001). This β2GPI does not have the advantages provided by attachment to an Fc region, as described earlier in the present application. Nonetheless, binding of this dimer to cells with exposed PS validates the use of Fc-β2GPI dimers to bind to PS-positive cells.

Figure 24:
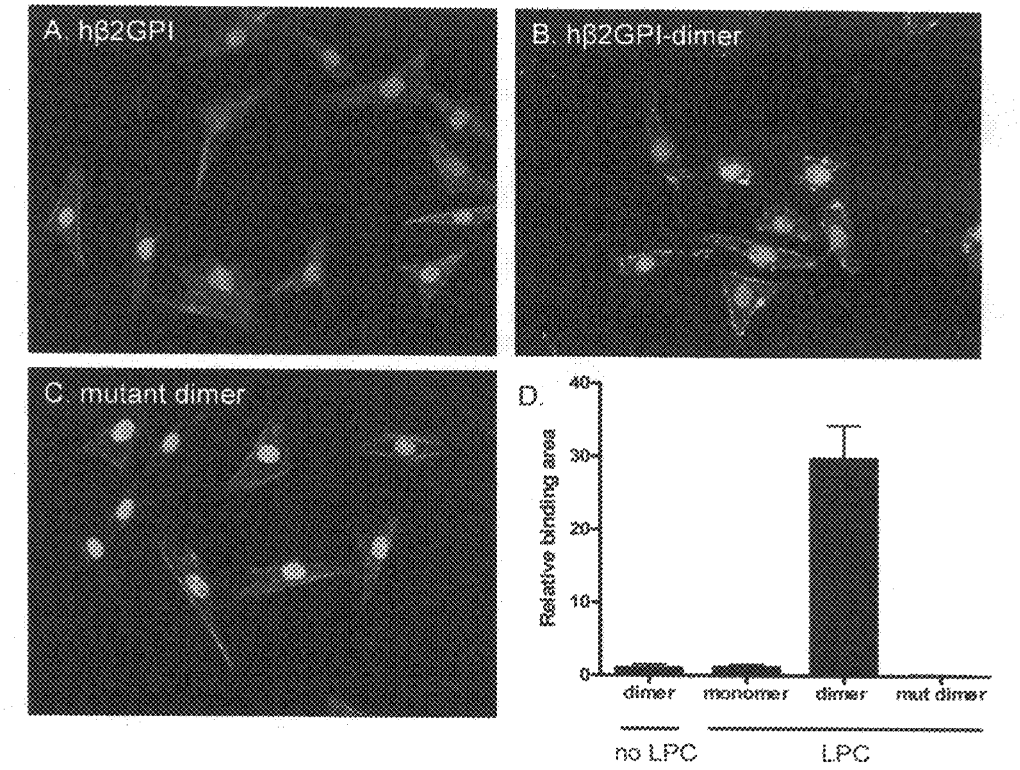
FIG. 24A, FIG. 24B, FIG. 24C and FIG. 24D. An artificial dimeric β2GPI construct binds endothelial cells with exposed PS. ABAE cells were incubated for 30 min with 200 μM LPC in DMEM+10% FBS plus purified hβ2GPI-monomer (FIG. 24A), hβ2GPI-dimer (FIG. 24B), or a mutant hβ2GPI-dimer unable to bind lipid (FIG. 24C). Cells were then washed and incubated with anti-β2GPI to detect hβ2GPI monomers and dimers. The anti-β2GPI antibody does not recognize bovine β2GPI; therefore, the presence of 10% FBS did not inhibit detection of hβ2GPI-monomers or hβ2GPI-dimers. Cells were then washed, fixed and stained with fluorescent markers. The cytoskeleton appears red, nuclei appear blue, and hβ2GPI-monomers and hβ2GPI-dimers appear green.

ABAE cells were treated with LPC to induce PS exposure and incubated with purified hβ2GPI, hβ2GPI-dimer, or a mutant hβ2GPI-dimer containing a disrupted lipid binding domain. As expected, binding of the monomeric hβ2GPI to LPC-treated ABAE cells was negligible (FIG. 24A). In contrast, the hβ2GPI-dimer bound strongly to LPC-treated cells (FIG. 24B), but not to non LPC-treated cells (FIG. 24D). Binding of the hβ2GPI-dimer was also found to be dependent upon a functional lipid binding domain (FIG. 24C). These data indicate that divalent β2GPI constructs bind to cells with exposed PS.

The Fc-β2GPI dimers of the present invention will also bind to cells with exposed PS, such as tumor vascular endothelial cells, tumor cells, virally infected cells and viral particles. However, the Fc-β2GPI constructs will have the additional advantage that the Fc region will promote host effector functions to enhance treatment of disease. Additional agents may also be attached to the Fc-β2GPI constructs, such as toxins, cytokines, radioisotopes, drugs and such like, to deliver a therapeutic payload to the PS-positive target cells.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Abrams and Oldham, *In: Monoclonal Antibody Therapy of Human Cancer*, Foon and Morgan (Eds.), Martinus Nijhoff Publishing, Boston, pp. 103-120, 1985.

Adler, Ng, Rote, "Monoclonal antiphosphatidylserine antibody inhibits intercellular fusion of the choriocarcinoma line, JAR," *Biol. Reprod.,* 53(4):905-910, 1995.

Alving, Banerji, Fogler and Alving, "Lupus anticoagulant activities of murine monoclonal antibodies to liposomal phosphatidylinositol phosphate", *Clin. Exp. Immunol.,* 69:403-408, 1987.

Anderson, Croyle, Lingrel, "Primary structure of a gene encoding rat T-kininogen," *Gene,* 81(1):119:28, 1989.

Andree, Reutelingsperger, Hauptmann, Hemker, Hermens, Willems, "Binding of vascular anticoagulant α (VACα) to planar phospholipid bilayers," *J. Biol. Chem.,* 265:4923-4928, 1990.

Antibodies: *A Laboratory Manual, Cold Spring Harbor Laboratory,* 1988.

Aoki, Uenaka, Aoki, Umeda and Inoue, "A novel peptide probe for studying the transbilayer movement of phosphatidylethanolamine," *J. Biochem.,* 116:291-297, 1994.

Asano, Yukita, Matsumoto, Kondo, Suzuki, "Inhibition of tumor growth and metastasis by an immunoneutralizing monoclonal antibody to human vascular endothelial growth factor/vascular permeability factor," *Cancer Res.,* 55:5296-5301, 1995.

Baca et al., "Antibody humanization using monovalent phage display," *J. Biol. Chem.,* 272(16):10678-84, 1997.

Balasubramanian, Chandra, Schroit, "Immune clearance of phosphatidylserine-expressing cells by phagocytes; the role of beta2-glycoprotein I in macrophage recognition," *J. Biol. Chem.,* 272:31113-17, 1997a.

Balasubramanian, Chandra, Schroit, "Macrophage recognition of phosphatidylserine-expressing cells: the role of beta (2)-glycoprotein I in immune clearance," *Blood,* 90:2864, 1997b.

Balasubramanian, Schroit, "Characterization of phosphatidylserinedependent beta(2)-glycoprotein I macrophage interactions—implications for apoptotic cell clearance by phagocytes," *J. Biol. Chem.,* 273:29272-77, 1998.

Balasubramanian and Schroit, "Aminophospholipid asymmetry: a matter of life and death," *Annu. Rev. Physiol.,* 65:701-734, 2003.

Balasubramanian, Maiti, Schroit, "Recruitment of beta-2-glycoprotein 1 to cell surfaces in extrinsic and intrinsic apoptosis, *Apoptosis,* 10:439-446, 2005.

Barbas, Kang, Lerner, Benkovic, "Assembly of combinatorial antibody libraries on phage surfaces: the gene III site," *Proc. Natl. Acad. Sci., USA,* 88(18):7978-7982, 1991.

Barbas et al., *Proc. Natl. Acad. Sci., USA,* 88:4457-4461, 1992.

Barras, Bain, Hoekstra and Lerner, "Semisynthetic combinatorial antibody libraries: a chemical solution to the diversity problem," *Proc. Natl. Acad. Sci. USA,* 89:4457-4461, 1992.

Beck, Luster, Miller, "Combination of a monoclonal anti-phosphatidylserine antibody with gemcitabine strongly inhibits the growth and metastasis of orthotopic pancreatic tumors in mice," *Int. J. Cancer*, published online: 13 Dec. 2005, DOI: 10.1002/ijc.21684, to be published in volume 118, edition 10, 2006.

Berman, Mellis, Pollock, Smith, Suh, Heinke, Kowal, Surti, Chess, Cantor, et al., "Content and organization of the human Ig VH locus: definition of three new VH families and linkage to the Ig CH locus," *EMBO J.,* 7(3):727-738, 1988.

Bernier and Jolles, "Purification and characterization of a basic 23 kDa cytosolic protein from bovine brain," *Biochim. Biophys. Acta,* 790(2):174-181, 1984.

Bernier, Tresca, Jolles, "Ligand-binding studies with a 23 kDa protein purified from bovine brain cytosol," *Biochim. Biophys. Acta,* 871(1):19-23, 1986.

Bevers, Rosing, Zwaal, "Development of procoagulant binding sites on the platelet surface," *Adv. Exp. Med. Biol.,* 192:359-371, 1985.

Bevers, Zwaal, Willems, "The effect of phospholipids on the formation of immune complexes between autoantibodies and beta(2)-glycoprotein I or prothrombin," *Clin. Immunol.,* 112:150-160, 2004.

Bevers, Janssen, Comfurius, et al., "Quantitative determination of the binding of beta(2)-glycoprotein I and prothrombin to phosphatidylserine-exposing blood platelets," *Biochem. J.,* 386:271-279, 2005.

Bevilacqua, "Endothelial-leukocyte adhesion molecules," *Ann. Rev. Immunol.,* 11:767-804, 1993.

Bitbol, Fellmann, Zachowski, Devaux, "Ion regulation of phosphatidylserine and phosphatidylethanolamine outside-inside translocation in human erythrocytes," *Biochim. Biophys. Acta,* 904(2):268-282, 1987.

Blackwood and Ernst, "Characterization of Ca2(+)-dependent phospholipid binding, vesicle aggregation and membrane fusion by annexins," *Biochem. J.,* 266(1):195-200, 1990.

Blankenberg, Katsikis, Tait, Davis, Naumovski, Ohtsuki, Kopiwoda, Abrams, Darkes, Robbins, Maecker, Strauss, "In vivo detection and imaging of phosphatidylserine expression during programmed cell death," *Proc. Natl. Acad. Sci., USA,* 95(11):6349-6354, 1998.

Bocci, "Efficient labeling of serum proteins with 1311 using chloramine T," *Int. J. Appl. Radiat. Isot.,* 15:449-456, 1964.

Bombeli, Karsan, Tait, Harlan, "Apoptotic vascular endothelial cells become procoagulant," *Blood,* 89(7):2429-2442, 1997.

Borgstrom et al., "Complete inhibition of angiogenesis and growth of microtumors by anti-vascular endothelial growth factor neutralizing antibody: novel concepts of angiostatic therapy from intravital videomicroscopy," *Cancer Res.,* 56(17):4032-1439, 1996.

Borgstrom et al., "Neutralizing anti-vascular endothelial growth factor antibody completely inhibits angiogenesis and growth of human prostate carcinoma micro tumors in vivo," *Prostate,* 35(1):1-10, 1998.

Bornstein, "Thrombospondins: structure and regulation of expression," *FASEB J*, 6(14):3290-3299, 1992.
Borrebaeck and Moller, "In vitro immunization. Effect of growth and differentiation factors on antigen-specific B cell activation and production of monoclonal antibodies to autologous antigens and weak immunogens," *J. Immunol.*, 136(10):3710-3715, 1986.
Boustead, Brown, Walker, "Isolation, characterization and localization of annexin V from chicken liver," *Biochem. J.*, 291:601-608, 1993.
Boyle, Pohlman, Cornejo, Verrier, "Endothelial cell injury in cardiovascular surgery: ischemia-reperfusion," *Ann. Thor. Surg.*, 62(6):1868-1875, 1996.
Bradford, "A rapid and sensitive method for the quantitation of microgram quantities of protein utilizing the principle of protein-dye binding," *Anal. Biochem.*, 72:248-254, 1976.
Branch, Rote, Dostal, Scott, "Association of lupus anticoagulant with antibody against phosphatidylserine," *Clin. Immun. Immunopathol.*, 42:63-75, 1987.
Breier, Blum, Peli, Groot, M., Wild, Risau, Reichmann, "Transforming growth factor-B and RAS regulate the VEGF/VEGF-Receptor system during tumor angiogenesis," *Int. J. Cancer*, 97:142-148, 2002.
Brem, "Angiogenesis antagonists: current clinical trials," *Angiogenesis*, 2:9-20, 1998.
Bresnahan, Boldogh, Thompson, and Albrecht, "Human Cytomegalovirus inhibits cellular DNA synthesis and arrests productively infected cells in late G1", *Virology*, 224:150-160, 1996.
Bruggemann, Williams, Bindon, Clark, Walker, Jefferis, Waldmann, Neuberger, "Comparison of the effector functions of human immunoglobulins using a matched set of chimeric antibodies," *J. Exp. Med.*, 166:1351-1361, 1987.
Bruijn and Dinklo, "Distinct patterns of expression of intercellular adhesion molecule-1, vascular cell adhesion molecule-1, and endothelial-leukocyte adhesion molecule-1 in renal disease," *Lab. Invest.*, 69:329-335, 1993.
Burke et al., "Cloning of large segments of exogenous DNA into yeast by means of artificial chromosome vectors", *Science*, 236, 806-812, 1987.
Burrows, Watanabe, Thorpe, "A murine model for antibody-directed targeting of vascular endothelial cells in solid tumors," *Cancer Res.*, 52:5954-5962, 1992.
Burrows and Thorpe, "Eradication of large solid tumors in mice with an immunotoxin directed against tumor vasculature," *Proc. Natl. Acad. Sci. USA*, 90:8996-9000, 1993.
Calderon and DeVries, "Lipid composition and phospholipid asymmetry of membranes from a schwann cell line," *J. Neuro. Res.*, 49:372-380, 1997.
Callahan et al., *J. Immunol.*, 170:4840-4845, 2003
Campbell, In: *Monoclonal Antibody Technology, Laboratory Techniques in Biochemistry and Molecular Biology*, Vol. 13, Burden and Von Knippenberg (Eds.), Elseview, Amsterdam, pp. 75-83, 1984.
Carnemolla et al., "A tumor-associated fibronectin isoform generated by alternative splicing of messenger RNA precursors," *J. Cell Biol.*, 108:1139-1148, 1989.
Chen, Stone, Woon et al., "Antiphospholipid antibodies bind to activated but not resting endothelial cells: is an independent triggering event required to induce antiphospholipid antibody-mediated disease?" *Thrombosis Res.*, 114:101-111, 2004.
Cheng, Huang, Nagane, Ji, Wang, Shih, Arap, Huang, Cavenee, "Suppression of glioblastoma angiogenicity and tumorigenicity by inhibition of endogenous expression of vascular endothelial growth factor," *Proc. Natl. Acad. Sci. USA*, 93:8502-8507, 1996.
Chonn, Semple, Cullis, "Beta 2 glycoprotein I is a major protein associated with very rapidly cleared liposomes in vivo, suggesting a significant role in the immune clearance of 'non-self' particles," *J. Biol. Chem.*, 270:25845-49, 1995.
Choung, Kobayashi, Inoue, Takemoto, Ishitsuka and Inoue, "Hemolytic activity of a cyclic peptide Ro09-0198 isolated from *Streptoverticillium*," *Biochim. Biophys. Acta.*, 940:171-179, 1988a.
Choung, Kobayashi, Takemoto, Ishitsuka and Inoue, "Interaction of a cyclic peptide, Ro09-0198, with phosphatidylethanolamine in liposomal membranes," *Biochem. Biophys. Acta*, 940:180-187, 1988b.
Christiansen, Sims, Hamilton, "Complement C5b-9 increases plasminogen binding and activation on human endothelial cells," *Arterioscler. Thromb. Vasc. Biol.*, 17(1):164-171, 1997.
Clapp et al., "The 16-kilodalton N-terminal fragment of human prolactin is a potent inhibitor of angiogenesis," *Endocrinology*, 133(3): 1292-1299, 1993.
Clark, "Antibody Engineering IgG Effector Mechanisms," *Chemical Immunology*, 65:88-110, 1997.
Cleve, Rittner, "Further family studies on the genetic control of beta 2-glycoprotein I concentration in human serum," *Humangenetik*, 7:93-97, 1969.
Comfurius, Senden, Tilly, et al., "Loss of membrane phospholipid asymmetry in platelets and red cells may be associated with calcium-induced shedding of plasma membrane and inhibition of aminophospholipid translocase," *Biochim. Biophys. Acta.*, 1026(2):153-160, 1990.
Contreras, Villar, Alonso, Kolesnick, and Goni, "Sphingomyelinase activity causes transbilayer lipid translocation in model and cell membranes," *J. Biol. Chem.*, 278:37169-37174, 2003.
Coughlin et al., "Interleukin-12 and interleukin-18 synergistically induce murine tumor regression which involves inhibition of angiogenesis," *J. Clin. Invest.*, 101(6):1441-1452, 1998.
D'Amato et al., "Thalidomide is an inhibitor of angiogenesis," *Proc. Natl. Acad. Sci. USA*, 91(9):4082-4085, 1994.
D'Angelo et al., "Activation of mitogen-activated protein kinases by vascular endothelial growth factor and basic fibroblast growth factor in capillary endothelial cells is inhibited by the antiangiogenic factor 16-kDa N-terminal fragment of prolactin," *Proc. Natl. Acad. Sci. USA*, 92(14):6374-6378, 1995.
Dachary-Prigent, Toti, Satta, Pasquet, Uzan, Freyssinet, "Physiopathological significance of catalytic phospholipids in the generation of thrombin," *Seminars in Thrombosis and Hemostasis*, 22:157-164, 1996.
Daleke, "Regulation of transbilayer plasma membrane phospholipid asymmetry," *J. Lipid Res.*, 44:233-242, 2003.
Daum, "Lipids of mitochondria," *Biochim. Biophys. Acta*, 822(1):1-42, 1985.
Davis and Yancopoulos, "The angiopoietins: Yin and Yang in angiogenesis", *Curr. Top. Microbiol. Immunol.*, 237:173-85, 1999.
Demo, Masuda, Rossi, et al., "Quantitative measurement of mast cell degranulation using a novel flow cytomeric annexin-V binding assay," *Cytometry*, 36(4):340-348, 1999.
de Laat, Derksen, de Groot, "beta(2)-glycoprotein I, the playmaker of the antiphospholipid syndrome," *Clin. Immunol.*, 112:161-168, 2004a.
de Laat, Derksen, Urbanus, Roest, de Groot, "beta(2)-glycoprotein I-dependent lupus anticoagulant highly correlates with thrombosis in the antiphospholipid syndrome," *Blood,* 104:3598-3602, 2004b.

de Laat, Derksen, Urbanus, de Groot, "IgG antibodies that recognize epitope Gly40-Arg43 in domain I of beta(2)-glycoprotein I cause LAC, and their presence correlates strongly with thrombosis," *Blood,* 105:1540-1545, 2005a.

de Laat, Derksen, van Lummel, Pennings, de Groot, "Pathogenic anti-beta(2)-glycoprotein I antibodies recognize domain I of beta(2)-glycoprotein I only after a conformational change," *Blood*, published online: DOI 10.1182/blood-2005-05-1943, 2005b.

Deleze, Alarconsegovia, Valdesmacho, Oria, Deleon, "Relationship between antiphospholipid antibodies and recurrent fetal loss in patients with systemic lupus-erythematosus and apparently healthy women, *J. Rheumatol.,* 16:768-772, 1989.

Denekamp, "Vascular attack as a therapeutic strategy for cancer," *Cancer Metastasis Rev.,* 9:267-282, 1990.

Devaux, "Protein involvement in transmembrane lipid asymmetry," *Annu. Rev. Biophys. Biomol. Struct.,* 21:417-439, 1992.

Devitt, Pierce, Oldreive, Shingler, Gregory, "CD14-dependent clearance of apoptotic cells by human macrophages: the role of phosphatidylserine," *Cell Death Differ.,* 10:371-382, 2003.

DeVore et al., "Phase I study of the antineovascularization drug CM101,*" Clin. Cancer Res.,* 3(3):365-372, 1997.

Diehl, Pfreundschuh, Fonatsch, Stein, Falk, Burrichter, Schaadt, "Phenotypic genotypic analysis of Hodgkin's disease derived cell lines: histopathological and clinical implications," *Cancer Surveys,* 4:399-416, 1985.

Dillon, Mancini, Rosen, et al., "Annexin V binds to viable B cells and colocalizes with a marker of lipid rafts upon B cell receptor activation," *J. Immunol.,* 164(3):1322-1332, 2000.

Donati and Falanga, "Pathogenic mechanisms of thrombosis in malignancy," *Acta Haematol.,* 106(1-2):18-24, 2001.

Drouvalakis and Buchanan, "Phospholipid specificity of autoimmune and drug induced lupus anticoagulants; association of phosphatidylethanolamine reactivity with thrombosis in autoimmune disease," *J. Rheumatol.,* 25(2): 290-295, 1998.

Droz, Patey, Paraf, Chretien, Gogusev, "Composition of extracellular matrix and distribution of cell adhesion molecules in renal cell tumors," *Lab. Invest.,* 71:710-718, 1994.

Dvorak, Nagy, Dvorak, "Structure of solid tumors and their vasculature: implications for therapy with monoclonal antibodies," *Cancer Cells,* 3(3):77-85, 1991.

Edgington, Mackman, Brand, Ruf, "The structural biology of expression and function of tissue factor," *Thromb. Haemost.,* 66(1):67-79, 1991.

Emoto, Kobayashi, Yamaji, Aizawa, Yahara, Inoue and Umeda, "Redistribution of phosphatidylethanolamine at the cleavage furrow of dividing cells during cytokinesis," *Proc. Natl. Acad. Sci.,* 93:12867-12872, 1996.

Emoto, Toyama-Sorimachi, Karasuyama, Inoue and Umeda, "Exposure of phosphatidylethanolamine on the surface of apoptotic cells," *Exp. Cell Res.,* 232:430-434, 1997.

Fadok, Bratton, Konowal, Freed, Westcott, Henson, "Macrophages that have ingested apoptotic cells in vitro inhibit proinflammatory cytokine production through autocrine/paracrine mechanisms involving TGF-beta, PGE2, and PAF," *J. Clin. Invest.,* 101:890-898, 1998.

Fadok, Bratton, Rose, Pearson, Ezekewitz, Henson, "A receptor for phosphatidylserinespecific clearance of apoptotic cells," *Nature,* 405:85-90, 2000.

Fadok, de Cathelineau, Daleke, Henson, Bratton, "Loss of phospholipid asymmetry and surface exposure of phosphatidylserine is required for phagocytosis of apoptotic cells by microphages and fibroblasts," *J. Biol. Chem.,* 276: 1071-1077, 2001a.

Fadok, Bratton, Guthrie, Henson, "Differential effects of apoptotic versus lysed cells on macrophage production of cytokines: role of proteases," *J. Immunol.,* 166:6847-6854, 2001b.

Ferrara, Clapp, Weiner, "The 16K fragment of prolactin specifically inhibits basal or fibroblast growth factor stimulated growth of capillary endothelial cells," *Endocrinology,* 129(2):896-900, 1991.

Folkman et al., "Angiogenesis inhibition and tumor regression caused by heparin or a heparin fragment in the presence of cortisone," *Science,* 221:719-725, 1983.

Fotsis et al., "The endogenous oestrogen metabolite 2-methoxyoestradiol inhibits angiogenesis and suppresses tumour growth," *Nature,* 368(6468):237-239, 1994.

Frankel, "Genetically Engineered Toxins", Editor Arthur E. Frankel, Marcel Dekker Inc., New York, N.Y., 1992.

Frater-Schroder et al., "Tumor necrosis factor type alpha, a potent inhibitor of endothelial cell growth in vitro, is angiogenic in vivo," *Proc. Natl. Acad. Sci. USA,* 84(15):5277-5281, 1987.

Frazier, "Thrombospondins," *Curr. Opin. Cell Biol.,* 3(5): 792-799, 1991.

Fridrikksson, Shipkiva, Sheets, Holowka, Baird and McLafferty, "Quantitative analysis of phospholipids in functionally important membrane domains from RBL-2H3 mast cells using tandem high-resolution mass spectrometry: Biochemistry, 38: 8056-8063, 1999.

Fries, Williams, Atkins, Newman, Lipscomb, Collins, "Expression of VCAM-1 and E-selectin in an in vivo model of endothelial activation," *Am. J. Pathol.,* 143:725-737, 1993.

Gaffet, Bettache, Bienvenüe, "Transverse redistribution of phospholipids during human platelet activation: evidence for a vectorial outflux specific to aminophospholipids," *Biochem.,* 34:6762-6769, 1995.

Gagliardi, Hadd, Collins, "Inhibition of angiogenesis by suramin," *Cancer Res.,* 52(18):5073-5075, 1992.

Gagliardi and Collins, "Inhibition of angiogenesis by antiestrogens," *Cancer Res.,* 53(3):533-535, 1993.

Gagliardi et al., "Antiangiogenic and antiproliferative activity of suramin analogues," *Cancer Chemother. Pharmacol.,* 41(2):117-124, 1998.

Galli, Comfurius, Maassen Hemker, de Baets, van Breda-Vriesman, Barbui, Zwaal, Bevers, "Anticardiolipin antibodies (ACA) directed not to cardiolipin but to a plasma protein cofactor," *Lancet,* 335(8705):1544-1547, 1990.

Galli, Barbui, Zwaal, Comfurius, Bevers, "Antiphospholipid antibodies: involvement of protein cofactors," *Haematologica,* 78(1):1-4, 1993.

Gallucci and Matzinger, "Danger signals: SOS to the immune system," *Curr. Opin. Immunol.,* 13:114-119, 2001.

Gavrieli, Sherman, Ben-Sasson, "Identification of programmed cell death in situ via specific labeling of nuclear DNA fragmentation," *J. Cell Biol.,* 119(3):493-501, 1992.

Gefter et al., "A simple method for polyethylene glycol-promoted hybridization of mouse myeloma cells," *Somatic Cell Genet.,* 3:231-236, 1977.

Giovarelli et al., "Tumor rejection and immune memory elicited by locally released LEC chemokine are associated with an impressive recruitment of APCs, lymphocytes, and granulocytes", *J. Immunol.,* 164, 3200-3206, 2000.

Goding, *In: Monoclonal Antibodies: Principles and Practice, 2nd Edition*, Academic Press, Orlando, Fla., pp. 60-61, 65-66, 71-74, 1986.

Good et al., "A tumor suppressor-dependent inhibitor of angiogenesis is immunologically and functionally indistinguishable from a fragment of thrombospondin," *Proc. Natl. Acad. Sci. USA,* 87(17):6624-6628, 1990.

Graham, et al., "Primary respiratory syncytial virus infection in mice," *J. Med. Virol.,* 26(2):153-62, 1988.

Grant et al., "Fibronectin fragments modulate human retinal capillary cell proliferation and migration," *Diabetes,* 47(8):1335-1340, 1998.

Hammill, Uhr, Scheuermann, "Annexin V staining due to loss of membrane asymmetry can be reversible and precede commitment to apoptotic death," *Exp. Cell Res.,* 251(1): 16-21, 1999.

Hamon, Broccardo, Chambenoit, Luciani, Toti, Chaslin, Freyssinet, Devaux, McNeish, Marguet, Chimini, "ABC1 promotes engulfment of apoptotic cells and transbilayer redistribution of phosphatidylserine," *Nat. Cell Biol.,* 2:399-406, 2000

Haran et al., "Tamoxifen enhances cell death in implanted MCF7 breast cancer by inhibiting endothelium growth," *Cancer Res.,* 54(21):5511-5514, 1994.

Harris, Zhang, Moghaddam, Fox, Scott, Pattison, Gatter, Stratford, Bicknell, "Breast cancer angiogenesis—new approaches to therapy via antiangiogenesis, hypoxic activated drugs, and vascular targeting," *Breast Cancer Res. Treat.,* 38(1):97-108, 1996.

Hasegawa, Suzuki, Ishii, Takakuwa, Tanaka, "Establishment of two distinct anti-cardiolipin antibody-producing cell lines from the same individual by Epstein-Barr virus transformation," *Throm. Res.,* 74(1):77-84, 1994.

Hasselaar and Sage, "SPARC antagonizes the effect of basic fibroblast growth factor on the migration of bovine aortic endothelial cells," *J. Cell Biochem.,* 49(3):272-283, 1992.

Hastie, Patton, Hechtmann, Sherpo, "Filamin redistribution in an endothelial cell reoxygenation injury model," *Free Rad. Biol. Med.,* 22:955-966, 1997.

Hayashi, Nagashima, Terui, Kawamura, Matsumoto and Itazaki, "The structure of PA48009; the revised structure of duramycin," *J. Antibiotics*, XLIII(11):1421-1430, 1990.

Hellerqvist et al., "Antitumor effects of GBS toxin: a polysaccharide exotoxin from group B beta-hemolytic streptococcus," *J. Cancer Res. Clin. Oncol.,* 120(1-2):63-70, 1993.

Henson, Bratton, Fadok, "The phosphatidylserine receptor: a crucial molecular switch?" *Nat. Rev. Mol. Cell Biol.,* 2:627-633, 2001.

Herrmann and Devaux, "Alteration of the aminophospholipid translocase activity during in vivo and artificial aging of human erythrocytes," *Biochim. Biophys. Acta.,* 1027(1): 41-46, 1990.

Hinkovska-Galcheva, Petkova, Koumanov, "Changes in the phospholipid composition and phospholipid asymmetry of ram sperm plasma membranes after cryopreservation," *Cryobiology,* 26(1):70-75, 1989.

Hiscox and Jiang, "Interleukin-12, an emerging anti-tumour cytokine," *In Vivo,* 11(2):125-132, 1997.

Holash et al., "Vessel cooption, regression, and growth in tumors mediated by angiopoietins and VEGF", *Science,* 284:1994-1998, 1999.

Hori, Chae, Murakawa, Matoba, Fukushima, Okubo, Matsubara, "A human cDNA sequence homologue of bovine phosphatidylethanolamine-binding protein," *Gene,* 140(2):293-294, 1994.

Hori et al., "Differential effects of angiostatic steroids and dexamethasone on angiogenesis and cytokine levels in rat sponge implants," *Br. J. Pharmacol.,* 118(7):1584-1591, 1996.

Hotchkiss, Ashton, Mahmood, Russell, Sparano, Schwartz, "Inhibition of endothelial cell function in vitro and angiogenesis in vivo by docetaxel (Taxotere): association with impaired repositioning of the microtubule organizing center", *Mol. Cancer Ther.,* 1 (13):1191-200, 2002.

Hristova and Needham, *In: Stealth Liposomes*, Lasic D. and Martin, F., Eds. CRC Press, Boca Raton, pp. 35-49, 1993.

Huang, Molema, King, Watkins, Edgington, Thorpe, "Tumor infarction in mice by antibody-directed targeting of tissue factor to tumor vasculature," *Science,* 275:547-550, 1997.

Huang, Bennett, Thorpe, "A monoclonal antibody that binds anionic phospholipids on tumor blood vessels enhances the antitumor effect of docetaxel on human breast tumors in mice," *Cancer Res.,* 65:4408-4416, 2005.

Hughes, Harris, Gharavi, "The anticardiolipin syndrome," *J. Rheumatol.,* 13:486-489, 1986.

Hunt, Simpson, Krilis, "Identification of a region of beta-2-glycoprotein-I critical for lipid-binding and anticardiolipin antibody cofactor activity," *Proc. Natl. Acad. Sci. USA,* 90:2141-2145, 1993.

Hunt and Krilis, "The 5th domain of beta(2)-glycoprotein-I contains a phospholipid-binding site (Cys281-Cys288) and a region recognized by anticardiolipin antibodies," *J. Immunol.,* 152:653-659, 1994.

Huse, Sastry, Iverson, Kang, Alting-Mees, Burton, Benkovic, Lerner, *Science,* 246(4935):1275-1281, 1989.

Igarashi, Umeda, Tokita, Soo Nam, Inoue, "Effective induction of anti-phospholipid and anticoagulant antibodies in normal mouse," *Thrombosis Res.,* 61:135-148, 1991.

Ingber et al., "Angioinhibins: Synthetic analogues of fumagillin which inhibit angiogenesis and suppress tumor growth," *Nature,* 48:555-557, 1990.

Iwamoto et al., "Inhibition of angiogenesis, tumour growth and experimental metastasis of human fibrosarcoma cells HT1080 by a multimeric form of the laminin sequence Tyr-Ile-Gly-Ser-Arg (YIGSR)," *Br. J. Cancer,* 73(5):589-595, 1996.

Jackson et al., "Stimulation and inhibition of angiogenesis by placental proliferin and proliferin-related protein," *Science,* 266(5190):1581-1584, 1994.

Jankowski, Vreys, Wittevrongel et al., "Thrombogenicity of beta(2)-glycoprotein I-dependent antiphospholipid antibodies in a photochemically induced thrombosis model in the hamster," *Blood,* 101:157-162, 2003.

Jendraschak and Sage, "Regulation of angiogenesis by SPARC and angiostatin: implications for tumor cell biology," *Semin. Cancer Biol.,* 7(3):139-146, 1996.

Jirholt, Ohlin, Borrebaeck, Soderlind, "Exploiting Sequence Space: Shuffling In Vivo Formed Complementarity Determining Regions Into a Master Framework," *Gene,* 215: 471-476, 1998.

Jones and Hall, "A 23 kDa protein from rat sperm plasma membranes shows sequence similarity and phospholipid binding properties to a bovine brain cytosolic protein," *Biochim. Biophys. Acta,* 1080(1):78-82, 1991.

Jones, Dear, Foote, Neuberger, Winter, *Nature,* 321(6069): 522-525, 1986.

Julien, Tournier, Tocanne, "Differences in the transbilayer and lateral motions of fluorescent analogs of phosphatidylcholine and phosphatidylethanolamine in the apical plasma membrane of bovine aortic endothelial cells," *Exp. Cell. Res.,* 208(2):387-389, 1993.

Julien, Tournier, Tocanne, "Basic fibroblast growth factor modulates the aminophospholipid translocase activity present in the plasma membrane of bovine aortic endothelial cells," *Eur. J. Biochem.,* 230:287-297, 1995.

Julien, Millot, Tocanne, Tournier, "12-O-Tetradecanoylphorbol-13-Acetate inhibits aminophospholipid translocase activity and modifies the lateral motions of fluorescent phospholipid analogs in the plasma membrane of bovine aortic endothelial cells," *Experimental Cell Res.,* 234:125-131, 1997.

Kabat et al., "Sequences of Proteins of Immunological Interest" 5th Ed. Public Health Service, National Institutes of Health, Bethesda, Md., 1991, pp 647-669 in particular.

Kang, Barbas, Janda, Benkovic, Lemer, *Proc. Natl. Acad. Sci., U.S.A,* 88(10):4363-4366, 1991.

Katsuragawa, Kanzaki, Inoue, Hirano, Mori, Rote, "Monoclonal antibody against phosphatidylserine inhibits in vitro human trophoblastic hormone production and invasion," *Biology of Reproduction,* 56:50-58, 1997.

Kellermann, Lottspeich, Henschen, Muller-Esterl, "Completion of the primary structure of human high-molecular-mass kininogen. The amino acid sequence of the entire heavy chain and evidence for its evolution by gene triplication," *Eur. J. Biochem.,* 154(2):471-478, 1986.

Kendall and Thomas, "Inhibition of vascular endothelial cell growth factor activity by an endogenously encoded soluble receptor," *Proc. Natl. Acad. Sci. USA,* 90:10705-10709, 1993.

Kenyon, Browne, D'Amato, "Effects of thalidomide and related metabolites in a mouse corneal model of neovascularization," *Exp. Eye Res.,* 64(6):971-978, 1997.

Keyt et al., "Identification of vascular endothelial growth factor determinants for binding KDR and FLT-1 receptors. Generation of receptor-selective VEGF variants by site-directed mutagenesis," *J. Biol. Chem.,* 271(10):5638-46, 1996.

Kim, Li, Houck, Winer, Ferrara, "The vascular endothelial growth factor proteins: identification of biologically relevant regions by neutralizing monoclonal antibodies," *Growth Factors,* 7:53-64, 1992.

Kim et al., "Inhibition of vascular endothelial growth factor-induced angiogenesis suppresses tumour growth in vivo," *Nature,* 362:841-844, 1993.

Kim, Kwak, Ahn, So, Liu, Koh, Koh, "Molecular cloning and characterization of a novel angiopoietin family protein, angiopoietin-3", *FEBS Lett.,* 443(3):353-6, 1999.

Kim et al., "Immunohistological analysis of immune cell infiltration of a human colon tumor xenograft after treatment with Stealth liposome-encapsulated tumor necrosis factor-alpha and radiation", *Int. J. Oncol.,* 21(5):973-9, 2002.

Kisch, and Johnson, "A plaque assay for respiratory syncytial virus," *Proc. Soc. Exp. Biol. Med.,* 112:583-9, 1963.

Kitamura, Takagaki, Furuto, Tanaka, Nawa, Nakanishi, "A single gene for bovine high molecular weight and low molecular weight kininogens," *Nature,* 305(5934):545-549, 1983.

Kitamura, Kitagawa, Fukushima, Takagaki, Miyata, Nakanishi, "Structural organization of the human kininogen gene and a model for its evolution," *J. Biol. Chem.,* 260(14): 8610-8617, 1985.

Kitamura, Ohkubo, Nakanishi, "Molecular biology of the angiotensinogen and kininogen genes," *J. Cardiovasc. Pharmacol.,* 10(Suppl 7):S49-S53, 1987.

Kitamura, Nawa, Takagaki, Furuto-Kato, Nakanishi, "Cloning of cDNAs and genomic DNAs for high-molecular-weight and low-molecular-weight kininogens," *Methods Enzymol.,* 163:230-240, 1988.

Kleinman et al., "The laminins: a family of basement membrane glycoproteins important in cell differentiation and tumor metastases," *Vitam. Horm.,* 47:161-186, 1993.

Kogure, Nakashima, Tsuchie, Tokumura, Fukuzawa, "Temporary membrane distortion of vascular smooth muscle cells is responsible for their apoptosis induced by platelet-activating factor-like oxidized phospholipids and their degradation product, lysophosphatidylcholine," *Chemistry and Physics of Lipids,* 126:29-38, 2003.

Kohler and Milstein, "Continuous cultures of fused cells secreting antibody of predefined specificity," *Nature,* 256: 495-497, 1975.

Kohler and Milstein, "Derivation of specific antibody-producing tissue culture and tumor lines by cell fusion," *Eur. J. Immunol.,* 6:511-519, 1976.

Kondo, Asano, Suzuki, "Significance of vascular endothelial growth factor/vascular permeability factor for solid tumor growth, and its inhibition by the antibody," *Biochem. Biophys. Res. Commun.,* 194:1234-1241, 1993.

Konieczny, Bobrzecka, Laidler, Rybarska, "The combination of IgM subunits and proteolytic IgG fragment by controlled formation of interchain disulphides," *Haematologia,* 14(1):95-99, 1981.

Krajewska, Wang, Krajewski, et al., "Immunohistochemical analysis of in vivo patterns of expression of CPP32 (Caspase-3), a cell death protease," *Cancer Res.,* 57(8): 1605-1613, 1997.

Kuzu, Bicknell, Fletcher, Gatter, "Expression of adhesion molecules on the endothelium of normal tissue vessels and vascular tumors," *Lab. Invest.,* 69(3):322-328, 1993.

Kyte and Doolittle, "A simple method for displaying the hydropathic character of a protein," *J. Mol. Biol.,* 157(1): 105-132, 1982.

Lane, Iruela-Arispe, Sage, "Regulation of gene expression by SPARC during angiogenesis in vitro. Changes in fibronectin, thrombospondin-1, and plasminogen activator inhibitor-1," *J. Biol. Chem.,* 267(23):16736-16745, 1992.

Lee et al., "Inhibition of urokinase activity by the antiangiogenic factor 16K prolactin: activation of plasminogen activator inhibitor 1 expression," *Endocrinology,* 139(9): 3696-3703, 1998.

Leppink, Bishop, Sedmak, Henry, Ferguson, Streeter, Butcher, Orosz, "Inducible expression of an endothelial cell antigen on murine myocardial vasculature in association with interstitial cellular infiltration," *Transplantation,* 48(5):874-877, 1989.

Levy, Gharavi, Sammaritano, Habina, Lockshin, "Fatty acid chain is a critical epitope for antiphospholipid antibody," *J. Clin. Immunol.,* 10(3):141-145, 1990.

Lichtenbeld, Van Dam-Mieras, Hillen, "Tumour angiogenesis: pathophysiology and clinical significance," *Neth. J. Med.,* 49(1):42-51, 1996.

Lin, Buxton, Acheson, Radziejewski, Maisonpierre, Yancopoulos, Channon, Hale, Dewhirst, George, Peters, "Anti-angiogenic gene therapy targeting the endothelium-specific receptor tyrosine kinase Tie2", *Proc. Natl. Acad. Sci., USA,* 95(15):8829-34, 1998.

Lin, Sankar, Shan, Dewhirst, Polverini, Quinn, Peters, "Inhibition of tumor growth by targeting tumor endothelium using a soluble vascular endothelial growth factor receptor," *Cell Growth Differ.,* 9:49-58, 1998b.

Linder and Borden, "Effects of tamoxifen and interferon-beta or the combination on tumor-induced angiogenesis," *Int. J. Cancer,* 71(3):456-461, 1997.

Lingen, Polverini, Bouck, "Inhibition of squamous cell carcinoma angiogenesis by direct interaction of retinoic acid with endothelial cells," *Lab. Invest.,* 74(2):476-483, 1996.

Lingen, Polverini, Bouck, "Retinoic acid and interferon alpha act synergistically as antiangiogenic and antitumor agents against human head and neck squamous cell carcinoma," *Cancer Res.,* 58(23):5551-5558, 1998.

Liu, Moy, Kim, Xia, Rajasekaran, Navarro, Knudsen, Bander, "Monoclonal antibodies to the extracellular domain of prostate-specific membrane antigen also react with tumor vascular endothelium", *Cancer Res.,* 57:3629-3634, 1997.

Lucas, Garcia, Donati, Hribar, Mandriota, Giroud, Buurman, Fransen, Suter, Nunez, Pepper, Grau, "Both TNF receptors are required for direct TNF-mediated cytotoxicity in microvascular endothelial cells," *Eur. J. Immunol.,* 28(11): 3577-3586, 1998.

Luo, Toyoda, Shibuya, "Differential inhibition of fluid accumulation and tumor growth in two mouse ascites tumors by an antivascular endothelial growth factor/permeability factor neutralizing antibody," *Cancer Res.,* 58(12):2594-2600, 1998a.

Luo et al., "Significant expression of vascular endothelial growth factor/vascular permeability factor in mouse ascites tumors," *Cancer Res.,* 58(12):2652-2660, 1998b.

Lupu, Moldovan, Ryan, Stem, Simionescu, "Intrinsic procoagulant surface induced by hypercholestrolaemia on rabbit aortic endothelium," *Blood Coagul. Fibrinolysis,* 4(5):743-752, 1993.

Lutters, Meijers, Derksen, Arnout, de Groot, "Dimers of beta (2)-glycoprotein I mimic the in vitro effects of beta(2)-glycoprotein I-anti-beta(2)-glycoprotein I antibody complexes," *J. Biol. Chem.,* 276:3060-3067, 2001.

Majewski et al., "Vitamin D3 is a potent inhibitor of tumor cell-induced angiogenesis," *J. Investig. Dermatol. Symp. Proc.,* 1(1):97-101, 1996.

Maneta-Peyret, Bessoule, Geffard, Cassagne, "Demonstration of high specificity antibodies against phosphatidylserine," *J. Immun. Meth.,* 108:123-127, 1988.

Maneta-Peyret, Freyburger, Bessoule, Cassagne, "Specific immunocytochemical visualization of phosphatidylserine," *J. Immun. Methods,* 122:155-159, 1989.

Manetti et al., "Synthesis and binding mode of heterocyclic analogues of suramin inhibiting the human basic fibroblast growth factor," *Bioorg. Med. Chem.,* 6(7):947-958, 1998.

Manfredi, Rovere, Galati, Heltai, Bozzolo, Soldini, Davoust, Balestrieri, Tincani, Sabbadini, "Apoptotic cell clearance in systemic lupus erythematosus—I. Opsonization by antiphospholipid antibodies," *Arthritis and Rheumatism,* 41:205-214, 1998.

Martin, Reutelingsperger, McGahon, et al., "Early redistribution of plasma membrane phosphatidylserine is a general feature of apoptosis regardless of the initiating stimulus: inhibition by overexpression of Bcl-2 and Abl," *J. Exp. Med.,* 182:1545-1556, 1995.

Massey et al., *Nature,* 328:457-458, 1987.

Matzinger, "An innate sense of danger," *Semin. Immunol.,* 10:399-415, 1998.

McEvoy, Williamson, Schlegel, "Membrane phospholipid asymmetry as a determinant of erythrocyte recognition by macrophages," *Proc. Natl. Acad. Sci. USA,* 83(10):3311-3315, 1986.

McNeil, Simpson, Chesterman, Krilis, "Anti-phospholipid antibodies are directed against a complex antigen that includes a lipid-binding inhibitor of coagulation: beta 2-glycoprotein I (apolipoprotein H)," *Proc. Natl. Acad. Sci. USA,* 87(11):4120-4124, 1990.

Mehdi, Naqvi, Kamboh, "A hydrophobic sequence at position 313-316 (Leu-Ala-Phe-Trp) in the fifth domain of apolipoprotein H (beta(2)-glycoprotein I) is crucial for cardiolipin binding," *Eur. J. Biochem.,* 267:1770-1776, 2000.

Menon, Rahman, Ravirajan, Kandiah, Longhurst, McNally, Williams, Latchman, Isenberg, "The production, binding characteristics and sequence analysis of four human IgG monoclonal antiphospholipid antibodies", *J. Autoimmunity,* 10:43-57, 1997.

Mesiano, Ferrara, Jaffe, "Role of vascular endothelial growth factor in ovarian cancer: inhibition of ascites formation by immunoneutralization," *Am. J. Pathol.,* 153(4):1249-1256, 1998.

Millauer, Longhi, Plate, Shawver, Risau, Ullrich, Strawn, "Dominant-negative inhibition of Flk-1 suppresses the growth of many tumor types in vivo," *Cancer Res.,* 56:1615-1620, 1996.

Mills, Brooker, Camerini-Otero, "Sequences of human immunoglobulin switch regions: implications for recombination and transcription," *Nucl. Acids Res.,* 18:7305-7316, 1990.

Miyakis, Robertson Krilis, "Beta-2 glycoprotein I and its role in antiphospholipid syndrome-lessons from knockout mice," *Clin. Immunol.,* 112:136-143, 2004.

Moldovan, Moldovan, Simionescu, "Binding of vascular anticoagulant alpha (annexin V) to the aortic intima of the hypercholesterolemic rabbit. An autoradiographic study," *Blood Coagul. Fibrinolysis,* 5:921-928, 1994.

Moore et al., "Tumor angiogenesis is regulated by CXC chemokines," *J. Lab. Clin. Med.,* β2(2):97-103, 1998.

Morrison, Johnson, Herzenberg, Oi, "Chimeric human antibody molecules: mouse antigen-binding domains with human constant region domains," *Proc. Natl. Acad. Sci. USA,* 81(21):6851-6855, 1984.

Morrison, Wims, Kobrin, Oi, "Production of novel immunoglobulin molecules by gene transfection," *Mt. Sinai J. Med.,* 53(3):175, 1986.

Muller, et al., "VEGF and the Fab fragment of a humanized neutralizing antibody: crystal structure of the complex at 2.4 A resolution and mutational analysis of the interface," *Structure,* 6(9): 1153-67, 1998.

Muyldermans, Cambillau and Wyne, "Recognition of Antigens by Single-Domain Antibody Fragments: The Superfluous Luxury of Paired Domains," *TRENDS,* 26(4):230-235, 2001.

Munro, "Endothelial-leukocyte adhesive interactions in inflammatory diseases," *European. Heart Journal,* 14:72-77, 1993.

Nagler, Feferman, Shoshan, "Reduction in basic fibroblast growth factor mediated angiogenesis in vivo by linomide," *Connect Tissue Res.,* 37(1-2):61-68, 1998.

Nakamura et al., Enzyme Immunoassays: Heterogeneous and Homogeneous Systems, Chapter 27.

Nakamura and Racker, "Inhibitory Effect of Duramycin or Partial Reactions Catalyzed by ($Na^+$, $K^+$)-Adenosinetriphosphatase from Dog Kidney," *Biochemistry,* 23(2):385-389, 1984.

Nakanishi, Ohkubo, Nawa, Kitamura, Kageyama, Ujihara, "Angiotensinogen and kininogen: closing and sequence analysis of the cDNAs," *Clin. Exp. Hypertens.,* 5(7-8):997-1003, 1983.

Nilsson, Kosmehl, Zardi, Neri, "Targeted delivery of tissue factor to the ED-B domain of fibronectin, a marker of angiogenesis, mediates the infarction of solid tumors in mice," *Cancer Res.,* 61(2):711-716, 2001.

Nimpf, Bevers, Bomans et al., "Prothrombinase activity of human-platelets is inhibited by beta-2-glycoprotein-I," *Biochimica et Biophysica Acta,* 884:142-149, 1986.

Nimpf, Wurm, Kostner, "Beta2-glycoprotein-I (Apo-H) inhibits the release reaction of human-platelets during Adp-induced aggregation," *Atherosclerosis,* 63:109-114, 1987.

Nimpf, Wurm, Kostner, "Interaction of beta-2-glycoprotein-I with human-blood platelets—influence upon the Adp-induced aggregation," *Thrombosis and Haemostasis,* 54:397-401, 1985.

Nuttall, Irving and Hudson, "Immunoglobulin $V_H$ Domains and beyond: Design and Selection of Single-Domain Binding and Targeting Reagents," *Current Pharma. Biotech.,* 1(3):253-262, 2000.

Ohizumi, Tsunoda, Taniguchi, Saito, Esaki, Makimoto, Wakai, Tsutsumi, Nakagawa, Utoguchi, Kaiho, Ohsugi, Mayumi, "Antibody-based therapy targeting tumor vascular endothelial cells suppresses solid tumor growth in rats," *Biochem. Biophys. Res. Comm.,* 236:493-496, 1997.

Oikawa et al., "A highly potent antiangiogenic activity of retinoids," *Cancer Lett.,* 48(2):157-162, 1989.

O'Reilly et al., "Angiostatin: a novel angiogenesis inhibitor that mediates the suppression of metastases by a Lewis lung carcinoma," *Cell,* 79:315-328, 1994.

O'Reilly et al., "Endostatin: an endogenous inhibitor of angiogenesis and tumor growth," *Cell,* 88(2):277-285, 1997.

Orr, Wang, Lafrenie, Scherbarth, Nance, "Interactions between cancer cells and the endothelium in metastasis," *J. Pathology,* 190:310-329, 2000.

Padlan, "Anatomy of the Antibody Molecule," *Mol. Immunol.,* 31:169-217, 1994.

Parmley and Smith, "Antibody-selectable filamentous fd phage vectors: affinity purification of target genes," *Gene,* 73(2):305-318, 1988.

Patey, Vazeux, Canioni, Potter, Gallatin, Brousse, "Intercellular adhesiong molecule-3 on endothelial cells: Expression in tumors but not in inflammatory responses," *Am. J. Pathol.,* 148:465-472, 1996.

Pepper et al., "Leukemia inhibitory factor (LIF) inhibits angiogenesis in vitro," *J. Cell Sci.,* 108(Pt 1):73-83, 1995.

Perry, Hall, Bell, Jones, "Sequence analysis of a mammalian phospholipid-binding protein from testis and epididymis and its distribution between spermatozoa and extracellular secretions," *Biochem. J.,* 301(Pt 1):235-242, 1994.

Pierangeli, Colden-Stanfield, Liu et al., "Antiphospholipid antibodies from antiphospholipid syndrome patients activate endothelial cells in vitro and in vivo," *Circulation,* 99:1997-2002, 1999.

Polz, Wurm, Kostner, "Investigations on beta-2-glycoprotein-I in the rat—isolation from serum and demonstration in lipoprotein density fractions," *Int. J. Biochem.,* 11:265-270, 1980.

Presta, Chen, O'Connor, Chisholm, Meng, Krummen, Winkler, Ferrara, "Humanization of an anti-vascular endothelial growth factor monoclonal antibody for the therapy of solid tumors and other disorders," *Cancer Res.,* 57:4593-4599, 1997.

Price, "Metastasis from human breast cancer cell lines," *Breast Cancer Research Treatment.,* 39:93-102, 1996.

Qamar, Gharavi, Levy, Lockshin, "Lysophosphatidylethanolamine is the antigen to which apparent antibody to phosphatidylethanolamine binds," *J. Clin. Immunol.,* 10(4):200-203, 1990.

Qu, Conroy, Walker, Wooding, Lucy, "Phosphatidylserine-mediated adhesion of T-cells to endothelial cells," *J. Biochem.,* 317(Pt 2):343-346, 1996.

Quinn et al., CM101, a polysaccharide antitumor agent, does not inhibit wound healing in murine models," *J. Cancer Res. Clin. Oncol.,* 121(4):253-256, 1995.

Ran, Gao, Duffy, Watkins, Rote, Thorpe, "Infarction of solid Hodgkin's tumors in mice by antibody-directed targeting of tissue factor to tumor vasculature," *Cancer Res.,* 58(20): 4646-4653, 1998.

Ran, Downes, Thorpe, "Increased exposure of anionic phospholipids on the surface of activated endothelial cells and tumor blood vessels," *Proceedings of AACR,* No. 2615 (Abstract):527, 2002a.

Ran, Downes, Thorpe, "Increased exposure of anionic phospholipids on the surface of tumor blood vessels," *Cancer Res.,* 62 6132-6140, 2002b.

Ran and Thorpe, "Phosphatidylserine is a marker of tumor vasculature and a potential target for cancer imaging and therapy," *Int. J. Radiat. Oncol. Biol. Phys.,* 54: 1479-1484, 2002.

Ran, Huang, Downes, Thorpe, "Evaluation of novel anti-mouse VEGFR2 antibodies as potential antiangiogenic or vascular targeting agents for tumor therapy," *Neoplasia,* 5:297-307, 2003.

Ran, He, Huang, et al., "Antitumor effects of a monoclonal antibody that binds anionic phospholipids on the surface of tumor blood vessels in mice," *Clin Cancer Res.,* 11:1551-1562, 2005.

Rao, Tait, Hoang, "Binding of annexin V to a human ovarian carcinoma cell line (OC-2008). Contrasting effects on cell surface factor VIIa/tissue factor activity and prothrombinase activity," *Thromb. Res.,* 67(5):517-531, 1992.

Rauch, Tannenbaum, Tannenbaum, Ramelson, Cullis, Tilcock, Hope, Janoff, "Human hybridoma lupus anticoagulants distinguish between lamellar and hexagonal phase lipid systems," *J. Biol. Chem.,* 261(21):9672-9677, 1986.

Rauch and Janoff, "Phospholipid in the hexagonal II phase is immunogenic: evidence for immunorecognition of nonbilayer lipid phases in vivo," *Proc. Natl. Acad. Sci., USA,* 87(11):4112-4114, 1990.

Ravirajan, Harmer, McNally, Hohmann, Mackworth-Young, Isenberg, "Phospholipid binding specificities and idiotype expression of hybridoma derived monoclonal autoantibodies from splenic cells of patients with systemic lupus erythematosus", *Ann. Rheumatic Diseases,* 54:471-476, 1995.

RayChaudhury and D'Amore, "Endothelial cell regulation by transforming growth factor-beta," *J. Cell Biochem.,* 47(3):224-229, 1991.

Richer and Lo, "Introduction of human DNA into mouse eggs by injection of dissected human chromosome fragments", *Science* 245, 175-177, 1989.

Riechmann, Clark, Waldmann, Winter, "Reshaping human antibodies for therapy," *Nature,* 332(6162):323-327, 1988.

Riechmann and Muyldermans, "Single Domain Antibodies: Comparison of Camel VH and Camelised Human VH Domains," *J. Immunol. Methods.,* 231:25-38, 1999.

Rimassa et al., "Unexpected low efficacy of stealth liposomal doxorubicin (Caelyx) and vinorelbine in the treatment of metastatic breast cancer", *Breast Cancer Research and Treatment,* 77 (2):185-8, 2003.

Rosenthal et al., "A phase I study of SPI-077 (Stealth liposomal cisplatin) concurrent with radiation therapy for locally advanced head and neck cancer", *Investigational New Drugs,* 20(3)343-9: 2002.

Rote, Ng, Dostal-Johnson, Nicholson, Siekman, "Immunologic detection of phosphatidylserine externalization during thrombin-induced platelet activation," *Clin. Immunol. Immunopathol.,* 66:193-200, 1993.
Rote, Chang, Katsuragawa, Ng, Lyden, Mori, "Expression of phosphatidylserine-dependent antigens on the surface of differentiating BeWo human choriocarcinoma cells," *Am. J. Reprod. Immun.,* 33:114-121, 1995.
Rote, "Antiphospholipid antibodies and recurrent pregnancy loss," *Am. J. Reprod. Immun.,* 35:394-401, 1996.
Roubey, Eisenberg, Harper, Winfield, "Anticardiolipin autoantibodies recognize beta(2)-glycoprotein-I in the absence of phospholipid—importance of Ag density and bivalent binding," *J. Immunol.,* 154:954-960, 1995.
Ruf, Rehemtulla, Edgington, "Phospholipid-independent and -dependent interactions required for tissue factor receptor and cofactor function," *Biol. Chem.,* 266:2158-2166, 1991.
Ruf and Edgington, "Structural biology of tissue factor, the initiator of thrombogenesis in vivo," *FASEB J.,* 8:385-390, 1994.
Sakamoto et al., "Heparin plus cortisone acetate inhibit tumor growth by blocking endothelial cell proliferation," *Canc. J.,* 1:55-58, 1986.
Saleh, Stacker, Wilks, "Inhibition of growth of C6 glioma cells in vivo by expression of antisense vascular endothelial growth factor sequence," *Cancer Res.,* 56:393-401, 1996.
Sambrook, Fritsch, Maniatis, *Molecular Cloning: A Laboratory Manual,* 2nd Ed., Cold Spring Harbor Press, Cold Spring Harbor, N.Y., 1989.
Sang, "Complex role of matrix metalloproteinases in angiogenesis," *Cell Res.,* 8(3):171-177, 1998.
Sanlioglu, Williams, Samavati, Butler, Wang, McCray, Ritchie, Hunninghake, Zandi, and Engelhardt, *J. Biol. Chem.,* 32:30188, 2001.
Schlaepfer, Mehlman, Burgess, Haigler, "Structural and functional characterization of endonexin II, a calcium- and phospholipid-binding protein," *Proc. Natl. Acad. Sci. USA,* 84(17):6078-6082, 1987.
Schoentgen, Saccoccio, Jolles, Bernier, Jolles, "Complete amino acid sequence of a basic 21-kDa protein from bovine brain cytosol," *Eur. J. Biochem.,* 166(2):333-338, 1987.
Schorer, Rick, Swaim, Moldow, "Structural features of endotoxin required for stimulation of endothelial cell tissue factor production; exposure of preformed tissue factor after oxidant-mediated endothelial cell injury," *J. Lab. Clin. Med.,* 106:38-42, 1985.
Schousboe, "Beta-2-glycoprotein-I—a plasma inhibitor of the contact activation of the intrinsic blood-coagulation pathway," *Blood,* 66:1086-1091, 1985.
Seigneuret and Devaux, "ATP-dependent asymmetric distribution of spin-labeled phospholipids in the erythrocyte membrane: relation to shape changes," *Proc. Natl. Acad. Sci. USA,* 81(12):3751-3755, 1984.
Sessions and Horwitz, "Myoblast aminophospholipid asymmetry differs from that of fibroblasts," *FEBS Lett.,* 134(1):75-78, 1981.
Shaughnessy, Buchanan, Turple, Richardson, Orr, "Walker carcinosarcoma cells damage endothelial cells by the generation of reactive oxygen species" *Am. J. Path.,* 134(4):787-796, 1989.
Sheibani and Frazier, "Thrombospondin 1 expression in transformed endothelial cells restores a normal phenotype and suppresses their tumorigenesis," *Proc. Natl. Acad. Sci. USA,* 92(15):6788-6792, 1995.
Sheng, Sali, Herzog, Lahnstein, Krilis, "Site-directed mutagenesis of recombinant human beta(2)-glycoprotein I identifies a cluster of lysine residues that are critical for phospholipid binding and anti-cardiolipin antibody activity," *J. Immunol.,* 157:3744-3751, 1996.
Sheu et al., "Inhibition of angiogenesis in vitro and in vivo: comparison of the relative activities of triflavin, an Arg-Gly-Asp-containing peptide and anti-alpha(v)beta3 integrin monoclonal antibody," *Biochim. Biophys. Acta,* 1336 (3):445-454, 1997.
Shotwell, Stodola, Michael, Lindenfelser, Dworschack and Pridham, "Antibiotics Against Plant Disease. III. Duramycin, a New Antibiotic from *Streptomyces Cinnamomeus* Forma *Azacoluta, N. Utiliza. Res. Dev. Div.,* 80:3912-3915, 1958.
Sideras, Mizuta, Kanamori, Suzuki, Okamoto, Kuze, Ohno, Doi, Fukuhara, Hassan, et al., "Production of sterile transcripts of C gamma genes in an IgM-producing human neoplastic B cell line that switches to IgG-producing cells," *Intl. Immunol.,* 1(6):631-642, 1989.
Siemann, Mercer, Lepler, Rojiani, "Vascular targeting agents enhance chemotherapeutic agent activities in solid tumor therapy," *Int. J. Cancer,* 99:1-6, 2002.
Siemeister, Martiny-Baron, Marme, "The pivotal role of VEGF in tumor angiogenesis: molecular facts and therapeutic opportunities," *Cancer Metastasis Rev.,* 17(2):241-248., 1998.
Siim, Lee, Shalal-Zwain, Prujin, McKeage, Wilson, "Marked potentiation of the antitumor activity of chemotherapeutic drugs by the antivascular agent 5, 6-dimethlyxanthenone-4-acetic acid (DMXAA)," *Cancer Chemother. Pharmacol.,* 51:43-52, 2004.
Simantov, Lasala, Lo et al., "Activation of cultured vascular endothelial-cells by antiphospholipid antibodies," *J. Clin. Invest.,* 96:2211-2219, 1995.
Singh et al., "Stealth monensin liposomes as a potentiator of adriamycin in cancer treatment", *Journal of Controlled Release,* 59(1):43-53, 1999.
Sioussat, Dvorak, Brock, Senger, "Inhibition of vascular permeability factor (vascular endothelial growth factor) with antipeptide antibodies," *Arch. Biochem. Biophys.,* 301:15-20, 1993.
Sipos et al., "Inhibition of tumor angiogenesis," *Ann. NY Acad. Sci.,* 732:263-272, 1994.
Sluiter, Pietersma, Lamers, Koster, "Leukocyte adhesion molecules on the vascular endothelium: their role in the pathogenesis of cardiovascular disease and the mechanisms underlying their expression," *J. Cardiol. Pharmacol.,* 22:S37-S44, 1993.
Smirnov, Triplett, Comp, Esmon, Esmon, "On the role of phosphatidylethanolamine in the inhibition of activated protein C activity by antiphospholipid antibodies," *J. Clin. Invest.,* 95(1):309-316, 1995.
Soares, Shaughnessy, MacLarkey, Orr, "Quantification and morphologic demonstration of reactive oxygen species produced by Walker 256 tumor cells in vitro and during metastasis in vivo," *Laboratory Invest.,* 71(4):480-489, 1994.
Soderlind, Ohlin and Carlsson, "Complementarity-Determining Region (CDR) Implantation: A Theme of Recombination," *Immunotech.,* 4:279-285, 1999.
Soderlind, Strandberg, Jirholt, Kobayashi, Alexeiva, Aberg, Nilsson, Jansson, Ohlin, Wingren, Danielsson, Carisson and Borrebaeck, "Recombining Germline-Derived CDR Sequences for Creating Diverse Single-Framework Antibody Libraries," *Nature Biotech.,* 18:852-856, 2000.

Soff et al., "Expression of plasminogen activator inhibitor type 1 by human prostate carcinoma cells inhibits primary tumor growth, tumor-associated angiogenesis, and metastasis to lung and liver in an athymic mouse model," *J. Clin. Invest.,* 96(6):2593-2600, 1995.

Staal-van den Brekel, Thunnissen, Buurman, Wouters, "Expression of E-selectin, intercellular adhesion molecule (ICAM)-1 and vascular cell adhesion molecule (VCAM)-1 in non-small-cell lung carcinoma," *Virchows Arch.,* 428: 21-27, 1996.

Staub, Harris, Khamashta, Savidge, Chahade, Hughes, "Antibody to phosphatidylethanolamine in a patient with lupus anticoagulant and thrombosis," *Ann. Rheum. Dis.,* 48(2): 166-169, 1989.

Steinkasserer, Barlow, Willis et al., "Activity, disulfide mapping and structural modeling of the 5th domain of human-beta-2-glycoprotein-I," *FEBS Letters,* 313:193-197, 1992.

Steinkasserer, Estaller, Weiss, Sim, Day, "Complete nucleotide and deduced amino-acid-sequence of human beta-2-glycoprotein-I, Biochem. J., 277:387-391, 1991.

Stella et al., "Prodrugs: A chemical approach to targeted drug delivery", *Directed Drug Delivery*, Borchardt et al., Eds. Human Press, 1985, pp 247-267.

Stone, Ruf, Miles, Edgington, Wright, "Recombinant soluble human tissue factor secreted by Saccharomyces cerevisiae and refolded from *E. coli* inclusion bodies: glycosylation of mutants, activity, and physical characterization," *Biochem. J.,* 310(2):605-614, 1995.

Sunderkotter, Steinbrink, Goebeler, Bhardwaj, Sorg, "Macrophages and angiogenesis," *J. Leukocyte Biol.,* 55:410-422, 1994.

Sugi and McIntyre, "Autoantibodies to phosphatidylethanolamine (PE) recognize a kininogen-PE complex," *Blood,* 86(8):3083-3089, 1995.

Sugi and McIntyre, "Phosphatidylethanolamine induces specific conformational changes in the kininogens recognizable by antiphosphatidylethanolamine antibodies," *Thromb. Haemost.,* 76(3):354-360, 1996a.

Sugi and McIntyre, "Autoantibodies to kininogen-phosphatidylethanolamine complexes augment thrombin-induced platelet aggregation," *Thromb. Res.,* 84(2):97-109, 1996b.

Sugimura, Donato, Kakar, Scully, "Annexin V as a probe of the contribution of anionic phospholipids to the procoagulant activity of tumor cell surfaces," *Blood Coagul. Fibrinolysis,* 5(3):365-373, 1994.

Symon et al., "Selective delivery of doxorubicin to patients with breast carcinoma metastases by stealth liposomes", *Cancer,* 86(1):72-8, 1999.

Tada et al., "Inhibition of tubular morphogenesis in human microvascular endothelial cells by co-culture with chondrocytes and involvement of transforming growth factor beta: a model for avascularity in human cartilage," *Biochim. Biophys. Acta,* 1201(2):135-142, 1994.

Tait and Smith, "Phosphatidylserine receptors: role of CD36 in binding of anionic phospholipid vesicles to monocytic cells," *J. Biol. Chem.,* 274(5):3048-3054, 1999.

Takano et al., "Suramin, an anticancer and angiosuppressive agent, inhibits endothelial cell binding of basic fibroblast growth factor, migration, proliferation, and induction of urokinase-type plasminogen activator," *Cancer Res.,* 54(10):2654-2660, 1994.

Tanaka et al., "Viral vector-mediated transduction of a modified platelet factor 4 cDNA inhibits angiogenesis and tumor growth," *Nat. Med.,* 3(4):437-442, 1997.

Test and Mitsuyoshi, "Activation of the alternative pathway of complement by calcium-loaded erythrocytes resulting from loss of membrane phospholipid asymmetry," *J. Lab. Clin. Med.,* 130(2):169-182, 1997.

Thornhill, Kyan-Aung, Haskard, "IL-4 increases human endothelial cell adhesiveness for T cells but not for neutrophils," *J. Immunol.,* 144:3060-3065, 1990.

Thorpe et al., "Heparin-Steroid Conjugates: New Angiogenesis Inhibitors with Antitumor Activity in Mice," *Cancer Res.,* 53:3000-3007, 1993.

Thorpe and Ran, "Tumor infarction by targeting tissue factor to tumor vasculature", *Cancer J. Sci. Am.,* 6(Suppl 3):S237-S244, 2000.

Thorpe, "Vascular targeting agents as cancer therapeutics," *Clin. Cancer Res.,* 10:415-427, 2004.

Tolsma et al., "Peptides derived from two separate domains of the matrix protein thrombospondin-1 have anti-angiogenic activity," *J. Cell Biol.,* 122(2):497-511, 1993.

Tryggvason, "The laminin family," *Curr. Opin. Cell Biol.,* 5(5):877-882, 1993.

Tsavaris, Kosmas, Vadiaka, Kanelopoulos, Boulamatsis, "Immune changes in patients with advanced breast cancer undergoing chemotherapy with taxanes", *Brit. J. Cancer,* 87(1):21-7, 2002.

Umeda, Igarashi, Nam, Inoue, "Effective production of monoclonal antibodies against phosphatidylserine: Stereo-specific recognition of phosphatidylserine by monoclonal antibody," *J. Immun.,* 143(7):2273-2279, 1989.

Umeda and Emoto, "Membrane Phospholipid Dynamics During Cytokinesis: Regulation of Actin Filament Assembly by Redistribution of Membrane Surface Phospholipid", *Chem. Phys. Lipids,* 101:81-91, 1999.

Utsugi, Schroit, Connor, Bucana, Fidler, "Elevated expression of phosphatidylserine in the outer membrane leaflet of human tumor cells and recognition by activated human blood monocytes," *Cancer Res.,* 51(11):3062-3066, 1991.

Valenzuela, Griffiths, Rojas, Aldrich, Jones, Zhou, McClain, Copeland, Gilbert, Jenkins, Huang, Papadopoulos, Maisonpierre, Davis, Yancopoulos, "Angiopoietins 3 and 4: diverging gene counterparts in mice and humans", *Proc. Natl. Acad. Sci., USA,* 96(5): 1904-9, 1999.

van Dijk, Warnaar, van Eendenburg, Thienpont, Braakman, Boot, Fleuren, Bolhuis, "Induction of tumor-cell lysis by bi-specific monoclonal antibodies recognizing renal-cell carcinoma and CD3 antigen," *Int. J. Cancer,* 43:344-349, 1989.

van Gorp, Broers, Reutelingsperger, Bronnenberg, Hornstra, Dam-Mieras, Heemskerk, "Peroxide-induced membrane blebbing in endothelial cells associated with glutathione oxidation but not apoptosis," *Am. J. Physiol.,* 277:C20-C28, 1999.

van Gorp, Hornstra, Van Dam-Mieras, Heemskerk, "Function of glutathione peroxidase in endothelial cell vitality," *Arch. Biochem. Biophys.,* 382(1):63-71, 2000.

van Gorp, Heeneman, Broers, Bronnenberg, Van Dam-Mieras, Heemskerk, "Glutathione oxidation in calcium- and p38 MAPK-dependent membrane blebbing of endothelial cells," *Biochim. Biophys. Acta,* 1591(1-3):129-138, 2002.

van Lummel, Pennings, Derksen, Urbanus, Lutters, Kaldenhoven, de Groot, "The binding site in β2-glycoprotein I for ApoER2' on platelets is located in domain V," *J. Biol. Chem.,* 280(44):36729-36, 2005.

Vitetta et al., "Phase I immunotoxin trial in patients with B-cell lymphoma," *Cancer Res.,* 15:4052-4058, 1991.

Vlachoyiannopoulos, Beigbeder, Duelanes, Youinou, Hunt, Krilis, Moutsopoulos, "Antibodies to phosphatidylethanolamine in antiphospholipid syndrome and systemic lupus erythematosus: their correlation with anticardiolipin antibodies and beta 2 glycoprotein-I plasma levels," *Autoimmunity,* 16(4):245-249, 1993.

Vogt, Ng, Rote, "A model for the antiphospholipid antibody syndrome: Monoclonal antiphosphatidylserine antibody induces intrauterine growth restriction in mice," *Am. J. Obstet. Gynecol.,* 174:700-707, 1996.

Vogt, Ng, Rote, "Antiphosphatidylserine antibody removes Annexin V and facilitates the binding prothrombin at the surface of a choriocarcinoma model of trophoblast differentiation," *Am. J. Obstet. Gynecol.,* 177:964-972, 1997.

Volpert, Lawler, Bouck, "A human fibrosarcoma inhibits systemic angiogenesis and the growth of experimental metastases via thrombospondin-1," *Proc. Natl. Acad. Sci. USA,* 95(11):6343-6348, 1998.

Vukanovic et al., "Antiangiogenic effects of the quinoline-3-carboxamide linomide," *Cancer Res.,* 53(8):1833-1837, 1993.

Wakamatsu, Choung, Kobayashi, Inoue, Higashijima and Miyazawa, "Complex Formation of Peptide Antibiotic Ro09-0198 with Lysophosphatidylethanolamine: $^1$H NMR Analysis in Dimethyl Sulfoxide Solution," *Biochemistry,* 29(1):113-118, 1986.

Waltenberger et al., "Suramin is a potent inhibitor of vascular endothelial growth factor. A contribution to the molecular basis of its antiangiogenic action," *J. Mol. Cell Cardiol.,* 28(7):1523-1529, 1996.

Wamil et al., "Soluble E-selectin in cancer patients as a marker of the therapeutic efficacy of CM101, a tumor-inhibiting anti-neovascularization agent, evaluated in phase I clinical trail," *J. Cancer Res. Clin. Oncol.,* 123(3): 173-179, 1997.

Wang and Joseph, "Mechanisms of hydrogen peroxide-induced calcium dysregulation in PC12 cells," *Free Rad. Biol. Med.,* 28(8):1222-1231, 2000.

Wells, "Starving cancer into submission", *Chem. Biol.,* 5(4): R87-88, 1998.

Whitworth, Pak, Esgro, Kleinerman, Fidler, "Macrophages and Cancer," *Cancer Meta. Rev.,* 8:319-351, 1990.

Wiesmann, et al., "Crystal structure at 1.7 A resolution of VEGF in complex with domain 2 of the Flt-1 receptor," *Cell,* 91(5):695-704, 1997.

Weiss, Young, LoBuglio, Slivka and Nimeh, "Role of Hydrogen Peroxide in Neutrophil-Mediated Destruction of Cultured Endothelial Cells," *J. Clin. Invest.,* 68:714-721, 1981.

Williamson and Schlegel, "Back and forth: the regulation and function of transbilayer phospholipid movement in eukaryotic cells," *Molec. Mem. Biol.,* 11:199-216, 1994.

Willems, Janssen, Pelsers et al., "Role of divalency in the high-affinity binding of anticardiolipin antibody-beta(2)-glycoprotein I complexes to lipid membranes," *Biochemistry,* 35:13833-13842, 1996.

Willman et al., "Prodrugs in cancer therapy", *Biochem. Soc. Trans.,* 14:375-382, 1988.

Winter and Milstein, "Man-made antibodies," *Nature,* 349: 293-299, 1991.

Wolff et al., "Dexamethasone inhibits glioma-induced formation of capillary like structures in vitro and angiogenesis in vivo," *Klin. Padiatr.,* 209(4):275-277, 1997.

Woodle, Engbers, Zalipsky, *Bioconjugate Chem.,* 5:493-496, 1994.

Wurm, "beta 2-Glycoprotein-I (apolipoprotein H) interactions with phospholipid vesicles," *Int. J. Biochem.,* 16:511-15, 1984.

Xie, Padron, Liao, Wang, Roth and De Brabander, "Salicylihalamide A inhibits the $V_0$ sector of the V-ATPase through a mechanism distinct from bafilomycin $A_1$," *J. Biol. Chem.,* 279(19):19755-63, 2004.

Yamada, Moldow, Sacks, Craddock, Boogaens and Jacob, "Deleterious Effects of Endotoxin on Cultured Endothelial Cells: An in vitro Model of Vascular injury," *Inflammation,* 5:115-116, 1981.

Yamamura et al., "Effect of Matrigel and laminin peptide YIGSR on tumor growth and metastasis," *Semin. Cancer Biol.,* 4(4):259-265, 1993.

Yasuda, Tsutsumi, Chiba et al., "Beta(2)-glycoprotein I deficiency: prevalence, genetic background and effects on plasma lipoprotein metabolism and hemostasis," *Atherosclerosis,* 152:337-346, 2000.

Yasuda et al., *Blood,* 103:3766-3772, 2004.

Yoon et al., "Inhibitory effect of Korean mistletoe (*Viscum album coloratum*) extract on tumour angiogenesis and metastasis of haematogenous and non-haematogenous tumour cells in mice," *Cancer Lett.,* 97(1):83-91, 1995.

Yoshida et al., "Suppression of hepatoma growth and angiogenesis by a fumagillin derivative TNP470: possible involvement of nitric oxide synthase," *Cancer Res.,* 58(16):3751-3756, 1998.

Zapata et al., *Protein Eng.,* 8(10):1057-1062, 1995.

Zhao, Zhou, Wiedmer, Sims, "Level of expression of phospholipid scramblase regulates induced movement of phosphatidylserine to the cell surface," *J. Biol. Chem.,* 273: 6603-6606, 1998.

Zhou, Zhao, Stout, Luhm, Wiedmer, Sims, "Molecular cloning of human plasma membrane phospholipid scramblase. A protein mediating transbilayer movement of plasma membrane phospholipids," *J. Biol. Chem.,* 272(29): 18240-18244, 1997.

Ziche et al., "Linomide blocks angiogenesis by breast carcinoma vascular endothelial growth factor transfectants," *Br. J. Cancer,* 77(7):1123-1129, 1998.

Zulueta, Yu, Hertig, Thannickal, Hassoun, "Release of hydrogen peroxide in response to hypoxia-reoxygenation: role of an NAD(P)H oxidase-like enzyme in endothelial cell plasma membrane," *Am. J. Respir. Cell Mol. Biol.,* 12(1): 41-49, 1995.

Zwaal, Bevers, Comfurius, Rosing, Tilly, Verhallen, "Loss of membrane phospholipid asymmetry during activation of blood platelets and sickled red cells; mechanisms and physiological significance," *Mol. Cell. Biochem.,* 91:23-31, 1989.

Zwaal and Schroit, "Pathophysiologic implications of membrane phospholipid asymmetry in blood cells," *Blood,* 89(4):1121-1132, 1997.

---

What is claimed is:

1. A construct comprising an antibody Fc region operatively attached to two β2-glycoprotein I (β2GPI) polypeptides, wherein said β2GPI polypeptides each comprise at least an intact domain V of β2GPI, wherein said intact domain V binds to phosphatidylserine, wherein said β2GPI polypeptides form a dimer when attached to said antibody Fc region and wherein said construct retains the property of binding to phosphatidylserine.

2. The construct of claim 1, wherein said β2GPI polypeptides each comprise at least an intact domain V of β2GPI and domain I of β2GPI.

3. The construct of claim 1, wherein said β2GPI polypeptides each comprise at least domain IV and an intact domain V of β2GPI.

4. The construct of claim 3, wherein said β2GPI polypeptides each comprise at least domain III, domain IV and an intact domain V of β2GPI.

5. The construct of claim 4, wherein said β2GPI polypeptides each comprise at least domain II, domain III, domain IV and an intact domain V of β2GPI.

6. The construct of claim 5, wherein said β2GPI polypeptides each comprise domain II, domain III, domain IV and an intact domain V of β2GPI.

7. The construct of claim 5, wherein said β2GPI polypeptides each comprise domain I, domain II, domain III, domain IV and an intact domain V of β2GPI.

8. The construct of claim 1, wherein said β2GPI polypeptides each comprise at least an intact domain V of human β2GPI.

9. The construct of claim 1, wherein said antibody Fc region comprises an antibody hinge and antibody heavy chain constant domains $C_H2$ and $C_H3$.

10. The construct of claim 1, wherein said antibody Fc region comprises an antibody hinge, antibody heavy chain constant domains $C_H2$ and $C_H3$, and at least one of antibody heavy chain constant domains $C_H1$ or $C_H4$.

11. The construct of claim 1, wherein said antibody Fc region is a human antibody Fc region.

12. The construct of claim 1, wherein said antibody Fc region is an Fc region from a human IgG1 (γ1), human IgG3 (γ3), mouse IgG2a (γ2a) or mouse IgG2b (γ2b) antibody.

13. The construct of claim 1, wherein said construct is further operatively attached to at least a first biological agent, diagnostic agent, imaging agent or therapeutic agent.

14. The construct of claim 13, wherein said construct is further operatively attached to an anticellular or cytotoxic agent, cytokine, chemokine, V-type ATPase inhibitor, protein synthesis inhibitor, chemotherapeutic agent, anti-angiogenic agent, apoptosis-inducing agent, anti-tubulin drug, tubulin polymerization inhibitor, radioisotope, coagulant or anti-viral agent.

15. The construct of claim 14, wherein said construct is further operatively attached to:

(a) a ricin, gelonin, abrin, diphtheria, *pseudomonas* or pertussis toxin;

(b) IL-2, IL-12, TNF-α, an interferon or LEC;

(c) the V-type ATPase inhibitor, salicylihalamide;

(d) taxol, docetaxel, paclitaxel, cisplatin, gemcitabine, a combretastatin, dolastatin, auristatin PE, doxorubicin or adriamycin;
(e) an arsenic radioisotope;
(f) truncated Tissue Factor;
(g) a nucleoside reverse transcriptase inhibitor, a non-nucleoside reverse transcriptase inhibitor or a protease inhibitor; or
(h) AZT, cidofovir or ribavirin.

16. The construct of claim 1, wherein said construct is comprised in a liposomal formulation.

17. The construct of claim 1, wherein said construct is comprised in a pharmaceutically acceptable formulation.

18. The construct of claim 17, wherein said pharmaceutically acceptable formulation further comprises at least a second therapeutic agent, anti-cancer agent or anti-viral agent.

19. A construct comprising an antibody Fc region operatively attached to two β2GPI polypeptides, wherein said β2GPI polypeptides each comprise at least an intact domain V of β2GPI, wherein said intact domain V binds to phosphatidylserine, wherein said β2GPI polypeptides form a dimer when attached to said antibody Fc region; and wherein said construct retains the phosphatidylserine binding property of said intact domain V and retains the effector functions of said antibody Fc region.

20. A construct comprising an antibody Fc region operatively attached to two β2GPI polypeptides; wherein said β2GPI polypeptides each comprise at least domain I of β2GPI and an intact domain V of β2GPI, wherein said intact domain V binds to phosphatidylserine; wherein said β2GPI polypeptides form a dimer when attached to said antibody Fc region; and wherein said construct retains the phosphatidylserine binding property of said intact domain V and retains the effector functions of said antibody Fc region.

21. A construct comprising an antibody Fc region operatively attached to a first and second β2GPI polypeptide; wherein said first and second β2GPI polypeptides each comprise at least an intact domain V of β2GPI, wherein said intact domain V binds to phosphatidylserine, and said first and second β2GPI polypeptides form an Fc-β2GPI dimer when attached to said antibody Fc region; and wherein said construct retains the phosphatidylserine binding property of said intact domain V and retains the complement activation and antibody-dependent cellular cytotoxicity (ADCC) functions of said antibody Fc region.

22. The construct of claim 21, wherein said first and second β2GPI polypeptides each comprise domain I of β2GPI.

23. The construct of claim 21, wherein said construct is further operatively-attached to at least a first diagnostic agent, imaging agent or therapeutic agent.

24. The construct of claim 1, wherein said antibody Fc region is operatively attached to said β2GPI polypeptides by a direct covalent bond or via a peptide or chemical crosslinker.

25. The construct of claim 1, wherein said antibody Fc region is operatively attached to said β2GPI polypeptides by recombinant expression as a fusion protein.

26. The construct of claim 1, wherein said β2GPI polypeptides each comprise at least an intact domain V of β2GPI and lack domain I of β2GP1.

27. The construct of claim 1, wherein said construct retains the complement activation and antibody-dependent cellular cytotoxicity (ADCC) functions of said antibody Fc region.

28. The construct of claim 21, wherein said first and second β2GPI polypeptides each lack domain I of β2GPI.

29. A construct comprising an antibody Fc region operatively attached to two β2GPI polypeptides; wherein said β2GPI polypeptides each lack domain I of β2GPI and each comprise at least an intact domain V of β2GPI, wherein said intact domain V binds to phosphatidylserine; wherein said β2GPI polypeptides form a dimer when attached to said antibody Fc region; and wherein said construct retains the phosphatidylserine binding property of said intact domain V and retains the effector functions of said antibody Fc region.

30. A construct comprising an antibody Fc region operatively attached to two β2GPI polypeptides; wherein said β2GPI polypeptides each comprise at least an intact domain V of β2GPI and one or more of the other four domains of β2GPI, wherein said intact domain V binds to phosphatidylserine; wherein said β2GPI polypeptides form a dimer when attached to said antibody Fc region; and wherein said construct retains the phosphatidylserine binding property of said intact domain V and retains the complement activation and antibody-dependent cellular cytotoxicity (ADCC) functions of said antibody Fc region.

31. A construct comprising an antibody Fc region operatively attached to two β2GPI polypeptides; wherein said β2GPI polypeptides each lack domain I of β2GPI and each comprise at least an intact domain V of β2GPI, wherein said intact domain V binds to phosphatidylserine; wherein said β2GPI polypeptides form a dimer when attached to said antibody Fc region; and wherein said construct retains the phosphatidylserine binding property of said intact domain V and retains the complement activation and antibody-dependent cellular cytotoxicity (ADCC) functions of said antibody Fc region.

* * * * *

UNITED STATES PATENT AND TRADEMARK OFFICE

CERTIFICATE OF CORRECTION

PATENT NO. : 8,956,616 B2
APPLICATION NO. : 11/339392
DATED : February 17, 2015
INVENTOR(S) : Thorpe et al.

It is certified that error appears in the above-identified patent and that said Letters Patent is hereby corrected as shown below:

In the Specification,

Column 35, line 13, delete “cytoskeletalal”, insert --cytoskeletal--.

Column 40, line 31, delete “foreoing”, insert --foregoing--.

Column 44, line 59, delete “eleicit”, insert --elicit--.

Column 55, line 65, delete “collasen”, insert --collagen--.

Column 50, line 61, in Table G, delete “iphosphate”, insert --triphophate--.

Column 62, line 41, delete “tree”, insert --three--.

Signed and Sealed this
Twenty-fifth Day of August, 2015

Michelle K. Lee

Michelle K. Lee
*Director of the United States Patent and Trademark Office*

SEQUENCE LISTING

```
<160> NUMBER OF SEQ ID NOS: 25

<210> SEQ ID NO 1
<211> LENGTH: 519
<212> TYPE: DNA
<213> ORGANISM: Mus musculus
```

<400> SEQUENCE: 1
atgggatgga cctggatctt tattttaatc ctgtcagtaa ctacaggtgt ccactctgag 60
gtccagctgc agcagtctgg acctgagctg gagaagcctg gcgcttcagt gaagctatcc 120
tgcaaggctt ctggttactc attcactggc tacaacatga actgggtgaa acagagccat 180
ggaaagagcc ttgaatggat tggacatatt gatccttact atggtgatac ttcctacaac 240
cagaagttca ggggcaaggc cacattgact gtagacaaat cctccagcac agcctacatg 300
cagctcaaga gcctgacatc tgaggactct gcagtctatt actgtgtaaa gggggggttac 360 tacgggcact ggtacttcga tgtctggggc gcagggacca cggtcaccgt ctcctcagct 420
acaacaacag ccccatctgt ctatcccttg gtcccgggcg gatcccccgg gctgcaggaa 480
ttcgatatca agcttatcga taccgtcgac ctcgagggg 519

<210> SEQ ID NO 2
<211> LENGTH: 152
<212> TYPE: PRT
<213> ORGANISM: Mus musculus

<400> SEQUENCE: 2

Met Gly Trp Thr Trp Ile Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Leu Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly His Ile Asp Pro Tyr Tyr Gly Asp Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Val Lys Gly Gly Tyr Tyr Gly His Trp Tyr Phe Asp Val
        115                 120                 125

Trp Gly Ala Gly Thr Thr Val Thr Val Ser Ser Ala Thr Thr Thr Ala
    130                 135                 140

Pro Ser Val Tyr Pro Leu Val Pro
145                 150

<210> SEQ ID NO 3
<211> LENGTH: 435
<212> TYPE: DNA
<213> ORGANISM: Mus musculus

<400> SEQUENCE: 3
atggacatga gggctcctgc acagattttg ggcttcttgt tgctcttgtt tccaggtacc 60
agatgtgaca tccagatgac ccagtctcca tcctccttat ctgcctctct gggagaaaga 120
gtcagtctca cttgtcgggc aagtcaggac attggtagta gcttaaactg gcttcagcag 180
ggaccagatg gaactattaa acgcctgatc tacgccacat ccagtttaga ttctggtgtc 240
cccaaaaggt tcagtggcag taggtctggg tcagattatt ctctcaccat cagcagcctt 300
gagtctgaag attttgtaga ctattactgt ctacaatatg ttagttctcc tcccacgttc 360
ggtgctggga ccaagctgga gctgaaacgg gctgatgctg caccaactgt cttcatcttc 420
gggcggatcc cccgg 435

<210> SEQ ID NO 4
<211> LENGTH: 144
<212> TYPE: PRT
<213> ORGANISM: Mus musculus

<400> SEQUENCE: 4

Met Asp Met Arg Ala Pro Ala Gln Ile Leu Gly Phe Leu Leu Leu Leu
1 5 10 15

Phe Pro Gly Thr Arg Cys Asp Ile Gln Met Thr Gln Ser Pro Ser Ser
20 25 30

Leu Ser Ala Ser Leu Gly Glu Arg Val Ser Leu Thr Cys Arg Ala Ser
35 40 45

Gln Asp Ile Gly Ser Ser Leu Asn Trp Leu Gln Gln Gly Pro Asp Gly
50 55 60

Thr Ile Lys Arg Leu Ile Tyr Ala Thr Ser Ser Leu Asp Ser Gly Val
65 70 75 80

Pro Lys Arg Phe Ser Gly Ser Arg Ser Gly Ser Asp Tyr Ser Leu Thr
85 90 95

Ile Ser Ser Leu Glu Ser Glu Asp Phe Val Asp Tyr Tyr Cys Leu Gln
100 105 110

Tyr Val Ser Ser Pro Pro Thr Phe Gly Ala Gly Thr Lys Leu Glu Leu
115 120 125

Lys Arg Ala Asp Ala Ala Pro Thr Val Phe Ile Phe Gly Arg Ile Pro
130 135 140

<210> SEQ ID NO 5
<211> LENGTH: 783
<212> TYPE: DNA
<213> ORGANISM: Artificial
<220> FEATURE:
<223> OTHER INFORMATION: Synthetic Oligonucleotide

<400> SEQUENCE: 5
gcccagccgg ccatggccga ggtgcagctg gtggagtctg ggggaggcgt ggtccagcct 60
gggaggtccc tgagactctc ctgtgcagcc tctggattca ccttcagtag ctatggcatg 120
cactgggtcc gccaggctcc aggcaagggg ctggagtggg tggcagttat atcatatgat 180
ggaagtaata aatactatgc agactccgtg aagggccgat tcaccatctc cagagacaat 240
tccaagaaca cgctgtatct gcaaatgaac agcctgagag ctgaggacac ggccgtgtat 300
tactgtgcaa gattgcatgc tcagacttgg ggccaaggta ccctggtcac cgtctcgagt 360
ggtggaggcg gttcaggcgg aggtggctct ggcggtagtg cacttcagtc tgtgctgacg 420
cagccgcctt cagtgtctgc ggccccagga cagaaggtca ccatctcctg ctctggaagc 480
agctccgaca tggggaatta tgcggtatcc tggtaccagc agctcccagg aacagccccc 540
aaactcctca tctatgaaaa taataagcga ccctcaggga ttcctgaccg attctctggc 600
tccaagtctg gcacctcagc caccctgggc atcactggcc tctggcctga ggacgaggcc 660
gattattact gcttagcatg ggataccagc ccgcggaatg tattcggcgg agggaccaag 720
ctgaccgtcc taggtgcggc cgcacatcat catcaccatc acggggccgc agaacaaaaa 780
ctc 783

<210> SEQ ID NO 6

<211> LENGTH: 261
<212> TYPE: PRT
<213> ORGANISM: Artificial
<220> FEATURE:
<223> OTHER INFORMATION: Synthetic Polypeptide

<400> SEQUENCE: 6

Ala Gln Pro Ala Met Ala Glu Val Gln Leu Val Glu Ser Gly Gly Gly
1 5 10 15

Val Val Gln Pro Gly Arg Ser Leu Arg Leu Ser Cys Ala Ala Ser Gly
20 25 30

Phe Thr Phe Ser Ser Tyr Gly Met His Trp Val Arg Gln Ala Pro Gly
35 40 45

Lys Gly Leu Glu Trp Val Ala Val Ile Ser Tyr Asp Gly Ser Asn Lys
50 55 60

Tyr Tyr Ala Asp Ser Val Lys Gly Arg Phe Thr Ile Ser Arg Asp Asn
65 70 75 80

Ser Lys Asn Thr Leu Tyr Leu Gln Met Asn Ser Leu Arg Ala Glu Asp
85 90 95

Thr Ala Val Tyr Tyr Cys Ala Arg Leu His Ala Gln Thr Trp Gly Gln
100 105 110

Gly Thr Leu Val Thr Val Ser Ser Gly Gly Gly Gly Ser Gly Gly Gly
115 120 125

Gly Ser Gly Gly Ser Ala Leu Gln Ser Val Leu Thr Gln Pro Pro Ser
130 135 140

Val Ser Ala Ala Pro Gly Gln Lys Val Thr Ile Ser Cys Ser Gly Ser
145 150 155 160

Ser Ser Asp Met Gly Asn Tyr Ala Val Ser Trp Tyr Gln Gln Leu Pro
165 170 175

Gly Thr Ala Pro Lys Leu Leu Ile Tyr Glu Asn Asn Lys Arg Pro Ser
180 185 190

Gly Ile Pro Asp Arg Phe Ser Gly Ser Lys Ser Gly Thr Ser Ala Thr
195 200 205

Leu Gly Ile Thr Gly Leu Trp Pro Glu Asp Glu Ala Asp Tyr Tyr Cys
210 215 220

Leu Ala Trp Asp Thr Ser Pro Arg Asn Val Phe Gly Gly Gly Thr Lys
225 230 235 240

Leu Thr Val Leu Gly Ala Ala Ala His His His His His His Gly Ala
245 250 255

Ala Glu Gln Lys Leu
260

<210> SEQ ID NO 7
<211> LENGTH: 20
<212> TYPE: PRT
<213> ORGANISM: Homo sapiens

<400> SEQUENCE: 7

Ala Ser Thr Lys Gly Pro Ser Val Phe Pro Leu Ala Pro Ser Ser Lys
1 5 10 15

Ser Thr Ser Gly
20

<210> SEQ ID NO 8
<211> LENGTH: 15
<212> TYPE: PRT
<213> ORGANISM: Homo sapiens

<400> SEQUENCE: 8

Ile Phe Pro Pro Ser Asp Glu Gln Leu Lys Ser Gly Thr Ala Ser
1               5                   10                  15

<210> SEQ ID NO 9
<211> LENGTH: 19
<212> TYPE: PRT
<213> ORGANISM: Streptomyces cinnamoneus
<220> FEATURE:
<221> NAME/KEY: MISC_FEATURE
<222> LOCATION: (11)..(18)
<223> OTHER INFORMATION: Xaa = Abu

<400> SEQUENCE: 9

Ala Lys Gln Ala Ala Ala Phe Gly Pro Phe Xaa Phe Val Ala Asp Gly
1               5                   10                  15

Asn Xaa Lys

<210> SEQ ID NO 10
<211> LENGTH: 468
<212> TYPE: PRT
<213> ORGANISM: Mus musculus

<400> SEQUENCE: 10

Met Gly Trp Thr Trp Ile Phe Ile Leu Ile Leu Ser Val Thr Thr Gly
1               5                   10                  15

Val His Ser Glu Val Gln Leu Gln Gln Ser Gly Pro Glu Leu Glu Lys
            20                  25                  30

Pro Gly Ala Ser Val Lys Leu Ser Cys Lys Ala Ser Gly Tyr Ser Phe
        35                  40                  45

Thr Gly Tyr Asn Met Asn Trp Val Lys Gln Ser His Gly Lys Ser Leu
    50                  55                  60

Glu Trp Ile Gly His Ile Asp Pro Tyr Tyr Gly Asp Thr Ser Tyr Asn
65                  70                  75                  80

Gln Lys Phe Arg Gly Lys Ala Thr Leu Thr Val Asp Lys Ser Ser Ser
                85                  90                  95

Thr Ala Tyr Met Gln Leu Lys Ser Leu Thr Ser Glu Asp Ser Ala Val
            100                 105                 110

Tyr Tyr Cys Val Lys Gly Gly Tyr Tyr Gly His Trp Tyr Phe Asp Val
        115                 120                 125

Trp Gly Ala Gly Thr Thr Val Thr Val Ser Ser Ala Lys Thr Thr Ala
    130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Glu Pro Arg Gly Pro
225                 230                 235                 240

Thr Ile Lys Pro Cys Pro Pro Cys Lys Cys Pro Ala Pro Asn Leu Leu
                245                 250                 255

Gly Gly Pro Ser Val Phe Ile Phe Pro Pro Lys Ile Lys Asp Val Leu

```
            260                 265                 270

Met Ile Ser Leu Ser Pro Ile Val Thr Cys Val Val Val Asp Val Ser
        275                 280                 285

Glu Asp Asp Pro Asp Val Gln Ile Ser Trp Phe Val Asn Asn Val Glu
    290                 295                 300

Val His Thr Ala Gln Thr Gln Thr His Arg Glu Asp Tyr Asn Ser Thr
305                 310                 315                 320

Leu Arg Val Val Ser Ala Leu Pro Ile Gln His Gln Asp Trp Met Ser
                325                 330                 335

Gly Lys Glu Phe Lys Cys Lys Val Asn Asn Lys Asp Leu Pro Ala Pro
            340                 345                 350

Ile Glu Arg Thr Ile Ser Lys Pro Lys Gly Ser Val Arg Ala Pro Gln
        355                 360                 365

Val Tyr Val Leu Pro Pro Pro Glu Glu Glu Met Thr Lys Lys Gln Val
    370                 375                 380

Thr Leu Thr Cys Met Val Thr Asp Phe Met Pro Glu Asp Ile Tyr Val
385                 390                 395                 400

Glu Trp Thr Asn Asn Gly Lys Thr Glu Leu Asn Tyr Lys Asn Thr Glu
                405                 410                 415

Pro Val Leu Asp Ser Asp Gly Ser Tyr Phe Met Tyr Ser Lys Leu Arg
            420                 425                 430

Val Glu Lys Lys Asn Trp Val Glu Arg Asn Ser Tyr Ser Cys Ser Val
        435                 440                 445

Val His Glu Gly Leu His Asn His His Thr Thr Lys Ser Phe Ser Arg
    450                 455                 460

Thr Pro Gly Lys
465


<210> SEQ ID NO 11
<211> LENGTH: 236
<212> TYPE: PRT
<213> ORGANISM: Mus musculus

<400> SEQUENCE: 11

Met Asp Met Arg Ala Pro Ala Gln Ile Leu Gly Phe Leu Leu Leu Leu
1               5                   10                  15

Phe Pro Gly Thr Arg Cys Asp Ile Gln Met Thr Gln Ser Pro Ser Ser
            20                  25                  30

Leu Ser Ala Ser Leu Gly Glu Arg Val Ser Leu Thr Cys Arg Ala Ser
        35                  40                  45

Gln Asp Ile Gly Ser Ser Leu Asn Trp Leu Gln Gln Gly Pro Asp Gly
    50                  55                  60

Thr Ile Lys Arg Leu Ile Tyr Ala Thr Ser Ser Leu Asp Ser Gly Val
65                  70                  75                  80

Pro Lys Arg Phe Ser Gly Ser Arg Ser Gly Ser Asp Tyr Ser Leu Thr
                85                  90                  95

Ile Ser Ser Leu Glu Ser Glu Asp Phe Val Asp Tyr Tyr Cys Leu Gln
            100                 105                 110

Tyr Val Ser Ser Pro Pro Thr Phe Gly Ala Gly Thr Lys Leu Glu Leu
        115                 120                 125

Lys Arg Ala Asp Ala Ala Pro Thr Val Ser Ile Phe Pro Pro Ser Ser
    130                 135                 140

Glu Gln Leu Thr Ser Gly Gly Ala Ser Val Val Cys Phe Leu Asn Asn
145                 150                 155                 160
```

-continued

```
Phe Tyr Pro Lys Asp Ile Asn Val Lys Trp Lys Ile Asp Gly Ser Glu
                165                 170                 175

Arg Gln Asn Gly Val Leu Asn Ser Trp Thr Asp Gln Asp Ser Lys Asp
            180                 185                 190

Ser Thr Tyr Ser Met Ser Ser Thr Leu Thr Leu Thr Lys Asp Glu Tyr
        195                 200                 205

Glu Arg His Asn Ser Tyr Thr Cys Glu Ala Thr His Lys Thr Ser Thr
    210                 215                 220

Ser Pro Ile Val Lys Ser Phe Asn Arg Asn Glu Cys
225                 230                 235
```

<210> SEQ ID NO 12
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 12
ggaattcgga cggacctgtc ccaagc 26

<210> SEQ ID NO 13
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 13
ggaattcgta tgtccttttg c 21

<210> SEQ ID NO 14
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 14
ggaattcgct cccatcatct gc 22

<210> SEQ ID NO 15
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 15
ggaattcgta aaatgcccat tc 22

<210> SEQ ID NO 16
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 16
ggaattcgca tcttgtaaag tac 23

<210> SEQ ID NO 17
<211> LENGTH: 22
<212> TYPE: DNA

<213> ORGANISM: Artificial
<220> FEATURE:
<223> OTHER INFORMATION: Synthetic Oligonucleotide

<400> SEQUENCE: 17
ttctagatta gcatggcttt ac 22

<210> SEQ ID NO 18
<211> LENGTH: 24
<212> TYPE: PRT
<213> ORGANISM: Mus musculus

<400> SEQUENCE: 18

Met Asp Met Arg Ala Pro Ala Gln Ile Leu Gly Phe Leu Leu Leu Leu
1 5 10 15

Phe Pro Gly Thr Arg Cys Leu Arg
20

<210> SEQ ID NO 19
<211> LENGTH: 561
<212> TYPE: PRT
<213> ORGANISM: Mus musculus

<400> SEQUENCE: 19

Glu Pro Arg Gly Pro Thr Ile Lys Pro Cys Pro Pro Cys Lys Cys Pro
1 5 10 15

Ala Pro Asn Leu Leu Gly Gly Pro Ser Val Phe Ile Phe Pro Pro Lys
20 25 30

Ile Lys Asp Val Leu Met Ile Ser Leu Ser Pro Ile Val Thr Cys Val
35 40 45

Val Val Asp Val Ser Glu Asp Asp Pro Asp Val Gln Ile Ser Trp Phe
50 55 60

Val Asn Asn Val Glu Val His Thr Ala Gln Thr Gln Thr His Arg Glu
65 70 75 80

Asp Tyr Asn Ser Thr Leu Arg Val Val Ser Ala Leu Pro Ile Gln His
85 90 95

Gln Asp Trp Met Ser Gly Lys Glu Phe Lys Cys Lys Val Asn Asn Lys
100 105 110

Asp Leu Pro Ala Pro Ile Glu Arg Thr Ile Ser Lys Pro Lys Gly Ser
115 120 125

Val Arg Ala Pro Gln Val Tyr Val Leu Pro Pro Pro Glu Glu Glu Met
130 135 140

Thr Lys Lys Gln Val Thr Leu Thr Cys Met Val Thr Asp Phe Met Pro
145 150 155 160

Glu Asp Ile Tyr Val Glu Trp Thr Asn Asn Gly Lys Thr Glu Leu Asn
165 170 175

Tyr Lys Asn Thr Glu Pro Val Leu Asp Ser Asp Gly Ser Tyr Phe Met
180 185 190

Tyr Ser Lys Leu Arg Val Glu Lys Lys Asn Trp Val Glu Arg Asn Ser
195 200 205

Tyr Ser Cys Ser Val Val His Glu Gly Leu His Asn His His Thr Thr
210 215 220

Lys Ser Phe Ser Arg Thr Pro Gly Lys Thr Gly Gly Arg Ile Cys Pro
225 230 235 240

Lys Pro Asp Asp Leu Pro Phe Ala Thr Val Val Pro Leu Lys Thr Ser
245 250 255

Tyr Asp Pro Gly Glu Gln Ile Val Tyr Ser Cys Lys Pro Gly Tyr Val

```
            260                 265                 270

Ser Arg Gly Gly Met Arg Arg Phe Thr Cys Pro Leu Thr Gly Met Trp
        275                 280                 285

Pro Ile Asn Thr Leu Arg Cys Val Pro Arg Val Cys Pro Phe Ala Gly
    290                 295                 300

Ile Leu Glu Asn Gly Ile Val Arg Tyr Thr Ser Phe Glu Tyr Pro Lys
305                 310                 315                 320

Asn Ile Ser Phe Ala Cys Asn Pro Gly Phe Phe Leu Asn Gly Thr Ser
                325                 330                 335

Ser Ser Lys Cys Thr Glu Glu Gly Lys Trp Ser Pro Asp Ile Pro Ala
            340                 345                 350

Cys Ala Arg Ile Thr Cys Pro Pro Pro Pro Val Pro Lys Phe Ala Leu
        355                 360                 365

Leu Lys Asp Tyr Arg Pro Ser Ala Gly Asn Asn Ser Leu Tyr Gln Asp
    370                 375                 380

Thr Val Val Phe Lys Cys Leu Pro His Phe Ala Met Ile Gly Asn Asp
385                 390                 395                 400

Thr Val Met Cys Thr Glu Gln Gly Asn Trp Thr Arg Leu Pro Glu Cys
                405                 410                 415

Leu Glu Val Lys Cys Pro Phe Pro Pro Arg Pro Glu Asn Gly Tyr Val
            420                 425                 430

Asn Tyr Pro Ala Lys Pro Val Leu Leu Tyr Lys Asp Lys Ala Thr Phe
        435                 440                 445

Gly Cys His Glu Thr Tyr Lys Leu Asp Gly Pro Glu Glu Ala Glu Cys
    450                 455                 460

Thr Lys Thr Arg Thr Trp Ser Phe Leu Pro Thr Cys Arg Glu Ser Cys
465                 470                 475                 480

Lys Leu Pro Val Lys Lys Ala Thr Val Leu Tyr Gln Gly Met Arg Val
                485                 490                 495

Lys Ile Gln Glu Gln Phe Lys Asn Gly Met Met His Gly Asp Lys Ile
            500                 505                 510

His Phe Tyr Cys Lys Asn Lys Glu Lys Lys Cys Ser Tyr Thr Val Glu
        515                 520                 525

Ala His Cys Arg Asp Gly Thr Ile Glu Ile Pro Ser Cys Phe Lys Glu
    530                 535                 540

His Ser Ser Leu Ala Phe Trp Lys Thr Asp Ala Ser Glu Leu Thr Pro
545                 550                 555                 560

Cys


<210> SEQ ID NO 20
<211> LENGTH: 36
<212> TYPE: PRT
<213> ORGANISM: Mus musculus

<400> SEQUENCE: 20

Lys Asn Lys Glu Lys Lys Cys Ser Tyr Thr Val Glu Ala His Cys Arg
1               5                   10                  15

Asp Gly Thr Ile Glu Ile Pro Ser Cys Phe Lys Glu His Ser Ser Leu
            20                  25                  30

Ala Phe Trp Lys
        35


<210> SEQ ID NO 21
<211> LENGTH: 329
<212> TYPE: PRT
```

<213> ORGANISM: Homo sapiens

<400> SEQUENCE: 21

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325
```

<210> SEQ ID NO 22
<211> LENGTH: 326
<212> TYPE: PRT
<213> ORGANISM: Homo sapiens

<400> SEQUENCE: 22

```
Gly Arg Thr Cys Pro Lys Pro Asp Asp Leu Pro Phe Ser Thr Val Val
1               5                   10                  15

Pro Leu Lys Thr Phe Tyr Glu Pro Gly Glu Glu Ile Thr Tyr Ser Cys
```

```
            20                  25                  30

Lys Pro Gly Tyr Val Ser Arg Gly Gly Met Arg Lys Phe Ile Cys Pro
        35                  40                  45

Leu Thr Gly Leu Trp Pro Ile Asn Thr Leu Lys Cys Thr Pro Arg Val
    50                  55                  60

Cys Pro Phe Ala Gly Ile Leu Glu Asn Gly Ala Val Arg Tyr Thr Thr
65                  70                  75                  80

Phe Glu Tyr Pro Asn Thr Ile Ser Phe Ser Cys Asn Thr Gly Phe Tyr
                85                  90                  95

Leu Asn Gly Ala Asp Ser Ala Lys Cys Thr Glu Glu Gly Lys Trp Ser
            100                 105                 110

Pro Glu Leu Pro Val Cys Ala Pro Ile Ile Cys Pro Pro Pro Ser Ile
        115                 120                 125

Pro Thr Phe Ala Thr Leu Arg Val Tyr Lys Pro Ser Ala Gly Asn Asn
    130                 135                 140

Ser Leu Tyr Arg Asp Thr Ala Val Phe Glu Cys Leu Pro Gln His Ala
145                 150                 155                 160

Met Phe Gly Asn Asp Thr Ile Thr Cys Thr Thr His Gly Asn Trp Thr
                165                 170                 175

Lys Leu Pro Glu Cys Arg Glu Val Lys Cys Pro Phe Pro Ser Arg Pro
            180                 185                 190

Asp Asn Gly Phe Val Asn Tyr Pro Ala Lys Pro Thr Leu Tyr Tyr Lys
        195                 200                 205

Asp Lys Ala Thr Phe Gly Cys His Asp Gly Tyr Ser Leu Asp Gly Pro
    210                 215                 220

Glu Glu Ile Glu Cys Thr Lys Leu Gly Asn Trp Ser Ala Met Pro Ser
225                 230                 235                 240

Cys Lys Ala Ser Cys Lys Leu Pro Val Lys Lys Ala Thr Val Val Tyr
                245                 250                 255

Gln Gly Glu Arg Val Lys Ile Gln Glu Lys Phe Lys Asn Gly Met Leu
            260                 265                 270

His Gly Asp Lys Val Ser Phe Phe Cys Lys Asn Lys Glu Lys Lys Cys
        275                 280                 285

Ser Tyr Thr Glu Asp Ala Gln Cys Ile Asp Gly Thr Ile Glu Val Pro
    290                 295                 300

Lys Cys Phe Lys Glu His Ser Ser Leu Ala Phe Trp Lys Thr Asp Ala
305                 310                 315                 320

Ser Asp Val Lys Pro Cys
                325


<210> SEQ ID NO 23
<211> LENGTH: 557
<212> TYPE: PRT
<213> ORGANISM: Homo sapiens

<400> SEQUENCE: 23

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60
```

```
Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Arg Thr Cys Pro Lys Pro Asp Asp
225                 230                 235                 240

Leu Pro Phe Ser Thr Val Val Pro Leu Lys Thr Phe Tyr Glu Pro Gly
                245                 250                 255

Glu Glu Ile Thr Tyr Ser Cys Lys Pro Gly Tyr Val Ser Arg Gly Gly
            260                 265                 270

Met Arg Lys Phe Ile Cys Pro Leu Thr Gly Leu Trp Pro Ile Asn Thr
        275                 280                 285

Leu Lys Cys Thr Pro Arg Val Cys Pro Phe Ala Gly Ile Leu Glu Asn
    290                 295                 300

Gly Ala Val Arg Tyr Thr Thr Phe Glu Tyr Pro Asn Thr Ile Ser Phe
305                 310                 315                 320

Ser Cys Asn Thr Gly Phe Tyr Leu Asn Gly Ala Asp Ser Ala Lys Cys
                325                 330                 335

Thr Glu Glu Gly Lys Trp Ser Pro Glu Leu Pro Val Cys Ala Pro Ile
            340                 345                 350

Ile Cys Pro Pro Pro Ser Ile Pro Thr Phe Ala Thr Leu Arg Val Tyr
        355                 360                 365

Lys Pro Ser Ala Gly Asn Asn Ser Leu Tyr Arg Asp Thr Ala Val Phe
    370                 375                 380

Glu Cys Leu Pro Gln His Ala Met Phe Gly Asn Asp Thr Ile Thr Cys
385                 390                 395                 400

Thr Thr His Gly Asn Trp Thr Lys Leu Pro Glu Cys Arg Glu Val Lys
                405                 410                 415

Cys Pro Phe Pro Ser Arg Pro Asp Asn Gly Phe Val Asn Tyr Pro Ala
            420                 425                 430

Lys Pro Thr Leu Tyr Tyr Lys Asp Lys Ala Thr Phe Gly Cys His Asp
        435                 440                 445

Gly Tyr Ser Leu Asp Gly Pro Glu Glu Ile Glu Cys Thr Lys Leu Gly
    450                 455                 460

Asn Trp Ser Ala Met Pro Ser Cys Lys Ala Ser Cys Lys Leu Pro Val
465                 470                 475                 480

Lys Lys Ala Thr Val Val Tyr Gln Gly Glu Arg Val Lys Ile Gln Glu
```

```
                485                 490                 495

Lys Phe Lys Asn Gly Met Leu His Gly Asp Lys Val Ser Phe Phe Cys
            500                 505                 510

Lys Asn Lys Glu Lys Lys Cys Ser Tyr Thr Glu Asp Ala Gln Cys Ile
        515                 520                 525

Asp Gly Thr Ile Glu Val Pro Lys Cys Phe Lys Glu His Ser Ser Leu
    530                 535                 540

Ala Phe Trp Lys Thr Asp Ala Ser Asp Val Lys Pro Cys
545                 550                 555


<210> SEQ ID NO 24
<211> LENGTH: 36
<212> TYPE: PRT
<213> ORGANISM: Homo sapiens

<400> SEQUENCE: 24

Lys Asn Lys Glu Lys Lys Cys Ser Tyr Thr Glu Asp Ala Gln Cys Ile
1               5                   10                  15

Asp Gly Thr Ile Glu Val Pro Lys Cys Phe Lys Glu His Ser Ser Leu
            20                  25                  30

Ala Phe Trp Lys
        35


<210> SEQ ID NO 25
<211> LENGTH: 9546
<212> TYPE: DNA
<213> ORGANISM: Mus musculus

<400> SEQUENCE: 25

agcttcgcga cgtacgttcg aacccgggcc gccaccatgg acatgagggc tcctgcacag      60

attttgggct tcttgttgct cttgtttcca ggtaccagat gcctaaggga gcccagaggg     120

cccacaatca agccctgtcc tccatgcaaa tgcccaggta agtcactaga ccagagctcc     180

acccgggaga atggtaagtg ctgtaaacat ccctgcacta gaggataagc catgtacaga     240

tccatttcca tctctcctca tcagcaccta acctcttggg tggaccatcc gtcttcatct     300

tccctccaaa gatcaaggat gtactcatga tctccctgag ccccatagtc acatgtgtgg     360

tggtggatgt gagcgaggat gacccagatg tccagatcag ctggtttgtg aacaacgtgg     420

aagtacacac agctcagaca caaacccata gagaggatta caacagtact ctccgggtgg     480

tcagtgccct ccccatccag caccaggact ggatgagtgg caaggagttc aaatgcaagg     540

tcaacaacaa agacctccca gcgcccatcg agagaaccat ctcaaaaccc aaaggtgaga     600

gctgcagcct gactgcatgg gggctgggat gggcataagg ataaaggtct gtgtggacag     660

ccttctgctt cagccatgac ctttgtgtat gtttctaccc tcacagggtc agtaagagct     720

ccacaggtat atgtcttgcc tccaccagaa gaagagatga ctaagaaaca ggtcactctg     780

acctgcatgg tcacagactt catgcctgaa gacatttacg tggagtggac caacaacggg     840

aaaacagagc taaactacaa gaacactgaa ccagtcctgg actctgatgg ttcttacttc     900

atgtacagca agctgagagt ggaaaagaag aactgggtgg aaagaaatag ctactcctgt     960

tcagtggtcc acgagggtct gcacaatcac cacacgacta agagcttctc tcggactccg    1020

ggtaaaaccg gggacggat ctgtccgaag ccggatgacc taccatttgc tacggttgtc    1080

cccttaaaga catcctacga ccctggggag cagattgtct actcctgcaa gccaggctac    1140

gtgtccaggg gagggatgag acggtttacc tgtcctctca caggaatgtg gcccatcaac    1200
```

```
accctgagat gtgtccccag agtatgtcct ttcgctggaa tcttagaaaa tggaattgta   1260
cgctacacga gttttgaata tcccaagaac atcagttttg cttgtaaccc tgggtttttt   1320
ctgaatggga ccagctcatc taagtgcacg gaggaaggaa aatggagccc agatattcct   1380
gcttgtgctc gcatcacctg cccgccacca ccagttccaa agtttgcact ccttaaggat   1440
tataggcctt cagctgggaa caactctttg tatcaggaca cagtggtctt taaatgcttg   1500
ccacactttg ccatgatcgg aaatgacaca gtcatgtgca cagaacaagg aaactggacc   1560
cgattgccag aatgcctgga agtaaaatgt cccttccctc cgaggccaga aaatgggtat   1620
gtgaattatc ctgcaaagcc ggtgcttcta tataaggata aagccacatt tggttgccat   1680
gagacataca agctggacgg cccagaagaa gcggaatgta ccaagacgag aacttggtcc   1740
ttcttgccga cctgtagaga gtcttgcaaa ctccccgtta agaaagccac cgtgctgtac   1800
caagggatga gggtgaagat ccaggaacag tttaagaatg ggatgatgca tggcgacaaa   1860
attcacttct actgcaaaaa caaagagaag aagtgcagct acactgtgga ggctcattgc   1920
agagatggca ctatcgagat tccctcgtgc ttcaaggagc acagttctct ggctttctgg   1980
aaaacggatg catcagaact gacaccgtgc tgaagtcgaa ttcattgatc ataatcagcc   2040
ataccacatt tgtagaggtt ttacttgctt taaaaaacct cccacacctc cccctgaacc   2100
tgaaacataa aatgaatgca attgttgttg ttaacttgtt tattgcagct tataatggtt   2160
acaaataaag caatagcatc acaaatttca caaataaagc atttttttca ctgcattcta   2220
gttgtggttt gtccaaactc atcaatgtat cttatcatgt ctggcggccg cgacctgcag   2280
gcgcagaact ggtaggtatg gaagatccct cgagatccat tgtgctggcg gtaggcgagc   2340
agcgcctgcc tgaagctgcg ggcattccca gtcagaaatg agcgccagtc gtcgtcggct   2400
ctcggcaccg aagtgctatg attctccgcc agcatggctt cggccagtgc gtcgagcagc   2460
gcccgcttgt tcctgaagtg ccagtaaagc gccggctgct gaacccccaa ccgttccgcc   2520
agtttgcgtg tcgtcagacc gtctacgccg acctcgttca acaggtccag ggcggcacgg   2580
atcactgtat tcggctgcaa ctttgtcatg cttgacactt tatcactgat aaacataata   2640
tgtccaccaa cttatcagtg ataaagaatc cgcgccagca caatggatct cgaggtcgag   2700
ggatctctag aggatcctct acgccggacg catcgtggcc ggcatcaccg gcgccacagg   2760
tgcggttgct ggcgcctata tcgccgacat caccgatggg gaagatcggg ctcgccactt   2820
cgggctcatg agcgcttgtt tcggcgtggg tatggtggca ggccccgtgg ccgggggact   2880
gttgggcgcc atctccttgc atgcaccatt ccttgcggcg gcggtgctca acggcctcaa   2940
cctactactg ggctgcttcc taatgcagga gtcgcataag ggagagcgtc gacctcgggc   3000
cgcgttgctg gcgtttttcc ataggctccg cccccctgac gagcatcaca aaaatcgacg   3060
ctcaagtcag aggtggcgaa acccgacagg actataaaga taccaggcgt ttccccctgg   3120
aagctccctc gtgcgctctc ctgttccgac cctgccgctt accggatacc tgtccgcctt   3180
tctcccttcg ggaagcgtgg cgctttctca tagctcacgc tgtaggtatc tcagttcggt   3240
gtaggtcgtt cgctccaagc tgggctgtgt gcacgaaccc cccgttcagc ccgaccgctg   3300
cgccttatcc ggtaactatc gtcttgagtc caacccggta agacacgact tatcgccact   3360
ggcagcagcc actggtaaca ggattagcag agcgaggtat gtaggcggtg ctacagagtt   3420
cttgaagtgg tggcctaact acggctacac tagaagaaca gtatttggta tctgcgctct   3480
gctgaagcca gttaccttcg gaaaaagagt tggtagctct tgatccggca aacaaaccac   3540
cgctggtagc ggtggttttt ttgtttgcaa gcagcagatt acgcgcagaa aaaaaggatc   3600
```

-continued

```
tcaagaagat cctttgatct tttctacggg gtctgacgct cagtggaacg aaaactcacg   3660
ttaagggatt ttggtcatga gattatcaaa aaggatcttc acctagatcc ttttaaatta   3720
aaaatgaagt tttaaatcaa tctaaagtat atatgagtaa acttggtctg acagttacca   3780
atgcttaatc agtgaggcac ctatctcagc gatctgtcta tttcgttcat ccatagttgc   3840
ctgactcccc gtcgtgtaga taactacgat acgggagggc ttaccatctg gccccagtgc   3900
tgcaatgata ccgcgagacc cacgctcacc ggctccagat ttatcagcaa taaaccagcc   3960
agccggaagg gccgagcgca gaagtggtcc tgcaacttta tccgcctcca tccagtctat   4020
taattgttgc cgggaagcta gagtaagtag ttcgccagtt aatagtttgc gcaacgttgt   4080
tgccattgct acaggcatcg tggtgtcacg ctcgtcgttt ggtatggctt cattcagctc   4140
cggttcccaa cgatcaaggc gagttacatg atcccccatg ttgtgcaaaa aagcggttag   4200
ctccttcggt cctccgatcg ttgtcagaag taagttggcc gcagtgttat cactcatggt   4260
tatggcagca ctgcataatt ctcttactgt catgccatcc gtaagatgct tttctgtgac   4320
tggtgagtac tcaaccaagt cattctgaga atagtgtatg cggcgaccga gttgctcttg   4380
cccggcgtca atacgggata ataccgcgcc acatagcaga actttaaaag tgctcatcat   4440
tggaaaacgt tcttcggggc gaaaactctc aaggatctta ccgctgttga gatccagttc   4500
gatgtaaccc actcgtgcac ccaactgatc ttcagcatct tttactttca ccagcgtttc   4560
tgggtgagca aaaacaggaa ggcaaaatgc cgcaaaaaag ggaataaggg cgacacggaa   4620
atgttgaata ctcatactct tcctttttca atattattga agcatttatc agggttattg   4680
tctcatgagc ggatacatat ttgaatgtat ttagaaaaat aaacaaatag gggttccgcg   4740
cacatttccc cgaaaagtgc cacctgacgt ctaagaaacc attattatca tgacattaac   4800
ctataaaaat aggcgtatca cgaggccctg atggctcttt gcggcaccca tcgttcgtaa   4860
tgttccgtgg caccgaggac aaccctcaag agaaaatgta atcacactgg ctcaccttcg   4920
ggtgggcctt tctgcgttta taaggagaca ctttatgttt aagaaggttg gtaaattcct   4980
tgcggctttg gcagccaagc tagatccggc tgtggaatgt gtgtcagtta gggtgtggaa   5040
agtccccagg ctccccagca ggcagaagta tgcaaagcat gcatctcaat tagtcagcaa   5100
ccaggtgtgg aaagtcccca ggctccccag caggcagaag tatgcaaagc atgcatctca   5160
attagtcagc aaccatagtc ccgcccctaa ctccgcccat cccgccccta actccgccca   5220
gttccgccca ttctccgccc catggctgac taattttttt tatttatgca gaggccgagg   5280
ccgcctcggc ctctgagcta ttccagaagt agtgaggagg cttttttgga ggcctaggct   5340
tttgcaaaaa gctagcttgg ggccaccgct cagagcacct tccaccatgg ccacctcagc   5400
aagttcccac ttgaacaaaa acatcaagca aatgtacttg tgcctgcccc agggtgagaa   5460
agtccaagcc atgtatatct gggttgatgg tactggagaa ggactgcgct gcaaaacccg   5520
caccctggac tgtgagccca agtgtgtaga agagttacct gagtggaatt ttgatggctc   5580
tagtaccttt cagtctgagg gctccaacag tgacatgtat ctcagccctg ttgccatgtt   5640
tcgggacccc ttccgcagag atcccaacaa gctggtgttc tgtgaagttt tcaagtacaa   5700
ccggaagcct gcagagacca atttaaggca ctcgtgtaaa cggataatgg acatggtgag   5760
caaccagcac ccctggtttg gaatggaaca ggagtatact ctgatgggaa cagatgggca   5820
ccccttttggt tggccttcca atggctttcc tgggccccaa ggtccgtatt actgtggtgt   5880
gggcgcagac aaagcctatg gcagggatat cgtggaggct cactaccgcg cctgcttgta   5940
```

-continued

```
tgctggggtc aagattacag gaacaaatgc tgaggtcatg cctgcccagt gggaactcca   6000
aataggaccc tgtgaaggaa tccgcatggg agatcatctc tgggtggccc gtttcatctt   6060
gcatcgagta tgtgaagact ttggggtaat agcaaccttt gaccccaagc ccattcctgg   6120
gaactggaat ggtgcaggct gccataccaa ctttagcacc aaggccatgc gggaggagaa   6180
tggtctgaag cacatcgagg aggccatcga gaaactaagc aagcggcacc ggtaccacat   6240
tcgagcctac gatcccaagg ggggcctgga caatgcccgt ggtctgactg ggttccacga   6300
aacgtccaac atcaacgact tttctgctgg tgtcgccaat cgcagtgcca gcatccgcat   6360
tccccggact gtcggccagg agaagaaagg ttactttgaa gaccgcggcc cctctgccaa   6420
ttgtgacccc tttgcagtga cagaagccat cgtccgcaca tgccttctca atgagactgg   6480
cgacgagccc ttccaataca aaaactaatt agactttgag tgatcttgag cctttcctag   6540
ttcatcccac cccgccccag agagatcttt gtgaaggaac cttacttctg tggtgtgaca   6600
taattggaca aactacctac agagatttaa agctctaagg taaatataaa atttttaagt   6660
gtataatgtg ttaaactact gattctaatt gtttgtgtat tttagattcc aacctatgga   6720
actgatgaat gggagcagtg gtggaatgcc tttaatgagg aaaacctgtt ttgctcagaa   6780
gaaatgccat ctagtgatga tgaggctact gctgactctc aacattctac tcctccaaaa   6840
aagaagagaa aggtagaaga ccccaaggac tttccttcag aattgctaag tttttgagt    6900
catgctgtgt ttagtaatag aactcttgct tgctttgcta tttacaccac aaaggaaaaa   6960
gctgcactgc tatacaagaa aattatggaa aaatattctg taacctttat aagtaggcat   7020
aacagttata atcataacat actgtttttt cttactccac acaggcatag agtgtctgct   7080
attaataact atgctcaaaa attgtgtacc tttagctttt taatttgtaa aggggttaat   7140
aaggaatatt tgatgtatag tgccttgact agagatcata atcagccata ccacatttgt   7200
agaggtttta cttgctttaa aaaacctccc acacctcccc ctgaacctga aacataaaat   7260
gaatgcaatt gttgttgtta acttgtttat tgcagcttat aatggttaca aataaagcaa   7320
tagcatcaca aatttcacaa ataaagcatt tttttcactg cattctagtt gtggtttgtc   7380
caaactcatc aatgtatctt atcatgtctg gatctagctt cgtgtcaagg acggtgactg   7440
cagtgaataa taaaatgtgt gtttgtccga aatacgcgtt ttgagatttc tgtcgccgac   7500
taaattcatg tcgcgcgata gtggtgttta tcgccgatag agatggcgat attggaaaaa   7560
tcgatatttg aaaatatggc atattgaaaa tgtcgccgat gtgagtttct gtgtaactga   7620
tatcgccatt tttccaaaag tgatttttgg gcatacgcga tatctggcga tagcgcttat   7680
atcgtttacg ggggatggcg atagacgact ttggtgactt gggcgattct gtgtgtcgca   7740
aatatcgcag tttcgatata ggtgacagac gatatgaggc tatatcgccg atagaggcga   7800
catcaagctg gcacatggcc aatgcatatc gatctataca ttgaatcaat attggccatt   7860
agccatatta ttcattggtt atatagcata aatcaatatt ggctattggc cattgcatac   7920
gttgtatcca tatcataata tgtacattta tattggctca tgtccaacat taccgccatg   7980
ttgacattga ttattgacta gttattaata gtaatcaatt acggggtcat tagttcatag   8040
cccatatatg gagttccgcg ttacataact tacggtaaat ggcccgcctg gctgaccgcc   8100
caacgacccc cgcccattga cgtcaataat gacgtatgtt cccatagtaa cgccaatagg   8160
gactttccat tgacgtcaat gggtggagta tttacggtaa actgcccact tggcagtaca   8220
tcaagtgtat catatgccaa gtacgccccc tattgacgtc aatgacggta aatggcccgc   8280
ctggcattat gcccagtaca tgaccttatg ggactttcct acttggcagt acatctacgt   8340
```

-continued

```
attagtcatc gctattacca tggtgatgcg gttttggcag tacatcaatg ggcgtggata   8400

gcggtttgac tcacggggat ttccaagtct ccaccccatt gacgtcaatg ggagtttgtt   8460

ttggcaccaa aatcaacggg actttccaaa atgtcgtaac aactccgccc cattgacgca   8520

aatgggcggt aggcgtgtac ggtgggaggt ctatataagc agagctcgtt tagtgaaccg   8580

tcagatcgcc tggagacgcc atccacgctg ttttgacctc catagaagac accgggaccg   8640

atccagcctc cgcggccggg aacggtgcat tggaacgcgg attccccgtg ccaagagtga   8700

cgtaagtacc gcctatagag tctataggcc cacccccttg gcttcttatg catgctatac   8760

tgtttttggc ttggggtcta tacacccccg cttcctcatg ttataggtga tggtatagct   8820

tagcctatag gtgtgggtta ttgaccatta ttgaccactc ccctattggt gacgatactt   8880

tccattacta atccataaca tggctctttg ccacaactct ctttattggc tatatgccaa   8940

tacactgtcc ttcagagact gacacggact ctgtattttt acaggatggg gtctcattta   9000

ttatttacaa attcacatat acaacaccac cgtccccagt gcccgcagtt tttattaaac   9060

ataacgtggg atctccacgc gaatctcggg tacgtgttcc ggacatgggc tcttctccgg   9120

tagcggcgga gcttctacat ccgagccctg ctcccatgcc tccagcgact catggtcgct   9180

cggcagctcc ttgctcctaa cagtggaggc cagacttagg cacagcacga tgcccaccac   9240

caccagtgtg ccgcacaagg ccgtggcggt agggtatgtg tctgaaaatg agctcgggga   9300

gcgggcttgc accgctgacg catttggaag acttaaggca gcggcagaag aagatgcagg   9360

cagctgagtt gttgtgttct gataagagtc agaggtaact cccgttgcgg tgctgttaac   9420

ggtggagggc agtgtagtct gagcagtact cgttgctgcc gcgcgcgcca ccagacataa   9480

tagctgacag actaacagac tgttcctttc catgggtctt ttctgcagtc accgtccttg   9540

acacga                                                              9546
```